(12) United States Patent
Martin et al.

(10) Patent No.: US 8,999,993 B2
(45) Date of Patent: Apr. 7, 2015

(54) RADIOPROTECTOR COMPOUNDS AND METHODS

(75) Inventors: Roger Francis Martin, Ivanhoe (AU); Jonathan White, Wheelers Hill (AU); Pavel Lobachevsky, Montmorency (AU); David Winkler, Malvern (AU); Colin Skene, Glen Waverly (AU); Sebastian Marcuccio, Endeavour Hills (AU)

(73) Assignee: Peter MacCallum Cancer Institute, East Melbourne (AU)

( * ) Notice: Subject to any disclaimer, the term of this patent is extended or adjusted under 35 U.S.C. 154(b) by 190 days.

(21) Appl. No.: 13/640,188

(22) PCT Filed: Apr. 6, 2011

(86) PCT No.: PCT/AU2011/000392
§ 371 (c)(1),
(2), (4) Date: Dec. 21, 2012

(87) PCT Pub. No.: WO2011/123890
PCT Pub. Date: Oct. 13, 2011

(65) Prior Publication Data
US 2013/0109678 A1    May 2, 2013

Related U.S. Application Data

(60) Provisional application No. 61/321,288, filed on Apr. 6, 2010.

(51) Int. Cl.
| | | |
|---|---|---|
| A61K 31/496 | (2006.01) | |
| C07D 235/20 | (2006.01) | |
| C07D 401/14 | (2006.01) | |
| C07D 235/18 | (2006.01) | |
| C07D 403/14 | (2006.01) | |
| C07D 405/14 | (2006.01) | |
| C07D 413/04 | (2006.01) | |
| C07D 413/14 | (2006.01) | |

(52) U.S. Cl.
CPC ............ C07D 401/14 (2013.01); C07D 235/18 (2013.01); C07D 403/14 (2013.01); C07D 405/14 (2013.01); C07D 413/04 (2013.10); C07D 413/14 (2013.01)

(58) Field of Classification Search
USPC ...................................... 514/254.06; 544/370
See application file for complete search history.

(56) References Cited

FOREIGN PATENT DOCUMENTS

| WO | 97/04776 A1 | 2/1997 |
|---|---|---|
| WO | 2004/063170 A1 | 7/2004 |
| WO | 2008/074091 A1 | 6/2008 |

OTHER PUBLICATIONS

International Preliminary Report on Patentability for Application No. PCT/AU2011/000392 dated Oct. 9, 2012.
Tawar et al.; Influence of Phenyl Ring Disubstitution on Bisbenzimidazole and Terbenzimidazole Cytotoxicity: Synthesis and Biological Evaluation as Radioprotectors, J. Med. Chem. 2003, vol. 46, No. 18, pp. 3785-3792.

*Primary Examiner* — Paul Zarek
(74) *Attorney, Agent, or Firm* — Sughrue Mion, PLLC

(57) ABSTRACT

The invention relates to novel compounds, processes for their preparation and their use in protecting biological materials from radiation damage (radioprotection). Preferred compounds of the invention are those of Formula II, as follows:

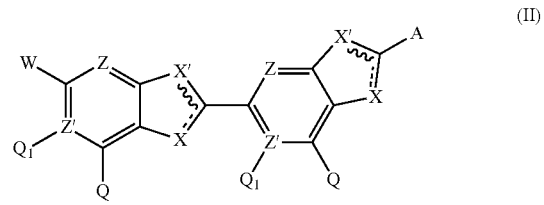

(II)

wherein W represents —N($R_1R_2$) where $R_1$ and $R_2$ are not both hydrogen and where they may together form a 5, 6 or 7 membered ring structure, —NHN($R_1R_2$), —NHR$_3$N($R_1R_2$), —NHR$_3$OR$_2$, —N($R_3$)R$_3$OR$_2$, —N($R_1$)R$_3$OR$_3$OR$_3$, —OR$_3$NR$_1R_2$, —OR$_3$ or W represents piperidyl, piperazinyl, morpholinyl, thiomorpholinyl or diazepanyl each of which may be optionally substituted by $C_1$ to $C_4$ alkyl, $C_2$ to $C_4$ alkenyl, —N(CO)N ($R_1R_2$), —N(CO)OR$_1$, —N(CO)OR$_3$OH, —(CO)NR$_1R_2$, —R$_3$(CO)NR$_1R_2$, —R$_3$OR$_1$, —OR$_1$, —N($R_1R_2$) or —NH—;
$R_1$ and $R_2$ are the same or different and are selected from hydrogen, $C_1$ to $C_4$ alkyl or $C_2$ to $C_4$ alkenyl;
$R_3$ is a $C_1$ to $C_4$ alkyl or $C_2$ to $C_4$ alkenyl group or chain;
Z is the same or different and represents N or CH;
Z' is the same or different and represents N or C;
X represents CH, N or NH, where ----- is a double bond when X is CH or N and a single bond when X is NH;
X' represents N or NH, wherein when X is CH or NX' is NH and wherein X and X' are different and further where ~~~ is a double bond when X' is N and a single bond when X' is NH;
Q represents H, alkoxyl, —NR$_1R_2$, F or Cl;
$Q_1$ is absent when Z' is N and when Z' is C it represents H, alkoxyl, —NR$_1R_2$, F or Cl;
A represents a five to ten membered single or multiple ring structure with heterocyclic N or O located at the ortho position, said ring including optional double bonds, substitutions and/or other heteroatoms
and pharmaceutically acceptable derivatives thereof.

15 Claims, 6 Drawing Sheets

RADIOPROTECTOR COMPOUNDS AND METHODS

CROSS REFERENCE TO RELATED APPLICATIONS

This application is a National Stage of International Application No. PCT/AU2011/000392, filed on Apr. 6, 2011, which claims priority from U.S. Provisional Application No. 61/321,288, filed on Apr. 6, 2010.

FIELD OF THE INVENTION

The invention relates to novel compounds, processes for their preparation and their use in protecting biological materials from radiation damage (radioprotection). In diagnostic and therapeutic radiology, particularly in cancer radiotherapy, radioprotectors may be used to protect certain normal tissues or structures from radiation damage. Radioprotectors also have uses in decreasing the effects of irradiation in non-medical scenarios, both civil and military. The invention relates in particular to novel compounds derived from a bibenzimidazole scaffold that are characterised by having at what can be considered the "right hand side" of the molecule, a five to ten membered single or multiple ring structure with heterocyclic N or O located at the ortho position. The compounds of the invention may exhibit reduced cytotoxicity and/or improved radioprotector activity relative to known radioprotector compounds.

BACKGROUND OF THE INVENTION

It is generally accepted that DNA is the crucial target in the cytotoxic effects of ionising radiation. There is considerable evidence to support the view that DNA double-stranded (ds) breaks are particularly important. The DNA damage results from both direct ionisation in the DNA molecule (direct effect) and by indirect effects mediated by the radiolysis products of water. Carbon-centred radicals on the deoxyribose moiety of DNA are thought to be important precursors of strand breaks. Ionising radiation also induces damage in DNA bases. If the level of cellular DNA damage is sufficient, the consequence of irradiation is cell kill, and thus ionising radiation is used as a mode of cancer therapy. For irradiated normal tissues, the cell killing can result in temporary or permanent impairment of tissue and organ function. The extent of such effects is dependant upon the radiation dose, and if sufficient, can be lethal to the organism. For humans and other animals, hematopoiesis is the most radiosensitive organ/function, followed by the gastrointestinal mucosa. Even if radiation induced DNA damage is sublethal, mutagenic lesions can have serious long term consequences, including carcinogenesis.

The medical strategies or countermeasures aimed at reducing the extent of radiation-induced effects are broadly described as radioprotectors (which to be effective, generally need to be administered prior to radiation exposure), mitigants/mitigators (which can be effective if administered after irradiation, but before the appearance of symptoms), and treatments which are generally administered after the appearance of symptoms. A sub-class of the prophylactic radioprotectors are drugs that reduce the extent of the initial radiation-induced DNA damage, and it is this sub-class that is the major focus of the present invention.

The commercial potential of radioprotectors resides primarily in two distinct arenas. One of these relates to the need to protect normal tissues in cancer radiotherapy patients, and the other concerns the need to assuage the consequences of unplanned irradiation associated with civil scenarios, such as radiation accidents and radiation terrorism, as well as irradiation in military contexts. This second scenario would also include planned exposure to ionising radiation in medical diagnostic procedures, in which administration of radioprotectors could ameliorate the health risks associated with low or modest radiation doses, without interfering with diagnostic imaging processes.

The treatment of tumours with ionising radiation (hereinafter referred to as "cancer radiotherapy") is used extensively in cancer therapy. The goal of such treatment is the destruction of tumour cells and inhibition of tumour cell growth presumably through DNA damage, while minimising damage to non-tumour cells and tissues. The potential for damage to non-tumour cells in the vicinity of the tumour limits the radiation dose that can be administered, which in turn often limits the effectiveness of radiotherapy against certain tumours. This is especially the case in relation to brain tumours and tumours in the abdominal cavity.

Cancer radiotherapy is a very significant public health activity. Given the incidence of cancer in the population and the international assessment that more than 50% of cancer patients benefit from inclusion of radiotherapy in their treatment, more than 10% of the population are likely to experience cancer radiotherapy in their lifetime.

The dominant consideration in prescribing radiation doses for cancer radiotherapy is the assessment of tolerance of the most radiosensitive normal tissues/organs in the treatment field. This assessment, together with the expected radiation dose required to eradicate a tumour, often determines whether the treatment strategy is aimed at cure or palliation. In many cases, the maximum tolerable doses are insufficient to eradicate the tumour. This dilemma is embodied in the concept of therapeutic ratio, which represents the ratio of probabilities of tumour control versus normal tissue morbidity. Approaches to improving the therapeutic ratio include:

(a) optimising the physical targeting of the radiation to the tumour;
(b) fractionation of the radiation dose; and
(c) the use of radiomodifiers (which includes both radioprotectors and radiosensitisers, the latter of which can be used to increase the level of cell kill per unit of radiation dose).

Improving the physical delivery of radiation has had a considerable impact on the practice of radiotherapy. For example, increasing the energy of x-ray photons from several hundred kilovolts to the present-day megavoltage beams enables the zone of maximum radiation dose to be set at depths of several centimetres, whereas with the older machines the maximum dose was near the skin surface. There are a number of more sophisticated approaches to "tailoring" treatment beams in various stages of development and implementation. Brachytherapy, the use of implanted radioactive sources rather than external beams, is a further approach to improving the physical dose distribution.

Almost without exception, curative external beam radiotherapy involves fractionation of the radiation dose. An example of a conventional schedule would be a total of 60 Gray given in thirty 2 Gray fractions. Since cells have the capacity to repair radiation damage between fractions, the fractionated treatment results in much less cell-kill than a single dose of 60 Gray. However, normal cells generally have a greater repair capacity than do tumour cells, so the "sparing" effect of fractionation is more marked for normal tissues. In short, fractionation improves the therapeutic ratio.

Exploration of radiomodifiers such as radioprotectors and radiosensitisers has focussed on hypoxic cell sensitisers such as metranidazole and misonidazole. Radioprotectors have received much less attention than radiosensitisers at the clinical level. The nuclear era spawned considerable effort in the development of radioprotectors with more than 4000 compounds being synthesised and tested at the Walter Reed Army Institute of Research in the United States of America in the 1960's. With the exception of a compound that was called WR2728 (later called Ethyol and now known as Amifostine) none of the compounds have proved useful for cancer radiotherapy, and even WR2728 was considered too toxic for administration in either the military or industrial contexts (i.e., protection against total body irradiation). More recently, for example, Metz and co-workers (Metz et al, *Clin Cancer Res.* 10, 6411-17, 2004) (15) developed the radioprotective compound known as TEMPOL, which demonstrates only limited efficacy even at very high concentrations, and Burdelya and colleagues (Burdelya et al Science 320, 226-30, 2008) (16) developed the compound known as the TOLL receptor agonist which suffers from the necessity for it to be administered systemically.

It is important to note the interplay between the three approaches (a)-(c), above, to improving the therapeutic ratio. A combination of improved physical targeting, fractionation and radiomodifiers could transform the intent in some radiotherapy situations from palliative to curative. For curative schedules, successful application of radiomodifiers would relax the requirement for fractionation and hence reduce overall costs of treatment, which to a large extent is proportional to the number of treatment fractions per patient.

A particularly important role for radioprotectors has emerged from the recognition that accelerated repopulation of tumour cells during radiotherapy can seriously compromise the effectiveness of treatment. The main consequences of this have been as follows:

(i) The development of accelerated treatment schedules to reduce the overall time of radiotherapy treatment. In such accelerated schedules, acute reactions are a particular problem. For example, acute oral mucositis in head and neck cancer patients indicates a clear need for radioprotectors.

(ii) The recognition that the interruption of radiotherapy treatment due to normal tissue reactions will reduce the probability of tumour control. Accordingly, the use of radioprotectors to prevent toxicity-induced treatment interruption would be clearly beneficial.

The events of 11 Sep. 2001 prompted assessments of vulnerability to many types of terrorism scenarios, amongst which is a collection described as radiological terrorism. An example is the so-called "dirty bomb" involving dispersal of some form a radioactivity with conventional explosive. Whilst attention is focused on the acute radiation syndrome (ARS; also referred to as "radiation sickness"), which describes the consequences of whole-body exposure to radiation doses greater than 1 Gy, there are also concerns about the longer-term effects of low doses, namely radiation-induced mutagenesis and carcinogenesis (1). This general situation, and the realisation that no prophylactic agents are available to provide protection against exposure to ionising radiation, has generated significant research and political activity.

The mean lethal dose of radiation required to kill 50% of humans 60 days after whole-body irradiation ($LD_{50/60}$) is between 3.25 and 4 Gy without supportive care, and 6-7 Gy when antibiotics and transfusion support are provided (1). The mortality is largely attributed to the haematopoietic syndrome, a consequence of hypoplasia or aplasia of the bone marrow. Cytopenias develop as a result of radiation-induced and normal attrition of mature functional cells, combined with the failure of replacement because of radiation-induced depletion of haematopoietic stem cells and progenitors. The time and extent of cytopenia generally correlate with radiation dose and prognosis, but the kinetics of depletion and recovery of blood cells also varies between the erythropoiesis, myelopoiesis and thrombopoiesis lineages, thrombopoiesis being the slowest.

The gastrointestinal syndrome results from ablation of stem cells in intestinal crypts, which in turn leads to denudation of the intestinal mucosa. This injury occurs after whole-body doses in the range of 3-15 Gy and in rodents doses at the upper end of this range usually result in death within about 1 week after irradiation.

Countermeasures against unplanned irradiation include a wide range of potential molecular and cellular interventions. However, the mechanistic simplicity of chemical radioprotection—that is, reduction of radiation-induced DNA damage—is attractive because of its widespread potential. In this context, the possible need for protection of individuals at risk of exposure to low radiation doses, to thereby minimise long-term radiation effects such as mutagenesis and carcinogenesis, is particularly important. Such individuals would include emergency personnel involved in response to unplanned exposures, as well as those subject to occupational exposure to ionising radiation.

A further group would be patients exposed to ionizing radiation during diagnostic medical procedures conducted in diagnostic radiology and nuclear medicine departments of hospitals and outpatient facilities.

The radioprotective properties of the minor groove binding DNA ligand Hoechst 33342 were first described by Smith, P. J. and Anderson, C. O. (2), who used clonogenic survival assays of irradiated cultured cells. Young, S. D. and Hill, R. P. (3) reported similar effects in cultured cells, but extended their studies to in vivo experiments. They concluded that the lack of radioprotection in their in vivo experiments was due to insufficient levels of Hoechst 33342 being delivered to target cells following intravenous injection. The findings of Hill and Young underline an important requirement for effective radioprotectors, namely potency. If the radioprotector is more potent, then it is more likely to achieve the required concentrations in an in vivo setting.

There is another aspect to be considered apart from potency. The concentration required for radioprotection must be non-toxic regardless of the potency of the radioprotector. If the radioprotector is delivered systemically, then this lack of toxicity requirement includes not just the cells and tissues to be protected from the radiation, but extends to the toxicity to the subject as a whole. In the case of Hoechst 33342 toxicity limits the extent to which it is useful as a radioprotector.

There is also a substantial conceptual problem in using radioprotectors in cancer radiotherapy. In attempting to decrease the effect of radiation on normal tissues by application of radioprotectors, there is a fear that some of the radioprotector will reach the tumour, thereby compromising tumour cell kill. The existing radioprotectors, e.g. WR2721 (Amifostine) and its active metabolite WR1065, are relatively small, diffusible molecules which do not avidly bind to tissue components and can therefore penetrate effectively through cell layers, so that they can reach the tumour via the circulation.

There is a need for radioprotectors that have limited penetration through cell layers. Such a property enables radioprotectors to be applied locally or topically to critical radiosensitive normal tissues in the vicinity of the tumour.

Limited penetration restricts the extent to which the radioprotector reaches the capillary bed and is taken up into the circulation thereby reaching the tumour by systemic delivery in sufficient concentrations to confer significant radioprotection to the tumour.

The limited diffusion of DNA-binding ligands such as Hoechst 33342 through cell layers is known and has been exploited in mapping the location of cells in multi-cellular spheroids and in vivo, with respect to perfusion. Thus perfusion of Hoechst 33342 is considered a surrogate marker for perfusion of oxygen. In addition to restricting access to the tumour by systemic uptake following local or topical application to normal tissues, there is a further potential advantage of limited penetration in the context of cancer radiotherapy. This advantage stems from the view that the vasculature, in particular the endothelial cells, are the critical targets that determine the damaging effects of radiation. Furthermore, most radioresistant cells in the tumour are those viable cells that are most distant from the capillaries. The radioresistance of these cells is due to their hypoxic state, which in turn reflects their remoteness from the capillaries.

Consequently, radioprotectors having limited diffusion, when administered intravenously, will be delivered more efficiently to critical radiosensitive cells in normal tissues, than to the hypoxic subpopulation of cells in tumours which limit the effectiveness of radiotherapy generally. Thus, the use of such radioprotectors would be expected to enable higher radiation doses to be used, with increased probability of killing the hypoxic cells in the tumour.

However, the potential of the combination of these radiobiological features and the characteristics of DNA-binding radioprotectors can only be useful in cancer radiotherapy provided that an over-riding and necessary requirement of the radioprotectors exists, namely that the radioprotectors are sufficiently potent as to confer demonstrable radioprotection at non-toxic concentrations, when applied topically or systemically. A further practical requirement is that the extent of the limited penetration is sufficient to prevent significant systemic uptake following topical application, but not so pronounced so as to prevent sufficient concentrations from reaching the cells that determine the radiosensitivity of the tissue to be protected from the effects of ionising radiation, by topical or local application.

The extent of radioprotection (in the contexts of both cancer radiotherapy and protection from unplanned radiation exposure) is generally described in terms of dose modification factor (DMF), which is defined as the ratio of radiation doses required to produce the equivalent radiation-induced effect (molecular, cellular or in vivo endpoint) in the presence and absence of the radioprotector. When the radioprotective effect is observed on the basis of an in vivo endpoint, mechanisms other than modification of the initial radiation-induced damage may be involved. For example, for both the haematopoietic syndrome and the gastrointestinal syndrome, infection plays an important role in ultimate mortality, as a consequence of neutropenia and breach of the intestinal mucosal barrier, respectively. Thus, some immunostimulants have potential as mitigators of the radiation response. Immunostimulants can also be effective post-irradiation.

International patent publication No. WO97/04776 and the subsequent publication by Martin et at (4) disclose certain bibenzimidazole compounds characterised by substitution with sterically hindering and electron donating groups. Although these compounds demonstrate strong radioprotective activity there is scope to reduce the inherent cytotoxicity of compounds of this general class. The challenge, however, is to do so while retaining, and preferably improving, radioprotective activity (measured as dose modification factor). The disclosures of WO97/04776 are included herein in their entirety by way of reference.

International patent publication No. WO/2008/074091 also discloses bibenzimidazole compounds substituted with fluorine and/or chlorine and which, relative to known radioprotector compounds such as those of International patent publication No. WO97/04776, exhibit reduced cytotoxicity activity. While the cytotoxicity of the fluorine and chlorine substituted bibenzimidazole compounds was improved there is still a need for development of alternative radioprotective compounds, and preferably compounds that can be used in cancer radiotherapy, in protection of biological material from effects of radiation exposure and/or in protection of humans or animals from the effects of unplanned irradiation, which demonstrate low cytotoxicity but that retain radioprotective potency, and preferably that penetrate through cell layers to a limited extent. In particular it is desirable in some contexts that such compounds can be administered topically to protect tissues such as the skin, oral mucosa, oesophageal mucosa, rectal mucosa, vaginal mucosa and bladder epithelium, as well as parenterally to protect organs such as the lung and brain.

SUMMARY OF THE INVENTION

According to one embodiment of the present invention there is provided a radioprotector compound of Formula I:

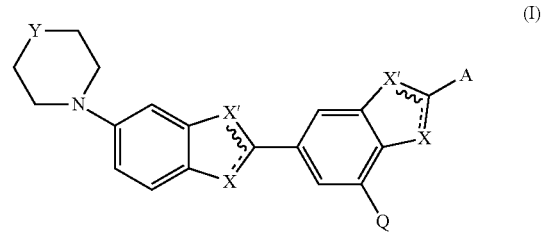

wherein X represents N or NH, where ----- is a double bond when X is N and a single bond when X is NH;

X' represents N or NH, where X and X' are different and where ∼∼∼ is a double bond when X' is N and a single bond when X' is NH;

Q represents methoxyl or H;

Y represents O, methylene, hydroxymethyl or methylamino; and

A represents optionally substituted 2-pyridyl, optionally substituted 2-pyrimidyl, optionally substituted 2-pyrazinyl, optionally substituted 3-pyrazolyl, optionally substituted 5-pyrazolyl, optionally substituted 2-furanyl, optionally substituted 2-quinolinyl, optionally substituted 1-isoquinolinyl or optionally substituted 3-isoquinolinyl;

and pharmaceutically acceptable derivatives thereof.

In one aspect Y represents methylamino or hydroxymethyl and in another aspect A represents optionally substituted 2-pyridyl.

According to another embodiment of the present invention there is provided a radioprotector compound of Formula II:

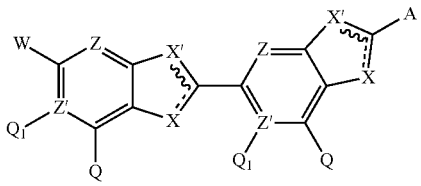

(II)

wherein W represents —N($R_1R_2$) where $R_1$ and $R_2$ are not both hydrogen and where they may together form a 5, 6 or 7 membered ring structure, —NHN($R_1R_2$), —NH$R_3$N($R_1R_2$), —NH$R_3$O$R_2$, —N($R_3$)$R_3$O$R_2$, —N($R_1$)$R_3$O$R_3$O$R_3$, —O$R_3$N$R_1R_2$, —O$R_3$ or W represents piperidyl, piperazinyl, morpholinyl, thiomorpholinyl or diazepanyl each of which may be optionally substituted by $C_1$ to $C_4$ alkyl, $C_2$ to $C_4$ alkenyl, —N(CO)N($R_1R_2$), —N(CO)O$R_1$, —N(CO)O$R_3$OH, —(CO)N$R_1R_2$, —$R_3$(CO)N$R_1R_2$, —$R_3$O$R_1$, —O$R_1$, —N($R_1R_2$) or —NH—.

$R_1$ and $R_2$ are the same or different and are selected from hydrogen, $C_1$ to $C_4$ alkyl or $C_2$ to $C_4$ alkenyl;

$R_3$ is a $C_1$ to $C_4$ alkyl or $C_2$ to $C_4$ alkenyl group or chain;

Z is the same or different and represents N or CH;

Z' is the same or different and represents N or C;

X represents CH, N or NH, where ----- is a double bond when X is CH or N and a single bond when X is NH;

X' represents N or NH, wherein when X is CH or NX' is NH and wherein X and X' are different and further where ⁓ is a double bond when X' is N and a single bond when X' is NH;

Q represents H, alkoxyl, —N$R_1R_2$, F or Cl;

$Q_1$ is absent when Z' is N and when Z' is C it represents H, alkoxyl, —N$R_1R_2$, F or Cl;

A represents a five to ten membered single or multiple ring structure with heterocyclic N or O located at the ortho position, said ring including optional double bonds, substitutions and/or other heteroatoms and pharmaceutically acceptable derivatives thereof.

In one aspect A represents optionally substituted 2-pyridyl, optionally substituted 2-pyrimidyl, optionally substituted 2-pyrazinyl, optionally substituted 3-pyrazolyl, optionally substituted 5-pyrazolyl, optionally substituted 2-furanyl, optionally substituted 2-quinolinyl, optionally substituted 1-isoquinolinyl or optionally substituted 3-isoquinolinyl.

In another aspect the optional substitution of A is by chloro, fluoro, $C_1$ to $C_4$ fluoroalkyl, $C_1$ to $C_4$ alkyl, $C_2$ to $C_4$ alkenyl, $C_1$ to $C_4$ alkoxy, $C_1$ to $C_4$ alkoxyalkyl, $C_1$ to $C_4$ alkylamino, $C_2$ to $C_4$ di-alkylamino or $C_1$ to $C_4$ aminoalkyl.

In another aspect at least one Q represents methoxyl.

According to another embodiment of the present invention there is provided a method of protecting biological material from damaging effects of ionising radiation comprising administering to said material an effective amount of a compound of either Formula I or Formula II prior to or in conjunction with exposure of the material to ionising radiation.

According to another embodiment of the present invention there is provided use of a compound of either Formula I or Formula II in protection of a biological material from damaging effects of ionising radiation.

According to another embodiment of the present invention there is provided use of a compound of either Formula I or Formula II in preparation of a medicament for protection of biological material from damaging effects of ionising radiation.

In one aspect the biological material comprises a human or animal patient undergoing radiation therapy.

BRIEF DESCRIPTION OF THE FIGURES

Within the following detailed description and examples reference will be made to the figures, wherein.

DETAILED DESCRIPTION OF THE INVENTION

Figure 1:
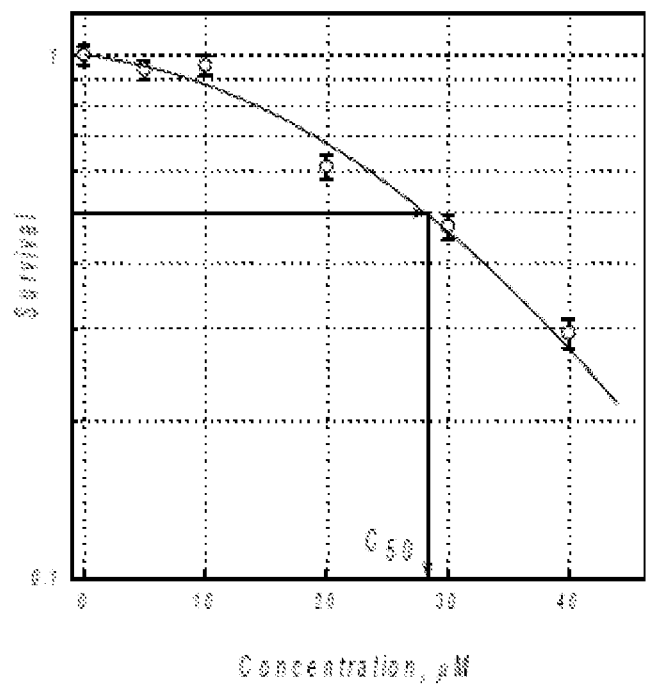
FIG. 1 shows the clonogenic survival of keratinocytes following incubation with various concentrations of a radioprotector. This is of assistance to demonstrate that the cytotoxicity parameter C50 is defined as a concentration of the drug that results in 50% clonogenic survival.

Throughout this specification, unless the context requires otherwise, the word "comprise", or variations such as "comprises" or "comprising", will be understood to imply the inclusion of a stated integer or group of integers but not the exclusion of any other integer or group of integers.

The reference to any prior art in this specification is not, and should not be taken as, an acknowledgment or any form of suggestion that that prior art forms part of the common general knowledge in Australia.

Throughout this specification the terms "compounds of the invention", "the compounds", "radioprotectors", "radioprotective compounds", "radioprotector compounds" "active agents", "active ingredients" or their singular forms are used synonymously to denote compounds according to Formulae (I) or (II), which demonstrate radioprotective activity. The compounds generally have, or are derived from, a bibenzimazole basic structure or scaffold (although elements of the basic bibenzimidazole scaffold may have been substituted, added or removed) with a five to ten membered single or multiple ring structure (shown as "A" in Formula (II)) with heterocyclic N or O located at the ortho position relative to the point of attachment of A located at the right hand side of the compounds. Other substitutions to the basic scaffold are apparent from the structures shown in Formulae (I) and (II). The compounds of the invention exhibit radioprotective activity—in that the compounds are effective to reduce the level of damage to biological material resulting from radiation exposure.

While not wishing to be limited by theory it is believed that the radiation protection conferred by the compounds according to the invention is achieved by electron donation (reduction) by the radioprotector of transient radiation induced oxidizing species on DNA, which is accompanied by proton donation from the radioprotector. While this proton donation could be from NH groups, for example within benzimidazole or similar units of the radioprotector compound to DNA, it is also possible that the proton transfer is an intra-molecular process. The role of an heterocylic oxygen or nitrogen at the ortho position (relative to the point of attachment of the ring structure to the main scaffold of the molecule) of the five to ten membered ring structure known as "A" in Formulae I and II, could be either to boost acidity of any adjacent NH groups on the main scaffold, or to act as a proton acceptor.

In this specification "optionally substituted" means that a group may or may not be further substituted with one or more groups selected from alkyl, alkenyl, alkynyl, aryl, halo, haloalkyl, haloalkenyl, haloalkynyl, haloaryl, hydroxy, alkoxy, alkenyloxy, alkynyloxy, aryloxy, carboxy, benzyloxy haloalkoxy, haloalkenyloxy, haloalkynyloxy, haloaryloxy, nitro, nitroalkyl, nitroalkenyl, nitroalkynyl, nitroaryl, nitroheterocyclyl, azido, amino, alkylamino, alkenylamino, alkynylamino, arylamino, benzylamino, acyl, alkenylacyl, alkynylacyl, arylacyl, acylamino, acyloxy, aldehydro, alkylsulphonyl, arylsulphonyl, alkylsulphonylamino, arylsulphonylamino, alkylsulphonyloxy, arylsulphonyloxy, heterocyclyl, heterocycloxy, heterocyclylamino, haloheterocyclyl, alkylsulphenyl, arylsulphenyl, carboalkoxy, carboaryloxy, mercapto, alkylthio, arylthio, acylthio and the like.

The term "alkyl" used either alone or in phrases such as "optionally substituted alkyl", "optionally substituted alkylamino" or "optionally substituted alkylene" is intended to encompass straight chain, branched or mono- or poly-cyclic alkyl, which is preferably $C_1$ to $C_{30}$ alkyl or cycloalkyl, for example $C_1$ to $C_{10}$ alkyl or cycloalkyl or $C_1$ to $C_4$ alkyl or cycloalkyl. Examples of straight chain and branched alkyl include methyl, ethyl, propyl, isopropyl, butyl, isobutyl, sec-butyl, tert-butyl, amyl, isoamyl, sec-amyl, 1,2-dimethylpropyl, 1,1-dimethylpropyl, hexyl, 4-methylpentyl, 1-methylpentyl, 2-methylpentyl, 3-methylpentyl, 1,1-dimethylbutyl, 2,2-dimethylbutyl, 3,3-dimethylbutyl, 1,2-dimethylbutyl, 1,3-dimethylbutyl, 1,2,2,-trimethylpropyl, 1,1,2-trimethylpropyl, heptyl, 5-methylhexyl, 1-methylhexyl, 2,2-dimethylpentyl, 3,3-dimethylpentyl, 4,4-dimethylpentyl, 1,2-dimethylpentyl, 1,3-dimethylpentyl, 1,4-dimethylpentyl, 1,2,3,-trimethylbutyl, 1,1,2-trimethylbutyl, 1,1,3-trimethylbutyl, octyl, 6-methylheptyl, 1-methylheptyl, 1,1,3,3-tetramethylbutyl, nonyl, 1-, 2-, 3-, 4-, 5-, 6- or 7-methyloctyl, 1-, 2-, 3-, 4- or 5-ethylheptyl, 1-, 2- or 3-propylhexyl, decyl, 1-, 2-, 3-, 4-, 5-, 6-, 7- and 8-methylnonyl, 1-, 2-, 3-, 4-, 5- or 6-ethyloctyl, 1-, 2-, 3- or 4-propylheptyl, undecyl 1-, 2-, 3-, 4-, 5-, 6-, 7-, 8- or 9-methyldecyl, 1-, 2-, 3-, 4-, 5-, 6- or 7-ethylnonyl, 1-, 2-, 3-, 4- or 5-propyloctyl, 1-, 2- or 3-butylheptyl, 1-pentylhexyl, dodecyl, 1-, 2-, 3-, 4-, 5-, 6-, 7-, 8-, 9- or 10-methylundecyl, 1-, 2-, 3-, 4-, 5-, 6-, 7- or 8-ethyldecyl, 1-, 2-, 3-, 4-, 5- or 6-propylnonyl, 1-, 2-, 3- or 4-butyloctyl, 1-2-pentylheptyl and the like. Examples of cyclic alkyl include cyclopropyl, cyclobutyl, cyclopentyl, cyclohexyl, cycloheptyl, cyclooctyl, cyclononyl and cyclodecyl and the like.

The term "alkenyl" used either alone or in compound words such as "optionally substituted alkenyl" denotes groups formed from straight chain, branched or mono- or poly-cyclic alkenes including ethylenically mono- or poly-unsaturated alkyl or cycloalkyl groups as defined above, preferably $C_{2-30}$ alkenyl, for example $C_{2-10}$ alkenyl or $C_{2-4}$ alkenyl. Examples of alkenyl include vinyl, allyl, 1-methylvinyl, butenyl, iso-butenyl, 3-methyl-2-butenyl, 1-pentenyl, cyclopentenyl, 1-methyl-cyclopentenyl, 1-hexenyl, 3-hexenyl, cyclohexenyl, 1-heptenyl, 3-heptenyl, 1-octenyl, cyclooctenyl, 1-nonenyl, 2-nonenyl, 3-nonenyl, 1-decenyl, 3-decenyl, 1,3-butadienyl, 1-4, pentadienyl, 1,3-cyclopentadienyl, 1,3-hexadienyl, 1,4-hexadienyl, 1,3-cyclohexadienyl, 1,4-cyclohexaidenyl, 1,3-cycloheptadienyl, 1,3,5-cycloheptatrienyl, 1,3,5,7-cycloocta-tetraenyl and the like.

The term "represents a five to ten membered single or multiple ring structure with heterocyclic N or O located at the ortho position relative to the point of attachment of A, said ring including optional double bonds, substitutions and/or other heteroatoms" (represented by "A" in Formula (II)) is used to denote structures including one, two or three connected or fused and saturated or unsaturated cyclic groups, such as cycloalkyl, cycloalkenyl, cycloalkynyl, aryl or mixed groups which contain from five up to ten atoms and at least include oxygen and/or nitrogen heteroatoms in the ortho position relative to the point of attachment of the ring structure to the main scaffold of the radioprotector molecule. Such ring structures may include one or more additional heteroatoms such as oxygen, nitrogen or sulphur. Examples of cycloalkyl and cycloalkenyl are described above. Aryl groups include single, polynuclear, conjugated and fused residues of aromatic hydrocarbons, such as, phenyl, biphenyl, naphthyl and the like.

Examples of heterocyclic groups meeting the requirement of "A" in Formula (II) include pyrrolyl, pyrrolinyl, imidazolyl, pyrazolyl, pyridyl, pyrimidinyl, pyrazinyl, pyridazinyl, triazolyl or tetrazolyl; saturated 3 to 6-membered heteromonocyclic groups containing 1 to 4 nitrogen atoms, such as, pyrrolidinyl, imidazolidinyl, piperidino or piperazinyl; unsaturated condensed heterocyclic groups containing 1 to 5 nitrogen atoms, such as, indolyl, isoindolyl, indolizinyl, benzimidazolyl, quinolyl, isoquinolyl, indazolyl, benzotriazolyl or tetrazolopyridazinyl; unsaturated 3 to 6-membered heteromonocyclic groups containing an oxygen atom, such as, pyranyl or furyl; unsaturated 3 to 6-membered heteromonocyclic groups containing 1 to 2 oxygen atoms and 1 to 3 nitrogen atoms, such as, oxazolyl, isoxazolyl or oxadiazolyl; saturated 3 to 6-membered heteromonocyclic groups containing 1 to 2 oxygen atoms and 1 to 3 nitrogen atoms, such as, morpholinyl; unsaturated condensed heterocyclic groups containing 1 to 2 oxygen atoms and 1 to 3 nitrogen atoms, such as, benzoxazolyl or benzoxadiazolyl; unsaturated 3 to 6-membered heteromonocyclic groups containing 1 to 2 sulphur atoms and 1 to 3 nitrogen atoms, such as, thiazolyl or thiadiazolyl; saturated 3 to 6-membered heteromonocyclic group containing 1 to 2 sulphur atoms and 1 to 3 nitrogen atoms, such as, thiazolidinyl; and unsaturated condensed heterocyclic group containing 1 to 2 sulphur atoms and 1 to 3 nitrogen atoms, such as, benzothiazolyl or benzothiadiazolyl, each of which may be optionally substituted. Preferred heterocyclic groups meeting the requirement of "A" in Formula (II) include optionally substituted 2-pyridyl, optionally substituted 2-pyrimidyl, optionally substituted 2-pyrazinyl, optionally substituted 3-pyrazolyl, optionally substituted 5-pyrazolyl, optionally substituted 2-furanyl, optionally substituted 2-quinolinyl, optionally substituted 1-isoquinolinyl or optionally substituted 3-isoquinolinyl. Example substituents include chloro, fluoro, $C_1$ to $C_4$ fluoroalkyl, $C_1$ to $C_4$ alkyl, $C_2$ to $C_4$ alkenyl, $C_1$ to $C_4$ alkoxy, $C_1$ to $C_4$ alkoxyalkyl, $C_1$ to $C_4$ alkylamino, $C_2$ to $C_4$ di-alkylamino or $C_1$ to $C_4$ aminoalkyl, and in particular methyl and methoxyl.

The salts of the compound of Formula (I) and (II) are preferably pharmaceutically acceptable, but it will be appreciated that non-pharmaceutically acceptable salts also fall within the scope of the present invention, since these are useful as intermediates in the preparation of pharmaceutically acceptable salts. Examples of pharmaceutically acceptable salts include salts of pharmaceutically acceptable cations such as sodium, potassium, lithium, calcium, magnesium, ammonium and alkylammonium; acid addition salts of pharmaceutically acceptable inorganic acids such as hydrochloric, orthophosphoric, sulphuric, phosphoric, nitric, carbonic, boric, sulfamic and hydrobromic acids; or salts of pharmaceutically acceptable organic acids such as acetic, propionic, butyric, tartaric, maleic, hydroxymaleic, fumaric, citric, lactic, mucic, gluconic, benzoic, succinic, oxalic, phenylacetic, methanesulphonic, trihalomethanesulphonic, toluenesulphonic, benzenesulphonic, salicyclic, sulphanilic, aspartic, glutamic, edetic, stearic, palmitic, oleic, lauric, pantothenic, tannic, ascorbic and valeric acids.

By "pharmaceutically acceptable derivative" is meant any pharmaceutically acceptable salt, hydrate, solvate, pro-drug or any other compound which, upon administration to the subject, is capable of providing (directly or indirectly) a compound of Formulae (I) or (II) or an active metabolite or residue thereof.

The term "pro-drug" is used herein in its broadest sense to include those compounds which are converted in vivo to compounds of Formulae (I) or (II).

The term "tautomer" is used herein in its broadest sense to include compounds of Formulae (I) or (II) which are capable of existing in a state of equilibrium between two isomeric forms. Such compounds may differ in the bond connecting two atoms or groups and the position of these atoms or groups in the compound. This term in particular encompasses keto-enol tautomers.

The compounds of the invention may be electrically neutral or be in the form of polycations with associated anions for electrical neutrality. Suitable associated anions include sulphate, tartrate, citrate, chloride, nitrate, nitrite, phosphate, perchlorate, halosulfonate or trihalomethylsulfonate.

Preferred compounds of Formulae (I) and/or (II) are those wherein A represents optionally substituted 2-pyridyl, optionally substituted 2-pyrimidyl, optionally substituted 2-pyrazinyl, optionally substituted 3-pyrazolyl, optionally substituted 5-pyrazolyl, optionally substituted 2-furanyl, optionally substituted 2-quinolinyl, optionally substituted 1-isoquinolinyl or optionally substituted 3-isoquinolinyl. Most preferably A represents optionally substituted 2-pyridyl.

In other preferred aspects of the invention A is optional substituted by chloro, fluoro, $C_1$ to $C_4$ fluoroalkyl, $C_1$ to $C_4$ alkyl, $C_2$ to $C_4$ alkenyl, $C_1$ to $C_4$ alkoxy, $C_1$ to $C_4$ alkoxyalkyl, $C_1$ to $C_4$ alkylamino, $C_2$ to $C_4$ di-alkylamino or $C_1$ to $C_4$ aminoalkyl.

In further preferred aspects of the invention W represents piperidyl, piperazinyl, morpholinyl, thiomorpholinyl or diazepanyl each of which may be optionally substituted by $C_1$ to $C_4$ alkyl, $C_2$ to $C_4$ alkenyl, —$OR_1$, —$N(R_1R_2)$ (for example including —$NH_2$ and $N(CH_3)_2$) or —NH—, where $R_1$ is hydrogen or $C_1$ to $C_4$ alkyl.

In particularly preferred aspects of the invention the radioprotectors are of Formula (III) below:

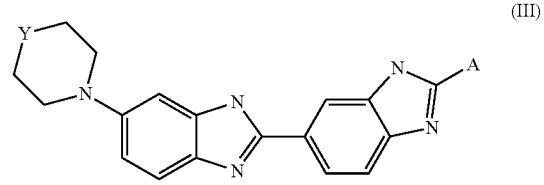

(III)

wherein:
Y represents O, methylene, hydroxymethyl or methylamino; and
A represents optionally substituted 2-pyridyl, optionally substituted 2-pyrimidyl, optionally substituted 2-pyrazinyl, optionally substituted 3-pyrazolyl, optionally substituted 5-pyrazolyl, optionally substituted 2-furanyl, optionally substituted 2-quinolinyl, optionally substituted 1-isoquinolinyl or optionally substituted 3-isoquinolinyl.

Specific examples of preferred compounds of the invention include:

2-(5'-(5"-(4'''-Methylpiperazin-1'''-yl)benzimidazol-2"-yl)benzimidazol-2'-yl)pyridine

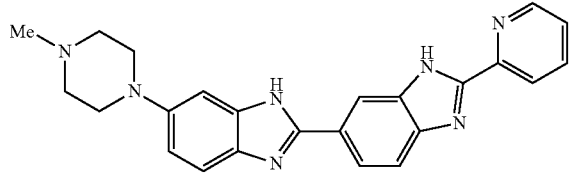

4-Methyl-2-(5'-(5"-(4'''-methylpiperazin-1'''-yl)benzimidazol-2"-yl)benzimidazol-2'-yl)pyridine

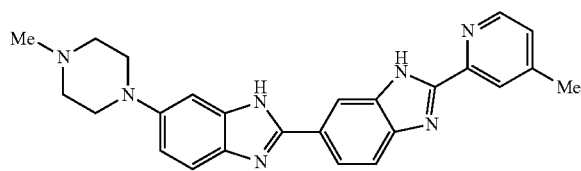 [SMILES: Cc1ccnc(-c2nc3ccc(-c4nc5ccc(N6CCN(C)CC6)cc5[nH]4)cc3[nH]2)c1]

4-Chloro-2-(5'-(5''-(4'''-methylpiperazin-1'''-yl)benz-
imidazol-2''-yl)benzimidazol-2'-yl)pyridine

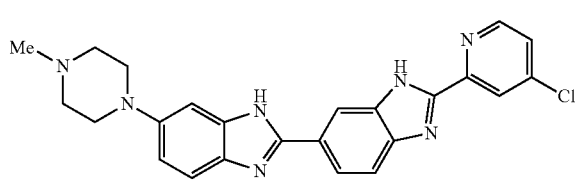 [SMILES: CN1CCN(c2ccc3nc(-c4ccc5nc(-c6cc(Cl)ccn6)[nH]c5c4)[nH]c3c2)CC1]

4-Methoxy-2-(5'-(5''-(4'''-methylpiperazin-1'''-yl)
benzimidazol-2''-yl)benzimidazol-2'-yl)pyridine

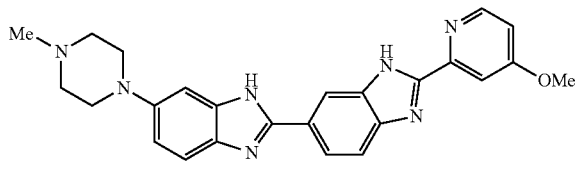 [SMILES: COc1ccnc(-c2nc3ccc(-c4nc5ccc(N6CCN(C)CC6)cc5[nH]4)cc3[nH]2)c1]

1-(5'-(5''-(4'''-Methylpiperazin-1'''-yl)benzimidazol-
2''-yl)benzimidazol-2'-yl)isoquinoline

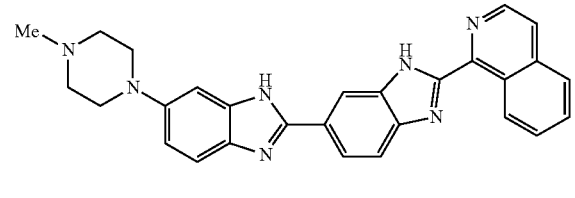 [SMILES: CN1CCN(c2ccc3nc(-c4ccc5nc(-c6nccc7ccccc67)[nH]c5c4)[nH]c3c2)CC1]

3-(5'-(5''-(4'''-Methylpiperazin-1'''-yl)benzimidazol-
2''-yl)benzimidazol-2'-yl)isoquinoline

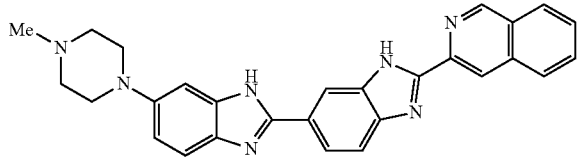 [SMILES: CN1CCN(c2ccc3nc(-c4ccc5nc(-c6cc7ccccc7cn6)[nH]c5c4)[nH]c3c2)CC1]

3-(5'-(5''-(4'''-Methylpiperazin-1'''-yl)benzimidazol-
2''-yl)benzimidazol-2'-yl)indazole

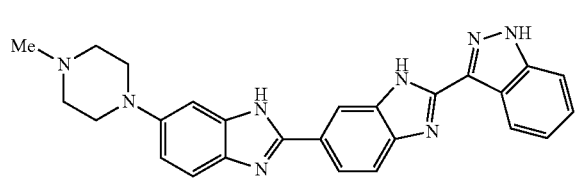 [SMILES: CN1CCN(c2ccc3nc(-c4ccc5nc(-c6n[nH]c7ccccc67)[nH]c5c4)[nH]c3c2)CC1]

2-(5'-(5''-Morpholinobenzimidazol-2''-yl)benzimida-
zol-2'-yl)pyridine

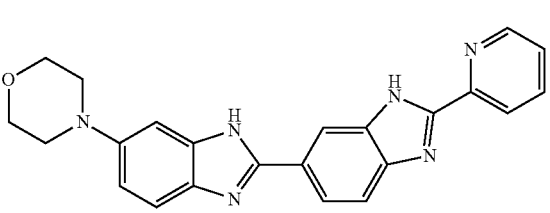 [SMILES: c1ccc(-c2nc3ccc(-c4nc5ccc(N6CCOCC6)cc5[nH]4)cc3[nH]2)nc1]

2-(5'-(5''-Morpholinobenzimidazol-2''-yl)benzimida-
zol-2'-yl)-4-methylpyridine

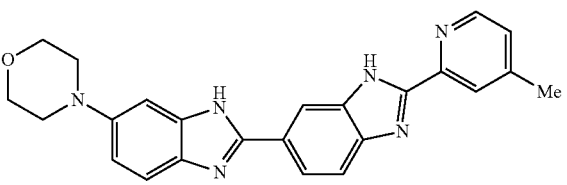 [SMILES: Cc1ccnc(-c2nc3ccc(-c4nc5ccc(N6CCOCC6)cc5[nH]4)cc3[nH]2)c1]

2-(5'-(5''-(4'''-Methyl-1''',4'''-diazepan-1'''-yl)benz-
imidazol-2''-yl)benzimidazol-2'-yl)pyridine

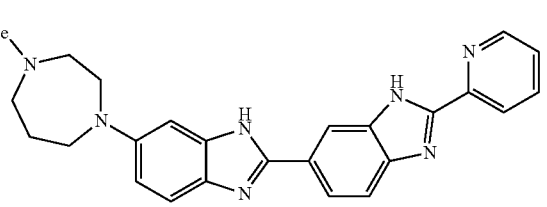

2-(5'-(5''-(4'''-Methoxypiperidin-1'''-yl)benzimidazol-
2''-yl)benzimidazol-2'-yl)pyridine

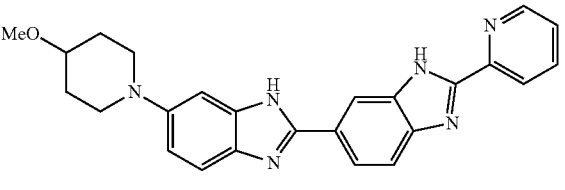 [SMILES: COC1CCN(c2ccc3nc(-c4ccc5nc(-c6ccccn6)[nH]c5c4)[nH]c3c2)CC1]

2-(4'-Methoxy-6'-(5''-(4'''-methylpiperazin-1'''-yl)
benzimidazol-2''-yl)benzimidazol-2'-yl)pyridine

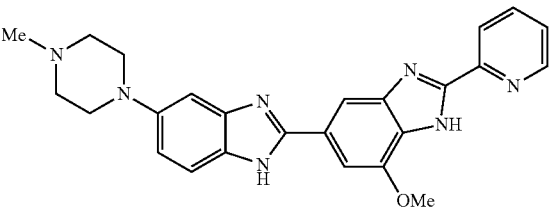 [SMILES: COc1cc(-c2nc3cc(N4CCN(C)CC4)ccc3[nH]2)cc2nc(-c3ccccn3)[nH]c12]

15

2-(6'-(5''-(4'''-Methylpiperazin-1'''-yl)benzimidazol-2''-yl)indol-2'-yl)pyridine

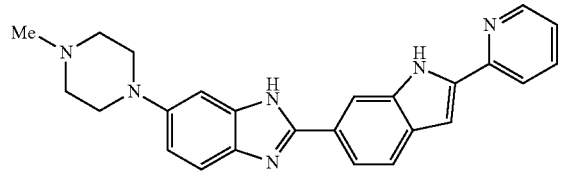 [SMILES: CN1CCN(c2ccc3nc(-c4ccc5cc(-c6ccccn6)[nH]c5c4)[nH]c3c2)CC1]

2-(5'-(5''-(Morpholinoamino)benzimidazol-2''-yl)benzimidazol-2'-yl)pyridine

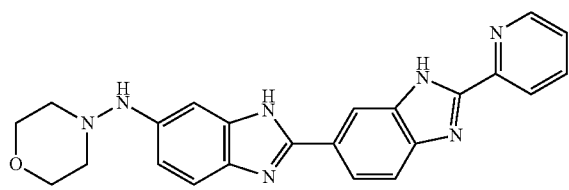 [SMILES: c1ccc(-c2nc3ccc(-c4nc5ccc(NN6CCOCC6)cc5[nH]4)cc3[nH]2)nc1]

2-(5'-(5''-(4'''-Isopropylpiperazin-1'''-yl)benzimidazol-2''-yl)benzimidazol-2'-yl)pyridine

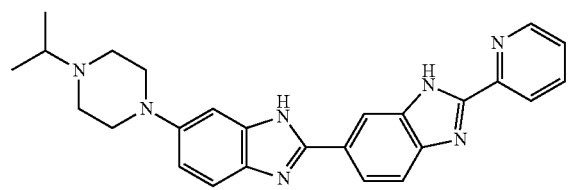 [SMILES: CC(C)N1CCN(c2ccc3nc(-c4ccc5nc(-c6ccccn6)[nH]c5c4)[nH]c3c2)CC1]

2-(5'-(5''-(4'''-Butylpiperazin-1'''-yl)benzimidazol-2''-yl)benzimidazol-2'-yl)pyridine

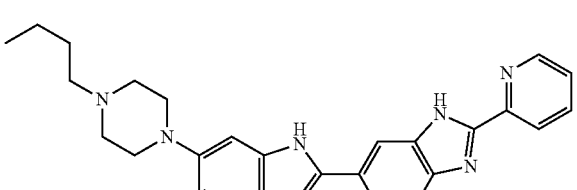

2-(5'-(5''-((2'''-Methoxyethyl)(methyl)amino)benzimidazol-2''-yl)benzimidazol-2'-yl)pyridine

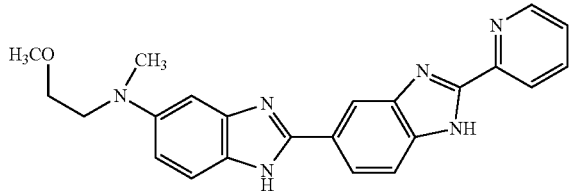 [SMILES: COCCN(C)c1ccc2[nH]c(-c3ccc4[nH]c(-c5ccccn5)nc4c3)nc2c1]

16

5-Methyl-2-(5'-(5''-(4'''-methylpiperazin-1'''-yl)benzimidazol-2''-yl)benzimidazol-2'-yl)pyridine

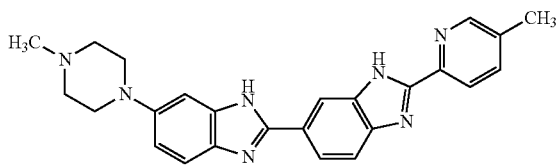

2-(5'-Methoxy-6'-(5''-(4'''-methylpiperazin-1'''-yl)benzimidazol-2''-yl)benzimidazol-2'-yl)pyridine

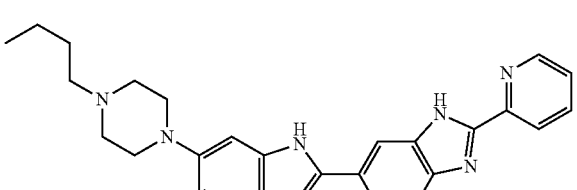

3-(5'-(5''-(4'''-Hydroxypiperidin-1'''-yl)benzimidazol-2''-yl)benzimidazol-2'-yl)isoquinoline

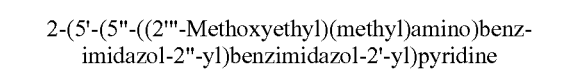

3-(5'-(5''-Morpholinobenzimidazol-2''-yl)benzimidazol-2'-yl)isoquinoline

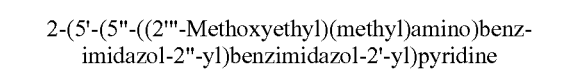

2-(5'-(5''-(4'''-(2''''-Methoxyethyl)piperazin-1'''-yl)benzimidazol-2''-yl)benzimidazol-2'-yl)pyridine

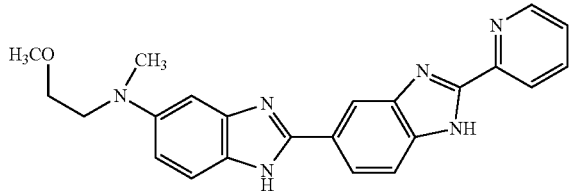 [SMILES: COCCN(C)c1ccc2[nH]c(-c3ccc4[nH]c(-c5ccccn5)nc4c3)nc2c1]

2-(5'-(5"-(2'''-(2''''-Methoxyethoxy)ethylamino)benz-imidazol-2"-yl)benzimidazol-2'-yl)pyridine

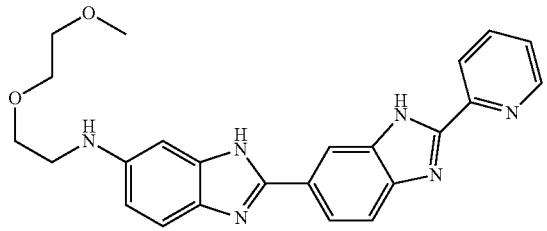 [SMILES: COCCOCCNc1ccc2nc(-c3ccc4nc(-c5ccccn5)[nH]c4c3)[nH]c2c1]

5-Fluoro-2-(5'-(5"-(4'''-methylpiperazin-1'''-yl)benz-imidazol-2"-yl)benzimidazol-2'-yl)pyridine

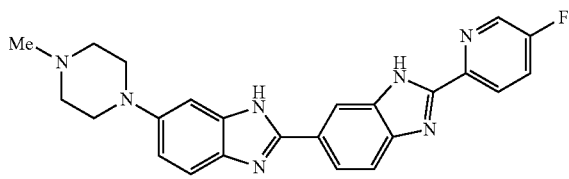 [SMILES: CN1CCN(c2ccc3nc(-c4ccc5nc(-c6ccc(F)cn6)[nH]c5c4)[nH]c3c2)CC1]

2-(5'-(5"-(4'''-Hydroxypiperidin-1'''-yl)benzimidazol-2"-yl)benzimidazol-2'-yl)-5-methylpyridine

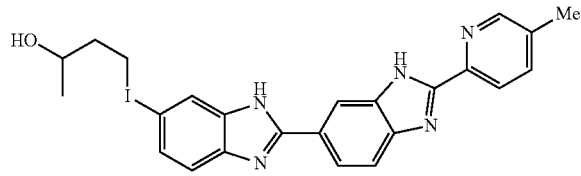

Specific examples of particularly preferred compounds include:
2-(5'-(5"-(4'''-Methylpiperazin-1'''-yl)benzimidazol-2"-yl)benzimidazol-2'-yl)pyridine
4-Chloro-2-(5'-(5"-(4'''-methylpiperazin-1'''-yl)benzimidazol-2"-yl)benzimidazol-2'-yl)pyridine
2-(5'-(5"-Morpholinobenzimidazol-2"-yl)benzimidazol-2'-yl)pyridine
2-(4'-Methoxy-6'-(5"-(4'''-methylpiperazin-1'''-yl)benzimidazol-2"-yl)benzimidazol-2'-yl)pyridine
2-(5'-(5"-(4'''-Butylpiperazin-1'''-yl)benzimidazol-2"-yl)benzimidazol-2'-yl)pyridine
2-(5'-Methoxy-6'-(5"-(4'''-methylpiperazin-1'''-yl)benzimidazol-2"-yl)benzimidazol-2'-yl)pyridine
4-Methoxy-2-(5'-(5"-(4'''-methylpiperazin-1'''-yl)benzimidazol-2"-yl)benzimidazol-2'-yl)pyridine
3-(5'-(5"-(4'''-Hydroxypiperidin-1'''-yl)benzimidazol-2"-yl)benzimidazol-2'-yl)isoquinoline
2-(5'-(5"-(2'''-(2''''-Methoxyethoxy)ethylamino)benzimidazol-2"-yl)benzimidazol-2'-yl)pyridine
2-(5'-(5"-(4'''-Isopropylpiperazin-1'''-yl)benzimidazol-2"-yl)benzimidazol-2'-yl)pyridine
5-Fluoro-2-(5'-(5"-(4'''-methylpiperazin-1'''-yl)benzimidazol-2"-yl)benzimidazol-2'-yl)pyridine The present invention also provides a method of protecting a subject or biological material from radiation damage, or of reducing radiation damage to a subject which comprises administering to the subject, or exposing the biological material to, an effective amount of a radioprotector compound according to the invention, such as falling with Formula (I) and/or Formula (II).

By the phrase "protecting from radiation damage" (or "prophylaxis from the damaging effects of radiation") it is implied that relative to damage expected to be incurred to tissues or cells within a subject or within biological material following exposure to a given amount of radiation (for example ionising, infra-red or ultra-violet radiation) damage is prevented, minimised or reduced due to presence of the radioprotector compound. The term "Dose Modification Factor" (DMF) refers to the ratio of the radiation dose required to produce a given effect in the presence of protector, to that required to produce the equivalent effect in the absence of radioprotector.

As shown in FIG. 1 the cytotoxicity parameter C50 is defined as a concentration of the drug that results in 50% clonogenic survival.

Figure 2:
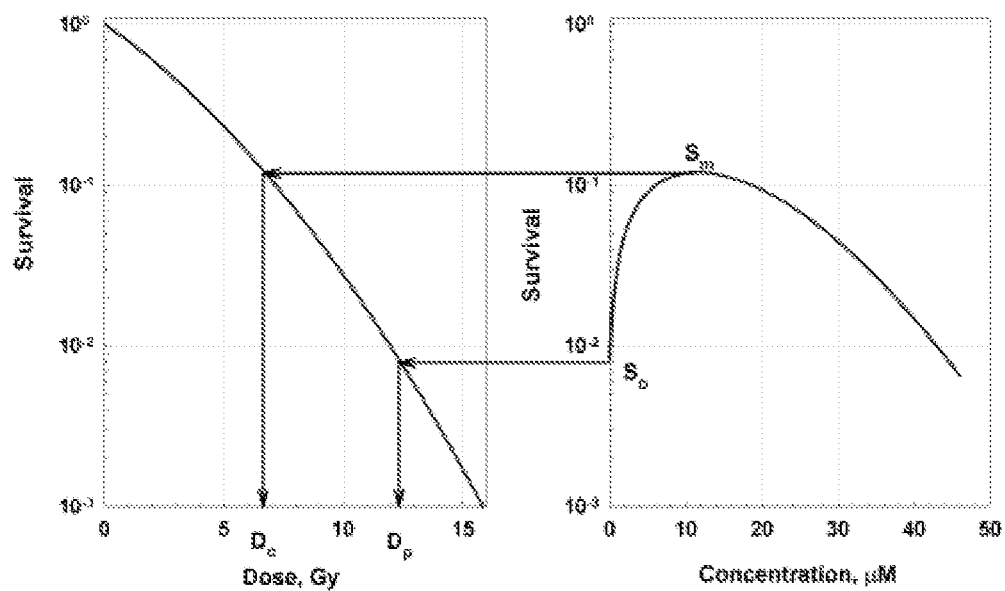
FIG. 2 shows graphs useful for demonstrating the calculation of Protection Factor (PF) and Dose Modification Factor (DMF). Clonogenic survival of keratinocytes irradiated at various doses (left panel) and at a dose of 12 Gy in the presence of various concentrations of a radioprotector (right panel). PF is defined as a ratio of survival at maximum protection Sm and survival after irradiation only So: PF=Sm/So. DMF is defined as a ratio of doses that result in survival level of Sm in the presence Dp and the absence Dc of radioprotector: DMF=Dp/Dc. DMF10 is define in a similar way except that instead of Sm a survival at 10 microM of radioprotector is used.
Figure 3:
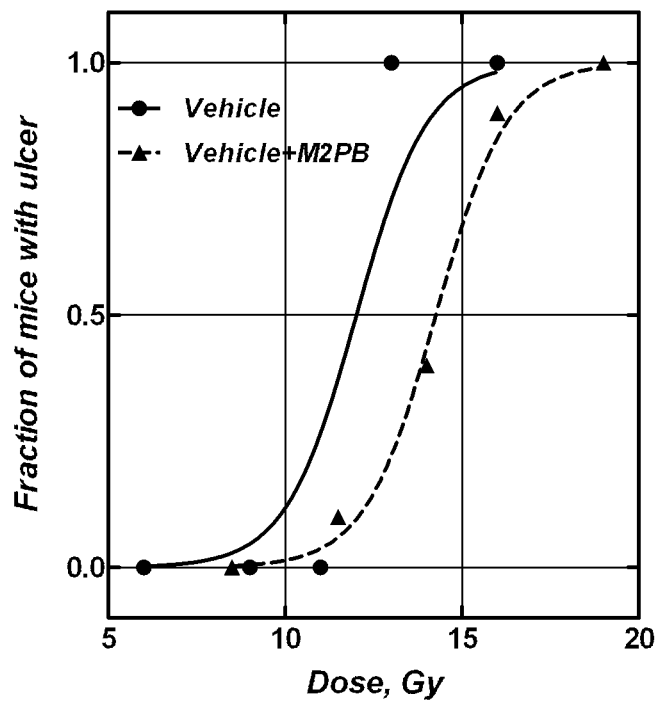
FIG. 3 shows dose (Gy)/effect (fraction of mice with ulcer) curves for mice treated with 10 mM M2PB (Example 19) in Formulation 1, compared to a mice treated with vehicle-only formulation. The respective $ED_{50}$ values were 14.3 and 12.0, yielding a dose reduction factor of 1.19.
Figure 4:
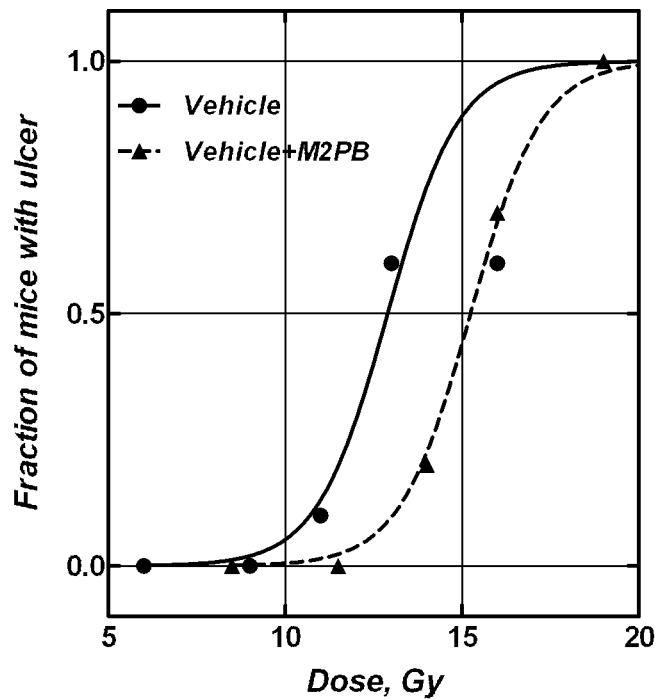
FIG. 4 shows dose (Gy)/effect (fraction of mice with ulcer) curves for 30 mM M2PB (Example 19) in Formulation 2 and the corresponding vehicle. The respective $ED_{50}$ values were 15.2 and 12.9, yielding a dose reduction factor of 1.18.
Figure 5:
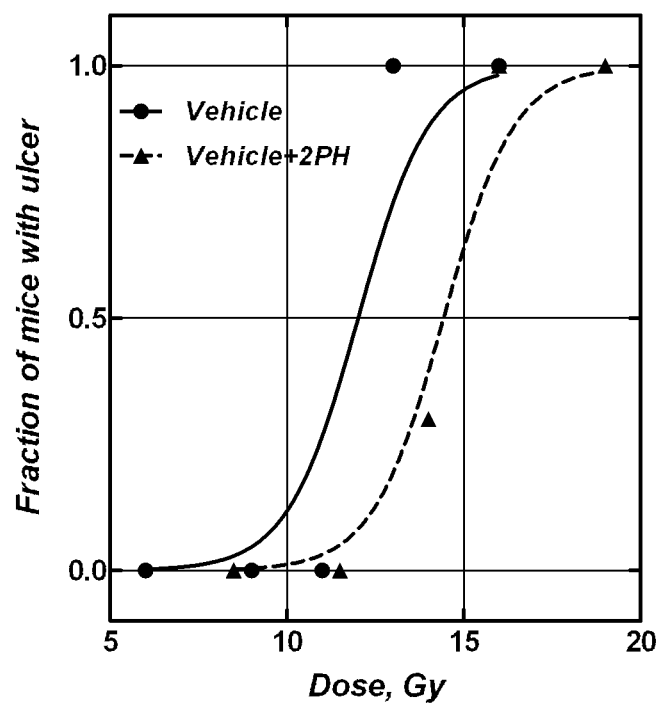
FIG. 5 shows dose (Gy)/effect (fraction of mice with ulcer) curves for 10 mM 2PH (Example 2) in Formulation 1. The respective $ED_{50}$ values were 14.4 and 12.0, yielding a dose reduction factor of 1.20.
Figure 6:
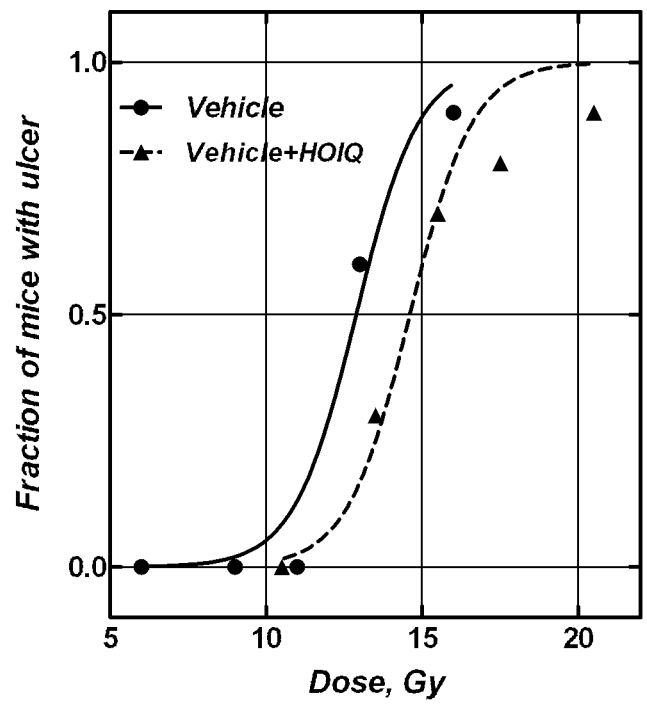
FIG. 6 shows dose (Gy)/effect (fraction of mice with ulcer) curves for 60 mM HOIQ (Example 23) in Formulation 3 and the corresponding blank formulation. The respective $ED_{50}$ values were 14.6 and 12.9, yielding a dose reduction factor of 1.13.
Figure 7:
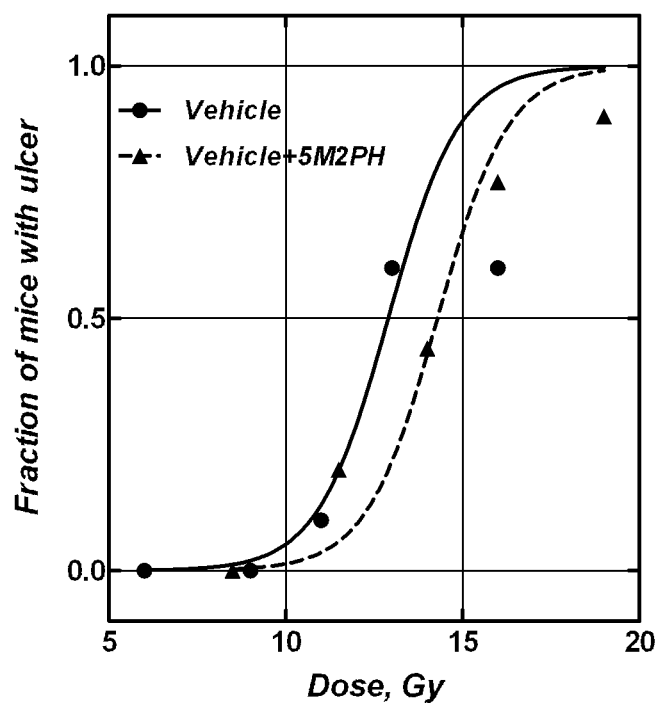
FIG. 7 shows dose (Gy)/effect (fraction of mice with ulcer) curves for 30 mM 2P5 MH (Example 6) in Formulation 2. The respective $ED_{50}$ values were 14.6 and 12.9, yielding a dose reduction factor of 1.13.

Clonogenic survival of keratinocytes irradiated at various doses (left panel) and at a dose of 12 Gy in the presence of various concentrations of a radioprotector (right panel) is shown in FIG. 2. PF (Protection Factor) is defined as a ratio of survival at maximum protection Sm and survival after irradiation only So:PF=Sm/So. DMF (Dose Modification Factor) is defined as a ratio of doses that result in survival level of Sm in the presence (Dp) and the absence (Dc) of radioprotector: DMF=Dp/Dc. DMF10 is defined in a similar way except that instead of Sm a survival at 10 microM of radioprotector is used.

Preferably the radioprotector compounds of the invention exhibit a DMF10 of at least 1.10, of at least 1.2, of at least 1.4, of at least 1.8 or at least 2.0.

The radiation damage may result from exposure to a radiation source, such as, ionising radiation. The term "ionising radiation" as used herein refers to photons or particles having sufficient energy to ionise a bond, and includes α, β and γ rays from radioactive nuclei and x-rays.

The term "biological material" is used herein in its broadest sense and includes any composition of matter which comprises at least one biologically-derived or derivable component. Biological material contemplated by the present invention includes proteins and other proteinaceous material including extracts of or including proteins and chemically modified proteins or extracts thereof; tissue fluids, tissue extracts or organs; animal, plant or microbiological tissue, fluid or extracts including products therefrom; biologically derived non-proteinaceous material such as, but not limited to, lipids, carbohydrates, hormones and vitamins including extracts and derivatives thereof; recombinant products including genetic material such as chromosomal material, genomic DNA, cDNA, mRNA, tRNA, ribosomes and nuclear material; and whole animal, plant or microbiological cells or extracts thereof.

As indicated the biological material of the invention can take the form of cells, tissues or organs or indeed of peptides, proteins or nucleic acids (for example) derived from a plant, animal or microorganism source, as well as those synthetically produced which mimic or are similar to naturally derived materials. The radioprotector compound can be used to protect from radiation damage for example in experimental systems, in whole live or dead organisms or on ex vivo cells, tissues or organs that may be returned to the original host, or transplanted into a new host, after therapy.

For example, the biological material can take the form of a human or animal subject such as an experimental animal (e.g. mouse, rat, guinea pig, rabbit), a companion animal (e.g. cat, dog), an agricultural animal (e.g. horse, cattle, sheep, donkey, goat, pig), a reptile, avian or captive wild animal. Preferably the subject is a mammal and most preferably the subject is a human. A significant application for the radioprotector compounds of the invention is for use in conjunction with radiotherapy in human subjects. However, the compounds can also be used to offer protection from exposure to, or from continuing exposure to, unplanned radiation such as in a terrorism, military or occupational context, or planned exposures associated with diagnostic radiology procedures.

Preferably the biological material (including to the human or animal subject) is exposed to the radioprotector compound for a sufficient period of time in advance of anticipated radiation exposure or continuing radiation exposure, such as between about 1 minute and about 3 days, preferably between about 10 minutes and about 6 hours, more preferably between about 20 minutes and about 4 hours and most preferably between about 30 minutes and about 2 hours. Preferably the time of administration of the radioprotector compound prior to radiation exposure is sufficient to allow association of the compound with DNA in the biological material. Preferably the radioprotector compound is administered preferentially to cells, tissues or organs likely to be exposed to radiation but that are intended to be protected from such radiation exposure. For example, in the case of administration in conjunction with cancer radiotherapy the compounds will preferably be administered preferentially to normal (non-tumour) tissues or cells surrounding a tumour or lesion that are likely to be exposed to radiation in the course of radiotherapy. Preferential administration can be achieved by way of direct application to the desired tumour or cells or, for example, by utilising a system for targeting specific cells or tissues. For example, it is possible to conjugate the compounds to agents that preferentially bind to specific cells or tissues, such as to receptors that are up-regulated in the particular cells or tissues concerned.

The compounds of the invention may be conjugated to agents, for example, via an interactive group, which will specifically deliver them to a desired tumour site. Suitable agents may include antibodies or proteins, such as, growth factors, for example, haemopoietic growth factor which will enable preferential radioprotection of haemopoietic stem cells to occur in the context of total body irradiation and bone marrow transplantation. The term "interactive group" is used herein in its broadest sense and refers to a group capable of forming a bond with a specific group on a target molecule or agent such as a protein or a derivative thereof. Examples of interactive groups include $N(CH_2)_nCOOH$, $N(CH_2)_nCO(CH_2)_mR$, $N(CH_2)_n-SH$, $N(CH_2)_n-NH_2$, $CH(CH_2)_nCOOH$, $CH(CH_2)_nCO(CH_2)_mR$, $CH(CH_2)_n-SH$ and $CH(CH_2)_n-NH_2$ wherein n is 1 to 10, m is 0 to 10 and R is optionally substituted alkyl.

The present invention still further provides a method of cancer radiotherapy which comprises administering to a subject in need of such therapy an effective amount of a radioprotector compound of the invention and subjecting the locus of the tumour to a radiation source. The term "cancer radiotherapy" is used herein in its broadest sense and includes radiotherapy involving tumours or lesions, which may be either benign or malignant.

The compounds of the invention may be used advantageously in therapy in combination with other medicaments, such as chemotherapeutic agents, for example, radiomimetic agents, which are cytotoxic agents that damage DNA in such a way that the lesions produced in DNA are similar to those resulting from ionising radiation. Examples of radiomimetic agents which cause DNA strand breaks include bleomycin, doxorubicin, adriamycin, 5 FU, neocarcinostatin, alkylating agents and other agents that produce DNA adducts. It is anticipated that the radioprotectors of the present invention will protect DNA from damage by some of these agents, in the same way as they protect against the effects of ionising radiation. In clinical applications, it is unlikely that the radioprotector would be administered systemically together with the chemotherapeutic agent, since this could compromise the action of this agent on the tumour. However, there are circumstances where topical application to problem tissues could be advantageous. For example, oral mucositis is a problem sideeffect for cytotoxic agents, such as, doxorubicin and administration of the present radioprotector as a mouth-wash before administration of the chemotherapeutic agent could ameliorate this side-effect without compromising the action of this agent on a tumour not located in the oral cavity. Similarly, the gastrointestinal tract could be protected by oral administration, the lungs by aerosol inhalation or the bladder by intravesical delivery, for example, via a catheter of the radioprotector. Hence a preferred method in accordance with the present invention utilises the compound of Formulae (I) or (II) in conjunction with another medicament, such as, a radiomimetic agent.

As earlier mentioned there is an ex vivo application of the compounds or conjugates of the invention and one example is in the context of bone marrow transplantation. Bone marrow transplantation generally involves obtaining and storing bone marrow samples from a subject in anticipation of a deterioration of the patient's condition. A rather drastic form of chemotherapy (i.e. a high dose) is then administered. This chemotherapy is such that it would normally be lethal due to the destruction of normal stem cells, but the subject is rescued by the administration of their own haemopoietic stem cells. The problem with this procedure is that the initial sample of stem cells is likely to be contaminated with tumour cells and various procedures are used therefore to purge the bone marrow preparations of the tumour cells. Radioprotectors conjugated for example to a haemopoietic growth factor, may be used in this context by being added to a suspension of bone marrow cells. The suspension may then be irradiated in the expectation that the normal bone marrow cells, but not the tumour cells, would be preferentially protected from the cellkilling effects of the radiation.

In the cancer radiotherapy setting, the compounds of Formulae (I) and (II) may be administered for therapy by any suitable route, including oral, rectal, nasal, topical (including buccal and sublingual), vaginal, intravesical and parenteral (including subcutaneous, intramuscular, intravenous, intrasternal and intradermal). Preferably, administration will be by the rectal, topical, vaginal or parenteral route. However it will be appreciated that the preferred route will vary with the condition and age of the subject, the tissue/tumour being treated, its location within the subject and the judgement of the physician or veterinarian. The compound of the invention may be administered directly into tissues surrounding or proximal to tumours to be irradiated.

In other settings where radioprotectors have utility, associated with planned or unplanned radiation exposure, the compounds of Formulae (I) and (II) may be administered by any suitable local or systemic route, but preferably by systemic routes, including parental and enteral.

The present invention also extends to a radioprotective composition which comprises a compound of Formula (I) or Formula (II) in association with a pharmaceutically or veterinarily acceptable carrier.

The compositions of the present invention comprise at least one radioprotector compound together with one or more pharmaceutically acceptable carriers, diluents, adjuvants and/or excipients and optionally other medicaments. Each carrier, diluent, adjuvant and/or excipient must be pharmaceutically "acceptable" in the sense of being compatible with the other ingredients of the composition and not injurious to the subject. Compositions include those suitable for oral, rectal, nasal, topical (including buccal and sublingual), vaginal, intravesical or parenteral (including subcutaneous, intramuscular, intravenous and intradermal) administration. The compositions may conveniently be presented in unit dosage form and may be prepared by methods well known in the art of pharmacy. Such methods include the step of bringing into association the active ingredient with the carrier, which constitutes one or more accessory ingredients. In general, the compositions are prepared by uniformly and intimately bringing into association the active ingredient with liquid carriers, diluents, adjuvants and/or excipients or finely divided solid carriers or both, and then if necessary shaping the product. The carriers also include agents that form molecular complexes with the radioprotector compound, and reduce the concentration of the free compound, and thus suppressing adverse effects such as taste, for oral formulations, local toxicity at the site of administration, for topical or subcutaneous, intramuscular, intravenous or intradermal formulations. Such complexing agents include cyclodextrins such as 2-hydroxypropyl-β-cyclodextrin and sulfobutylether-β-cyclodextrin. Further details of conventional pharmaceutical compositions are explained in Remington's Pharmaceutical Sciences, 18$^{th}$ Edition, Mack Publishing Co., Easton, Pa., USA, the disclosure of which is included in its entirety by way of reference.

The compositions of the present invention suitable for local or systemic administration may comprise at least one radioprotector compound presented as an oil-in-water liquid emulsion or a water-in-oil liquid emulsion, which may be in the form of vesicles such as micelles or liposomes, of nanometer to micrometer dimensions.

Compositions of the present invention suitable for oral administration may be presented as discrete units such as capsules, sachets or tablets each containing a predetermined amount of the active ingredient; as a powder or granules; as a solution or a suspension in an aqueous or non-aqueous liquid; or as an oil-in-water liquid emulsion or a water-in-oil liquid emulsion. The active ingredient may also be presented as a bolus, electuary or paste.

A tablet may be made by compression or moulding, optionally with one or more accessory ingredients. Compressed tablets may be prepared by compressing in a suitable machine the active ingredient in a free-flowing form such as a powder or as granules, optionally mixed with a binder (e.g. cross-linked povidone, cross-linked sodium carboxymethyl cellulose), inert diluent, preservative, disintegrant (e.g. sodium starch glycollate), surface-active agent and/or dispersing agent. Moulded tablets may be made by moulding in a suitable machine a mixture of the powdered compound moistened with an inert liquid diluent. The tablets may optionally be coated or scored and may be formulated so as to provide slow or controlled release of the active ingredient therein using, for example, hydroxypropylmethyl cellulose in varying proportions to provide the desired release profile. Tablets may optionally be provided with an enteric coating, to provide release in parts of the gut other than the stomach.

Compositions suitable for topical administration in the mouth include lozenges comprising the active ingredient in a flavoured basis, usually sucrose and acacia or tragacanth gum; pastilles comprising the active ingredient in an inert basis such as gelatin and glycerin, or sucrose and acacia gum; and mouthwashes or sprays comprising the active ingredient in a suitable liquid carrier.

For topical application to the skin, the active ingredient may be in the form of a cream, ointment, jelly, solution or suspension.

For topical application to the eye, the active ingredient may be in the form of a solution or suspension in a suitable sterile aqueous or non-aqueous vehicle. Additives, for instance buffers, preservatives including bactericidal and fungicidal agents, such as phenyl mercuric acetate or nitrate, benzalkonium chloride or chlorohexidine and thickening agents such as hypromellose may also be included.

Compositions for rectal administration may be presented as a suppository with a suitable non-irritating excipient which is solid at ordinary temperatures but liquid at the rectal temperature and will therefore melt in the rectum to release the active ingredient. Such excipients include cocoa butter or a salicylate.

Nasal compositions may be presented topically as nose drops or sprays or systemically in a form suitable for absorption through the nasal mucosa and/or the alveolar cells in the lungs.

Compositions suitable for vaginal administration may be presented as pessaries, tampons, creams, gels, pastes, foams or spray formulations containing in addition to the active ingredient such carriers as are known in the art to be appropriate.

Compositions suitable for parenteral administration include aqueous and non-aqueous isotonic sterile injection solutions which may contain anti-oxidants, buffers, bacteriostats and solutes which render the composition isotonic with the blood of the intended subject; and aqueous and non-aqueous sterile suspensions which may include suspending agents and thickening agents. The compositions may be presented in unit-dose or multi-dose sealed containers, for example, ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage compositions are those containing a daily dose or unit, daily sub-dose, as hereinabove described, or an appropriate fraction thereof, of an active ingredient. The compounds of the invention may be administered for example in amounts of between about 0.01 mg to about 500 mg per kg body weight of the subject per day (or preferably per incidence of radiation exposure), preferably between about 0.1 mg to about 100 mg, more preferably between about 1.0 mg to about 10 mg per kg body weight of the subject per day or per incidence of radiation exposure.

The compound of formula (I) may also be presented for use in the form of veterinary compositions, which may be prepared, for example, by methods that are conventional in the art. Examples of such veterinary compositions include those adapted for:
(a) oral administration, external application, for example drenches (e.g. aqueous or non-aqueous solutions or suspensions); tablets or boluses; powders, granules or pellets for admixture with feed stuffs; pastes for application to the tongue;
(b) parenteral administration for example by subcutaneous, intramuscular or intravenous injection, e.g. as a sterile solution or suspension; or (when appropriate) by intramammary injection where a suspension or solution is introduced into the udder via the teat;
(c) topical application, e.g. as a cream, ointment or spray applied to the skin; or
(d) intravaginally, e.g. as a pessary, cream or foam.

It should be understood that in addition to the ingredients particularly mentioned above, the compositions of this invention may include other agents conventional in the art having regard to the type of composition in question, for example, those suitable for oral administration may include such further agents as binders, sweeteners, thickeners, flavouring agents, disintegrating agents, coating agents, preservatives, lubricants and/or time delay agents.

Suitable sweeteners include sucrose, lactose, glucose, aspartame or saccharin. Suitable disintegrating agents include corn starch, methylcellulose, polyvinylpyrrolidone, xanthan gum, bentonite, alginic acid or agar. Suitable flavouring agents include peppermint oil, oil of wintergreen, cherry, orange or raspberry flavouring. Suitable coating agents include polymers or copolymers of acrylic acid and/or methacrylic acid and/or their esters, waxes, fatty alcohols, zein, shellac or gluten. Suitable preservatives include sodium benzoate, vitamin E, alpha-tocopherol, ascorbic acid, methyl paraben, propyl paraben or sodium bisulphite. Suitable lubricants include magnesium stearate, steric acid, sodium oleate, sodium chloride or talc. Suitable time delay agents include glyceryl monostearate or glyceryl distearate.

An important application of the radioprotector of the present invention is in cancer radiotherapy. Many of the normal tissues which are a problem in radiotherapy such as the skin, oral mucosa, oesophageal mucosa, rectal mucosa, vaginal mucosa and bladder epithelium can be topically protected by the radioprotectors of the present invention.

There are two distinct settings for such topical radioprotectors. Firstly, there is potential to decrease the distressing acute reactions that often occur in the normal tissues noted above. Although these acute reactions can be transient, their amelioration will obviously be of benefit to a subject. A different setting is the situation where acute reactions limit the dose of radiation that can be delivered to the tumour. An example is in the accelerated fractionation regime, in which acute reactions can be dose-limiting. Thus, the application of radioprotectors can enable the use of higher radiation doses, and hence improve prospects for cure.

Aside from topical application, the pharmaco-distribution properties of the radioprotectors of the present invention offer other ways of achieving an improved therapeutic ratio. Examples include tumours in the brain and lung.

In the case of the brain, endothelial cells are thought to be an important radiosensitive target in terms of the detrimental effects of radiation on normal brain tissue. The administration of the radioprotector of the present invention would protect the important endothelial cells in the normal brain. The corresponding cells in the tumour would also be protected, but these cells are well oxygenated and therefore are the most radiosensitive cells in the tumour. The more distant cells in the tumour, which are hypoxic, would therefore be out of reach of the radioprotector, if administered at an appropriate interval prior to irradiation. This means that the normal endothelial cells and oxic (radiosensitive) cells of the tumour would be protected equally. This radioprotection would then enable a higher dose of irradiation to be used which would increase the chance of killing the hypoxic cells in the tumour. The fact that the endothelial cells of both the tumour and normal tissue are affected equally has no impact on the therapeutic ratio. An increase in the therapeutic ratio could result because of the increase in kill of hypoxic tumour cells, without any debt in terms of normal tissue damage.

In the case of tumours in the lung, the radioprotector of the present invention would be delivered to alveolar cells. Although the endothelial cells of the lung tumour may also be protected, the more distant cells in the tumour would not. Moreover, the circulation of some lung tumours is provided not by the pulmonary artery but from the bronchial circulation, which will not be accessed until the next pass of the radioprotector in the circulation and hence exposed to lower concentrations.

The targeting of radioprotectors may also achieve improved therapeutic ratios in radiotherapy. A suitable example is the conjugation of the radioprotector of the present invention to haemopoietic growth factor to achieve preferential radioprotection of haemopoietic stem cells in the context of total body irradiation and bone marrow transplantation.

Outside the context of cancer radiotherapy, the radioprotectors of the present invention can be used as a prophylactic in high risk radiation situations. For example, the haemopoietic growth factor conjugate described above may be administered for this purpose. More generally, radioprotectors represented by Formula (I) and (II) can be used as a prophylactic in situations where there is a risk of exposure to radiation, or to mitigate against the effects of continuing exposure. In such situations, the compounds may be administered parentally (preferably subcutaneously) or orally, without any consideration for the concern associated with the cancer radiotherapy setting, namely delivery of the radioprotector to the tumour. In the case of subcutaneous administration, formulation of the radioprotector as a cyclodextrin complex may avoid a local toxicity reaction attributable to cytoxicity of transient exposure of the tissue to high local concentration of the uncomplexed radioprotector at the site of injection.

Compounds of Formula (I) and (II) as referred to above can, for example, be prepared by adopting one of synthetic Schemes 1 to 4, as below. The variables in the synthetic schemes are as provided in relation to Formula (II) (and Formula (I) in the case of Y).

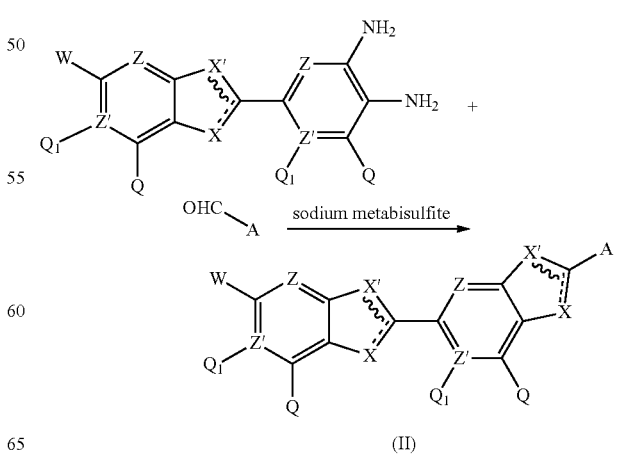

Scheme 2

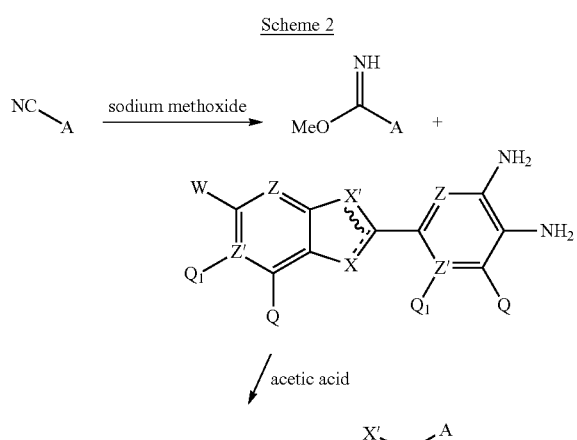

Scheme 3

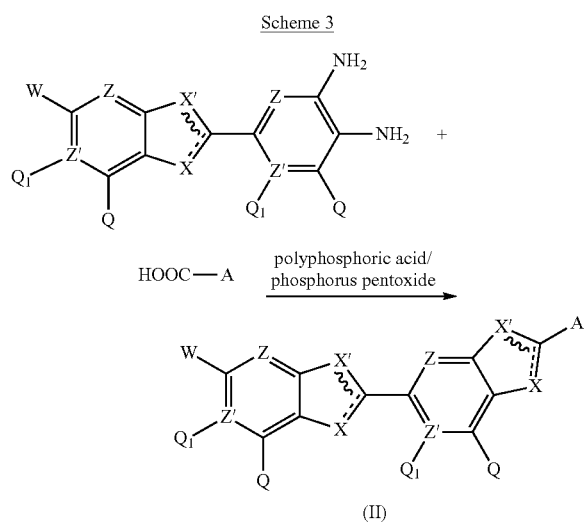

Scheme 4

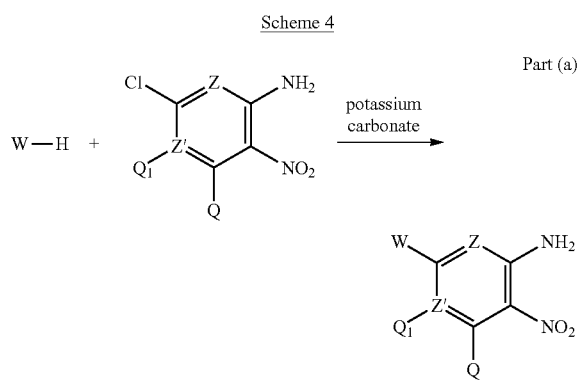

Part (a)

-continued

Part (b)

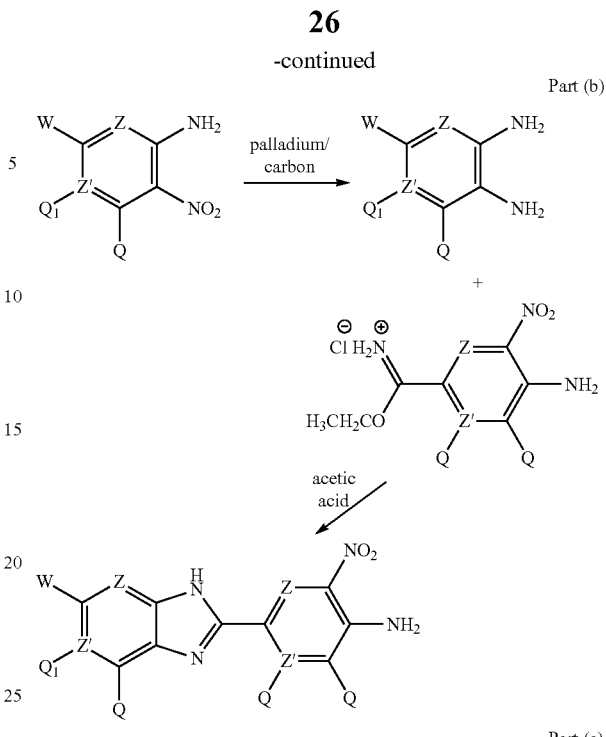

Part (c)

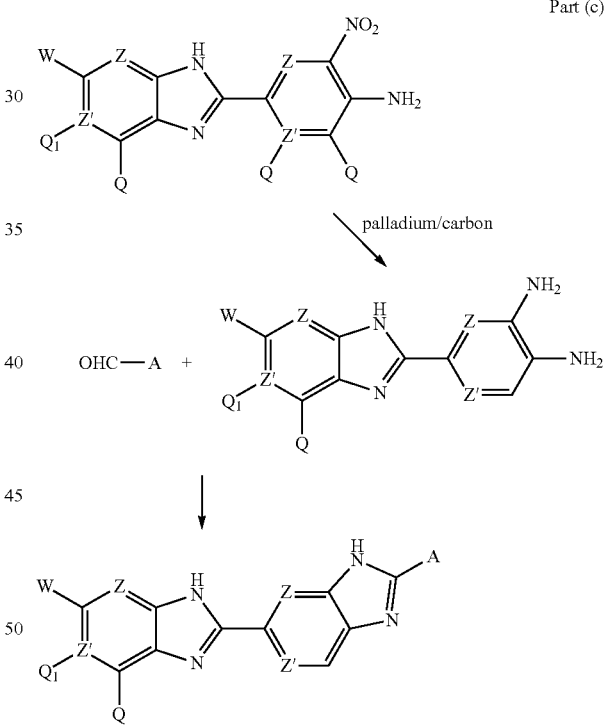

Those skilled in the art will appreciate that the invention described herein is susceptible to variations and modifications other than those specifically described. It is to be understood that the invention includes all such variations and modifications. The invention also includes all of the steps, features, compositions and compounds referred to or indicated in this specification, individually or collectively, and any and all combinations of any two or more of said steps or features.

The invention will now be described with reference to the following Examples. These Examples are not to be construed as limiting the invention in any way.

TABLE 1

Compound Example/Code/Name Correlation Table

| Example No. | Code | Compound Name |
|---|---|---|
| 1 | 2FuH | 2-(5'-(5''-(4'''-methylpiperazin-1'''-yl)benzimidazol-2''-yl)benzimidazol-2'-yl)furan |
| 2 | 2PH | 2-(5'-(5''-(4'''-methylpiperazin-1'''-yl)benzimidazol-2''-yl)benzimidazol-2'-yl)pyridine |
| 3 | F2PH | 3-fluoro-2-(5'-(5''-(4'''-methylpiperazin-1'''-yl)benzimidazol-2''-yl)benzimidazol-2'-yl)pyridine |
| 4 | CF32PH | 2-(5'-(5''-(4'''-methylpiperazin-1'''-yl)benzimidazol-2''-yl)benzimidazol-2'-yl)-3-trifluoromethylpyridine |
| 5 | 2P3MH | 6-methyl-2-(5'-(5''-(4'''-methylpiperazin-1'''-yl)benzimidazol-2''-yl)benzimidazol-2'-yl)pyridine |
| 6 | 2P5MH | 5-methyl-2-(5'-(5''-(4'''-methylpiperazin-1'''-yl)benzimidazol-2''-yl)benzimidazol-2'-yl)pyridine |
| 7 | 2P4MH | 4-methyl-2-(5'-(5''-(4'''-methylpiperazin-1'''-yl)benzimidazol-2''-yl)benzimidazol-2'-yl)pyridine |
| 8 | 4C2PH | 4-chloro-2-(5'-(5''-(4'''-methylpiperazin-1'''-yl)benzimidazol-2''-yl)benzimidazol-2'-yl)pyridine |
| 9 | 4MA2PH | 4-methylamino-2-(5'-(5''-(4'''-methylpiperazin-1'''-yl)benzimidazol-2''-yl)benzimidazol-2'-yl)pyridine |
| 10 | 4MN2PH | 4-dimethylamino-2-(5'-(5''-(4'''-methylpiperazin-1'''-yl)benzimidazol-2''-yl)benzimidazol-2'-yl)pyridine |
| 11 | 4MO2PH | 4-methoxy-2-(5'-(5''-(4'''-methylpiperazin-1'''-yl)benzimidazol-2''-yl)benzimidazol-2'-yl)pyridine |
| 12 | 2PHZ | 2-(5'-(5''-(4'''-methylpiperazin-1'''-yl)benzimidazol-2''-yl)benzimidazol-2'-yl)pyrazine |
| 13 | QHO | 2-(5'-(5''-(4'''-methylpiperazin-1'''-yl)benzimidazol-2''-yl)benzimidazol-2'-yl)quinoline |
| 14 | IQH | 3-(5'-(5''-(4'''-methylpiperazin-1'''-yl)benzimidazol-2''-yl)benzimidazol-2'-yl)isoquinoline |
| 15 | 3IQH | 1-(5'-(5''-(4'''-methylpiperazin-1'''-yl)benzimidazol-2''-yl)benzimidazol-2'-yl)isoquinoline |
| 16 | IZH | 3-(5'-(5''-(4'''-methylpiperazin-1'''-yl)benzimidazol-2''-yl)benzimidazol-2'-yl)indazole |
| 17 | MIZH | 1-methyl-3-(5'-(5''-(4'''-methylpiperazin-1'''-yl)benzimidazol-2''-yl)benzimidazol-2'-yl)indazole |
| 18 | 2PHO | 3-(5'-(5''-(4'''-methylpiperazin-1'''-yl)benzimidazol-2''-yl)benzimidazol-2'-yl)pyridin-2(1H)-one |
| 19 | M2PB | 2-(5'-(5''-morpholinobenzimidazol-2''-yl)benzimidazol-2'-yl)pyridine |
| 20 | MOIQ | 3-(5'-(5''-morpholinobenzimidazol-2''-yl)benzimidazol-2'-yl)isoquinoline |
| 21 | 2P4MM | 2-(5'-(5''-Morpholinobenzimidazol-2''-yl)benzimidazol-2'-yl)-4-methylpyridine |
| 22 | HOP2PH | 2-(5'-(5''-(4'''-hydroxypiperidin-1'''-yl)benzimidazol-2''-yl)benzimidazol-2'-yl)pyridine |
| 23 | HOIQ | 3-(5'-(5''-(4'''-hydroxypiperidin-1'''-yl)benzimidazol-2''-yl)benzimidazol-2'-yl)isoquinoline |
| 24 | 2PBP | 2-(5'-(5''-(piperidin-1'''-yl)benzimidazol-2''-yl)benzimidazol-2'-yl)pyridine |
| 25 | DZ2PB | 2-(5'-(5''-(4'''-methyl-1''',4'''-diazepan-1'''-yl)benzimidazol-2''-yl)benzimidazol-2'-yl)pyridine |
| 26 | 3HOP | 2-(5'-(5''-(3'''-hydroxypiperidin-1'''-yl)benzimidazol-2''-yl)benzimidazol-2'-yl)pyridine |
| 27 | MOP2PH | 2-(5'-(5''-(4'''-methoxypiperidin-1'''-yl)benzimidazol-2''-yl)benzimidazol-2'-yl)pyridine |
| 28 | 2PBD | 2-(5'-(5''-(dimethylamino)benzimidazol-2''-yl)benzimidazol-2'-yl)pyridine |
| 29 | 2PCH | 2-(5'-(5''-(4'''-(Dimethylamino)piperidin-1'''-yl)benzimidazol-2''-yl)benzimidazol-2'-yl)pyridine |
| 30 | 4M2PH | 2-(4'-methoxy-6'-(5''-(4'''-methylpiperazin-1'''-yl)benzimidazol-2''-yl)benzimidazol-2'-yl)pyridine |
| 31 | 2PBI | 2-(6'-(5''-(4'''-methylpiperazin-1'''-yl)benzimidazol-2''-yl)indol-2'-yl)pyridine |
| 32 | 5MO2PH | 2-(5'-methoxy-6'-(5''-(4'''-methylpiperazin-1'''-yl)benzimidazol-2''-yl)benzimidazol-2'-yl)pyridine |
| 33 | IP2PH | 2-(5'-(5''-(4'''-Isopropylpiperazin-1'''-yl)benzimidazol-2''-yl)benzimidazol-2'-yl)pyridine |
| 34 | B2PH | 2-(5'-(5''-(4'''-Butylpiperazin-1'''-yl)benzimidazol-2''-yl)benzimidazol-2'-yl)pyridine |
| 35 | M2PO | 2-(5'-(5''-(2'''-methoxyethylamino)benzimidazol-2''-yl)benzimidazol-2'-yl)pyridine |
| 36 | MT2P | 2-(5'-(5''-thiomorpholinobenzimidazol-2''-yl)benzimidazol-2'-yl)pyridine |
| 37 | CD2PH | 2-(5'-(5''-(4'''-(dimethylcarbamoyl)piperazin-1'''-yl)benzimidazol-2''-yl)benzimidazol-2'-yl)pyridine |
| 38 | 2BMOA | 2-(5'-(5''-((2'''-Methoxyethyl)(methyl)amino)benzimidazol-2''-yl)benzimidazol-2'-yl)pyridine |
| 39 | 2BMOEA | 2-(5'-(5''-(2'''-(2''''-methoxyethoxy)ethylamino)benzimidazol-2''-yl)benzimidazol-2'-yl)pyridine |
| 40 | 2BME | 2-(5'-(5''-(4'''-(2''''-methoxyethyl)piperazin-1'''-yl)benzimidazol-2''-yl)benzimidazol-2'-yl)pyridine |
| 41 | 2BPE | 2-(5'-(5''-(4'''-(2''''-hydroxyethyl)piperazin-1'''-yl)benzimidazol-2''-yl)benzimidazol-2'-yl)pyridine |
| 42 | MA2BP | 2-(5'-(5''-(morpholinoamino)benzimidazol-2''-yl)benzimidazol-2'-yl)pyridine |
| 43 | 2POP | 2-(5'-(5''-(2'''-(dimethylamino)ethylamino)benzimidazol-2''-yl)benzimidazol-2'-yl)pyridine |

TABLE 1-continued

Compound Example/Code/Name Correlation Table

| Example No. | Code | Compound Name |
|---|---|---|
| 44 | DAE2B | 2-(5'-(5''-(2'''-(dimethylamino)ethoxy)benzimidazol-2''-yl)benzimidazol-2'-yl)pyridine |
| 45 | cH2PH | 2-(5'-(5''-(tetrahydropyridazin-1'''-yl)benzimidazol-2''-yl)benzimidazol-2'-yl)pyridine |
| 46 | IDK | 2-(5'-(5''-(2''',2'''-dimethylhydrazinyl)benzimidazol-2''-yl)benzimidazol-2'-yl)pyridine |
| 47 | 2PHF | 5-fluoro-2-(5'-(5''-(4'''-methylpiperazin-1'''-yl)benzimidazol-2''-yl)benzimidazol-2'-yl)pyridine |
| 48 | 4TFMP | 2-(5'-(5''-(4'''-methylpiperazin-1'''-yl)benzimidazol-2''-yl)benzimidazol-2'-yl)-4-(trifluoromethyl)pyridine |
| 49 | 5TFMP | 2-(5'-(5''-(4'''-methylpiperazin-1'''-yl)benzimidazol-2''-yl)benzimidazol-2'-yl)-5-(trifluoromethyl)pyridine |
| 50 | HO2P4M | 2-(5'-(5''-(4'''-hydroxypiperidin-1'''-yl)benzimidazol-2''-yl)benzimidazol-2'-yl)-4-methylpyridine |
| 51 | HO2P5M | 2-(5'-(5''-(4'''-hydroxypiperidin-1'''-yl)benzimidazol-2''-yl)benzimidazol-2'-yl)-5-methylpyridine |
| 52 | MP2M | 2-(5'-(5''-(cis-2''',6'''-dimethylmorpholino)benzimidazol-2''-yl)benzimidazol-2'-yl)pyridine |
| 53 | 2PIB | 2-(5'-(5''-(4'''-methypiperazin-1'''-yl)-1H-indol-2''-yl)benzimidazol-2'-yl)pyridine |
| 54 | 2BMAE | 2-(5'-(5''-(3'''-hydroxyethyl-1'''-methylamino)benzimidazol-2''-yl)benzimidazol-2'-yl)pyridine |

EXAMPLES

Notes in Relation to the Examples i. In the naming of the examples, priority is generally given to the heterocyclic ring-system depicted on the right end of the molecule, with subsequent ring systems numbered accordingly. In appropriate cases, tautomers are drawn to illustrate potential hydrogen-bond donating configurations into the minor groove of DNA.

ii. 2-Amino-4-(5'-(4''-methylpiperazin-1''-yl)benzimidazol-2'-yl)aniline was prepared by hydrogenation of 4-(5'-(4''-methylpiperazin-1''-yl)benzimidazol-2'-yl)-2-nitroaniline, using a modification of the method of Kelly et al, *Aust. J. Chem.* 1994, 47, 247-262 (Reference 7).

iii. 2-Amino-4-(5'-(piperidin-1''-yl)benzimidazol-2'-yl)aniline was prepared by hydrogenation of 2-nitro-4-(5'-(piperidin-1''-yl)benzimidazol-2'-yl)aniline, using a modification of the method of Kelly et al, *Aust. J. Chem.* 1994, 47, 247-262 (Reference 7).

iv. Ethyl 4-amino-3-nitrobenzenecarboximidate hydrochloride was prepared by reaction of 4-amino-3-nitrobenzonitrile with dry HCl gas in ethanol, using the method of Kelly et al, *Aust. J. Chem.* 1994, 47, 247-262 (Reference 7).

v. 4-Amino-3-methoxy-5-nitrobenzonitrile was prepared using the method described in WO 2005/070906 A1 (Reference 11).

vi. 5-(4'-Methylpiperazin-1'-yl)-2-nitroaniline was prepared using a modification of the method of Kelly et al, *Aust. J. Chem.* 1994, 47, 247-262 (Reference 7).

vii. 2,4-Dichloro-5-nitropyrimidine was prepared using the method of Whittaker, *J. Chem. Soc.*, 1565, 1951 (Reference 12).

viii. The following chemicals were obtained from the chemical suppliers indicated: 2-furaldehyde (Aldrich), 2-pyridinecarboxaldehyde (Aldrich), 3-fluoropyridine-2-carbaldehyde (Maybridge), 3-trifluoromethylpyridine-2-carboxaldehyde (Apollo Scientific), 6-methyl-2-pyridinecarboxaldehyde (Matrix Scientific), 5-methylpyridine-2-carbonitrile (Apollo Scientific), 4-methyl-2-pyridinecarbonitrile (Aldrich), 4-chloro-2-pyridinecarbonitrile (Aldrich), 4-methoxypicolinonitrile (Combi-Blocks), pyrazinecarbonitrile (Aldrich), 2-quinolinecarbonitrile (Aldrich), 3-isoquinolinecarbonitrile (Aldrich), 1-isoquinolinecarboxylic acid (Aldrich), indazole-3-carboxylic acid (Aldrich), 2-hydroxynicotinic acid (Aldrich), 4-hydroxypiperidine (Aldrich), 1-methylhomopiperazine (Aldrich), 3-hydroxypiperidine (Aldrich), 4-(N-BOC-amino)piperidine (Aldrich), 4-methoxypiperidine (Acros), 4-methyl-3-nitrobenzonitrile (Aldrich), 5-chloro-2-nitroaniline (Aldrich), 2-cyanopyridine (Aldrich), methyl 4-amino-2-methoxybenzoic acid (Aldrich), 4-(trifluoromethyl)-2-pyridinecarbonitrile (Matrix Scientific), cis-2,6-dimethylmorpholine (Acros), 5-(trifluoromethyl)-2-pyridinecarbonitrile (Advanced Chemical Intermediates) and 5-fluoro-2-pyridinecarbonitrile (Advanced Chemical Intermediates).

ix. The following abbreviations are used: BOC (tert-butoxycarbonyl), obs (obscured), MeOH (methanol), TFA (trifluoroacetic acid), HOAc (acetic acid), TLC (thin layer chromatography), C50 (concentration of radioprotector that results in 50% clonogenic survival, PF (protection factor), DMF (dose modification factor), DMF10 (dose modification factor at a concentration of 10 microM of radioprotector).

Example numbers have been assigned based on the following:

1-5 N-methylpiperazines prepared using aldehyde/metabisulfite method 6-14 N-methylpiperazines prepared using nitrile/methoxide method 14-18 N-methylpiperazines prepared using carboxylic acid/PPA method 19-21 morpholino analogues 22-23 4-hydroxypiperidine analogues 24-29 other 5''-substituted 2-pyridyl analogues 30-32 4'-methoxy and indole/purine analogues 33-44 piperazinyl, amine, thiomorpholino and morpholino analogues 45-53 miscellaneous compounds.

x. Melting points were determined using an Electrothermal melting point apparatus, and are uncorrected. Proton ($^1$H) and carbon ($^{13}$C) nuclear magnetic resonance (nmr) spectroscopy were recorded as solutions in the stated solvent using a Varian Inova 400 or Varian Inova 500 spectrometer, at 399.77 or 499.69 MHz respectively for $^1$H, and at 100.52 or 125.66 MHz respectively for $^{13}$C. $^1$H nmr spectra were measured as chemical shifts quoted in parts per million (ppm) from tetramethylsilane, followed by multiplicity, coupling constant(s), number of equivalent nuclei, and assignment. The abbreviations s for singlet, d for doublet, t for triplet, q for quartet, br for broad and m for multiplet were used in the assignments of multiplicity. A value approximating the centre of a multiplet is quoted. The addition of a few drops of trifluoroacetic acid-d (d-TFA) to methanol-d4 solutions was found to reduce peak broadening and enhance the definition of multiplets in the aromatic region. The addition of a few drops of acetic acid to methanol-d4 solutions was used to enhance solubility for the acquisition of $^{13}C$ nmr spectra. Mass spectra were recorded on a Micromass Quattro II mass spectrometer and accurate mass analyses were carried out by the School of Chemistry at the University of Melbourne on a Finnigan LTQ-FT model high resolution mass spectrometer. Thin layer chromatography (TLC) was carried out using Merck silica gel 60 $F_{254}$ aluminium sheets or Merck neutral aluminium oxide 150 $F_{254}$ sheets. Flash column chromatography was carried out using Ajax silica gel 230-400 mesh.

xi. Clonogenic Survival Cell Culture Assay for Cytotoxicity and Radioprotective Activity The assay involves the transformed human keratinocyte cell line (FEP 1811) (as described by Smith et al (6)) and evaluation of cytotoxicity and radioprotective activity using the clonogenic survival endpoint. The details are described in detail in Martin et al (4) (the disclosure of which is included herein in its entirety by way of reference), but briefly, mid-log phase monolayer cultures are incubated with various concentrations of the test drugs for one hour, after which the monolayers are washed and dispersed into single cell suspensions using pronase, and finally appropriate numbers of cells are dispensed into Petri dishes. Colonies are counted after eight days incubation. For radioprotection studies, the monolayer cultures are irradiated in a $^{137}Cs$-Gamma-cell radiation source to a dose of 12 Gy. The irradiation (with a dose rate of 0.6 Gy per minute) is started 30 minutes after addition of the test drug. After completion of irradiation, incubation of cultures is continued until the total time of exposure to the drug reaches 60 minutes. Cultures are then washed and plated for clonogenic survival as described for the cytotoxicity experiments. The experiments include untreated cultures as controls, and the plating efficiency of these controls is used to adjust that of the test cultures, in order to calculate the overall clonogenic survival.

In general each experiment involves investigation of 4 or 5 different test concentrations of the drug under study, with and without irradiation. The data analysis for the experiments with un-irradiated cells generates curves showing the relationship between cell survival and drug concentration (FIG. 1), from which the drug concentration corresponding to 50% survival ($C_{50}$) is determined.

Example 1

2-(5'-(5"-(4'''-Methylpiperazin-1'''-yl)benzimidazol-2"-yl)benzimidazol-2'-yl)furan

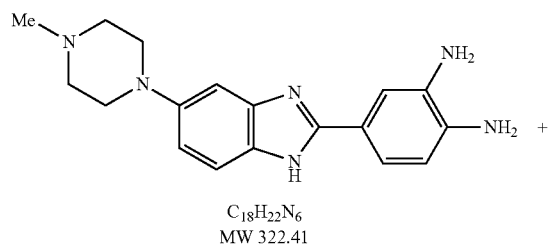

$C_{18}H_{22}N_6$
MW 322.41

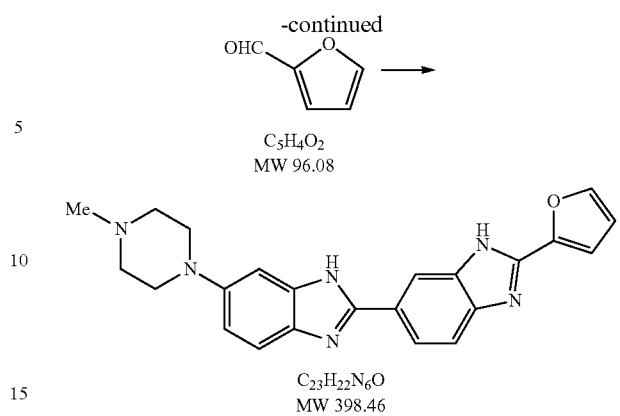

$C_5H_4O_2$
MW 96.08

$C_{23}H_{22}N_6O$
MW 398.46

To a solution of freshly distilled 2-furaldehyde (100 mg, 1.04 mmol) in ethanol (4 ml) was slowly added a solution of sodium metabisulfite (209 mg, 1.10 mmol) in water (1 ml). The resulting mixture was then added to a solution of 2-amino-4-(5'-(4"-methylpiperazin-1"-yl)benzimidazol-2'-yl)aniline (prepared by hydrogenation of 0.87 mmol of 4-(5'-(4"-methylpiperazin-1"-yl)benzimidazol-2'-yl)-2-nitroaniline)(7) in ethanol (6 ml), with additional ethanol (3 ml) used to aid the transfer. The mixture was refluxed under nitrogen for 18 h before cooling and removal of the solvent by rotary evaporator. The residue was treated with dilute ammonia solution (6%, 2×15 ml) and acetonitrile (2×10 ml) with centrifugation and removal of the supernatant following each treatment. Drying of the resultant solid under vacuum gave 2-(5'-(5"-(4'''-methylpiperazin-1'''-yl)benzimidazol-2"-yl)benzimidazol-2'-yl)furan as a yellow powder (331 mg, 94%), mp 202-224° C. (dec).

$^1H$ nmr (400 MHz, $d_4$-MeOH+4 drops d-TFA) δ 3.00, s, 3H, 4'''-MeN; 3.20, t (J=13.2 Hz), 2H, $NCH_2$; 3.34, m (obs), $NCH_2$; 3.68, d (J=12.0 Hz), 2H, $NCH_2$; 3.97, d (J=12.8 Hz), 2H, $NCH_2$; 6.90, ddd (J=3.6, 1.6, 0.4 Hz), 1H, H4; 7.35, d (J=2.4 Hz), 1H, H4"; 7.44, dd (J=9.2, 2.0 Hz), 1H, H6"; 7.69, d (J=3.6 Hz), 1H, H3; 7.75, d (J=9.2 Hz), 1H, H7"; 8.04, d, (J=8.8 Hz), 1H, H7'; 8.07, d (J=1.6 Hz), 1H, H5; 8.21, dd (J=8.4, 1.6 Hz), 1H, H6'; 8.54, d (J=1.6 Hz), 1H, H4'. $^{13}C$ nmr (100 MHz, $d_4$-MeOH+4 drops HOAc) δ 43.6, 4'''-MeN; ~49.2 (obs), C2'''/6'''; 54.6, C3'''/5'''; 102.4, C4"; 113.0, 113.4; C3, C4; 114.4; C4'; 116.2, 116.6, 116.9, C6", C7', C7"; 122.8, C6'; 123.6, C5'; 133.8, 138.6, 139.7, 141.6, C3a', C3a", C7a', C7a"; 145.8, 146.3, 147.1, C2, C2', C5; 148.6, C5"; 152.4, C2". MS (ESI+ve) m/z 399 ($MH^+$, 100%). HRMS (ESI+ve) m/z 399.19289, $C_{23}H_{23}N_6O$ requires 399.19279 (Δ=0.3 ppm).

Cytotoxicity and Radioprotection Results
C50=57.3
PF=7.7
DMFm=1.37
DMF10=1.14

Example 2

2-(5'-(5"-(4'''-Methylpiperazin-1'''-yl)benzimidazol-2"-yl)benzimidazol-2'-yl)pyridine

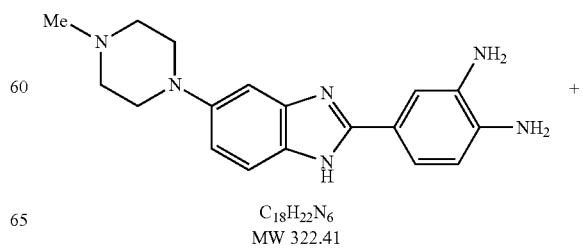

$C_{18}H_{22}N_6$
MW 322.41

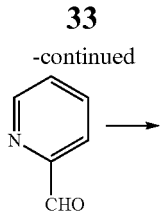

C₆H₅NO
MW 107.11

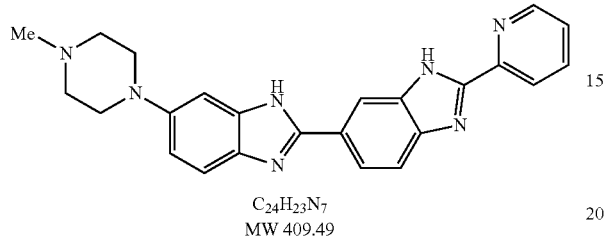

C₂₄H₂₃N₇
MW 409.49

2-Pyridinecarboxaldehyde (0.11 g, 1.02 mmol) was added to a solution of 2-amino-4-(5'-(4''-methylpiperazin-1''-yl)benzimidazol-2'-yl)aniline (prepared by hydrogenation of 0.85 mmol of 4-(5'-(4''-methylpiperazin-1''-yl)benzimidazol-2'-yl)-2-nitroaniline)(7) in ethanol (20 ml) and the mixture refluxed under nitrogen for 15 min before cooling. A solution of sodium metabisulfite (162 mg, 0.85 mmol) in water (2 ml) was then added and refluxing continued under nitrogen for a further 16 h. After cooling, the reaction mixture was centrifuged, the supernatant separated and the solid residue triturated with methanol (2×5 ml). The methanol was then combined with the supernatant before evaporating the solvents to give a glassy orange solid. The material was subjected to column chromatography with alumina (neutral, 35×120 mm) eluting with 50:3:1 ethyl acetate/methanol/triethylamine to give 2-(5'-(5''-(4'''-methylpiperazin-1'''-yl)benzimidazol-2''-yl)benzimidazol-2'-yl)pyridine as a light ochre powder (0.116 g, 33%), mp 178-180° C. (dec).

¹H nmr (400 MHz, d₄-MeOH+4 drops d-TFA) δ 3.00, s, 3H, 4'''-MeN; 3.21, t (J=11.6 Hz), 2H, NCH₂; 3.34, m (obs), NCH₂; 3.68, d (J=11.6 Hz), 2H, NCH₂; 3.96; d (J=13.2 Hz), 2H, NCH₂; 7.33, d (J=2.4 Hz), 1H, H4''; 7.41, dd (J=2.0, 8.8 Hz), 1H, H6''; 7.67, dd (J=4.8, 7.6 Hz), 1H, H5; 7.73, d (J=8.8 Hz), 1H, H7''; 8.06, d (J=8.8 Hz), 1H, H7'; 8.13, dt (J=1.6, 8.0 Hz), 1H, H4; 8.19, dd (J=1.6, 8.8 Hz), 1H, H6'; 8.40, d (J=8.0 Hz), 1H, H3; 8.58, d (J=1.6 Hz), 1H, H4'; 8.87, d (J=4.8 Hz), 1H, H6. ¹³C nmr (100 MHz, d₄-MeOH+3 drops HOAc) δ 43.6, 4'''-MeN; 49.4, C2'''/6'''; 54.6, C3'''/5'''; 102.6; C4''; 115.1; C4'; 116.4, 116.7, 116.9, C6'', C7', C7''; 122.7, C3 or C6'; 123.0, C6' or C3; 124.6, C5'; 126.1, C5; 134.7, C7a''; 138.4, C4; 139.2, 140.4, C3a', C3a''; 141.5, C7a'; 148.5, C5''; 148.7, C2; 150.8, C6; 153.1, 154.1, C2', C2''. MS (ESI+ve) m/z 410 (MH⁺, 100%). HRMS (ESI+ve) m/z 410.20859, C₂₄H₂₄N₇ requires 410.20877 (Δ=0.4 ppm).

Cytotoxicity and Radioprotection Results

C50=101.0

PF=18.2

DMFm=2.10

DMF10=1.93

Example 3

3-Fluoro-2-(5'-(5''-(4'''-methylpiperazin-1'''-yl)benzimidazol-2''-yl)benzimidazol-2'-yl)pyridine

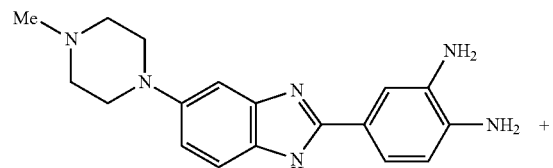

C₁₈H₂₂N₆
MW 322.41

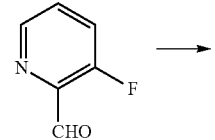

C₆H₄FNO
MW 125.10

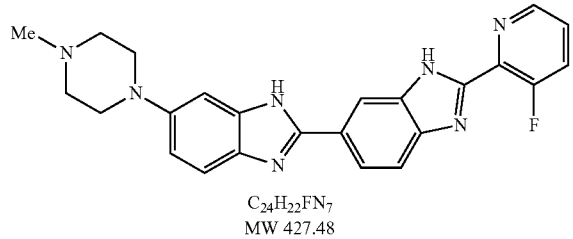

C₂₄H₂₂FN₇
MW 427.48

To a solution of 3-fluoropyridine-2-carbaldehyde (95 mg, 0.76 mmol) in ethanol (10 ml) was added a solution of sodium metabisulfite (159 mg, 0.84 mmol, 1.1 eq) in water (1 ml) and the mixture heated at 40-50° C. for 5 min. The mixture was then added to a suspension of 2-amino-4-(5'-(4''-methylpiperazin-1''-yl)benzimidazol-2'-yl)aniline (prepared by hydrogenation of 0.635 mmol of 4-(5'-(4''-methylpiperazin-1''-yl)benzimidazol-2'-yl)-2-nitroaniline)(7) in ethanol (10 ml) and the combined mixture gently refluxed under nitrogen for 18 h. After cooling the solvents were removed by rotary evaporator and the residue partitioned between n-butanol (20 ml) and dilute ammonia solution (2.7 M, 15 ml). The butanol extract was washed with brine (20 ml), dried (Na₂SO₄) and evaporated to give a glassy orange solid (285 mg). The material was dissolved in methanol (3 ml), applied to a plug of silica gel (30×70 mm) and eluted with methanol to give 3-fluoro-2-(5'-(5''-(4'''-methylpiperazin-1'''-yl)benzimidazol-2''-yl)benzimidazol-2'-yl)pyridine as an orange powder (177 mg, 65%), mp 201-214° C.

¹H nmr (500 MHz, d₄-MeOH+4 drops d-TFA) δ 3.01, s, 3H, 4'''-MeN; 3.21, t (J=11.8 Hz), 2H, NCH₂; 3.35, m (obs), NCH₂; 3.69, d (J=11.5 Hz), 2H, NCH₂; 3.97, d (J=13.5 Hz), 2H, NCH₂; 7.35, d (J=2.0 Hz), 1H, H4''; 7.44, dd (J=2.0, 9.0 Hz), 1H, H6''; 7.76, d (J=9.0 Hz), 1H, H7''; 7.80, ddd (J=4.3, 4.3, 8.6 Hz), 1H, H5; 7.99, ddd (J=1.0, 8.5, 10.1 Hz), 1H, H4; 8.10, d (J=8.5 Hz), 1H, H7'; 8.22, dd (J=1.7, 9.0 Hz), 1H, H6'; 8.62, d (J=1.5 Hz), 1H, H4'; 8.75, dt (J=4.8, 1.5 Hz), 1H, H6. ¹³C nmr (100 MHz, d₄-MeOH+4 drops HOAc) δ 43.6, 4'''-MeN; 49.4, C2'''/6'''; 54.7, C3'''/5'''; 102.7, C4''; 115.4, C4'; 116.4, 116.8, 117.2, C6'', C7', C7''; 123.3, C6'; 124.9, C5';

126.4, d ($^2J_{CF}$=19 Hz), C4; 127.8, d ($^3J_{CF}$=4 Hz), C5; 134.8, C7a"; 136.7, d ($^2J_{CF}$=9 Hz), C2; 139.4, 140.3, C3a', C3a"; 141.4, C7a'; 146.9, d ($^4J_{CF}$=5 Hz), C6; 148.5, C5"; 150.6, d ($^3J_{CF}$=8 Hz), C2'; 153.1, C2"; 159.1, d ($^1J_{CF}$=266 Hz), C3. MS (ESI+ve) m/z 428 (MH$^+$, 100%). HRMS (ESI+ve) m/z 428.19938, $C_{24}H_{23}FN_7$ requires 428.19935 ($\Delta$=0.1 ppm).

Cytotoxicity and Radioprotection Results
C50=93.1
PF=15.3
DMFm=1.80
DMF10=1.40

Example 4

2-(5'-(5"-(4'''-Methylpiperazin-1'''-yl)benzimidazol-2"-yl)benzimidazol-2'-yl)-3-trifluoromethylpyridine

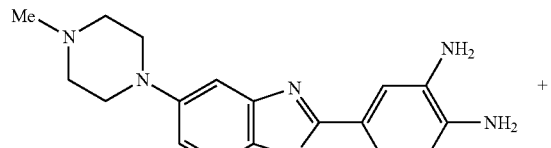

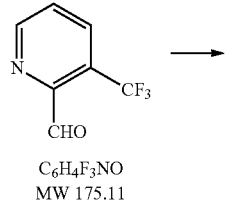

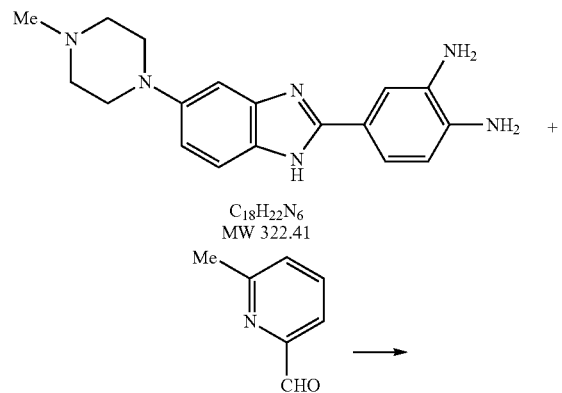

To a solution of 3-trifluoromethylpyridine-2-carboxaldehyde (150 mg, 0.85 mmol) in ethanol (10 ml) was added a solution of sodium metabisulfite (180 mg, 0.94 mmol, 1.1 eq.) in water (1 ml) and the mixture heated at 40-50° C. for 5 min. The mixture was then added over 5 min to a solution of 2-amino-4-(5'-(4"-methylpiperazin-1"-yl)benzimidazol-2'-yl)aniline (prepared by hydrogenation of 0.775 mmol of 4-(5'-(4"-methylpiperazin-1"-yl)benzimidazol-2'-yl)-2-nitroaniline)(7) in ethanol (15 ml) and the combined mixture gently refluxed under nitrogen for 16 h. After cooling, the solvents were removed by rotary evaporator and the residue treated with dilute ammonia solution (2.7 M, 10 ml) and stirred for 15 min to give an even suspension before centrifuging and removal of the supernatant. The solid was again treated with dilute ammonia solution (2.7 M, 5 ml), then acetonitrile (3×5 ml), with centrifugation and removal of the supernatant after each treatment. The remaining solid was dried under vacuum to give 2-(5'-(5"-(4'''-methylpiperazin-1'''-yl)benzimidazol-2"-yl)benzimidazol-2'-yl)-3-trifluoromethylpyridine as a yellow powder (178 mg, 48%), mp 189-191° C.

$^1$H nmr (400 MHz, $d_4$-MeOH+4 drops d-TFA) δ 3.00, s, 3H, 4'''-MeN; 3.20, t (J=11.8 Hz), 2H, NCH$_2$; 3.35, m (obs), NCH$_2$; 3.68, d (J=12.0 Hz), 2H, NCH$_2$; 3.96, d (J=13.6 Hz), 2H, NCH$_2$; 7.32, d (J=2.0 Hz), 1H, H4"; 7.42, dd (J=2.2, 9.0 Hz), 1H, H6"; 7.73, d (J=9.2 Hz), 1H, H7"; 7.80, dd (J=4.8, 8.4 Hz), 1H, H5; 8.00, dd (J=0.8, 8.8 Hz), 1H, H7'; 8.07, dd (J=1.8, 8.6 Hz), 1H, H6'; 8.41, dd (J=0.8, 8.0 Hz), 1H, H4; 8.53, dd (J=0.6, 1.4 Hz), 1H, H4'; 9.00, d (J=4.7 Hz), 1H, H6. $^{13}$C nmr (125 MHz, $d_4$-MeOH+4 drops HOAc) δ 43.6, 4'''-MeN; 49.5, C2"'/6"'; 54.7, C3"'/5"'; 103.0, C4"; 115.8, 116.5, 117.0, 117.4, C4', C6", C7', C7"; 123.4, C6'; 124.5, q ($^1J_{CF}$=266 Hz), 3-CF$_3$, 125.2, C5'; 125.9, C5; 126.9, q ($^2J_{CF}$=34 Hz), C3; 134.9, C7a"; 137.3, d ($^3J_{CF}$=5 Hz), C4; 139.6, 140.6, C3a', C3a"; 141.4, C7a'; 148.1, C2; 148.6, C5"; 152.0, C2'; 153.4, C2" and C6 (overlap). MS (ESI+ve) m/z 478 (MH$^+$, 100%), 239.7 (MH$_2^{2+}$, 60). HRMS (ESI+ve) m/z 478.19617, $C_{25}H_{23}F_3N_7$ requires 478.19615 ($\Delta$=0.04 ppm).

Cytotoxicity and Radioprotection Results
C50=190.0
PF=30.5
DMFm=1.99
DMF10=1.41

Example 5

6-Methyl-2-(5'-(5"-(4'''-methylpiperazin-1'''-yl)benzimidazol-2"-yl)benzimidazol-2'-yl)pyridine To a solution of 6-methyl-2-pyridinecarboxaldehyde (125 mg, 1.03 mmol) in ethanol (5 ml) was added a solution of sodium metabisulfite (211 mg, 1.11 mmol) in water (3 ml) and the combined mixture stirred for 5 min before being added to a solution of 2-amino-4-(5'-(4"-methylpiperazin-1"-yl)benzimidazol-2'-yl)aniline (prepared by hydrogenation of 0.956 mmol of 4-(5'-(4"-methylpiperazin-1"-yl)benzimidazol-2'-yl)-2-nitroaniline)(7) in ethanol (20 ml). The mixture was then refluxed under nitrogen for 22 h before cooling and the solvents removed by rotary evaporation. The residue was partitioned between dilute ammonia solution (2.7 M, 15 ml) and n-butanol (40 ml) and the n-butanol extract then washed with dilute ammonia (2.7 M, 30 ml), brine (30 ml), dried (Na$_2$SO$_4$) and evaporated to give a glassy green-brown solid (402 mg). The material (200 mg) was subjected to column chromatography with alumina (neutral, 33×270 mm) eluting with 50:3:1 ethyl acetate/methanol/triethylamine to give 6-methyl-2-(5'-(5"-(4'"-methylpiperazin-1'"-yl)benzimidazol-2"-yl)benzimidazol-2'-yl)pyridine as an olive-coloured glass (37 mg, 18%).

Additional material (50 mg, total yield 43%) was obtained by re-columning mixed fractions using the same chromatography conditions.

$^1$H nmr (400 MHz, d$_4$-MeOH+5 drops d-TFA) δ 2.67, s, 3H, 6-Me; 3.00, s, 3H, 4'"-MeN; 3.22, m (obs), NCH$_2$; 3.32, m (obs), NCH$_2$; 3.68, d (J=11.6 Hz), 2H, NCH$_2$; 3.94, d (J=12.8 Hz), 2H, NCH$_2$; 7.28, d (J=2.0 Hz), 1H, H4"; 7.36, dd (J=2.4, 9.2 Hz), 1H, H6"; 7.49, d (J=8.0 Hz), 1H, H5; 7.68, d (J=9.2 Hz), 1H, H7"; 7.96, t (J=7.8 Hz), 1H, H4; 8.00, d (J=8.8 Hz), 1H, H7'; 8.14, m, 2H, H3, H6'; 8.49, d (J=1.2 Hz), 1H, H4'. $^{13}$C nmr (100 MHz, d$_4$-MeOH+3 drops HOAc) δ 24.4, 6-Me; 43.6, 4'"-MeN; 49.3, C2"'/6'"; 54.7, C3'"/5'"; 102.6, C4"; 115.3, C4'; 116.3, 116.9, 117.1, C6", C7', C7"; 119.9, C3; 123.0, C6'; 123.9, C5'; 125.8, C5; 134.0, C7a"; 138.6, C4; 138.8, 140.5, C3a', C3a"; 141.6, C7a'; 147.9, C2; 148.7, C5"; 152.9, 154.5, C2'; C2". MS (ESI+ve) m/z 424 (MH$^+$, 100%), 213 (MH$_2^{2+}$, 45). HRMS (ESI+ve) m/z 424.22433, C$_{25}$H$_{26}$N$_7$ requires 424.22442 (Δ=0.2 ppm).

Cytotoxicity and Radioprotection Results

C50=73.3
PF=2.5
DMFm=1.22
DMF10=1.12

Example 6

5-Methyl-2-(5'-(5"-(4'"-methylpiperazin-1'"-yl)benzimidazol-2"-yl)benzimidazol-2'-yl)pyridine

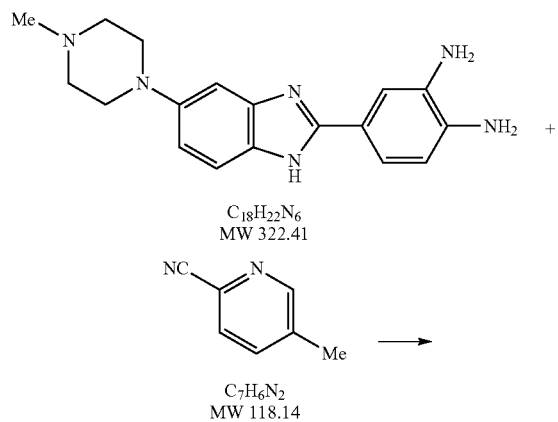

C$_{18}$H$_{22}$N$_6$
MW 322.41

C$_7$H$_6$N$_2$
MW 118.14

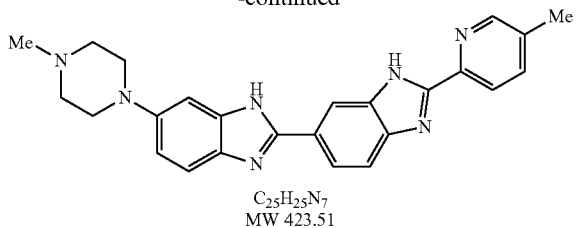

C$_{25}$H$_{25}$N$_7$
MW 423.51

To 5-methylpyridine-2-carbonitrile (107 mg, 0.90 mmol) was added a solution of sodium methoxide in methanol (0.087 M, 1.0 ml, 0.1 eq) and the solution heated under nitrogen in a 40° C. oil-bath for 2 h. A solution of 2-amino-4-(5'-(4"-methylpiperazin-1"-yl)benzimidazol-2'-yl)aniline (7) (193 mg, 0.60 mmol) in dry methanol (10 ml) and glacial acetic acid (0.10 ml, 1.75 mmol) was then added and the mixture gently refluxed under nitrogen for 16 h. After cooling the solvents were removed by rotary evaporator, the residue treated with dilute ammonia solution (2.7 M, 8 ml) and stirred for 30 min to give an even suspension of friable material. The suspension was centrifuged, the supernatant removed and the residue treated with additional dilute ammonia (2.7 M, 8 ml), followed by acetonitrile (3×3 ml), with centrifugation and removal of the supernatant between each treatment. The remaining solid was dried under vacuum to give a light grey powder (209 mg). The material was then applied to a short plug of silica gel (30×110 mm) and eluted with methanol to give 5-methyl-2-(5'-(5"-(4'"-methylpiperazin-1'"-yl)benzimidazol-2"-yl)benzimidazol-2'-yl)pyridine as a yellow-green powder (148 mg, 58%), mp 200-204° C.

$^1$H nmr (500 MHz, d$_4$-MeOH+4 drops d-TFA) δ 2.50, s, 3H, 5-Me; 3.00, s, 3H, 4'"-MeN; 3.21, t (J=12.0 Hz), 2H, NCH$_2$; 3.34, m (obs), NCH$_2$; 3.68, d (J=11.5 Hz), 2H, NCH$_2$; 3.97, d (J=13.5 Hz), 2H, NCH$_2$; 7.34, d (J=2.0 Hz), 1H, H4"; 7.43, dd (J=2.5, 9.0 Hz), 1H, H6"; 7.75, d (J=9.5 Hz), 1H, H7"; 7.97, m, 1H, H4; 8.06, d (J=9.0 Hz), 1H, H7'; 8.20, dd (J=1.5, 8.5 Hz), 1H, H6'; 8.30, d (J=8.0 Hz), 1H, H3; 8.58, d (J=1.5 Hz), 1H, H4'; 8.73, m, 1H, H6. $^{13}$C nmr (125 MHz, d$_4$-MeOH+4 drops HOAc) δ 18.4, 5-Me; 43.6, 4'"-MeN; 49.4, C2'"/6'"; 54.6, C3'"/5'"; 102.6, C4"; 114.9, C4'; 116.3, 116.7 (overlap), C6", C7', C7"; 122.3. 122.9, C3, C6'; 124.2, C5'; 134.4, C7a"; 136.6, C5; 138.6, C4; 139.1, 140.3, C3a', C3a"; 141.4; C7a'; 145.9, C2; 148.5, C5"; 151.1, C6; 153.0, 154.3, C2', C2". MS (ESI+ve) m/z 424 (MH$^+$, 100%). HRMS (ESI+ve) m/z 424.22406, C$_{25}$H$_{26}$N$_7$ requires 424.22442 (Δ=0.8 ppm).

Cytotoxicity and Radioprotection Results

C50=58.4
PF=26.2
DMFm=2.52
DMF10=2.43

Example 7

4-Methyl-2-(5'-(5"-(4'"-methylpiperazin-1'"-yl)benzimidazol-2"-yl)benzimidazol-2'-yl)pyridine

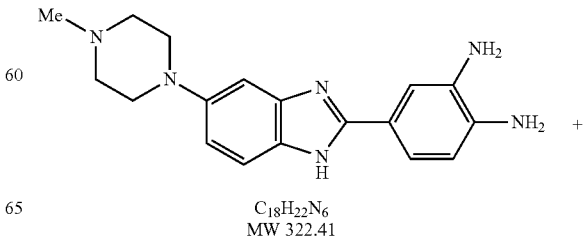

C$_{18}$H$_{22}$N$_6$
MW 322.41

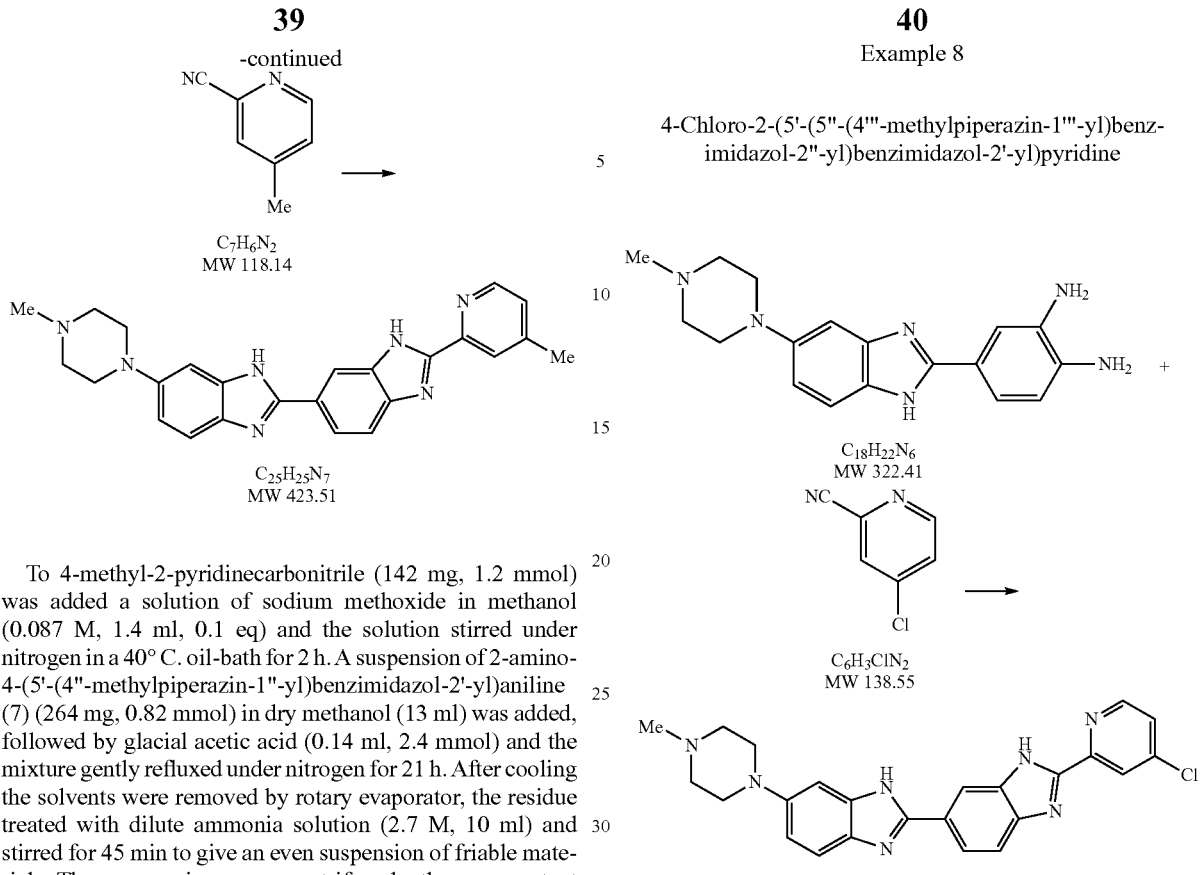

To 4-methyl-2-pyridinecarbonitrile (142 mg, 1.2 mmol) was added a solution of sodium methoxide in methanol (0.087 M, 1.4 ml, 0.1 eq) and the solution stirred under nitrogen in a 40° C. oil-bath for 2 h. A suspension of 2-amino-4-(5'-(4''-methylpiperazin-1''-yl)benzimidazol-2'-yl)aniline (7) (264 mg, 0.82 mmol) in dry methanol (13 ml) was added, followed by glacial acetic acid (0.14 ml, 2.4 mmol) and the mixture gently refluxed under nitrogen for 21 h. After cooling the solvents were removed by rotary evaporator, the residue treated with dilute ammonia solution (2.7 M, 10 ml) and stirred for 45 min to give an even suspension of friable material. The suspension was centrifuged, the supernatant removed and the residue treated with additional dilute ammonia (2.7 M, 5 ml), followed by acetonitrile (2×5 ml), with centrifugation and removal of the supernatant between each treatment. The remaining solid was then applied to a short plug of alumina (basic, Act I, 30×70 mm) and eluted with 50:3:1 ethyl acetate/methanol/triethylamine to give 4-methyl-2-(5'-(5''-(4'''-methylpiperazin-1'''-yl)benzimidazol-2''-yl)benzimidazol-2'-yl)pyridine as a yellow powder (281 mg, 83%), mp 200° C. (dec).

$^1$H nmr (400 MHz, $d_4$-MeOH+4 drops d-TFA) δ 2.58, s, 3H, 4-Me; 3.01, s, 3H, 4'''-MeN; 3.21, m (obs), $NCH_2$; 3.34, m (obs), $NCH_2$; 3.68, d (J=12.0 Hz), 2H, $NCH_2$; 3.97, d (J=12.4 Hz), 2H, $NCH_2$; 7.34, d (J=2.4 Hz), 1H, H4''; 7.43, dd (J=2.2, 9.0 Hz), 1H, H6''; 7.58, d (J=4.0 Hz), 1H, H5; 7.75, d (J=9.2 Hz), 1H, H7''; 8.08, d (J=8.8 Hz), 1H, H7'; 8.20, dd (J=1.6, 8.4 Hz), 1H, H6'; 8.29, s, 1H, H3; 8.60, d (J=1.6 Hz), 1H, H4'; 8.73, d (J=4.8 Hz), 1H, H6. $^{13}$C nmr (125 MHz, $d_4$-MeOH+4 drops HOAc) δ 21.1, 4-Me*; 43.6, 4'''-MeN; 49.3, C2'''/6'''; 54.6, C3'''/5'''; 102.4, C4''; 115.1, C4'; 116.3, C7''; 116.9 (overlap), C6'', C7'; 123.0, C6'; 123.5, C3, 123.9, C5'; 127.0, C5; 134.0, C7a''; 138.8, 140.3, 141.5, C3a', C3a'', C7a'; 148.4, 148.6, C2, C5''; 150.1, C4; 150.5, C6; 152.8, 154.2, C2', C2''. MS (ESI+ve) m/z 847 ($M_2H^+$, 8%), 424 ($MH^+$, 100), 213 ($MH_2^{2+}$, 14). HRMS (ESI+ve) m/z 424.22433, $C_{25}H_{26}N_7$ requires 424.22442 (Δ=0.2 ppm).

*Obscured by HOAc, observed indirectly by gHSQC experiment.

Cytotoxicity and Radioprotection Results

C50=130.5

PF=183.8

DMFm=2.55

DMF10=2.36

Example 8

4-Chloro-2-(5'-(5''-(4'''-methylpiperazin-1'''-yl)benzimidazol-2''-yl)benzimidazol-2'-yl)pyridine To 4-chloro-2-pyridinecarbonitrile (154 mg, 1.11 mmol) was added a solution of sodium methoxide in methanol (0.087 M, 1.2 ml, 0.1 eq) and the suspension heated under nitrogen in a 40° C. oil-bath for 2 h. A solution of 2-amino-4-(5'-(4''-methylpiperazin-1''-yl)benzimidazol-2'-yl)aniline (prepared by hydrogenation of 0.74 mmol of 4-(5'-(4''-methylpiperazin-1''-yl)benzimidazol-2'-yl)-2-nitroaniline)(7) in dry methanol (15 ml) was added, followed by glacial acetic acid (0.13 ml, 2.3 mmol) and the mixture gently refluxed under nitrogen for 72 h. After cooling, the solvents were removed by rotary evaporator and the residue treated with dilute ammonia solution (2.7 M, 20 ml) then extracted with n-butanol (2×20 ml). The butanol extract was washed with brine (20 ml) before evaporating to give a glassy solid. Column chromatography (silica gel) eluting with methanol afforded 4-chloro-2-(5'-(5''-(4'''-methylpiperazin-1'''-yl)benzimidazol-2''-yl)benzimidazol-2'-yl)pyridine as a yellow powder (245 mg, 75%), mp 195° C. (dec).

$^1$H nmr (500 MHz, $d_4$-MeOH+4 drops d-TFA) δ 3.00, s, 3H, 4'''-MeN; 3.19, t (J=12.0 Hz), 2H, $NCH_2$; 3.32, m (obs), $NCH_2$; 3.67, d (J=12.5 Hz), 2H, $NCH_2$; 3.89, d (J=12.0 Hz), 2H, $NCH_2$; 7.17, d (J=1.5 Hz), 1H, H4''; 7.27, dd (J=2.0, 9.0 Hz), 1H, H6''; 7.46, dd (J=1.8, 5.3 Hz), 1H, H5; 7.58, d (J=9.5 Hz), 1H, H7''; 7.78, d (J=8.5 Hz), 1H, H7'; 7.86, dd (J=1.5, 8.5 Hz), 1H, H6'; 8.17, d (J=1.5 Hz), 1H, H3 or H4'; 8.20, br s, 1H, H4' or H3; 8.56, d (J=5.0 Hz), 1H, H6. $^{13}$C nmr (125 MHz, $d_4$-MeOH+4 drops HOAc) δ 44.0, 4'''-MeN; 49.9, C2'''/6'''; 54.9, C3'''/5'''; 102.7, C4''; 114.9, C4'; 116.49, 116.55, 116.9, C6'', C7', C7''; 122.5, 123.1, C3; C6'; 125.5, C5'; 125.7, C5; 135.5, C7a''; 139.8, 140.3, 141.3, C3a', C3a'', C7a'; 146.0, C2 or C4; 148.5, C5''; 150.2, C4 or C2; 151.8, C6; 152.6, 153.2, C2', C2". MS (ESI+ve) m/z 444/446 (MH+, 100/35%), 223/224 (MH$_2^{2+}$, 60/20). HRMS (ESI+ve) m/z 444.16977, C$_{24}$H$_{23}$ClN$_7$ requires 444.16980 (Δ=0.1 ppm).
Cytotoxicity and Radioprotection Results
C50=80.0
PF=39.6
DMFm=2.20
DMF10=2.12

Example 9

4-Methylamino-2-(5'-(5"-(4'''-methylpiperazin-1'''-yl)benzimidazol-2"-yl)benzimidazol-2'-yl)pyridine

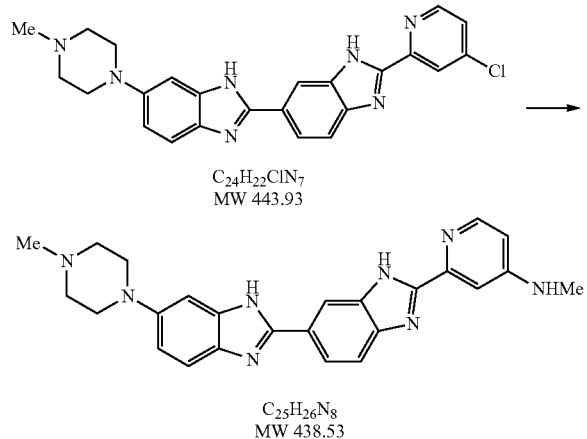

C$_{24}$H$_{22}$ClN$_7$
MW 443.93

C$_{25}$H$_{26}$N$_8$
MW 438.53

To a solution of 4-chloro-2-(5'-(5"-(4'''-methylpiperazin-1'''-yl)benzimidazol-2"-yl)benzimidazol-2'-yl)pyridine (48 mg, 0.11 mmol) (for preparation see Example 8) in ethanol (2 ml) was added potassium carbonate (20 mg, 0.145 mmol), followed by aqueous methylamine solution (30%, 3.0 ml, 26.1 mmol) and the mixture heated in a sealed tube in a 100° C. oil-bath for 114 h (CAUTION: High pressure). The reaction mixture was then cooled, diluted with water (10 ml) and extracted with n-butanol (10 ml). The n-butanol extract was washed with water (3×10 ml) and evaporated to give 4-methylamino-2-(5'-(5"-(4'''-methylpiperazin-1'''-yl)benzimidazol-2"-yl)benzimidazol-2'-yl)pyridine as a yellow glassy solid (41 mg, 67%), mp 220° C. (dec).
$^1$H nmr (400 MHz, d$_4$-MeOH+4 drops d-TFA) δ 3.00, s, 3H, 4'''-MeN; 3.08, br s, 4-MeN (minor); 3.14, br s, 4-MeN (major); 3.21, t (J=12.6 Hz), 2H, NCH$_2$; 3.34, m (obs), NCH$_2$; 3.69, d (J=12.4 Hz), 2H, NCH$_2$; 3.97, d (J=13.6 Hz), 2H, NCH$_2$; 6.94, m, 1H, H5; 7.33, d (J=2.4 Hz), 1H, H4"; 7.41, dd (J=2.4, 9.2 Hz), 1H, H6"; 7.56, br s, 0.4H, H3 (minor); 7.64, br s, 0.6H, H3 (major); 7.73, d (J=9.2 Hz), 1H, H7"; 8.00-8.26, m, 3H, H6, H6', H7'; 8.58, br s, 1H, H4'. $^{13}$C nmr (100 MHz, d$_4$-MeOH+4 drops HOAc) δ 29.7, 4-MeNH; 43.6, 4'''-MeN; 49.4, C2'''/6'''; 54.7, C3'''/5'''; 102.7, C4"; 105.5, br, C3 or C5; 108.6, br, C5 or C3; 115.5, 116.5, 116.9, 117.5, C4', C6", C7', C7"; 123.6, C6'; 125.2, C5'; 134.8, C7a"; 139.4, 140.6, 141.7, 142.7, C2 or C4, C3a', C3a", C7a'; 143.4, C6; 148.6, C5"; 148.7, C4 or C2; 152.8, C2"; 159.5, C2'. MS (ESI+ve) m/z 877 (M$_2$H$^+$, 8%), 439 (MH$^+$, 100), 220 (MH$_2^{2+}$, 25). HRMS (ESI+ve) m/z 439.23526, C$_{25}$H$_{27}$N$_8$ requires 439.23532 (Δ=0.1 ppm).
Cytotoxicity and Radioprotection Results
C50=59.9
PF=7.1
DMFm=1.55
DMF10=1.14

Example 10

4-Dimethylamino-2-(5'-(5"-(4'''-methylpiperazin-1'''-yl)benzimidazol-2"-yl)benzimidazol-2'-yl)pyridine C$_{24}$H$_{22}$ClN$_7$
MW 443.93

C$_{26}$H$_{28}$N$_8$
MW 452.55

To a solution of 4-chloro-2-(5'-(5"-(4'''-methylpiperazin-1'''-yl)benzimidazol-2"-yl)benzimidazol-2'-yl)pyridine (50 mg, 0.113 mmol) (for preparation see Example 8) in ethanol (2 ml) was added potassium carbonate (20 mg, 0.145 mmol), followed by aqueous dimethylamine solution (40%, 1.0 ml, 9.9 mmol) and the mixture heated in a sealed tube in a 100° C. oil-bath for 20 h (CAUTION: High pressure). The reaction mixture was then cooled, diluted with water (10 ml) and extracted with n-butanol (10 ml). The n-butanol extract was washed with water (3×10 ml) and evaporated to give 4-dimethylamino-2-(5'-(5"-(4'''-methylpiperazin-1'''-yl)benzimidazol-2"-yl)benzimidazol-2'-yl)pyridine as a yellow powder (48 mg, 94%), mp 216-220° C.
$^1$H nmr (400 MHz, d$_4$-MeOH+5 drops d-TFA) δ 3.00, s, 3H, 4'''-MeN; 3.20, t (J=12.4 Hz), 2H, NCH$_2$; 3.38, br m (obs.), 4-Me$_2$N and NCH$_2$; 3.68, d (J=12.0 Hz), 2H, NCH$_2$; 3.95, d (J=13.2 Hz), 2H, NCH$_2$; 7.07, dd (J=3.0, 7.4 Hz), 1H, H5; 7.33, d (J=2.0 Hz), 1H, H4"; 7.41, dd (J=2.2, 9.0 Hz), 1H, H6"; 7.73, d (J=8.8 Hz), 1H, H7"; 7.77, d (J=2.8 Hz), 1H, H3; 8.02, d (J=8.8 Hz), 1H, H7'; 8.08, dd (J=1.6, 8.8 Hz), 1H, H6'; 8.18, d (J=7.6 Hz), 1H, H6; 8.57, d (J=0.8 Hz), 1H, H4'. $^{13}$C nmr (100 MHz, d$_4$-MeOH+4 drops HOAc) δ 39.9, 4-Me$_2$N; 43.6, 4'''-MeN; 49.4, C2'''/6'''; 54.7, C3'''/5'''; 102.6, C4"; 105.5, 107.8, C3, C5; 115.1, C4'; 116.5, 116.8, 117.3, C6", C7', C7"; 123.3, C6'; 125.0, C5'; 134.9, C7a"; 139.4, 140.3, 141.4, 142.6, C2 or C4, C3a', C3a", C7a'; 143.9, C6; 148.5, C5"; 149.3, C4 or C2; 152.8, C2"; 157.6, C2'. MS (ESI+ve) m/z 453 (MH$^+$, 100%), 227 (MH$_2^{2+}$, 34). HRMS (ESI+ve) m/z 453.25107, C$_{26}$H$_{29}$N$_8$ requires 453.25097 (Δ=0.2 ppm).
Cytotoxicity and Radioprotection Results
C50=18.6
PF=10.1
DMFm=1.51
DMF10=1.39

Example 11

4-Methoxy-2-(5'-(5''-(4'''-methylpiperazin-1'''-yl)benzimidazol-2''-yl)benzimidazol-2'-yl)pyridine

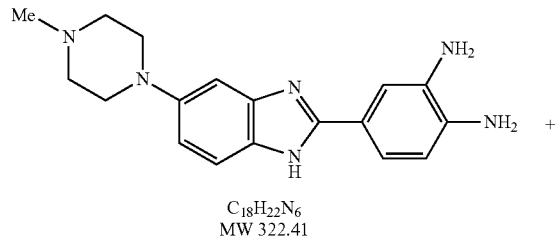

C$_{18}$H$_{22}$N$_6$
MW 322.41

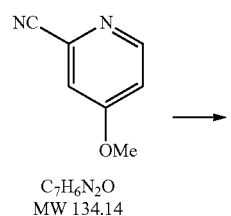

C$_7$H$_6$N$_2$O
MW 134.14

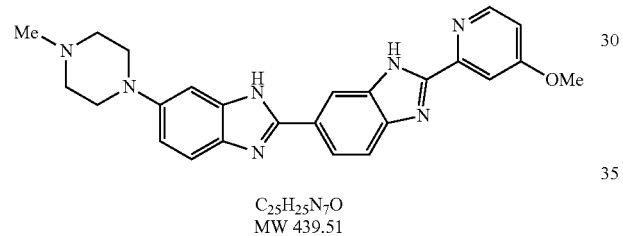

C$_{25}$H$_{25}$N$_7$O
MW 439.51

To 4-methoxypicolinonitrile (172 mg, 1.28 mmol) was added a solution of sodium methoxide in methanol (0.087 M, 1.5 ml, 0.1 eq) and the suspension stirred under nitrogen in a 40° C. oil-bath for 105 min. A solution of 2-amino-4-(5'-(4''-methylpiperazin-1''-yl)benzimidazol-2'-yl)aniline (prepared by hydrogenation of 0.87 mmol of 4-(5'-(4''-methylpiperazin-1''-yl)benzimidazol-2'-yl)-2-nitroaniline)(7) in dry methanol (10 ml) was added, followed by glacial acetic acid (0.15 ml, 2.6 mmol) and the mixture gently refluxed under nitrogen for 20 h. After cooling the solvents were removed by rotary evaporator and the residue treated with dilute ammonia solution (2.7 M, 23 ml) before extracting with n-butanol (3×6 ml). The butanol extract was washed with water (2×20 ml) after which a heavy tan precipitate had formed in the butanol layer. The suspension was centrifuged, the butanol supernatant removed and the solid treated with acetonitrile (2×4 ml) with centrifugation and removal of the supernatant after each treatment. The remaining solid was dried under vacuum to give 4-methoxy-2-(5'-(5''-(4'''-methylpiperazin-1'''-yl)benzimidazol-2''-yl)benzimidazol-2'-yl)pyridine as a light tan powder (174 mg, 46%), mp 190° C. (dec).

Additional material was obtained by evaporation of the n-butanol supernatant and treatment of the residue with acetonitrile (2×6 ml), with centrifugation and removal of the supernatant after each treatment. After drying under vacuum this afforded a further 153 mg of pure material (total yield 86%).

$^1$H nmr (500 MHz, d$_4$-MeOH+4 drops d-TFA) δ 3.00, s, 3H, 4'''-MeN; 3.21, t (J=12.3 Hz), 2H, NCH$_2$; 3.34, m (obs), NCH$_2$; 3.68, d (J=12.5 Hz), 2H, NCH$_2$; 3.96, d (J=11.5 Hz), 2H, NCH$_2$; 4.17, s, 3H, 4-Ome; 7.34, d (J=2.0 Hz), 1H, H4''; 7.42, dd (J=2.5, 9.0 Hz), 1H, H6''; 7.45, dd (J=2.5, 6.5 Hz), 1H, H5; 7.74, d (J=9.0 Hz), 1H, H7''; 8.07, d (J=8.5 Hz), 1H, H7'; 8.13, d (J=2.5 Hz), 1H, H3; 8.15, dd (J=2.0, 8.5 Hz), 1H, H6'; 8.61, d (J=1.0 Hz), 1H, H4'; 8.69, d (J=6.5 Hz), 1H, H6.
$^{13}$C nmr (125 MHz, d$_4$-MeOH+4 drops HOAc) δ 43.6, 4'''-MeN; 49.4, C2'''/6'''; 54.6, C3'''/5'''; 56.1, 4-Ome; 102.5, C4''; 108.5, 112.4, C3, C5; 115.1, C4'; 116.3, 116.8 (overlap), C6'', C7', C7''; 123.0, C6'; 124.3, C5'; 134.4, C7a''; 139.0, 140.3, 141.4, C3a', C3a'', C7a'; 148.5, C5''; 150.1, C2; 151.9, C6; 152.9, 154.0, C2', C2''; 168.0, C4. MS (ESI+ve) m/z 879 (M$_2$H$^+$, 10%), 440 (MH$^+$, 100), 221 (MH$_2$$^{2+}$, 7). HRMS (ESI+ve) m/z 440.21918, C$_{25}$H$_{26}$N$_7$O requires 440.21933 (Δ=0.3 ppm).

Cytotoxicity and Radioprotection Results

C50=53.6
PF=51.4
DMFm=2.28
DMF10=1.95

Example 12

2-(5'-(5''-(4'''-Methylpiperazin-1'''-yl)benzimidazol-2''-yl)benzimidazol-2'-yl)pyrazine (A) Preparation of Ethyl pyrazine-2-carbimidate Hydrochloride

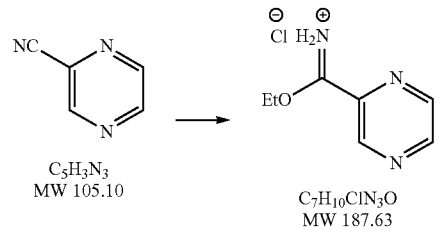 [SMILES: N#Cc1cnccn1 ; CCOC(=[NH2+])c1cnccn1 ; [Cl-]]

C$_5$H$_3$N$_3$
MW 105.10

C$_7$H$_{10}$ClN$_3$O
MW 187.63

To a solution of pyrazinecarbonitrile (1.00 g, 9.5 mmol) in dry ethanol (30 ml) was introduced a stream of dry HCl gas bubbled through the solution with stirring. Shortly after the HCl was introduced the temperature quickly rose requiring cooling with an ice/water bath. At this time a heavy white precipitate had formed and after 2 h the gas inlet was replaced with a calcium chloride drying tube and the reaction mixture stirred overnight. The HCl gas stream was re-introduced into the reaction mixture for 2 h before again replacing the gas inlet with a drying tube and stirring for 1 h. Dry diethyl ether (45 ml) was then added to the mixture and stirring continued for 10 min before the solid was filtered under nitrogen using a Schlenk apparatus. The collected material was washed with dry diethyl ether (3×20 ml) and dried under vacuum to give 1.59 g of a highly moisture-sensitive white powder. $^1$H nmr revealed the solid to be a mixture of the desired ethyl pyrazine-2-carbimidate hydrochloride (65%) and the two hydrolysis products pyrazine-2-carboxamide (30%) and ethyl pyrazine-2-carboxylate (5%).

$^1$H nmr (400 MHz, d$_6$-dmso) δ 1.49, t (J=7.0 Hz), 3H, OEt; 4.73, q (J=6.9 Hz), 2H, OEt; 7.85, br, 1H, C=NH$_2$$^+$; 8.24, br, 1H, C=NH$_2^+$; 8.93, dd (J=1.6, 2.4 Hz), 1H, H6; 9.06; d (J=2.4 Hz), 1H, H5; 9.33, d (J=1.2 Hz), 1H, H3.

(B) Preparation of 2-(5'-(5''-(4'''-methylpiperazin-1'''-yl)benzimidazol-2''-yl)benzimidazol-2'-yl)pyrazine

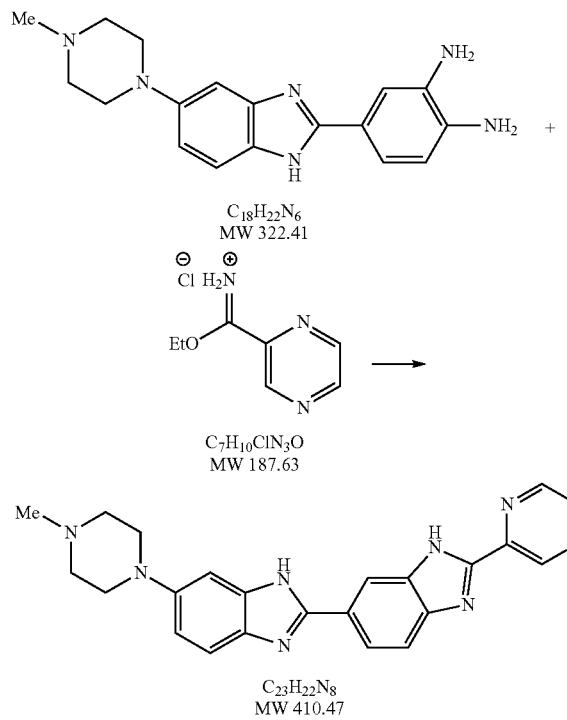

To 2-amino-4-(5'-(4''-methylpiperazin-1''-yl)benzimidazol-2'-yl)aniline (prepared by hydrogenation of 1.42 mmol of 4-(5'-(4''-methylpiperazin-1''-yl)benzimidazol-2'-yl)-2-nitroaniline)(7) was added the crude ethyl pyrazine-2-carbimidate hydrochloride (0.632 g, 65% pure, 2.2 mmol) followed by dry ethanol (10 ml) and glacial acetic acid (5 ml) and the combined mixture gently refluxed under nitrogen for 2 h. After cooling and stirring for 60 h at room temperature, refluxing was continued for a further 5 h. The solvents were then removed by rotary evaporator and the tan residue treated with dilute ammonia solution (2.7 M, 15 ml) and stirred for 16 h to give an even suspension before centrifuging and removal of the supernatant. The solid was again treated with dilute ammonia solution (2.7 M, 15 ml), then acetonitrile (3×15 ml), with centrifugation and removal of the supernatant after each treatment. The remaining solid was dried under vacuum to give a tan powder (379 mg), which $^1$H nmr showed to be only a 1:3 mixture of desired product and diamine. This material was re-treated with the crude ethyl pyrazine-2-carbimidate hydrochloride (0.94 g, 65% pure, 3.3 mmol) and again refluxed in 2:1 ethanol/glacial acetic acid (15 ml) for 23 h under nitrogen. A similar work-up afforded a brown powder (180 mg) consisting of equal amounts of the desired product and unreacted diamine. This was applied to a plug of alumina (basic, Act I, 70×30 mm) and eluted with 4:1:1 ethyl acetate/methanol/triethylamine to give 2-(5'-(5''-(4'''-methylpiperazin-1'''-yl)benzimidazol-2''-yl)benzimidazol-2'-yl)pyrazine as an orange-brown solid (71 mg, 12%), mp 175° C. (dec.).

$^1$H nmr (400 MHz, d$_4$-MeOH+4 drops d-TFA) δ 3.01, s, 3H, 4'''-MeN; 3.20, t (J=13.0 Hz), 2H, NCH$_2$; 3.35, m (obs), NCH$_2$; 3.68, d (J=12.0 Hz), 2H, NCH$_2$; 3.97, d (J=13.6 Hz), 2H, NCH$_2$; 7.32, d (J=2.0 Hz), 1H, H4''; 7.41, dd (J=2.4, 9.2 Hz), 1H, H6''; 7.73, d (J=8.8 Hz), 1H, H7''; 8.01, d (J=8.8 Hz), 1H, H7'; 8.09, dd (J=1.6, 8.4 Hz), 1H, H6'; 8.53, d (J=1.6 Hz), 1H, H4'; 8.79, d (J=2.8 Hz), 1H, H5; 8.84, dd (J=1.6, 2.4 Hz), 1H, H6; 9.55, d (J=1.2 Hz), 1H, H3. $^{13}$C nmr (100 MHz, d$_4$-MeOH+4 drops HOAc) δ 43.6, 4'''-MeN; 49.2, C2'''/6'''; 54.6, C3'''/5'''; 102.4, C4'',;115.2, C4'; 116.3, 116.7, 117.1, C6'', C7', C7''; 123.2, C6'; 124.5, C5'; 134.3, C7a''; 138.9, 140.4, C3a', C3a''; 141.4, C7a'; 143.7, C3, C5 or C6; 144.7, C2; 145.6, 146.1, C3, C5 or C6; 148.4, C5''; 151.5, 152.5, C2', C2''. MS (ESI+ve) m/z 411 (MH$^+$, 100%), 206 (MH$_2^+$, 15). HRMS (ESI+ve) m/z 411.20373, C$_{23}$H$_{23}$N$_8$ requires 411.20402 (Δ=0.7 ppm).

Cytotoxicity and Radioprotection Results
C50=54.2
PF=6.5
DMFm=1.29
DMF10=1.15

Example 13

2-(5'-(5''-(4'''-Methylpiperazin-1'''-yl)benzimidazol-2''-yl)benzimidazol-2'-yl)quinoline

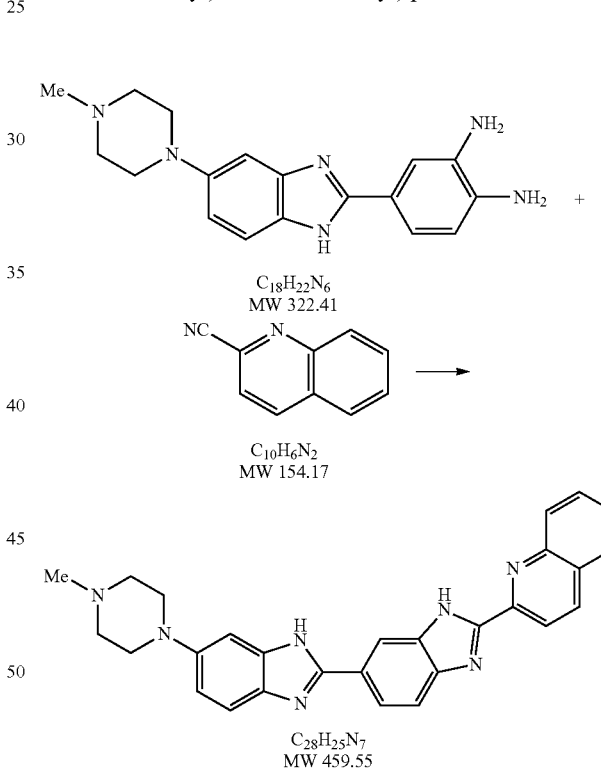

To 2-quinolinecarbonitrile (95 mg, 0.61 mmol) was added a solution of sodium methoxide in methanol (0.060 M, 1.0 ml, 0.1 eq) and the solution stirred under nitrogen in a 40° C. oil-bath for 2 h. A suspension of 2-amino-4-(5'-(4''-methylpiperazin-1''-yl)benzimidazol-2'-yl)aniline(7) (126 mg, 0.39 mmol) in dry methanol (10 ml) was added, followed by glacial acetic acid (0.07 ml, 1.2 mmol) and the mixture gently refluxed under nitrogen for 20 h. After cooling the solvents were removed by rotary evaporator, the residue treated with dilute ammonia solution (2.7 M, 5 ml) and resulting gum partitioned between n-butanol (20 ml) and additional dilute ammonia (2.7 M, 15 ml). The butanol extract was washed with water (3×20 ml) and evaporated. Treatment of the residue with methanol (2 ml) gave a heavy yellow precipitate, which was isolated by centrifugation and removal of the supernatant. The solid was further treated with acetonitrile (2 ml), centrifuged, the supernatant removed and the solid dried under vacuum to give 2-(5'-(5"-(4'"-methylpiperazin-1'"-yl)benzimidazol-2"-yl)benzimidazol-2'-yl)quinoline as a yellow powder (52 mg, 29%), mp>300° C.

Additional material was obtained by applying the methanol supernatant to a short plug of silica gel (45×30 mm) and eluting with methanol to give a further 87 mg (total yield 78%).

$^1$H nmr (500 MHz, d$_4$-MeOH+4 drops d-TFA) δ 3.01, s, 3H, 4'"-MeN; 3.20, t (J=12.0 Hz), 2H, NCH$_2$; 3.35, m (obs), NCH$_2$; 3.68, d (J=12.0 Hz), 2H, NCH$_2$; 3.94, d (J=13.0 Hz), 2H, NCH$_2$; 7.25, d (J=1.5 Hz), 1H, H4"; 7.36, dd (J=2.0, 9.5 Hz), 1H, H6"; 7.67, m, 2H, H6 or H7, H7"; 7.85, t (J=7.5 Hz), 1H, H7 or H6; 7.97, d (J=9.0 Hz), 1H, H5 or H8; 8.03, d (J=8.5 Hz), 1H, H7'; 8.10, br d (J=8.5 Hz), 1H, H6'; 8.22, d (J=8.5 Hz), 1H, H8 or H5; 8.38, d (J=8.5 Hz), 1H, H3 or H4; 8.49, s, 1H, H4'; 8.54, d (J=8.5 Hz), 1H, H4 or H3. $^{13}$C nmr (125 MHz, d$_4$-MeOH+4 drops HOAc) δ 43.6, 4'"-MeN; 49.1, C2'"/6'"; 54.6, C3'"/5'"; 102.0, C4"; 115.1, 116.0, 116.6, 116.8, C4', C6", C7', C7"; 119.6, C3; 122.8, C6'; 123.4, C5'; 128.3, 128.8, C5, C6, C7 or C8; 129.5, C4a; 130.2; 131.0, C5, C6, C7 or C8; 133.5, C7a"; 138.0, C4; 138.3, 140.2, 141.4, C3a', C3a", C7a'; 148.1, 148.4, 148.6, C2, C5", C8a; 152.2, 153.8, C2', C2". MS (ESI+ve) m/z 460 (MH$^+$, 100). HRMS (ESI+ve) m/z 460.22437, C$_{28}$H$_{26}$N$_7$ requires 460.22442 (Δ=0.1 ppm).

Cytotoxicity and Radioprotection Results
 C50=14.0
 PF=11.0
 DMFm=1.66
 DMF10=1.65

Example 14

3-(5'-(5"-(4'"-Methylpiperazin-1'"-yl)benzimidazol-2"-yl)benzimidazol-2'-yl)isoquinoline

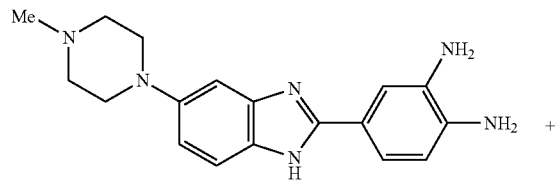

C$_{18}$H$_{22}$N$_6$
MW 322.41

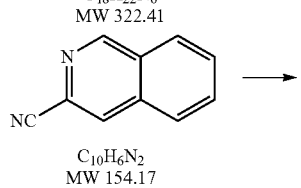

C$_{10}$H$_6$N$_2$
MW 154.17

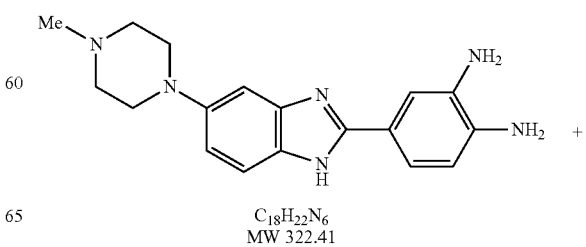

C$_{28}$H$_{25}$N$_7$
MW 459.55

To 3-isoquinolinecarbonitrile (154 mg, 1.0 mmol) was added a solution of sodium methoxide in methanol (0.087 M, 1.2 ml, 0.1 mmol, 0.1 eq) and the suspension stirred under nitrogen at room temperature for 3 h. Additional methanol (1.5 ml) was added before heating in a 40° C. oil-bath for 1 h to give a clear solution. A suspension of 2-amino-4-(5'-(4"-methylpiperazin-1"-yl)benzimidazol-2'-yl)aniline (prepared by hydrogenation of 0.72 mmol of 4-(5'-(4"-methylpiperazin-1"-yl)benzimidazol-2'-yl)-2-nitroaniline)(7) in dry methanol (13 ml) was added, followed by glacial acetic acid (0.12 ml, 2.1 mmol) and the mixture gently refluxed under nitrogen for 18 h. After cooling the solvents were removed by rotary evaporator and the residue treated with dilute ammonia solution (2.7 M, 10 ml) and the mixture then stirred for 1 h to give a foamy yellow suspension. The suspension was centrifuged, the supernatant removed and the solid treated with additional dilute ammonia solution (2.7 M, 10 ml), followed by acetonitrile (3×3 ml) with centrifugation and removal of the supernatant after each treatment. The remaining solid was dried under vacuum to give the crude product as a dull yellow powder (201 mg). The material was applied to a plug of silica gel (60×30 mm) and eluted with methanol to give 3-(5'-(5"-(4'"-methylpiperazin-1'"-yl)benzimidazol-2"-yl)benzimidazol-2'-yl)isoquinoline as a light yellow-green powder (138 mg, 42%), mp 224-229° C.

$^1$H nmr (400 MHz, d$_4$-MeOH+4 drops d-TFA) δ 3.01, s, 3H, 4'"-MeN; 3.20, t (J=12.0 Hz), 2H, NCH$_2$; 3.34, m (obs), NCH$_2$; 3.69, d (J=12.0 Hz), 2H, NCH$_2$; 3.96, d (J=13.6 Hz), 2H, NCH$_2$; 7.31, d (J=1.6 Hz), 1H, H4"; 7.41, dd (J=2.0, 9.2 Hz), 1H, H6", 7.73;,d (J=9.2 Hz), 1H, H7"; 7.88, app. t (J=7.0 Hz), 1H, H6 or H7; 7.95, app. t (J=7.0 Hz), 1H, H7 or H6; 8.10, d (J=8.4 Hz), 1H, H7'; 8.15, d (J=8.0 Hz), 1H, H5 or H8; 8.22; m, 2H, H6' and H8 or H5; 8.59, br s, 1H, H4'; 8.85, s, 1H, H1 or H4; 9.50, s, 1H, H4 or H1. $^{13}$C nmr (125 MHz, d$_4$-MeOH+4 drops HOAc) δ 43.6, 4'"-MeN; 49.0, C2'"/6'"; 54.5, C3'"/5'"; 101.8, C4"; 114.4, C4'; 115.9, 116.6 (overlap), C6", C7', C7"; 119.6, C4; 122.5, C6'; 122.7, C5'; 128.3, 128.6, 129.4, C5, C7, C8; 129.9, C8a; 132.0, C;, 133.1, C7a"; 136.7, 138.0, 139.6, 141.5 (overlap), C3, C3a', C3a", C4a, C7a'; 148.5, C5"; 152.1, C2' or C2"; C2; 153.4, C6; 154.2, C2" or C2'. MS (ESI+ve) m/z 919 (M$_2$H$^+$, 3%), 460 (MH$^+$, 100), 231 (MH$_2^{2+}$, 45). HRMS (ESI+ve) m/z 460.22436, C$_{28}$H$_{26}$N$_7$ requires 460.22442 (Δ=0.1 ppm).

Cytotoxicity and Radioprotection Results
 C50=26.0
 PF=25.1
 DMFm=2.45
 DMF10=2.34

Example 15

1-(5'-(5"-(4'"-Methylpiperazin-1'"-yl)benzimidazol-2"-yl)benzimidazol-2'-yl)isoquinoline

C$_{18}$H$_{22}$N$_6$
MW 322.41

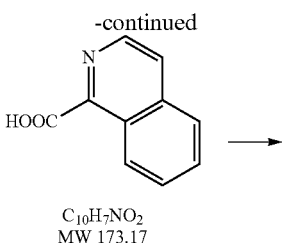

C₁₀H₇NO₂
MW 173.17

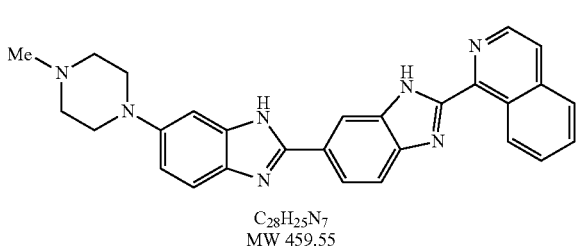

C₂₈H₂₅N₇
MW 459.55

Examples 16 and 17

3-(5'-(5''-(4'''-Methylpiperazin-1'''-yl)benzimidazol-2''-yl)benzimidazol-2'-yl)indazole and 1-methyl-3-(5'-(5''-(4'''-methylpiperazin-1'''-yl)benzimidazol-2''-yl)benzimidazol-2'-yl)indazole, Respectively

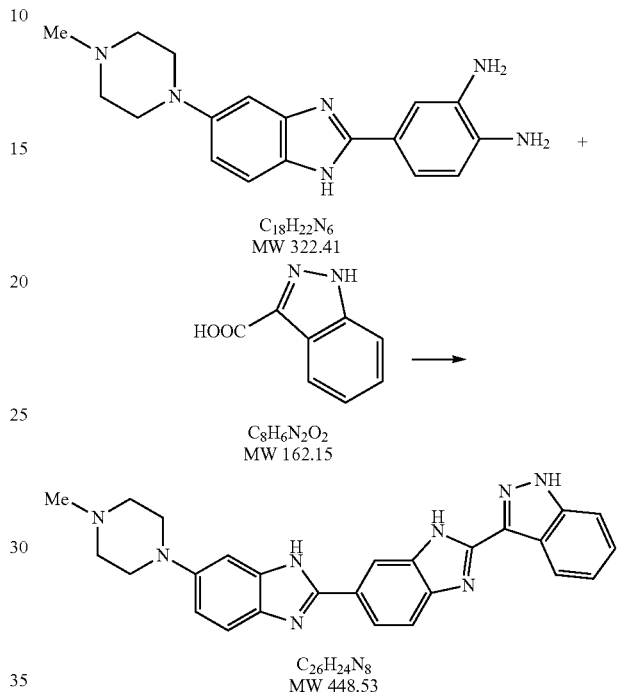

A mixture of 2-amino-4-(5'-(4''-methylpiperazin-1''-yl)benzimidazol-2'-yl)aniline(7) (86 mg, 0.27 mmol), 1-isoquinolinecarboxylic acid (83 mg, 0.48 mmol, 1.8 eq), polyphosphoric acid (3 g) and phosphorous pentoxide (0.6 g) was heated under nitrogen in a 180° C. oil-bath for 10 h. After cooling ice-water (30 ml) was added and the resultant heavy suspension basified (pH 8) with concentrated ammonia solution (6-8 ml). The suspension was then extracted with n-butanol (2×30 ml), the extract washed with water (2×45 ml) and evaporated to give a brown glassy solid. The material was subjected to column chromatography with alumina (basic, act. I, 22×200 mm) eluting with 15:1 ethyl acetate/methanol to give 1-(5'-(5''-(4'''-methylpiperazin-1'''-yl)benzimidazol-2''-yl)benzimidazol-2'-yl)isoquinoline as a dull yellow solid (70 mg), which was further purified by recrystallization from methanol (51 mg, 42%), mp 214-217° C.

¹H nmr (500 MHz, d₄-MeOH+4 drops d-TFA) δ 3.01, s, 3H, 4'''-MeN; 3.19, t (J=11.9 Hz), 2H, NCH₂; 3.33, m (obs), NCH₂; 3.68, d (J=12.0 Hz), 2H, NCH₂; 3.94, d (J=13.0 Hz), 2H, NCH₂; 7.25, d (J=2.0 Hz), 1H, H4''; 7.36, dd (J=2.0, 9.0 Hz), 1H, H6''; 7.67, d (J=9.0 Hz), 1H, H7''; 7.85, m, 2H, H6, H7; 7.97-8.06, m, 4H, H4, H5, H6', H7'; 8.50; d (J=1.0 Hz), 1H, H4'; 8.70, d (J=5.0 Hz), 1H, H3, 9.53, dd (J=1.0, 8.5 Hz), 1H, H8. ¹³C nmr (125 MHz, d₄-MeOH+5 drops HOAc) δ 43.5, 4'''-MeN; 49.1, C2'''/6'''; 54.5; C3'''/5'''; 102.1, C4''; 115.6, 116.1, 116.8, 117.0, C4', C6'', C7', C7''; 122.8, C4 or C6'; 123.3, C5'; 123.7, C6' or C4; 127.6, C8a; 128.1, 128.7, 129.5, 131.6, C5, C6, C7, C8; 133.4, C7a''; 138.29, 139.34, 140.5, 141.5, C3a', C3a'', C4a, C7a'; 142.7, C3; 147.6, 148.5, C1, C5''; 152.6, 154.3, C2', C2''. MS (ESI+ve) m/z 919 (M₂H⁺, 7%), 460 (MH⁺, 100). HRMS (ESI+ve) m/z 460.22445, C₂₈H₂₆N₇ requires 460.22442 (Δ=0.1 ppm).

Cytotoxicity and Radioprotection Results

C50=26.9

PF=36.9

DMFm=1.85

DMF10=1.70

A mixture of 2-amino-4-(5'-(4''-methylpiperazin-1''-yl)benzimidazol-2'-yl)aniline (prepared by hydrogenation of 0.71 mmol of 4-(5'-(4''-methylpiperazin-1''-yl)benzimidazol-2'-yl)-2-nitroaniline)(7), indazole-3-carboxylic acid (115 mg, 0.71 mmol), polyphosphoric acid (2.4 g) and phosphorous pentoxide (0.7 g) were heated under nitrogen in a 150° C. oil-bath for 6 h. After cooling ice-water (20 ml) was added and the resultant heavy suspension basified (pH 12) with concentrated ammonia solution (3-4 ml). After stirring for 20 min the heavy tan suspension was centrifuged, the supernatant removed and the residue treated with water (2×10 ml), then acetonitrile (2×4 ml), with centrifugation and removal of the supernatant after each treatment. The remaining solid was dried under vacuum to give the crude product as a light tan powder (216 mg), which was then subjected to silica gel column chromatography (26×300 mm) eluting with 50:3 methanol/triethylamine to give 3-(5'-(5''-(4'''-methylpiperazin-1'''-yl)benzimidazol-2''-yl)benzimidazol-2'-yl)indazole as a light tan glassy solid (111 mg, 35%), mp 235° C. (dec).

¹H nmr (500 MHz, d₄-MeOH+4 drops d-TFA) δ 3.00, s, 3H, 4'''-MeN; 3.20, m (obs), NCH₂; 3.32, m (obs), NCH₂; 3.68, d (J=12.0 Hz), 2H, NCH₂; 3.94, d (J=12.0 Hz), 2H, NCH₂; 7.29, d (J=2.0 Hz), 1H, H4''; 7.38, dd (J=2.5, 9.0 Hz), 1H, H6''; 7.45, m, 1H, H5 or H6; 7.54, m, 1H, H6 or H5; 7.70, m, 2H, H7, H7''; 8.03, d (J=8.5 Hz), 1H, H7'; 8.16, dd (J=2.0, 8.5 Hz), 1H, H6'; 8.40, d (J=8.5 Hz), 1H, H4; 8.53, d (J=1.5 Hz), 1H, H4'. ¹³C nmr (125 MHz, d₄-MeOH+5 drops HOAc) δ 43.5, 4'''-MeN; 48.9, C2'''/6'''; 54.4, C3'''/5'''; 101.7, C4''; 111.5, C7; 114.6, 115.8, 116.6, 117.0, C4', C6'', C7', C7'';

122.0, 122.2, C3a, C5'; 122.4, 122.5, 123.2, C4, C5, C6'; 128.1, C6; 132.5, 136.4, 137.6, 140.0, 142.0, 142.9, C3, C3a', C3a", C7a, C7a', C7a"; 148.7, C5"; 150.7, 152.2, C2', C2". MS (ESI+ve) m/z 449 (MH+, 100%). HRMS (ESI+ve) m/z 449.21947, $C_{26}H_{25}N_8$ requires 449.21967 (Δ=0.4 ppm).

An earlier eluting fraction was found to contain 1-methyl-3-(5'-(5"-(4'''-methylpiperazin-1'''-yl)benzimidazol-2"-yl)benzimidazol-2'-yl)indazole (53 mg, 16%), mp 106° C. (dec); presumably arising due to a trace amount of methanol (hydrogenation solvent) being present in the strongly acidic reaction mixture, resulting in N-alkylation.

$^1$H nmr (500 MHz, $d_4$-MeOH+4 drops d-TFA) δ 3.00, s, 3H, 4'''-MeN; 3.20, m (obs), NCH$_2$; 3.32, m (obs), NCH$_2$; 3.68, d (J=11.5 Hz), 2H, NCH$_2$; 3.94, d (J=13.5 Hz), 2H, NCH$_2$; 4.58, s, 3H, 1-Me; 7.29, d (J=2.5 Hz), 1H, H4"; 7.33, ddd (J=1.0, 6.5, 8.5 Hz), 1H, H5 or H6; 7.38, dd (J=2.5, 9.0 Hz), 1H, H6"; 7.42, ddd (J=1.0, 7.0, 8.5 Hz), 1H, H6 or H5; 7.70, d (J=9.0 Hz), 1H, H7"; 7.73, m, 1H, H7; 7.99, d (J=8.5 Hz), 1H, H7'; 8.02, m, 1H, H4; 8.04, dd (J=1.5, 8.5 Hz), 1H, H6'; 8.49, d (J=1.5 Hz), 1H, H4'. MS (ESI+ve) m/z 925 ($M_2H^+$, 6%), 463 (MH+, 100). HRMS (ESI+ve) m/z 463.23511, $C_{27}H_{27}N_8$ requires 463.23587 (Δ=1.6 ppm).

Cytotoxicity and Radioprotection Results for Example 16
C50=40.9
PF=18.3
DMFm=2.16
DMF10=1.78

Cytotoxicity and Radioprotection Results for Example 17
C50=76.5
PF=10.9
DMFm=1.68
DMF10=1.27

Example 18

3-(5'-(5"-(4'''-Methylpiperazin-1'''-yl)benzimidazol-2"-yl)benzimidazol-2'-yl)pyridin-2(1H)-one

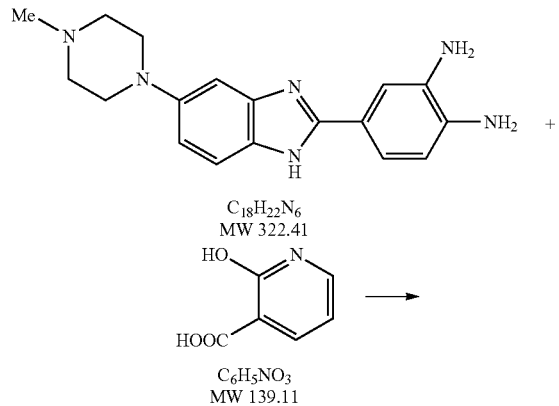

A mixture of 2-amino-4-(5'-(4"-methylpiperazin-1"-yl)benzimidazol-2'-yl)aniline(7) (86 mg, 0.27 mmol), 2-hydroxynicotinic acid (69.5 mg, 0.50 mmol, 1.9 eq), polyphosphoric acid (3 g) and phosphorous pentoxide (0.6 g) was heated under nitrogen in a 180° C. oil-bath for 12 h. After cooling ice-water (45 ml) was added and the resultant heavy suspension basified (pH 7) with 0.8 M sodium bicarbonate solution. The aqueous gum was then extracted with n-butanol (2×50 ml), the extract washed with water (2×80 ml) and evaporated to give a glassy solid. The material was dissolved in methanol (3 ml) and left to stand for 18 h during which time crystalline material had deposited. The crystals were collected, washed with acetonitrile (2×2 ml) and dried under vacuum to give 3-(5'-(5"-(4'''-methylpiperazin-1'''-yl)benzimidazol-2"-yl)benzimidazol-2'-yl)pyridin-2(1H)-one (17 mg, 15%) as a yellow crystalline powder, mp 244-248° C.

Additional material was obtained by combining the material from the methanolic filtrate and acetonitrile, subjecting it to alumina column chromatography (basic, act. I, 22×170 mm) and eluting with 1:1 ethyl acetate/methanol, methanol, then finally 5:1 methanol/acetic acid. The appropriate fractions (TLC) were concentrated and the material treated with 0.8 M sodium bicarbonate solution (12 ml) and extracted with n-butanol (3×5 ml). The n-butanol extract was washed with water (2×10 ml) and evaporated to give an additional 36 mg of yellow powder (total yield 47%).

$^1$H nmr (500 MHz, $d_4$-MeOH+5 drops d-TFA) δ 3.00, s, 3H, 4'''-MeN; 3.21, t (J=12.0 Hz), 2H, NCH$_2$; 3.32, m (obs), NCH$_2$; 3.68, d (J=12.0 Hz), 2H, NCH$_2$; 3.97, d (J=13.5 Hz), 2H, NCH$_2$; 6.75; dd (J=6.5, 7.5 Hz), 1H, H5; 7.35, d (J=2.0 Hz), 1H, H4"; 7.44, dd (J=1.8, 9.3 Hz), 1H, H6"; 7.76, d (J=9.0 Hz), 1H, H7"; 7.96, dd (J=2.0, 6.5 Hz), 1H, H4; 8.14, dd (J=0.8, 8.8 Hz), 1H, H7'; 8.24, dd (J=1.8, 8.8 Hz), 1H, H6'; 8.60, dd (J=0.8, 1.8 Hz), 1H, H4'; 8.71, dd (J=2.0, 7.5 Hz), 1H, H6. $^{13}$C nmr (100 MHz, $d_4$-MeOH+5 drops HOAc) δ 43.6, 4'''-MeN; 49.2, C2'''/6'''; 54.6, C3'''/5'''; 102.3, C4"; 108.5, C5; 114.6, C4'; 116.1, 116.6, 116.9, C6", C7', C7"; 118.8, C3; 122.7, C6'; 123.1; C5'; 133.4, C7a"; 138.4, C3a', C3a" or C7a'; 138.7, C4; 139.0, 140.6, C3a', C3a" or C7a'; 142.4, C6; 148.6, C5"; 151.8, 152.7, C2', C2"; 162.9, C2. MS (ESI+ve) m/z 426 (MH+, 100%), 214 ($MH_2^{2+}$, 79). HRMS (ESI+ve) m/z 426.20367, $C_{24}H_{24}N_7O$ requires 426.20368 (Δ=0.0 ppm).

Cytotoxicity and Radioprotection Results
C50=66.8
PF=1.1
DMFm=1.01
DMF10=1.00

Example 19

2-(5'-(5"-Morpholinobenzimidazol-2"-yl)benzimidazol-2'-yl)pyridine (A) Preparation of 5-morpholino-2-nitroaniline

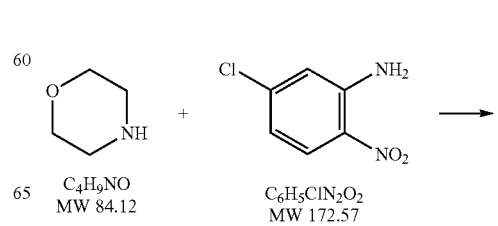

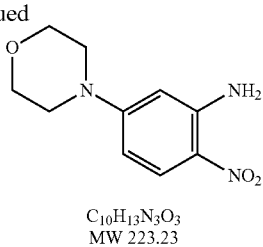

C₁₀H₁₃N₃O₃
MW 223.23

A mixture of 5-chloro-2-nitroaniline (4.0 g, 2.3 mmol), morpholine (3.45 ml, 41 mmol) and anhydrous potassium carbonate (3.2 g, 23 mmol) in N,N-dimethylacetamide (40 ml) was stirred at 130-140° C. under nitrogen overnight. The reaction mixture was then cooled to room temperature, poured onto ice and allowed to stand for 2-3 h. The yellow-brown precipitate was collected by filtration to afford 5-morpholino-2-nitroaniline (3.0 g, 58%), mp 183-185° C. (lit. (8) mp 187.5° C.).

¹H nmr (500 MHz, CDCl₃) δ 3.31, m, 4H, 2×CH₂N; 3.82, m, 4H, 2×CH₂O; 5.95, d (J=2.7 Hz), 1H, H6; 6.16, br, 2H, NH₂; 6.27, dd (J=9.5, 2.7 Hz), 1H, H4; 8.03, d (J=9.8 Hz), 1H, H3. ¹³C nmr (125 MHz, CDCl₃) δ 47.3, 2×CH₂N; 66.6, 2×CH₂O; 98.7, 105.6, C4, C6; 125.4, C2; 128.5, C3; 147.2, 155.9, C1, C5.

(B) Preparation of 4-(5'-morpholinobenzimidazol-2'-yl)-2-nitroaniline

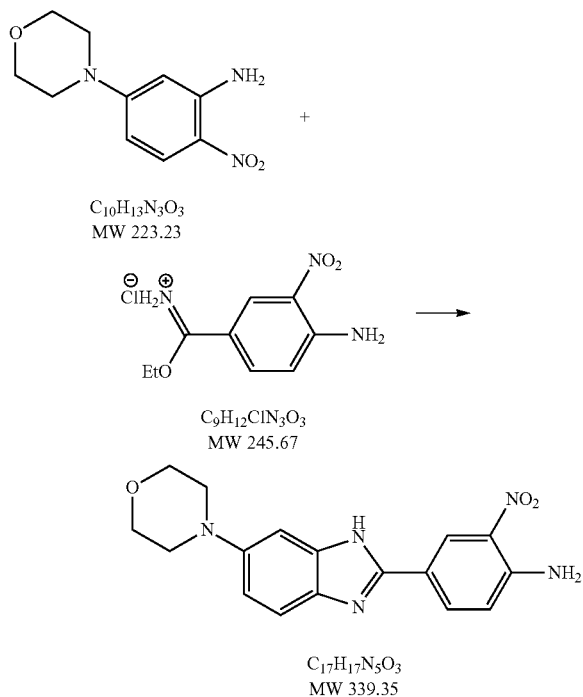

(i) Hydrogenation

To a solution of 5-morpholino-2-nitroaniline (0.50 g, 2.2 mmol) in 4:1 ethyl acetate/methanol (25 ml) was added 5% palladium on carbon (0.11 g) and the reaction mixture stirred under an atmosphere of hydrogen overnight. The reaction mixture was then filtered through celite, the filtered solid washed with methanol, and the combined filtrate and washings concentrated in vacuo to give the crude 2-amino-4-morpholinoaniline which was used immediately for the next step.

(ii) Coupling Reaction

The crude 2-amino-4-morpholinoaniline (prepared above in (i)) was dissolved in anhydrous ethanol (10 ml) and glacial acetic acid (5 ml), treated with ethyl 4-amino-3-nitrobenzenecarboximidate hydrochloride(7) (0.58 g, 2.4 mmol), then the mixture refluxed under nitrogen for 16 h. After cooling and concentrating in vacuo the residue was dissolved in water and basified with concentrated aqueous ammonia (pH 12) with vigorous stirring. The red precipitate formed was collected by filtration, washed with water then dried under vacuum to afford 4-(5'-morpholinobenzimidazol-2'-yl)-2-nitroaniline (0.67 g, 88%), mp 265-267° C.

¹H nmr (500 MHz, d₄-MeOH+4 drops d-TFA) δ 3.34, m (obs), 2×CH₂N; 3.91, m, 4H, 2×CH₂O; 7.25, d (J=9.0 Hz), 1H, H6; 7.28, d (J=1.5 Hz), 1H, H4'; 7.41, dd (J=2.2, 9.0 Hz), 1H, H6'; 7.66, d (J=9.0 Hz), 1H, H7'; 7.99, dd (J=2.2, 9.0 Hz), 1H, H5; 8.95, d (J=2.0 Hz), 1H, H3. ¹³C nmr (125 MHz, d₄-MeOH+4 drops d-TFA) δ 50.9, 2×CH₂N; 67.8, 2×CH₂O; 99.1, C4'; 110.6, C4; 114.9, 118.2, C6', C7'; 121.8, C6; 126.7, C2, C3a' or C7a'; 127.7, C3; 132.4, C2, C3a' or C7a'; 133.4, C5; 134.2, C2; C3a' or C7a'; 148.6, 150.1, 152.3, C1, C2' and C5'. MS (ESI+ve) m/z 340 (MH⁺, 100%). HRMS (ESI+ve) m/z 340.14047, C₁₇H₁₈N₅O₃ requires 340.14042 (Δ=0.1 ppm).

(C) Preparation of 2-(5'-(5''-Morpholinobenzimidazol-2''-yl)benzimidazol-2'-yl)pyridine

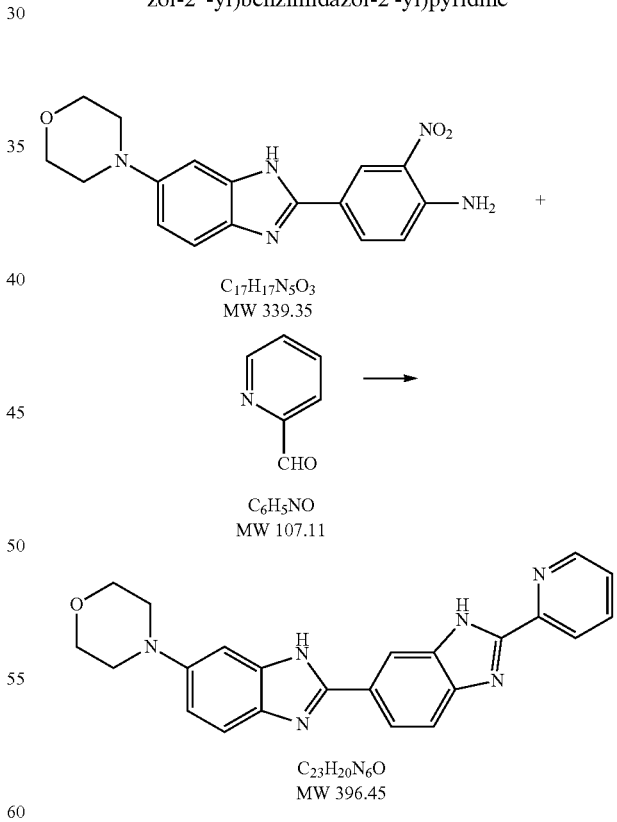

(i) Hydrogenation

To a solution of 4-(5'-morpholinobenzimidazol-2'-yl)-2-nitroaniline (0.25 g, 0.74 mmol) in 4:1 ethyl acetate/methanol (17.5 ml) was added 5% palladium on carbon (70 mg) and the reaction mixture stirred under an atmosphere of hydrogen overnight. The reaction mixture was then filtered through celite, the filtered solid washed with methanol, and the combined filtrate and washings concentrated in vacuo to give the crude 2-amino-4-(5'-morpholinobenzimidazol-2'-yl)aniline which was used immediately for the next step.

$^1$H nmr (400 MHz, d$_4$-MeOH+4 drops d-TFA) δ 3.32, m (obs), H3"/5"; 3.90, m, 4H, H2"/6"; 7.13, d (J=8.8 Hz), 1H, H6; 7.27, d (J=2.0 Hz), 1H, H4'; 7.37, dd (J=2.4, 9.2 Hz), 1H, H6'; 7.65, d (J=9.2 Hz), 1H, H7'; 7.81; dd (J=2.4, 8.8 Hz), 1H, H5; 7.89, d (J=2.4 Hz), 1H, H3.

(ii) Coupling Reaction

To a solution of the crude 2-amino-4-(5'-morpholinobenzimidazol-2'-yl)aniline (180 mg, 0.58 mmol, prepared above in (i)) in ethanol (10 ml) was added a solution of 2-pyridinecarboxaldehyde (79 mg, 0.74 mmol, 1.25 eq) in ethanol (3 ml) and the mixture gently refluxed under nitrogen for 10 min. After cooling, a solution of sodium metabisulfite (113 mg, 0.59 mmol) in water (1 ml) was added and refluxing under nitrogen continued for 20 h. The reaction mixture was then cooled, the solvents removed by rotary evaporator and the oily-brown semi-solid treated with dilute ammonia solution (2.7 M, 10 ml) and stirred for 20 min. The resulting suspension was centrifuged, the supernatant removed and the residue then re-treated with dilute ammonia (2.7 M, 10 ml), centrifuged and the supernatant again removed. The resulting dark red solid (221 mg after drying) was dissolved in methanol (2 ml) and applied to a plug of silica gel (30×75 mm) and eluted with ethyl acetate (3×50 ml), followed by 5, 10 and 20% methanol in ethyl acetate, to give 2-(5'-(5"-morpholinobenzimidazol-2"-yl)benzimidazol-2'-yl)pyridine (95 mg, 41%) as a light tan powder, mp 206-209° C.

$^1$H nmr (400 MHz, d$_4$-MeOH+5 drops d-TFA) δ 3.31, m (obs), H3'''/5'''; 3.90, m, 4H, H2'''/6'''; 7.26, d (J=2.0 Hz), 1H, H4"; 7.41; dd (J=2.4, 9.2 Hz), 1H, H6"; 7.70, m, 2H, H5, H7"; 8.08, dd (J=0.8, 8.8 Hz), 1H, H7'; 8.15, dt (J=1.2, 8.0 Hz), 1H, H4; 8.19, dd (J=1.8, 8.6 Hz), 1H, H6'; 8.41, br d (J=8.0 Hz), 1H, H3; 8.57, br d (J=1.2 Hz), 1H, H4'; 8.89, br d (J=4.4 Hz), 1H, H6. $^{13}$C nmr (100 MHz, d$_4$-MeOH+4 drops HOAc) δ 51.7, C3'''/5'''; 67.9, C2'''/6'''; 100.6, C4"; 115.4, 116.0, 116.5, 116.9, C4', C6", C7', C7"; 122.8, 122.9, C3 and C6'; 123.2, C5'; 126.2, C5; 132.5, C7a"; 137.9, C3a', C3a" or C7a'; 138.4, C4; 140.6, 141.6, C3a', C3a" or C7a'; 148.6, 150.6, C2, C5" and C2' or C2"; 150.9, C6; 151.9, C2; C5" and C2' or C2"; 154.4, C2" or C2'. MS (ESI+ve) m/z 397 (MH$^+$, 100%). HRMS (ESI+ve) m/z 397.17719, C$_{23}$H$_{20}$N$_6$O requires 397.17714 (Δ=0.1 ppm).

Cytotoxicity and Radioprotection Results

C50=149.9
PF=69.6
DMFm=2.26
DMF10=1.66

Example 20

3-(5'-(5"-Morpholinobenzimidazol-2"-yl)benzimidazol-2'-yl)isoquinoline

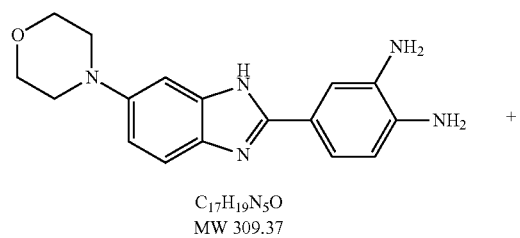

C$_{17}$H$_{19}$N$_5$O
MW 309.37

+

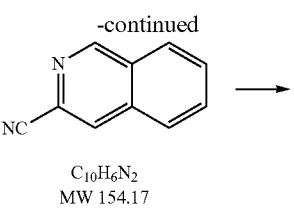

C$_{10}$H$_6$N$_2$
MW 154.17

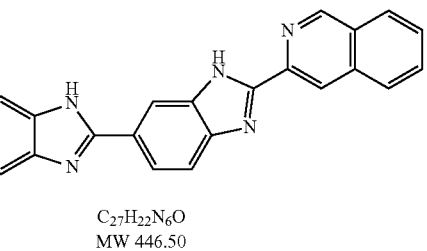

C$_{27}$H$_{22}$N$_6$O
MW 446.50

To 3-isoquinolinecarbonitrile (178 mg, 1.15 mmol) was added a solution of sodium methoxide in methanol (1.65 ml, 0.115 mmol, 0.07 M) and the resulting clear solution heated at 40° C. for 2 h under nitrogen. A solution of 2-amino-4-(5'-morpholinobenzimidazol-2'-yl)aniline (prepared by hydrogenation of 0.775 mmol of 4-(5'-morpholinobenzimidazol-2'-yl)-2-nitroaniline, for preparation see Example 19 part C(i)) in dry methanol (10 ml) and acetic acid (0.13 ml, 2.3 mmol) was added and the resulting dark brown solution refluxed for 20 h under nitrogen. The solvent was then removed under reduced pressure and dilute ammonia (2.7 M, 20 ml) was added before extraction with n-butanol (2×20 ml). The extract was then washed with brine (2×10 ml) and evaporated to give a glassy material which was purified by flash chromatography (silica gel), eluting with methanol to give 3-(5'-(5"-morpholinobenzimidazol-2"-yl)benzimidazol-2'-yl)isoquinoline (235 mg, 68%) as yellow powder, mp 202° C. (dec).

$^1$H NMR (400 MHz, d$_4$-MeOH+4 drops d-TFA) δ 3.16, m, 4H, H3'''/5'''; 3.83, m, 4H, H2'''/6'''; 6.96, d (J=2.0 Hz), 1H, H4"; 7.18, dd (J=2.2, 9.0 Hz), 1H, H6"; 7.49, d (J=8.8 Hz), 1H, H7"; 7.65, t (J=7.6 Hz), 1H, H6 or H7; 7.76, t (J=7.6 Hz), 1H, H7 or H6; 7.85, d (J=8.8 Hz), 1H, H7'; 7.90, dd (J=1.8. 8.6 Hz), 1H, H6'; 7.95, d (J=8.4 Hz), 1H, H5 or H8; 7.97, d (J=8.0 Hz), 1H, H8 or H5; 8.19, m, 1H, H4'; 8.52, s, 1H, H1 or H4, 9.24, s, 1H, H4 or H1. $^{13}$C NMR (125 MHz, d$_4$-MeOH+4 drops HOAc) δ 51.4, C3'''/5'''; 67.9, C2'''/6'''; 100.1, C4"; 114.4, C4'; 115.7, 116.0, 116.6, C6", C7', C7"; 119.5, C4; 122.1, C5'; 122.2, C6'; 128.3, 128.6, 129.4, C5, C7, C8; 129.9, C8a; 132.0 (overlap), C6, C7a"; 136.7, 137.4, 139.7, 141.4 (overlap), C3, C3a', C3a", C4a, C7a'; 150.2, C5"; 151.2, C2' or C2"; 153.4, C1; 154.3; C2" or C2'. MS (ESI+ve) m/z 447 (MH$^+$, 100%). HRMS (ESI+ve) m/z 447.19276, C$_{27}$H$_{23}$N$_6$O requires 447.19279 (Δ=0.1 ppm).

Cytotoxicity and Radioprotection Results

C50=171.9
PF=11.4
DMFm=1.57
DMF10=1.52

Example 21

2-(5'-(5''-Morpholinobenzimidazol-2''-yl)benzimidazol-2'-yl)-4-methylpyridine

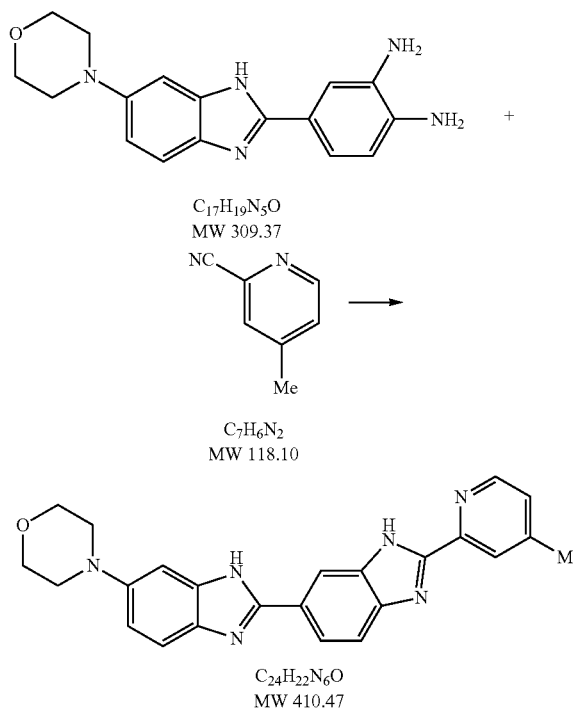

4-Methyl-2-pyridinecarbonitrile (105 mg, 0.89 mmol) was treated with a solution of sodium methoxide in methanol (0.087 M, 1.1 ml, 0.09 mmol) and the mixture heated at 40° C. under nitrogen for 90 min. A solution of 2-amino-4-(5'-morpholinobenzimidazol-2'-yl)aniline (121 mg, 0.39 mmol) (for preparation see Example 19 part C(i)) in dry methanol (13 ml) and glacial acetic acid (0.11 ml, 1.9 mmol) was then added and the mixture gently refluxed under nitrogen for 18 h. The solvent was then removed under reduced pressure and dilute ammonia (3.0 M, 10 ml) was added before diluting with water (10 ml) and extraction with n-butanol (20 ml). The n-butanol extract was washed with water (2×15 ml) then evaporated to give an orange glassy solid. The material was triturated with acetonitrile (4×3 ml) to give a tan powder (90 mg) that was further purified by column chromatography (silica gel, 20×150 mm), eluting with 9:1 ethyl acetate/methanol to give 2-(5'-(5''-morpholinobenzimidazol-2''-yl)benzimidazol-2'-yl)-4-methylpyridine as a pale yellow powder (67 mg, 42%), mp 214-230° C.

Additional material was obtained by column chromatography of the acetonitrile soluble material to give a further 51 mg (total yield 73%).

$^1$H nmr (500 MHz, $d_4$-MeOH+4 drops d-TFA) δ 2.58, s, 3H, 4-Me; 3.30, m (obs), H3'''/5'''; 3.90, m, 4H, H2'''/6'''; 7.24, d (J=2.0 Hz), 1H, H4''; 7.41, dd (J=2.5, 9.0 Hz), 1H, H6''; 7.57, br d (J=5.0 Hz), 1H, H5; 7.70, d (J=9.0 Hz), 1H, H7''; 8.06, d (J=8.5 Hz), 1H, H7'; 8.16, dd (J=1.8, 8.8 Hz), 1H, H6'; 8.27, br s, 1H, H3; 8.55, d (J=1.5 Hz), 1H, H4'; 8.72, d (J=5.5 Hz), 1H, H6. $^{13}$C nmr (125 MHz, $d_4$-MeOH+4 drops HOAc) δ 21.1, 4-Me; 51.3, C3'''/5'''; 67.8, C2'''/6'''; 100.1, C4''; 115.1, 115.7, 116.3, 116.9, C4', C6'', C7', C7''; 122.0, C5'; 122.6, 123.4, C3, C6'; 126.9, C5; 131.5, C7a''; 137.2, 140.1, 141.6, C3a', C3a'', C7a'; 150.0, C2'', C4 or C5''; 150.4,C6; 150.5, 151.2, C2'', C4 or C5''; 154.3, C2'. MS (ESI+ve) m/z 821 ($M_2H^+$, 8%), 411 ($MH^+$, 100). HRMS (ESI+ve) m/z 411.19274, $C_{24}H_{23}N_6O$ requires 411.19279 (Δ=0.1 ppm).

Cytotoxicity and Radioprotection Results
C50=213.4
PF=18.2
DMFm=1.77
DMF10=1.47

Example 22

2-(5'-(5''-(4'''-Hydroxypiperidin-1'''-yl)benzimidazol-2''-yl)benzimidazol-2'-yl)pyridine (A) Preparation of 5-(4'-hydroxypiperidin-1'-yl)-2-nitroaniline

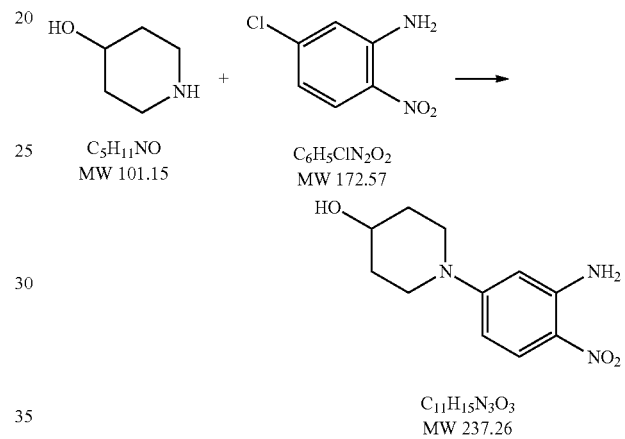

A mixture of 5-chloro-2-nitroaniline (1.0 g, 5.8 mmol), 4-hydroxypiperidine (1.06 g, 10.5 mmol) and anhydrous potassium carbonate (0.8 g, 6.0 mmol) in anhydrous N,N-dimethylacetamide (12 ml) was stirred at 130-140° C. under nitrogen overnight. The resultant mixture was cooled to room temperature, poured onto ice and stirred vigorously for 3 h. The yellow-brown precipitate was collected by filtration, washed carefully with water then dried to afford 5-(4'-hydroxypiperidin-1'-yl)-2-nitroaniline (0.86 g, 62%) and used in the next step without further purification.

$^1$H nmr (500 MHz, $d_4$-MeOH) δ 1.53, m, 2H, H3'/H5'; 1.91, m, 2H, H3'/5'; 3.12, m, 2H, H2'/6'; 3.78, m, 2H, H2'/6'; 3.84, m, 1H, H4'; 6.17, d (J=2.5 Hz), 1H, H6; 6.35, dd (J=2.3, 9.5 Hz), 1H, H4; 7.89, d (J=9.5 Hz), 1H, H3.

(B) Preparation of 4-(5'-(4''-hydroxypiperidin-1''-yl)benzimidazol-2'-yl)-2-nitroaniline

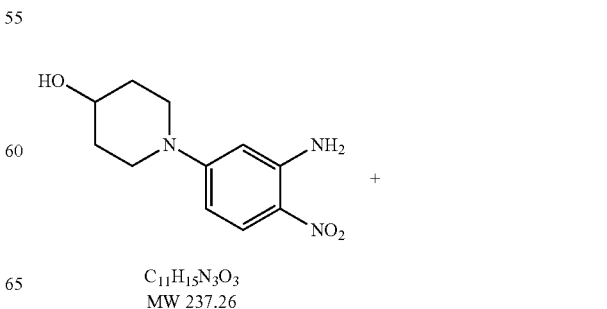

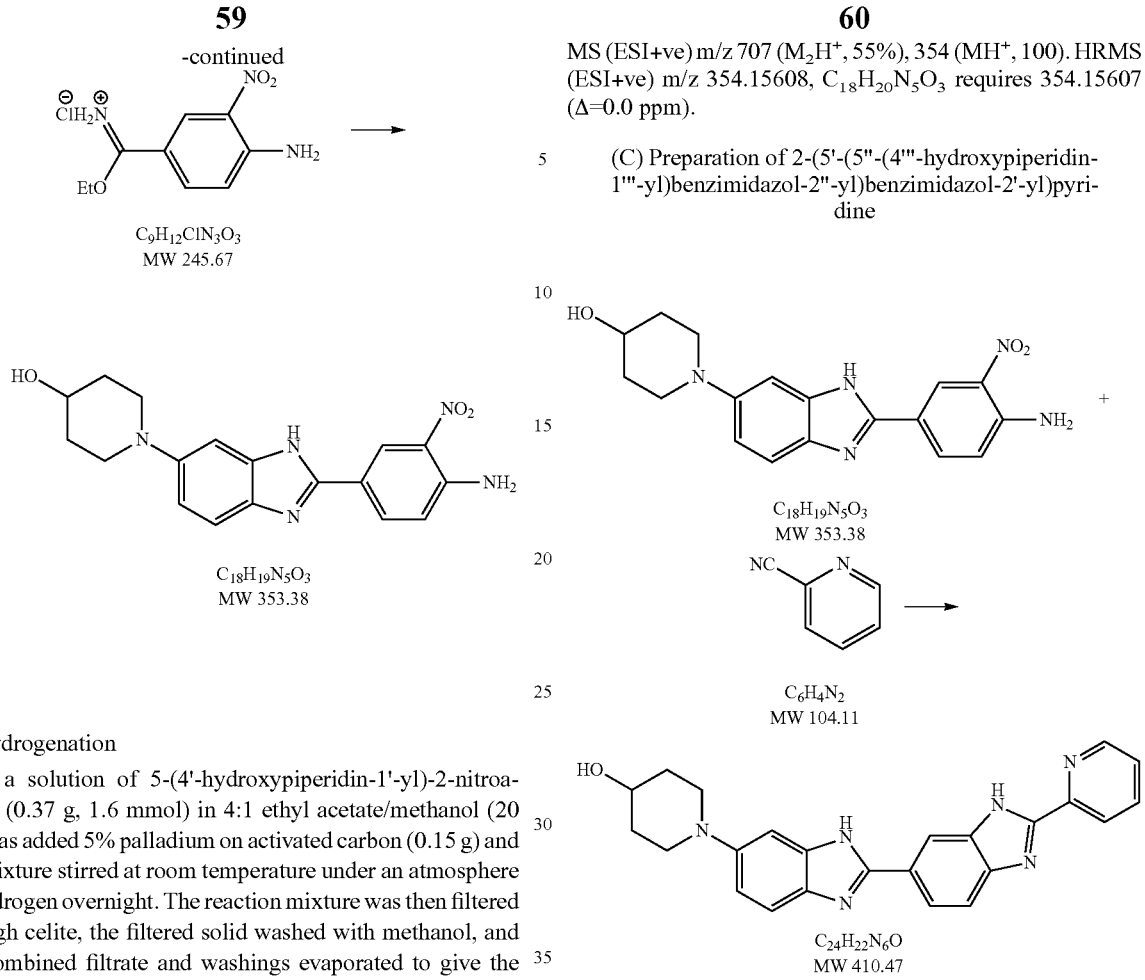

(i) Hydrogenation

To a solution of 5-(4'-hydroxypiperidin-1'-yl)-2-nitroaniline (0.37 g, 1.6 mmol) in 4:1 ethyl acetate/methanol (20 ml) was added 5% palladium on activated carbon (0.15 g) and the mixture stirred at room temperature under an atmosphere of hydrogen overnight. The reaction mixture was then filtered through celite, the filtered solid washed with methanol, and the combined filtrate and washings evaporated to give the crude 2-amino-4-(4'-hydroxypiperidin-1'-yl)aniline as a dark glassy solid (300 mg, 93%) that was used in the next step without further purification.

(ii) Coupling Reaction

The crude 2-amino-4-(4'-hydroxypiperidin-1'-yl)aniline (300 mg, 1.45 mmol, prepared above in (i)), was treated with ethyl 4-amino-3-nitrobenzenecarboximidate hydrochloride (7) (376 mg, 1.53 mmol) followed by dry ethanol (10 ml) and glacial acetic acid (5 ml). The reaction mixture was refluxed under nitrogen for 17 h, then cooled to room temperature and the solvents removed by rotary evaporator. The residue was partitioned between aqueous ammonia solution (2.7 M, 20 ml) and n-butanol (20 ml), the butanol extract washed with water (3×20 ml) and evaporated to give a red oil. The material was treated with ethanol (10 ml) and allowed to stand overnight resulting in a fine red precipitate, which was collected and dried to give 4-(5'-(4"-hydroxypiperidin-1"-yl)benzimidazol-2'-yl)-2-nitroaniline (349 mg, 68%) as a red powder, mp 206-209° C.

$^1$H nmr (400 MHz, $d_4$-MeOH+4 drops d-TFA) δ 2.02, m, 2H, H3"/5"; 2.24, m, 2H, H3"/5"; 3.61, m, 2H, H2"/6"; 3.91, m, 2H, H2"/6"; 4.09, tt (J=3.8, 7.6 Hz), 1H, H4"; 7.25, d (J=8.8 Hz), 1H, H6; 7.78, dd (J=2.2, 9.0 Hz), 1H, H6'; 7.89, d (J=9.2 Hz), 1H, H7'; 7.99, d (J=1.6 Hz), 1H, H4'; 8.04, dd (J=2.2, 9.0 Hz), 1H, H5; 9.02, d (J=2.4 Hz), 1H, H3. $^{13}$C nmr (125 MHz, $d_4$-MeOH+12 drops HOAc) δ 34.5, C3"/5"; 50.3, C2"/6"; 67.5; C4"; 102.1, C4'; 114.5, C4; 115.5, 117.8, 121.1, 126.2, C3, C6, C6', C7'; 131.4; 132.1, C2, C3a' or C7a'; 133.7, C5; 137.1, C2, C3a' or C7a'; 149.0, 149.2, 150.2, C1, C2', C5'.

MS (ESI+ve) m/z 707 ($M_2H^+$, 55%), 354 (MH$^+$, 100). HRMS (ESI+ve) m/z 354.15608, $C_{18}H_{20}N_5O_3$ requires 354.15607 (Δ=0.0 ppm).

(C) Preparation of 2-(5'-(5"-(4"'-hydroxypiperidin-1"'-yl)benzimidazol-2"-yl)benzimidazol-2'-yl)pyridine (i) Hydrogenation To a suspension of 4-(5'-(4"-hydroxypiperidin-1"-yl)benzimidazol-2'-yl)-2-nitroaniline (206 mg, 0.58 mmol) in 4:1 ethyl acetate/methanol (20 ml) was added 5% palladium on activated carbon (50 mg) and the reaction mixture stirred vigorously under an atmosphere of hydrogen for 20 h. The reaction mixture was then filtered through celite, the filtered solid washed with methanol, and the combined filtrate and washings evaporated to give the crude 2-amino-4-(5'-(4"-hydroxypiperidin-1"-yl)benzimidazol-2'-yl)aniline as a light orange solid, which was used immediately in the next step.

$^1$H nmr (400 MHz, $d_4$-MeOH+4 drops d-TFA) δ 2.04, m, 2H, H3"/5"; 2.28, m, 2H, H3"/5"; 3.65, m, 2H, H2"/6"; 3.91, m, 2H, H2"/6"; 4.10, m, 1H, H4"; 7.11, d (J=8.8 Hz), 1H, H6; 7.82, dd (J=2.2, 9.0 Hz), 1H, H6'; 7.90, m, 2H, H5, H7'; 8.00, d (J=2.0 Hz), 1H, H4'; 8.10, d (J=1.6 Hz), 1H, H3.

(ii) Coupling Reaction

To 2-cyanopyridine (87 mg, 0.84 mmol) was added a solution of sodium methoxide in methanol (0.087 M, 1.0 ml, 0.087 mmol) and the solution heated under nitrogen in a 40° C. oil-bath for 90 min. A solution of crude 2-amino-4-(5'-(4"-hydroxypiperidin-1"-yl)benzimidazol-2'-yl)aniline (0.58 mmol, prepared above in (i)) in dry methanol (7 ml) was then added followed by glacial acetic acid (0.1 ml, 1.75 mmol) and the mixture gently refluxed under nitrogen for 23 h. After cooling the solvents were removed by rotary evaporator and the residue treated with dilute ammonia solution (2.7 M, 15 ml). The mixture was stirred for 40 min to give an even suspension, which was centrifuged and the supernatant removed. The residue was further treated with additional dilute ammonia solution (2.7 M, 5 ml), then acetonitrile (2×5 ml), with centrifugation and removal of the supernatant after each treatment. The remaining solid was dried under vacuum to give 2-(5'-(5"-(4'''-hydroxypiperidin-1'''-yl)benzimidazol-2"-yl)benzimidazol-2'-yl)pyridine as a dull yellow powder (169 mg, 71%), mp 226-229° C.

$^1$H nmr (400 MHz, d$_4$-MeOH+4 drops d-TFA) δ 2.02, m, 2H, H3'''/H5'''; 2.25, m, 2H, H3'''/5'''; 3.62, m, 2H, H2'''/6'''; 3.92, m, 2H, H2'''/6'''; 4.10, tt (J=3.6, 7.2 Hz), 1H, H4'''; 7.70, ddd (J=1.0, 4.8, 7.8 Hz), 1H, H5; 7.75, dd (J=2.2, 9.0 Hz), 1H, H6"; 7.93, d (J=8.8 Hz), 1H, H7"; 8.01, d (J=2.0 Hz), 1H, H4"; 8.07, dd (J=0.8, 8.8 Hz), 1H, H7'; 8.15, dt (J=1.6, 8.0 Hz), 1H, H4; 8.27, dd (J=1.6, 8.8 Hz), 1H, H6'; 8.41, br d (J=8.0 Hz), 1H, H3; 8.64, d (J=1.2 Hz), 1H, H4'; 8.89, m, 1H, H6. $^{13}$C nmr (125 MHz, d$_4$-MeOH+4 drops HOAc) δ 34.8, C3'''/5'''; 49.9, C2'''/6'''; 68.0, C4'''; 101.3, C4"; 115.3, 115.6, 116.9, 117.6, C4', C6", C7', C7"; 122.1, C5'; 122.8 (overlap), C3, C6'; 126.1, C5; 131.4, C7a"; 137.2, C3a"; 138.3, C4; 140.3, C3a'; 141.6, C7a'; 148.4, C2; 150.1, C5"; 150.7, C6; 151.3, 154.3, C2', C2". MS (ESI+ve) m/z 821 (M$_2$H$^+$, 6%), 411 (MH$^+$, 100). HRMS (ESI+ve) m/z 411.19275, C$_{24}$H$_{23}$N$_6$O requires 411.19279 (Δ=0.1 ppm).

Cytotoxicity and Radioprotection Results

C50=266.0
PF=21.3
DMFm=2.20
DMF10=1.47

Example 23

3-(5'-(5"-(4'''-Hydroxypiperidin-1'''-yl)benzimidazol-2"-yl)benzimidazol-2'-yl)isoquinoline

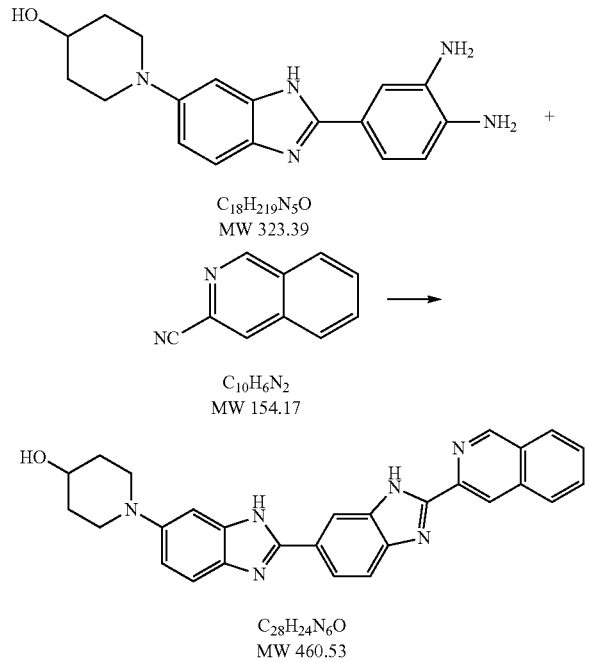

3-Isoquinolinecarbonitrile (170 mg, 1.1 mmol) was treated with methanolic sodium methoxide (0.07 M, 1.6 ml, 0.11 mmol), followed by dry methanol (1.5 ml) and heated under nitrogen in a 40° C. oil-bath for 2 h. A solution of 2-amino-4-(5'-(4"-hydroxypiperidin-1"-yl)benzimidazol-2'-yl)aniline (242 mg, 0.75 mmol) (for preparation see Example 22 part C(i)) in dry methanol (10 ml) was then added, followed by glacial acetic acid (0.13 ml, 2.2 mmol) and the dark mixture gently refluxed under nitrogen for 19 h. The solvents were then removed by rotary evaporator and the residue partitioned between dilute ammonia solution (0.9 M, 30 ml) and n-butanol (30 ml). The n-butanol extract was washed with water (3×30 ml) and evaporated to give a brown glassy solid (413 mg). The material was applied to a short column of basic alumina (40×120 mm) and eluted with 5:1 ethyl acetate/methanol to give 3-(5'-(5"-(4'''-hydroxypiperidin-1'''-yl)benzimidazol-2"-yl)benzimidazol-2'-yl)isoquinoline as a yellow powder (196 mg, 57%), mp 222° C. (dec).

$^1$H nmr (400 MHz, d$_4$-MeOH+4 drops d-TFA) δ 2.01, m, 2H, H3'''/H5'''; 2.24, m, 2H, H3'''/5'''; 3.61, m, 2H, H2'''/6'''; 3.91, m, 2H, H2'''/6'''; 4.09, m, 1H, H4'''; 7.71, dd (J=2.2, 9.0 Hz), 1H, H6"; 7.87, ddd (J=1.2, 7.6, 8.0 Hz), 1H, H6 or H7; 7.89, d (J=8.8 Hz), 1H, H7"; 7.94, m, 1H, H7 or H6; 7.96, d (J=2.0 Hz), 1H, H4"; 8.08, dd (J=0.6, 8.6 Hz), 1H, H7'; 8.15, d (J=7.6 Hz), 1H, H5 or H8; 8.22, d (J=8.0 Hz), 1H, H8 or H5; 8.27, dd (J=1.6, 8.8 Hz), 1H, H6'; 8.61, dd (J=0.4, 1.6 Hz), 1H, H4'; 8.83, s, 1H, H1 or H4, 9.49, s, 1H, H4 or H1. $^{13}$C nmr (125 MHz, d$_4$-MeOH+4 drops HOAc) δ 34.9, C3'''/5'''; 49.4, C2'''/6'''; 68.0, C4'''; 100.5, C4"; 114.4, 115.2, 116.7, 117.4, C4', C6", C7', C7"; 119.6, C4; 120.6, C5'; 122.1, C6'; 128.2, 128.5, 129.3, C5, C7, C8; 129.8, 130.1, C7a", C8a; 131.9, C6; 136.3, 136.5, 139.5, 141.1, 141.6, C3, C3a', C3a", C4a, C7a'; 150.2, 150.3, C2' or C2", C5"; 153.2, C1; 154.3, C2" or C2'. MS (ESI+ve) m/z 461 (MH$^+$, 100%). HRMS (ESI+ve) m/z 461.20849, C$_{28}$H$_{25}$N$_6$O requires 461.20844 (Δ=0.1 ppm).

Cytotoxicity and Radioprotection Results

C50=588.6
PF=36.5
DMFm=2.26
DMF10=2.13

Example 24

2-(5'-(5"-(Piperidin-1'''-yl)benzimidazol-2"-yl)benzimidazol-2'-yl)pyridine

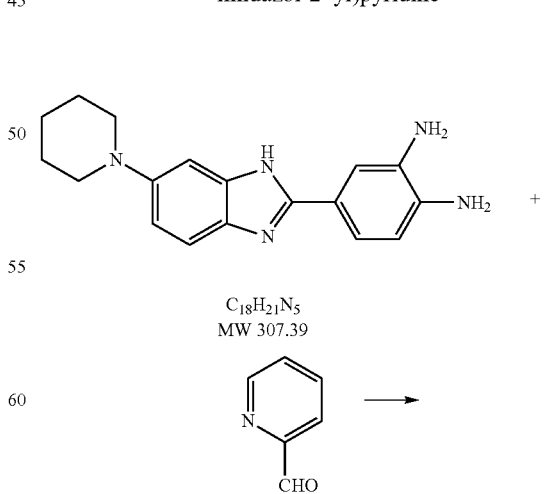

-continued

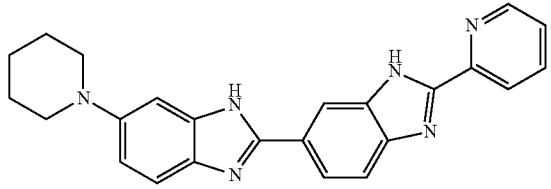

C₂₄H₂₂N₆
MW 394.47

A solution of 2-pyridinecarboxaldehyde (130 mg, 1.17 mmol) in ethanol (10 ml) was treated with a solution of sodium metabisulfite (0.25 g, 1.29 mmol) in water (2 ml), and the combined mixture added to a solution of 2-amino-4-(5'-(piperidin-1"-yl)benzimidazol-2'-yl)aniline (prepared by hydrogenation of 1.10 mmol of 2-nitro-4-(5'-(piperidin-1"-yl)benzimidazol-2'-yl)aniline)(7) in ethanol (15 ml). The mixture was gently refluxed under nitrogen overnight then the solvents removed by rotary evaporator and the residue treated with dilute ammonia solution (2.7 M, 20 ml) and stirred for 30 min to give an even suspension of friable solid. The resultant suspension was centrifuged, the supernatant removed and the solid then re-treated with dilute ammonia (2.7 M, 15 ml) followed by acetonitrile (2×5 ml) with centrifugation and removal of the supernatant between each treatment. The solid was then dried under vacuum to give 2-(5'-(5"-(piperidin-1'''-yl)benzimidazol-2"-yl)benzimidazol-2'-yl)pyridine (196 mg, 47%) as a tan powder, mp 196-203° C.

$^1$H nmr (500 MHz, d₄-MeOH+4 drops d-TFA) δ 1.84, m, 2H, H4'; 2.09, m, 4H, H3'''/5'''; 3.74, m, 4H, H2'''/6'''; 7.68, ddd (J=1.0, 4.8, 7.8 Hz), 1H, H5; 7.80, dd (J=2.3, 8.8 Hz), 1H, H6"; 7.96, d (J=9.0 Hz), 1H, H7"; 8.06, d (J=8.5 Hz), 1H, H7'; 8.13, m, 2H, H4, H4"; 8.28, dd (J=1.5, 8.5 Hz), 1H, H6'; 8.40, d (J=8.0 Hz), 1H, H3; 8.64, d (J=1.0 Hz), 1H, H4'; 8.88, br d (J=4.0 Hz), 1H, H6. $^{13}$C nmr (125 MHz, d₄-MeOH+4 drops HOAc) δ 24.7, C4'''; 26.7, C3'''/5'''; 53.8, C2'''/6'''; 102.2, C4'''; 115.3, 115.7, 116.9, 117.6, C4', C6", C7', C7"; 122.7, C5'; 122.77, 122.84, C3, C6'; 126.1, C5; 132.5, C7a"; 137.8, C3a' or C3a"; 138.3, C4; 140.4, C3a" or C3a'; 141.7, C7a'; 148.5, C2; 149.8, C5"; 150.8, C6; 151.9, C2' or C2"; 154.3, C2" or C2'. MS (ESI+ve) m/z 789 (M₂H⁺, 20%), 395 (MH⁺, 100). HRMS (ESI+ve) m/z 395.19784, C₂₄H₂₃N₆ requires 395.19787 (Δ=0.1 ppm).

Cytotoxicity and Radioprotection Results
C50=24.0
PF=7.5
DMFm=1.42
DMF10=1.35

Example 25

2-(5'-(5"-(4'''-Methyl-1''',4'''-diazepan-1'''-yl)benz-imidazol-2"-yl)benzimidazol-2'-yl)pyridine (A) Preparation of 5-(4'-methyl-1',4'-diazepan-1'-yl)-2-nitroaniline

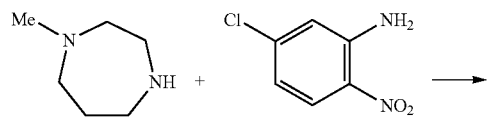

C₆H₁₄N₂
MW 114.19

C₆H₅ClN₂O₂
MW 172.57

-continued

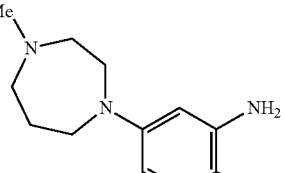

C₁₂H₁₈N₄O₂
MW 250.30

A mixture of 5-chloro-2-nitroaniline (1.20 g, 7.0 mmol), 1-methylhomopiperazine (1.03 g, 9.0 mmol, 1.3 eq) and anhydrous potassium carbonate (0.97 g, 7.0 mmol) in anhydrous N,N-dimethylacetamide (20 ml) was heated at 125° C. under nitrogen overnight. The resultant mixture was cooled to room temperature, poured into ice-water (30 ml) and extracted with n-butanol (2×50 ml). The extract was then evaporated and the red residue subjected to column chromatography (silica gel) eluting with methanol to give 5-(4'-methyl-1',4'-diazepan-1'-yl)-2-nitroaniline (1.21 g, 69%).

$^1$H nmr (9) (400 MHz, CDCl₃) δ 2.01, m, 2H, H6'; 2.39, s, 3H, 4'-MeN; 2.57, m, 2H, NCH₂; 2.70, m, 2H, NCH₂; 3.53, m, 2H, NCH₂; 3.60, m, 2H, NCH₂; 5.76, d (J=2.4 Hz), 1H, H6; 6.13, m, 3H, 1-NH₂; H4, 8.00, d (J=10.0 Hz), 1H, H3.

(B) Preparation of 4-(5'-(4"-methyl-1",4"-diazepan-1"-yl)benzimidazol-2'-yl)-2-nitroaniline

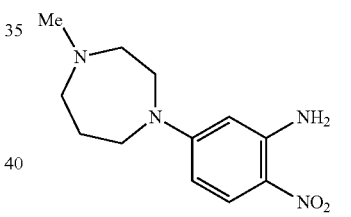

C₁₂H₁₈N₄O₂
MW 250.30

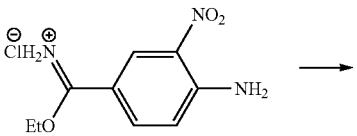

C₉H₁₂ClN₃O₃
MW 245.67

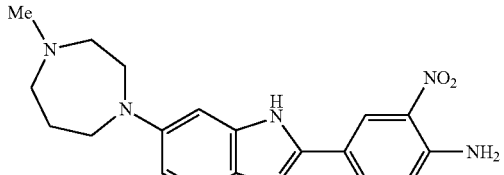

C₁₉H₂₂N₆O₂
MW 366.42

(i) Hydrogenation
To a solution of 5-(4'-methyl-1',4'-diazepan-1'-yl)-2-nitroaniline (0.415 g, 1.66 mmol) in 4:1 ethyl acetate/methanol (40 ml) was added 5% palladium on activated carbon (142 mg) and the mixture stirred at room temperature under an atmosphere of hydrogen overnight. The reaction mixture was then filtered through celite, the filtered solid washed with methanol, and the combined filtrate and washings evaporated to give the crude 2-amino-4-(4'-methyl-1',4'-diazepan-1'-yl) aniline as a dark red material that was used in the next step without further purification.

(ii) Coupling Reaction

The crude 2-amino-4-(4'-methyl-1',4'-diazepan-1'-yl) aniline (1.66 mmol, prepared above in (i)), was treated with ethyl 4-amino-3-nitrobenzenecarboximidate hydrochloride (7) (449 mg, 1.83 mmol) followed by dry ethanol (20 ml) and glacial acetic acid (10 ml). The reaction mixture was gently refluxed under nitrogen for 48 h, then cooled to room temperature and the solvents removed by rotary evaporator. The residue was dissolved in water (55 ml, basified with concentrated ammonia solution (pH 12) and stirred vigorously for 30 min at 0° C. to give an even black suspension. The material was collected by filtration, washed with water (2×10 ml) and dried to give a dark red solid. The material was subjected to column chromatography (silica gel) eluting with methanol to give 4-(5'-(4"-methyl-1",4"-diazepan-1"-yl)benzimidazol-2'-yl)-2-nitroaniline (262 mg, 43%) as a dark red powder, mp 237-238° C.

$^1$H nmr (500 MHz, $d_6$-dmso) δ 1.91, m, 2H, H6"; 2.25, s, 3H, 4"-MeN; 2.44, m, 2H, NCH$_2$; 2.63, m, 2H, NCH$_2$; 3.45, m, 2H, NCH$_2$; 3.52, m, 2H, NCH$_2$; 6.66, m, 2H, H4', H6'; 7.11, d (J=8.8 Hz), 1H, H6 or H7'; 7.33, d (J=9.2 Hz), 1H, H7' or H6; 7.72, br, 2H, 1-NH$_2$; 8.12, dd (J=2.0, 9.2 Hz), 1H, H5; 8.70, d (J=2.0 Hz), 1H, H3. MS (ESI+ve) m/z 367 (MH$^+$, 100%). HRMS (ESI+ve) m/z 367.18771, C$_{19}$H$_{23}$N$_6$O$_2$ requires 367.18770 (Δ=0 ppm).

(C) Preparation of 2-(5'-(5"-(4'''-methyl-1''',4'''-diazepan-1'''-yl)benzimidazol-2"-yl)benzimidazol-2'-yl)pyridine

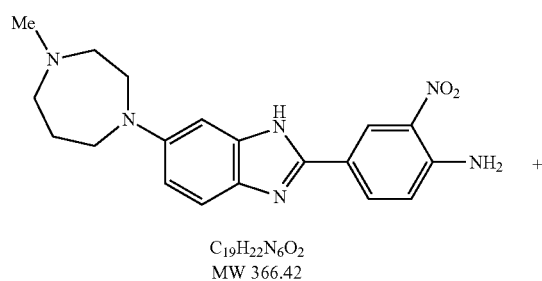

C$_{19}$H$_{22}$N$_6$O$_2$
MW 366.42

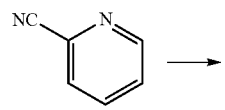

C$_6$H$_4$N$_2$
MW 104.11

-continued

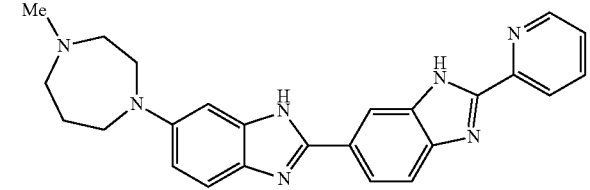

C$_{25}$H$_{25}$N$_7$
MW 423.51

(i) Hydrogenation

To a solution of 4-(5'-(4"-methyl-1",4"-diazepan-1"-yl) benzimidazol-2'-yl)-2-nitroaniline (209 mg, 0.57 mmol) in 4:1 ethyl acetate/methanol (25 ml) was added 5% palladium on carbon (71 mg) and the mixture stirred at room temperature under an atmosphere of hydrogen for 22 h. The reaction mixture was filtered through Celite, washed with methanol, and the combined filtrate and washings concentrated to give the crude 2-amino-4-(5'-(4"-methyl-1",4"-diazepan-1"-yl) benzimidazol-2'-yl)aniline as dark-red solid that was used in the next step without further purification.

(ii) Coupling Reaction

To 2-cyanopyridine (90 mg, 0.864 mmol) was added a solution of sodium methoxide in methanol (0.09 M, 1.0 ml, 0.09 mmol) and the solution heated at 50° C. for 1.5 h under nitrogen. A solution of the crude 2-amino-4-(5'-(4"-methyl-1",4"-diazepan-1"-yl)benzimidazol-2'-yl)aniline (0.57 mmol, prepared above in (i)) in dry methanol (15 ml) and acetic acid (0.105 ml) was then added and the now dark brown solution refluxed for 20 h under nitrogen. The reaction mixture was cooled to room temperature, the solvent removed under reduced pressure and the residue treated with ammonia solution (10 ml) before extraction with n-butanol (20 ml). The extract was washed with brine (20 ml) and evaporated to give a glassy material which was recrystallized from ethanol to give 2-(5'-(5"-(4'''-methyl-1''',4'''-diazepan-1'''-yl)benzimidazol-2"-yl)benzimidazol-2'-yl)pyridine (162 mg, 67%) as a tan solid, mp 185° C. (dec).

$^1$H nmr (500 MHz, $d_4$-MeOH+4 drops d-TFA) δ 2.36, m, H6'''; 2.98, s, 3H, 4'''-MeN; 3.40, m, 2H, NCH$_2$; 3.56-3.78, m, 4H, 2×NCH$_2$; 3.84-4.00, m, 2H, NCH$_2$; 7.06, d (J=2.0 Hz), 1H, H4"; 7.22, dd (J=2.2, 9.2 Hz), 1H, H6"; 7.70, m, 2H, H5, H7"; 8.08, d (J=8.5 Hz), 1H, H7'; 8.15, dt (J=1.5, 7.8 Hz), 1H, H4; 8.19, dd (J=1.5, 8.5 Hz), 1H, H6'; 8.42, d (J=7.5 Hz), 1H, H3; 8.59, app. s, 1H, H4'; 8.89, d (J=4.5 Hz), 1H, H6. $^{13}$C nmr (125 MHz, $d_4$-MeOH+10 drops HOAc) δ 25.6, C6'''; 44.9, 4'''-MeN; 46.4, C2'''; 48.8, C7'''; 57.1, 58.5, C3''', C5'''; 96.0, C4"; 113.6, C4'; 115.8 (overlap), 117.3, C6"; C7', C7"; 120.6, C5'; 123.0 (overlap), C3, C6'; 126.5, C5; 128.1, C7a"; 136.3, C3a' or C3a"; 138.6, C4; 140.6, C3a" or C3a'; 142.1, C7a'; 148.4. 148.6, C2, C5"; 150.2, C2' or C2"; 151.0, C6; 154.8, C2" or C2'. MS (ESI+ve) m/z 424 (MH$^+$, 100%). HRMS (ESI+ve) m/z 424.22421, C$_{25}$H$_{26}$N$_7$ requires 424.22442 (Δ=0.5 ppm).

Cytotoxicity and Radioprotection Results

C50=123.0

PF=16.7

DMFm=2.14

DMF10=1.77

Example 26

2-(5'-(5''-(3'''-Hydroxypiperidin-1'''-yl)benzimidazol-2''-yl)benzimidazol-2'-yl)pyridine

(A) Preparation of 5-(3'-hydroxypiperidin-1'-yl)-2-nitroaniline

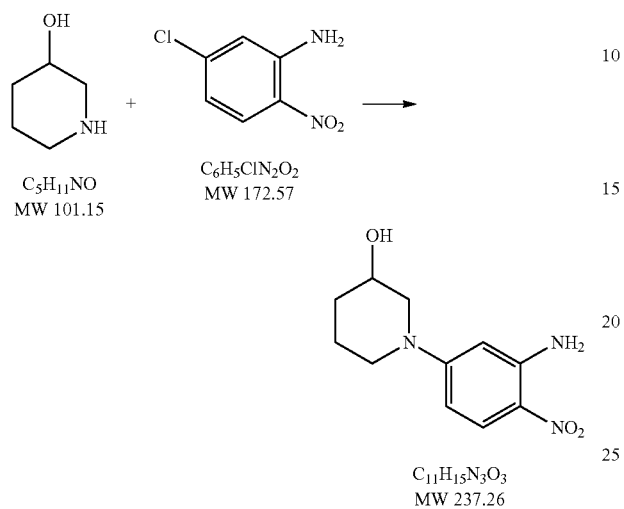

A mixture of 5-chloro-2-nitroaniline (1.73 g, 10 mmol), 3-hydroxypiperidine (2.53 g, 25 mmol) and anhydrous potassium carbonate (1.38 g, 10 mmol) in anhydrous N,N-dimethylacetamide (20 ml) was heated in a 120-130° C. oil-bath under nitrogen for 21 h. The reaction mixture was then cooled to room temperature, poured into cold water (100 ml) and stirred vigorously for 45 min to give a friable even suspension. The yellow-brown solid was collected by filtration, washed carefully with water (2×10 ml), then dried over phosphorous pentoxide to give 5-(3'-hydroxypiperidin-1'-yl)-2-nitroaniline (2.04 g, 86%) as a light ochre powder.

$^1$H nmr(10) (400 MHz, $d_6$-dmso) δ 1.32-1.49, m, 2H, H4' and/or H5'; 1.72, m, 1H, H4' or H5'; 1.88, m, 1H, H4' or H5'; 2.83, dd (J=8.8, 12.8 Hz), 1H, H2'; 2.96, m, 1H, H6'; 3.50, m, 1H, H3'; 3.59, m, 1H, H6'; 3.68, dd (J=4.0, 12.8 Hz), 1H, H2'; 4.90, d (J=4.4 Hz), 1H, 3'-OH; 6.18, d (J=2.8 Hz), 1H, H6; 6.33, dd (J=2.6, 9.8 Hz), 1H, H4; 7.22, br s, 2H, 1-NH$_2$; 7.77, d (J=10.0 Hz), 1H, H3. $^{13}$C nmr (100 MHz, $d_6$-dmso) δ 21.7, C5'; 32.4, C4'; 46.0, C6'; 53.3, C2'; 64.4, C3'; 96.2, 104.9, C4, C6; 121.9, C2; 126.8, C3; 148.0, 154.2, C1, C5.

(B) Preparation of 4-(5'-(3''-hydroxypiperidin-1''-yl)benzimidazol-2'-yl)-2-nitroaniline

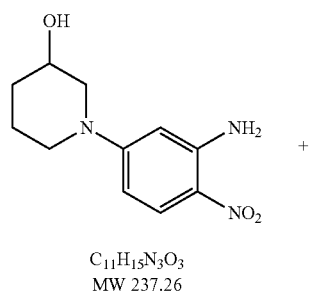

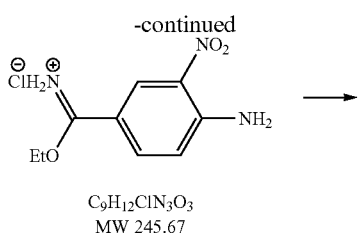

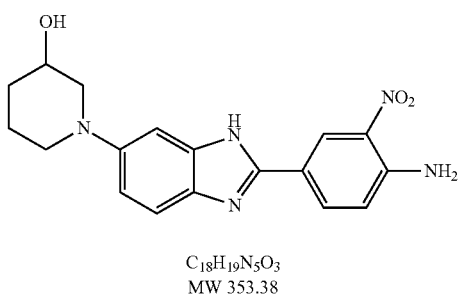

(i) Hydrogenation

To a solution of 5-(3'-hydroxypiperidin-1'-yl)-2-nitroaniline (593 mg, 2.5 mmol) in 4:1 ethyl acetate/methanol (40 ml) was added 5% palladium on activated carbon (160 mg) and the mixture stirred at room temperature under an atmosphere of hydrogen for 23 h. The reaction mixture was then filtered through filter-aid, the residue washed with methanol, and the combined filtrate and washings evaporated to give the crude 2-amino-4-(3'-hydroxypiperidin-1'-yl)aniline as a dark green oil (539 mg, 100%) that was used in the next step without further purification.

(ii) Coupling Reaction

The crude 2-amino-4-(3'-hydroxypiperidin-1'-yl)aniline (539 mg, 2.5 mmol) was treated with ethyl 4-amino-3-nitrobenzenecarboximidate hydrochloride(7) (650 mg, 2.65 mmol, 1.06 eq) followed by dry ethanol (20 ml) and glacial acetic acid (10 ml). The reaction mixture was refluxed under nitrogen for 21 h, then cooled to room temperature and the solvents removed by rotary evaporator. The residue was partitioned between aqueous dilute ammonia solution (2.7 M, 25 ml) and n-butanol (25 ml), the butanol extract washed with water (3×20 ml) and evaporated. The residue was triturated with ethanol (2×10 ml) and the ethanol insoluble material dried under vacuum to give 4-(5'-(3''-hydroxypiperidin-1''-yl)benzimidazol-2'-yl)-2-nitroaniline (645 mg, 73%) as a dark purple powder, mp 255-260° C. (dec).

$^1$H nmr (400 MHz, $d_4$-MeOH+4 drops d-TFA) δ 1.74, m, 1H, H4'' or H5''; 1.89,m, 1H, H4'' or H5''; 1.99, m, 1H, H4'' or H5''; 2.23, m, 1H, H4'' or H5''; 3.30, m (obs), H2'' or H6''; 3.40, m, 1H, H2'' or H6''; 3.70, m, 1H, H2'' or H6''; 3.75, dd (J=2.6, 12.0 Hz), 1H, H2'' or H6''; 4.10, tt (J=3.2, 6.4 Hz), 1H, H3''; 7.22, d (J=9.2 Hz), 1H, H6; 7.64, dd (J=2.0, 8.8 Hz), 1H, H6'; 7.79, m, 2H, H4', H7'; 8.02, dd (J=2.2, 9.0 Hz), 1H, H5; 8.95, d (J=2.4 Hz), 1H, H3. $^{13}$C nmr (125 MHz, $d_4$-MeOH+25 drops HOAc) δ 23.4, C5''; 32.9, C4''; 52.0, C6''; 58.8, C2''; 67.4, C3''; 101.1, C4'; 112.4, C4; 115.1, 118.3, 121.3, 126.8, C3, C6, C6', C7'; 128.8, 132.0, C2, C3a' or C7a'; 133.5, C5; 135.6, C2, C3a' or C7a'; 149.0, 149.2, 150.2, C1, C2', C5'. MS (ESI+ve) m/z 354 (MH⁺, 100%). HRMS (ESI+ve) m/z 354.15609, $C_{18}H_{20}N_5O_3$ requires 354.15607 (Δ=0.1 ppm).

(C) Preparation of 2-(5'-(5''-(3'''-hydroxypiperidin-1'''-yl)benzimidazol-2''-yl)benzimidazol-2'-yl)pyridine

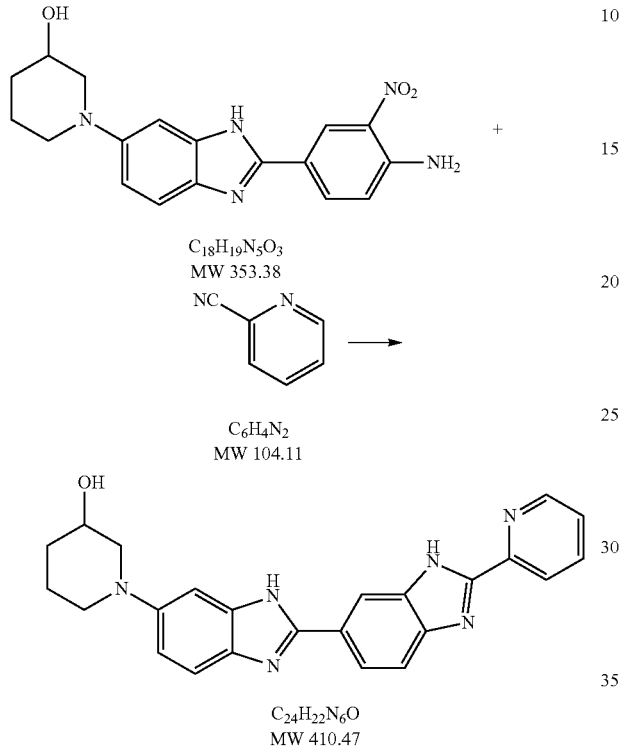

(i) Hydrogenation

To a suspension of 4-(5'-(3''-hydroxypiperidin-1''-yl)benzimidazol-2'-yl)-2-nitroaniline (219 mg, 0.62 mmol) in 2:1 ethyl acetate/methanol (24 ml) was added 5% palladium on activated carbon (50 mg) and the reaction mixture stirred vigorously at room temperature under an atmosphere of hydrogen for 20 h. The reaction mixture was then filtered through filter-aid, the residue washed with methanol (~130 ml) and the combined filtrate and washings evaporated to give the crude 2-amino-4-(5'-(3''-hydroxypiperidin-1''-yl)benzimidazol-2'-yl)aniline as a dull orange oil, which was used without further purification.

(ii) Coupling Reaction

To 2-cyanopyridine (102 mg, 0.98 mmol) was added a solution of sodium methoxide in methanol (0.087 M, 1.2 ml, 0.10 mmol) and the solution heated under nitrogen in a 40° C. oil-bath for 75 min. A solution of the crude 2-amino-4-(5'-(3''-hydroxypiperidin-1''-yl)benzimidazol-2'-yl)aniline (0.62 mmol, prepared above in (i)) in dry methanol (10 ml) was then added followed by glacial acetic acid (0.12 ml, 2.0 mmol) and the mixture gently refluxed under nitrogen for 21 h. After cooling the solvents were removed by rotary evaporator and the residue partitioned between dilute ammonia solution (2.7 M, 15 ml) and n-butanol (20 ml). The butanol extract was washed with water (2×15 ml) and evaporated to give a dark glassy solid. The material was treated with 9:1 ethyl acetate/methanol (10 ml) and stirred for 65 min to give an even suspension, which was centrifuged and the supernatant removed. The residue was further treated with additional 9:1 ethyl acetate/methanol (5 ml) with centrifugation and removal of the supernatant. The remaining grey-brown solid was then applied to a plug of silica gel (30×70 mm) and eluted with methanol to give 2-(5'-(5''-(3'''-hydroxypiperidin-1'''-yl)benzimidazol-2''-yl)benzimidazol-2'-yl)pyridine as a light tan powder (185 mg, 73%), mp 278-282° C.

¹H nmr (500 MHz, d₄-MeOH+4 drops d-TFA) δ 1.78, m, 1H, H4''' or H5'''; 1.92, m, 1H, H4''' or H5'''; 2.00, m, 1H, H4''' or H5'''; 2.28, m, 1H, H4''' or H5'''; 3.37, dd (J=6.0, 12.0 Hz), 1H, H2'''; 3.47, m, 1H, H6'''; 3.74, m, 1H, H6'''; 3.79, dd (J=2.5, 12.0 Hz); 1H, H2'''; 4.14, tt (J=3.5, 7.0 Hz); 1H, H3'''; 7.70, m, 2H, H5, H6''; 7.90, d (J=9.0 Hz), 1H, H7''; 7.93, d (J=2.5 Hz), 1H, H4''; 8.08, d (J=8.5 Hz), 1H, H7'; 8.14, dt (J=1.5, 7.8 Hz), 1H, H4; 8.27, dd (J=1.5, 8.5 Hz); 1H, H6'; 8.41, d (J=8.0 Hz), 1H, H3; 8.64, d (J=1.0 Hz), 1H, H4'; 8.89, d (J=4.5 Hz), 1H, H6. ¹³C nmr (125 MHz; d₄-MeOH+20 drops HOAc) δ 23.6, C5'''; 33.2, C4'''; 51.3, C6'''; 58.3, C2'''; 67.5, C3'''; 100.2, C4''; 115.0, 115.8, 117.2, 118.2, C4', C6'', C7', C7''; 119.2, C5'; 122.7, 123.1, C3, C6'; 126.4, C5; 128.0, C7a''; 135.1, C3a''; 138.5, C4; 140.0, C3a'; 141.9, C7a'; 147.8, C2; 149.7, C5''; 150.7, C6; 150.9, 154.4, C2', C2''. MS (ESI+ve) m/z 821 (M₂H⁺, 15%), 411 (MH⁺, 100). HRMS (ESI+ve) m/z 411.19270, $C_{24}H_{23}N_6O$ requires 411.19279 (Δ=0.2 ppm).

Cytotoxicity and Radioprotection Results
C50=77.9
PF=14.7
DMFm=1.90
DMF10=1.33

Example 27

2-(5'-(5''-(4'''-Methoxypiperidin-1'''-yl)benzimidazol-2''-yl)benzimidazol-2'-yl)pyridine (A) Preparation of 5-(4'-methoxypiperidin-1'-yl)-2-nitroaniline

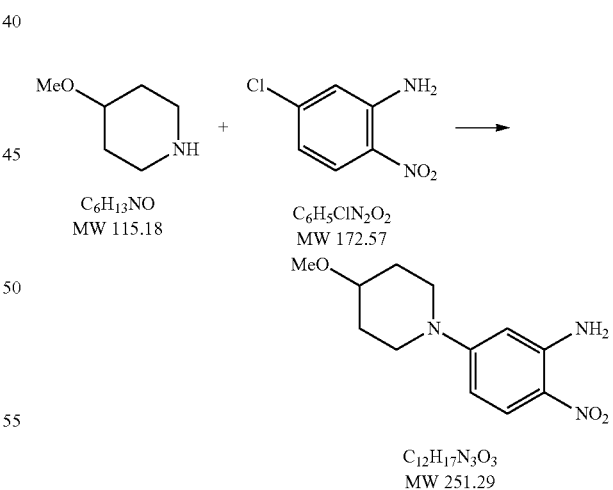

A mixture of 5-chloro-2-nitroaniline (0.375 g, 2.17 mmol), 4-methoxypiperidine (0.50 g, 4.34 mmol, 2.0 eq) and anhydrous potassium carbonate (0.36 g, 2.6 mmol) in anhydrous N,N-dimethylacetamide (5 ml) was heated at 110° C. under nitrogen for 21 h. The resultant mixture was cooled to room temperature, poured into water (30 ml) and stirred vigorously for 90 min to give an even suspension. The material was centrifuged, the supernatant removed and the residue treated with water (3×15 ml), then acetonitrile (2×2 ml) with centrifugation and removal of the supernatant between each treatment. The residue was then dried under vacuum to give 5-(4'-methoxypiperidin-1'-yl)-2-nitroaniline (0.312 g, 57%), as a dull yellow powder, mp 142-144° C.

Additional material was obtained by passing the acetonitrile soluble material through a plug of silica gel, eluting with 1:1 ethyl acetate/hexane to give a further 100 mg (total yield 75%).

$^1$H nmr (500 MHz, $d_6$-dmso) δ 1.44, m, 2H, H3'/H5'; 1.88, m, 2H, H3'/5'; 3.13, ddd (J=3.5, 9.5, 13.5 Hz), 2H, H2'/6'; 3.26, s, 3H, 4'-MeO; 3.42, app tt (J=4.0, 8.0 Hz), 1H, H4'; 3.61, m, 2H, H2'/6'; 6.21, d (J=2.5 Hz), 1H, H6; 6.37, dd (J=2.5, 9.5 Hz), 1H, H4; 7.21, br, 2H, 1-NH$_2$; 7.78, d (J=10.0 Hz), 1H, H3. $^{13}$C nmr (125 MHz, $d_6$-dmso) δ 30.0, C3'/5'; 44.2, C2'/6'; 55.1, 4'-MeO; 75.1, C4', 97.3; 105.6; C4, C6, 122.8; C2, 127.5; C3; 148.6, 154.7, C1, C5. MS (ESI+ve) m/z 252 (MH$^+$, 100%). HRMS (ESI+ve) m/z 252.13414, $C_{12}H_{18}N_3O_3$ requires 252.13427 (Δ=0.5 ppm).

(B) Preparation of 4-(5'-(4"-methoxypiperidin-1"-yl)benzimidazol-2'-yl)-2-nitroaniline

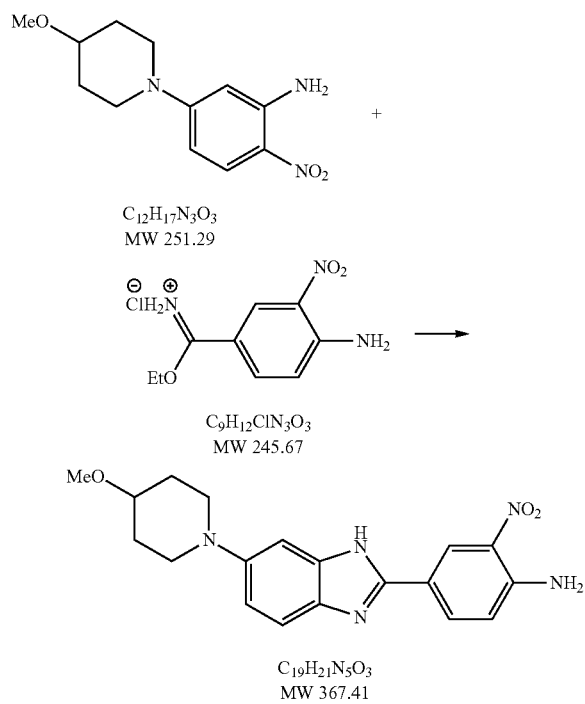

(i) Hydrogenation

To a solution of 5-(4'-methoxypiperidin-1'-yl)-2-nitroaniline (0.30 g, 1.2 mmol) in 2:1 ethyl acetate/methanol (45 ml) was added 10% palladium on activated carbon (50 mg) and the mixture stirred at room temperature under an atmosphere of hydrogen for 23 h. The reaction mixture was then filtered through filter-aid, the filtered solid washed with methanol, and the combined filtrate and washings evaporated to give the crude 2-amino-4-(4'-methoxypiperidin-1'-yl)aniline as a dark viscous oil (258 mg, 98%) that was used in the next step without further purification.

(ii) Coupling Reaction

The crude 2-amino-4-(4'-methoxypiperidin-1'-yl)aniline (258 mg, 1.16 mmol) was treated with ethyl 4-amino-3-nitrobenzenecarboximidate hydrochloride(7) (300 mg, 1.22 mmol) followed by dry ethanol (10 ml) and glacial acetic acid (5 ml). The reaction mixture was gently refluxed under nitrogen for 18 h, then cooled to room temperature and the solvents removed by rotary evaporator. The residue was treated with dilute ammonia solution (2.7 M, 20 ml) and stirred vigorously for 90 min to give an even fine red suspension. The material was centrifuged, the supernatant removed and the residue treated with water (2×10 ml), then acetonitrile (3×4 ml), with centrifugation and removal of the supernatant between each treatment. The residue was then dried under vacuum to give 4-(5'-(4"-methoxypiperidin-1"-yl)benzimidazol-2'-yl)-2-nitroaniline (336 mg, 78%) as a fine red powder, mp 193-197° C.

$^1$H nmr (400 MHz, $d_4$-MeOH+5 drops d-TFA) δ 2.13, m, 2H, H3"/5"; 2.26, m, 2H, H3"/5"; 3.44, s, 3H, 4"-MeO; 3.61, m, 2H, H2"/6"; 3.68, m, 1H, H4"; 3.86, m, 2H, H2"/6"; 7.25, d (J=9.2 Hz), 1H, H6; 7.78, dd (J=2.2, 9.0 Hz), 1H, H6'; 7.89, d (J=8.8 Hz), 1H, H7'; 8.01, d (J=1.6 Hz), 1H, H4'; 8.05, dd (J=2.4, 9.2 Hz), 1H, H5; 9.01, d (J=2.4 Hz), 1H, H3. $^{13}$C nmr (100 MHz, $d_4$-MeOH+15 drops HOAc) δ 31.1, C3"/5"; 50.0, C2"/6"; 56.0, 4"-MeO; 76.3, C4"; 102.1, C4'; 113.7, C4; 115.4, 117.9, 121.2, 126.5, C3, C6, C6', C7'; 130.8, 132.1, C2, C3a' or C7a'; 133.7, C5; 136.7, C2, C3a' or C7a'; 149.0, 149.1, 150.0, C1, C2', C5'. MS (ESI+ve) m/z 368 (MH$^+$, 100%). HRMS (ESI+ve) m/z 368.17154, $C_{19}H_{22}N_5O_3$ requires 368.17172 (Δ=0.5 ppm).

(C) Preparation of 2-(5'-(5"-(4"'-methoxypiperidin-1"'-yl)benzimidazol-2"-yl)benzimidazol-2'-yl)pyridine

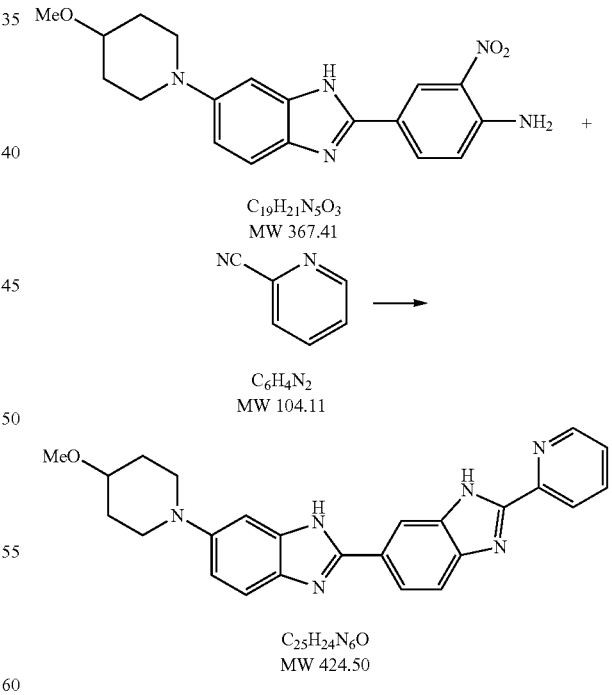

(i) Hydrogenation

To a solution of 4-(5'-(4"-methoxypiperidin-1"-yl)benzimidazol-2'-yl)-2-nitroaniline (281 mg, 0.765 mmol) in 4:1 ethyl acetate/methanol (25 ml) was added 5% palladium on carbon (55 mg) and the mixture stirred at room temperature under an atmosphere of hydrogen for 20 h. The reaction mixture was filtered through celite, washed with methanol, and the combined filtrate and washings concentrated to give the crude 2-amino-4-(5'-(4"-methoxypiperidin-1"-yl)benzimidazol-2'-yl)aniline as dark-red glassy solid that was used in the next step without further purification.

(ii) Coupling Reaction

To 2-cyanopyridine (119 mg, 1.14 mmol) was added a solution of sodium methoxide in methanol (0.09 M, 1.3 ml, 0.119 mmol) and the solution heated at 40° C. for 2 h under nitrogen. A solution of the crude 2-amino-4-(5'-(4"-methoxypiperidin-1"-yl)benzimidazol-2'-yl)aniline (0.765 mmol, prepared above in (i)) in dry methanol (15 ml) and acetic acid (0.13 ml) was then added and the now dark brown solution refluxed for 21 h under nitrogen. The reaction mixture was cooled to room temperature, the solvent removed under reduced pressure and the residue treated with ammonia solution (5 ml) before extraction with n-butanol (2×10 ml). The extract was washed with brine (10 ml) and evaporated to give a glassy material which was subjected to column chromatography (silica gel) eluting with 1:4 methanol/ethyl acetate to give 2-(5'-(5"-(4'''-methoxypiperidin-1'''-yl)benzimidazol-2"-yl)benzimidazol-2'-yl)pyridine (252 mg, 78%) as an orange powder, mp 203° C. (dec).

$^1$H nmr (500 MHz, d$_4$-MeOH+4 drops d-TFA) δ 2.04, m, 2H, H3'''/5'''; 2.23, m, 2H, H3'''/5'''; 3.43, s, 3H, 4'''-MeO; 3.49, m, 2H, H2'''/6'''; 3.64, tt (J=3.3, 6.5 Hz), 1H, H4'''; 3.79, m, 2H, H2'''/6'''; 7.62, m, 2H, H5, H6"; 7.82, d (J=8.5 Hz), 1H, H7"; 7.83, d (J=2.0 Hz), 1H, H4"; 7.96, d (J=8.5 Hz), 1H, H7'; 8.06, dt (J=1.5, 7.8 Hz), 1H, H4; 8.15, dd (J=1.8, 8.8 Hz), 1H, H6'; 8.34, dd (J=0.5, 8.0 Hz), 1H, H3; 8.51, s, 1H, H4'; 8.80, dd, (J=1.0, 4.5 Hz), 1H, H6. $^{13}$C nmr (125 MHz, d$_4$-MeOH+5 drops HOAc) δ 31.7, C3'''/C5'''; 49.9, C2'''/C6'''; 55.8, 4'''-MeO; 77.2, C4'''; 101.7, C4"; 115.1, 115.9, 116.9, 117.4, C4', C6", C7', C7"; 122.7, 122.8, C3, C6'; 123.6, C5'; 126.0, C5; 133.0, C7a"; 138.3 (overlap), C3a", C4; 140.5, C3a'; 141.5, C7a'; 148.6, C2; 150.1, C5"; 150.8, C6; 152.0, 154.2, C2', C2". MS (ESI+ve) m/z 425 (MH$^+$, 100%). HRMS (ESI+ve) m/z 425.20842, C$_{25}$H$_{25}$N$_6$O requires 425.20844 (Δ=0.1 ppm).

Cytotoxicity and Radioprotection Results
C50=69.3
PF=15.7
DMFm=1.70
DMF10=1.37

Example 28

2-(5'-(5"-(Dimethylamino)benzimidazol-2"-yl)benzimidazol-2'-yl)pyridine (A) Preparation of 5-dimethylamino-2-nitroaniline

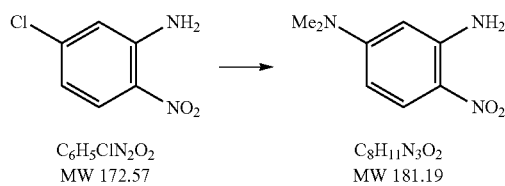 [SMILES: Nc1cc(Cl)ccc1[N+](=O)[O-] ; CN(C)c1ccc([N+](=O)[O-])c(N)c1]

To a solution of 5-chloro-2-nitroaniline (4.14 g, 24.0 mmol) in ethanol (62 ml) in a sealed thick-walled tube, was added aqueous 40% dimethylamine solution (22.5 ml, 178 mmol, 7.4 eq) and the mixture heated in a 90° C. oil-bath for 2 days (CAUTION: High pressure). After cooling, additional 40% dimethylamine solution (7.5 ml) was added and heating continued for a further 3 days. The reaction mixture was cooled to room temperature and the contents were tipped onto ice (250 ml). After stirring the suspension was filtered, washed with water (200 ml) and dried under vacuum to give 5-dimethylamino-2-nitroaniline as a bright yellow solid (4.16 g, 96%), mp 138.5-139.8° C. (lit. (8) mp 140° C.).

$^1$H nmr (500 MHz, CDCl$_3$) δ 3.04, s, 6H, Me$_2$N; 5.76, d (J=2.7 Hz), 1H, H6; 6.12, dd (J=2.7, 9.8 Hz), 1H, H4; 7.99, d (J=9.8 Hz), 1H, H3. $^{13}$C nmr (125 MHz, CDCl$_3$) δ 40.4, Me$_2$N; 96.0, C6; 104.5, C4; 124.2, C2; 128.6, C3; 147.4, C1; 155.1, C5.

(B) Preparation of 4-(5'-(dimethylamino)benzimidazol-2'-yl)-2-nitroaniline

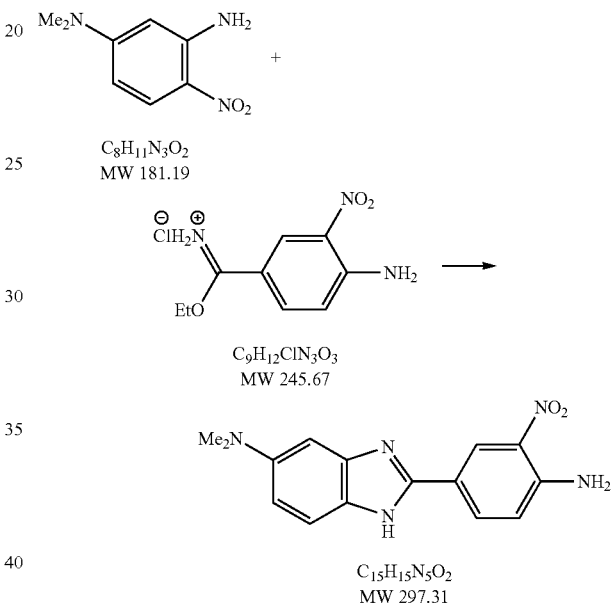

(i) Hydrogenation

A solution of 5-dimethylamino-2-nitroaniline (1.94 g, 10.7 mmol) in 4:1 ethyl acetate/methanol (200 ml) was treated with 5% palladium on carbon (1.12 g) and stirred under an atmosphere of hydrogen at room temperature for 20.5 h. The suspension was quickly filtered through celite, the residue washed with methanol and the combined filtrate and washings concentrated to give the crude 2-amino-4-(dimethylamino)aniline as a dark brown oil, which was used without further purification in the next step.

(ii) Coupling Reaction

The crude 2-amino-4-(dimethylamino)aniline (prepared above in (i)) and ethyl 4-amino-3-nitrobenzenecarboximidate hydrochloride(7) (2.79 g, 11.4 mmol) were refluxed in dry ethanol (60 ml) and glacial acetic acid (30 ml) under nitrogen for 20 h. After cooling to room temperature, the solvents were removed by rotary evaporator and the residue basified with dilute ammonia solution (2.7 M) then stirred at room temperature for 4 days. The suspension was filtered and the dark brown solid washed with water, then diethyl ether to give 4-(5'-(dimethylamino)benzimidazol-2'-yl)-2-nitroaniline as a dark red-brown solid (2.85 g, 90%), mp 249-251° C.

$^1$H nmr (500 MHz, d$_4$-MeOH+5 drops d-TFA) δ 3.27s, 6H, Me$_2$N; 7.26, d (J=9.0 Hz), 1H, H6; 7.53, dd (J=2.4, 9.0 Hz), 1H, H6'; 7.57, d (J=2.2 Hz), 1H, H4'; 7.79, dd (J=0.5, 9.0 Hz), 1H, H7'; 8.02, dd (J=2.4, 8.9 Hz), 1H, H5; 8.99, d (J=2.2 Hz), 1H, H3. $^{13}$C nmr (125 MHz, d$_4$-MeOH+5 drops HOAc) δ 41.4, Me$_2$N; 95.8, C4'; 113.3, C4; 113.5, 115.2, C6', C7'; 121.0, C6; 125.8, C3; 127.8, 131.8, C2, C7a'; 133.1, C5; 136.2, C3a'; 147.9, 148.8, 149.8, C1, C2', C5'. MS (ESI+ve) m/z 298 (MH$^+$, 100%). HRMS (ESI+ve) m/z 298.12984, C$_{15}$H$_{16}$N$_5$O$_2$ requires 298.12985 (Δ=0.0 ppm).

(C) Preparation of 2-(5'-(5"-(dimethylamino)benzimidazol-2"-yl)benzimidazol-2'-yl)pyridine

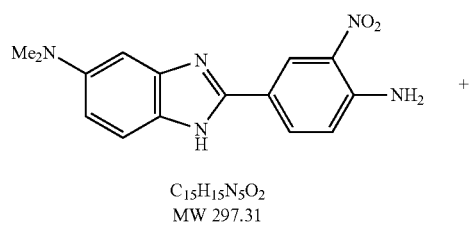

C$_{15}$H$_{15}$N$_5$O$_2$
MW 297.31

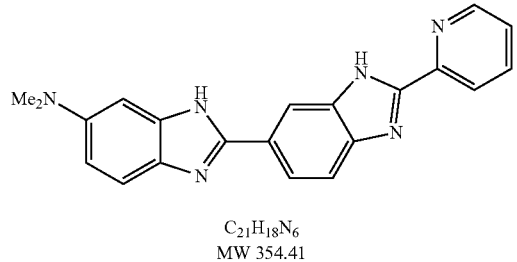

C$_{21}$H$_{18}$N$_6$
MW 354.41

(i) Hydrogenation

A solution of 4-(5'-(dimethylamino)benzimidazol-2'-yl)-2-nitroaniline (0.358 g, 1.20 mmol) in 4:1 ethyl acetate/methanol (40 ml) was treated with 5% palladium on carbon (0.20 g) and stirred under an atmosphere of hydrogen at room temperature for 17 h. The suspension was quickly filtered through celite, the residue washed with methanol and the combined filtrate and washings concentrated to give the crude 2-amino-4-(5'-(dimethylamino)benzimidazol-2'-yl)aniline as a brown solid, which was used without further purification in the next step.

(ii) Coupling Reaction

A solution of sodium metabisulfite (0.269 g, 1.41 mmol) in 1:1 ethanol/water (5 ml) was added to 2-pyridinecarboxaldehyde (0.157 g, 1.47 mmol) in ethanol (5 ml) and the mixture gently heated for 5 min. The solution was then added to a solution of 2-amino-4-(5'-(dimethylamino)benzimidazol-2'-yl)aniline (prepared above in (i)) in ethanol (40 ml) and the mixture refluxed under nitrogen for 22 h. After cooling the solvents were removed by rotary evaporator and the residue treated with dilute ammonia solution (2.7 M, 30 ml) and allowed to stand at 0° C. for 24 h. The resulting suspension was centrifuged, the supernatant removed and the dark brown residue treated with water (2×13 ml), diethyl ether (2×13 ml) and ethyl acetate (15 ml and 10 ml), with centrifugation and removal of supernatant after each treatment. Drying of the resultant solid under vacuum gave 2-(5'-(5"-(dimethylamino)benzimidazol-2"-yl)benzimidazol-2'-yl)pyridine as a light brown solid (0.190 g, 45%), mp 180° C. (dec).

$^1$H nmr (500 MHz, d$_4$-MeOH+5 drops d-TFA) δ 3.23, s, 6H, Me$_2$N; 7.41, d (J=1.2 Hz), 1H, H4"; 7.42, dd (J=2.2, 9.0 Hz), 1H, H6"; 7.70, dd (J=5.4, 7.5 Hz), 1H, H5; 7.78, d (J=9.0 Hz), 1H, H7"; 8.08, d (J=8.8 Hz), 1H, H7'; 8.15, dt (J=1.5, 8.0 Hz), 1H, H4; 8.21, dd (J=1.7, 8.5 Hz), 1H, H6'; 8.42, d (J=7.8 Hz), 1H, H3; 8.58, d (J=1.1 Hz), 1H, H4'; 8.90, d (J=4.4 Hz), 1H, H6. $^{13}$C nmr (125 MHz, d$_4$-MeOH+5 drops HOAc) δ 41.2, Me$_2$N; 95.5, C4"; 113.7, C6"; 115.2, C7"; 115.4, C4'; 117.1, C7'; 120.2, C5'; 122.5, C6'; 122.8, C3; 126.3, C5; 127.3, C7a"; 135.9, C3a"; 138.4, C4; 140.3, C3a'; 142.0, C7a'; 148.4, C2; 149.3, C2"; 150.0, C5"; 150.8, C6; 154.6, C2'. MS (ESI+ve) m/z 355 (MH$^+$, 100%). HRMS (ESI+ve) m/z 355.16654, C$_{21}$H$_{19}$N$_6$ requires 355.16657 (Δ=0.1 ppm).

Cytotoxicity and Radioprotection Results
C50=60.8
PF=13.5
DMFm=1.57
DMF10=1.30

Example 29

2-(5'-(5"-(4'"-(Dimethylamino)piperidin-1'"-yl)benzimidazol-2"-yl)benzimidazol-2'-yl)pyridine (A) Preparation of 5-(4'-(N-BOC-amino)piperidin-1'-yl)-2-nitroaniline

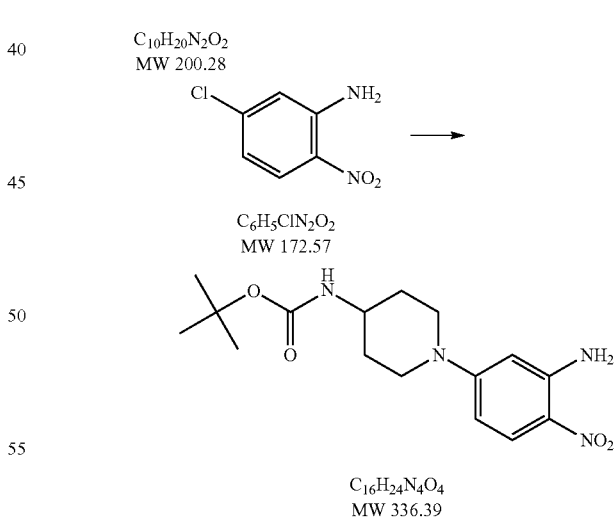

A mixture of 5-chloro-2-nitroaniline (0.86 g, 5.0 mmol), 4-(N-BOC-amino)piperidine (1.50 g, 7.5 mmol) and potassium carbonate (0.72 g, 5.2 mmol) in anhydrous N,N-dimethylacetamide (9 ml) was stirred in a 125-135° C. oil-bath under nitrogen for 25 h. The resultant mixture was cooled to room temperature, ice (50 ml) added, then stirred vigorously for 18 h. The heavy precipitate was collected by filtration, washed carefully with water (3×15 ml), followed by diethyl ether (2×15 ml), then dried under vacuum to give a dull yellow powder (1.46 g). A portion was applied to a plug of silica gel (40×60 mm) and eluted with ethyl acetate to afford pure 5-(4'-(N-BOC-amino)piperidin-1'-yl)-2-nitroaniline (0.57 g) as a yellow powder.

$^1$H nmr (400 MHz, base-washed CDCl$_3$) δ 1.45, m, 11H, O-t-Bu and H3'/5'; 2.04, m, 2H, H3'/5'; 3.01, dt (J=2.4, 12.4 Hz), 2H, H2'/6'; 3.70, br, 1H, H4'; 3.82, br d, 2H, H2'/6'; 4.46, br, 1H, NH; 5.94, d (J=2.8 Hz), 1H, H6; 6.13, br, 2H, NH$_2$; 6.26, dd (J=2.6, 9.8 Hz), 1H, H4; 8.00, d (J=9.2 Hz), 1H, H3.

(B) Preparation of 4-(5'-(4''-(N-BOC-amino)piperidin-1''-yl)benzimidazol-2'-yl)-2-nitroaniline

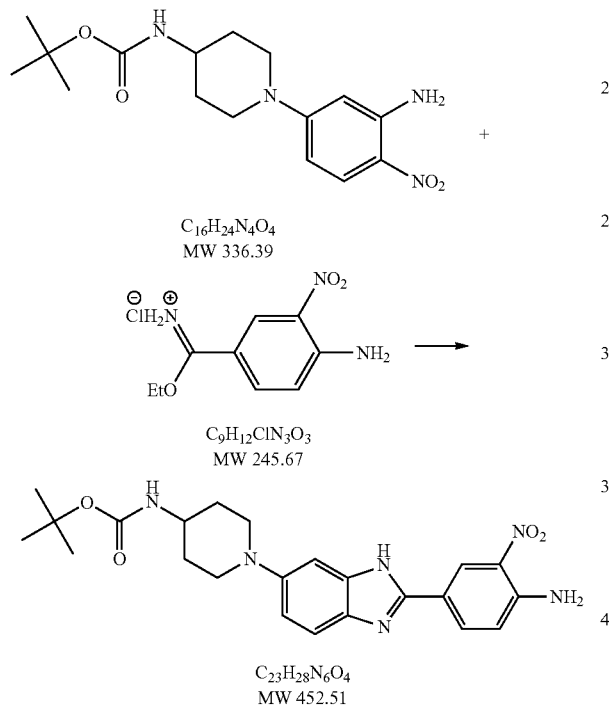

(i) Hydrogenation

To a suspension of 5-(4'-(N-BOC-amino)piperidin-1'-yl)-2-nitroaniline (0.57 g, 1.7 mmol) in 2:1 ethyl acetate/methanol (60 ml) was added 10% activated palladium on carbon (0.10 g) and the mixture stirred at room temperature under an atmosphere of hydrogen for 18 h. The reaction mixture was then filtered through filter-aid, the filtered solid washed with methanol (150 ml), and the combined filtrate and washings evaporated to give the crude 2-amino-4-(4'-(N-BOC-amino)piperidin-1'-yl)aniline as a dull khaki-coloured solid (0.51 g, 98%) that was used in the next step without further purification.

$^1$H nmr (400 MHz, base-washed CDCl$_3$) δ 1.45, s, 9H, O-t-Bu, 1.54, m, 2H, H3'/5'; 2.02, m, 2H, H3'/5'; 2.71, dt (J=2.4, 12.0 Hz), 2H, H2'/6'; 3.39, m, 2H, H2'/6'; 3.55, br, 1H, H4'; 4.47, br, 1H, BOC-NH; 6.32, dd (J=2.8, 8.4 Hz), 1H, H5; 6.37, d (J=2.4 Hz), 1H, H3; 6.62, d (J=8.4 Hz), 1H, H6.

(ii) Coupling Reaction

The crude 2-amino-4-(4'-(N-BOC-amino)piperidin-1'-yl) aniline (0.51 g, 1.66 mmol) was treated with ethyl 4-amino-3-nitrobenzenecarboximidate hydrochloride[7] (0.429 g, 1.74 mmol) followed by dry ethanol (20 ml) and glacial acetic acid (10 ml). The reaction mixture was refluxed under nitrogen for 19 h, then cooled to room temperature and the solvents removed by rotary evaporator. The residue was treated with dilute ammonia solution (2.7 M, 20 ml) and stirred for 40 min to give a fine red precipitate. The suspension was centrifuged, the supernatant removed and the residue treated with water (2×10 ml), then acetonitrile (2×4 ml), with centrifugation and removal of the supernatant between each treatment. The residue was dried under vacuum to give 4-(5'-(4''-(N-BOC-amino)piperidin-1''-yl)benzimidazol-2'-yl)-2-nitroaniline (0.498 g, 66%) as a dark red powder, mp 155-160° C.

$^1$H nmr (400 MHz, d$_4$-MeOH+4 drops d-TFA) δ 1.46, s, 9H, O-t-Bu, 1.97, m, 2H, H3''/5''; 2.24, m, 2H, H3''/5''; 3.63, dt (J=1.3, 12.0 Hz), 2H, H2''/6''; 3.79, m, 3H, H2''/6''; H4''; 7.25, d (J=9.2 Hz), 1H, H6; 7.74, dd (J=2.2, 9.0 Hz), 1H, H6'; 7.86, d (J=8.8 Hz), 1H, H7'; 7.92, d (J=2.0 Hz), 1H, H4'; 8.04, dd (J=2.4, 9.2 Hz), 1H, H5; 9.01, d (J=2.4 Hz), 1H, H3. $^{13}$C nmr (125 MHz, d$_4$-MeOH+25 drops HOAc) δ 28.8, OCMe$_3$; 32.6, C3''/5''; 48.4, C4''; 51.3, C2''/6''; 80.3, OCMe$_3$; 101.5, C4'; 113.0, C4; 115.2, 118.2, 121.3, 126.7, C3, C6, C6', C7'; 129.7, 132.1, C2, C3a' or C7a'; 133.6, C5; 136.0, C2, C3a' or C7a'; 149.2, 149.5, 149.6, C1, C2', C5'; 157.7, O(C=O)N. MS (ESI+ve) m/z 905 (M$_2$H$^+$, 22%), 453 (MH$^+$, 100). HRMS (ESI+ve) m/z 453.22448, C$_{23}$H$_{29}$N$_6$O$_4$ requires 453.22448 (Δ=0.0 ppm).

(C) Preparation of 2-(5'-(5''-(4'''-(N-BOC-amino) piperidin-1'''-yl)benzimidazol-2''-yl)benzimidazol-2'-yl)pyridine

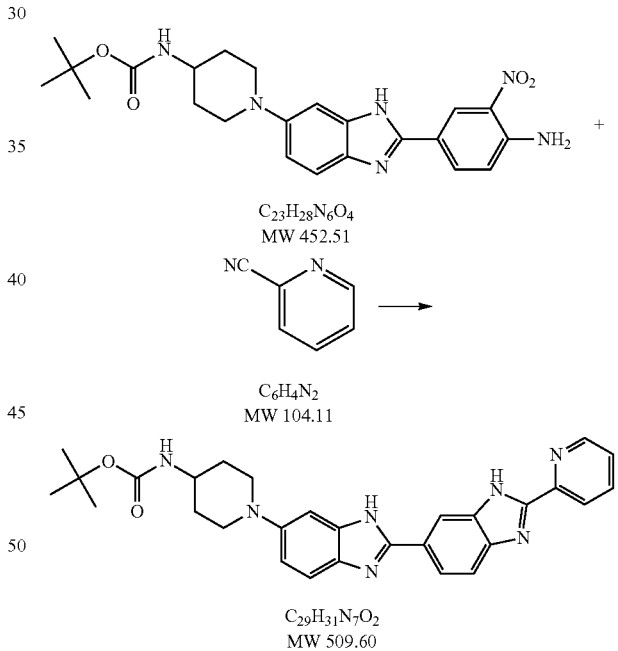

(i) Hydrogenation

To a suspension of 4-(5'-(4''-(N-BOC-amino)piperidin-1''-yl)benzimidazol-2'-yl)-2-nitroaniline (350 mg, 0.77 mmol) in 1:1 ethyl acetate/methanol (20 ml) was added 10% palladium on carbon (50 mg) and the reaction mixture stirred vigorously under an atmosphere of hydrogen for 21 h. The reaction mixture was then filtered through filter-aid, the residue washed with methanol (~100 ml) and the combined filtrate and washings evaporated to give the crude 2-amino-4-(5'-(4''-(N-BOC -amino)piperidin-1''-yl)benzimidazol-2'-yl) aniline (331 mg, 99%) as an orange-brown solid, which was used without further purification.

¹H nmr (400 MHz, d₄-MeOH+4 drops d-TFA) δ 1.46, s, 9H, O-t-Bu; 1.94, m, 2H, H3″/5″; 2.23, m, 2H, H3″/5″; 3.62, dt (J=2.8, 12.0 Hz), 2H, H2″/6″; 3.79, m, 3H, H2″/6″, H4″; 7.11, d (J=8.8 Hz), 1H, H6; 7.71, dd (J=2.2, 9.0 Hz), 1H, H6′; 7.85, m, 2H, H5, H7′; 7.91, d (J=1.6 Hz), 1H, H4′; 7.95, d (J=2.0 Hz), 1H, H3.

(ii) Coupling Reaction

To 2-cyanopyridine (133 mg, 1.28 mmol) was added a solution of sodium methoxide in methanol (0.075 M, 1.7 ml, 0.128 mmol, 0.1 eq) and the solution heated under nitrogen in a 40° C. oil-bath for 80 min. A solution of the crude 2-amino-4-(5′-(4″-(N-BOC-amino)piperidin-1″-yl)benzimidazol-2′-yl)aniline (331 mg, 0.78 mmol) in dry methanol (15 ml) was then added followed by glacial acetic acid (0.14 ml, 2.45 mmol) and the mixture gently refluxed under nitrogen for 16 h. After cooling the solvents were removed by rotary evaporator, the residue treated with dilute ammonia solution (2.7 M, 20 ml) and stirred for 40 min to give an even suspension, which was centrifuged and the supernatant removed. The residue was treated with water (15 ml), then acetonitrile (4×3 ml), with centrifugation and removal of the supernatant after each treatment. The remaining solid was applied to a short plug of silica gel (30×70 mm) and eluted with methanol to give 2-(5′-(5″-(4′″-(N-BOC-amino)piperidin-1′″-yl)benzimidazol-2″-yl)benzimidazol-2′-yl)pyridine as a brown powder (261 mg, 65%), mp 197° C. (dec).

¹H nmr (400 MHz, d₄-MeOH+4 drops d-TFA) δ 1.47, s, 9H, O-t-Bu, 1.93, m, 2H, H3′″/H5′″; 2.23, m, 2H, H3′″/5′″; 3.59, dt (J=2.6, 12.0 Hz), 2H, H2′″/6′″; 3.80, m, 3H, H2′″/6′″, H4′″; 7.71, m, 2H, H5, H6″; 7.89, m, 2H, H4″, H7″; 8.08, d (J=8.8 Hz), 1H, H7′; 8.16, dt (J=1.6, 8.0 Hz), 1H, H4; 8.23, dd (J=1.8, 8.6 Hz), 1H, H6′; 8.41, d (J=7.6 Hz), 1H, H3; 8.63, d (J=0.8 Hz), 1H, H4′; 8.90, m, 1H, H6. ¹³C nmr (125 MHz, d₄-MeOH+4 drops HOAc) δ 28.8, OCMe₃; 33.0, C3′″/5′″; 48.8, C4′″; 51.1, C2′″/6′″; 80.1, OCMe₃; 101.2, C4″; 115.3, 115.6, 116.9, 117.6, C4′, C6″, C7′, C7″; 122.2, C5′; 122.8 (overlap), C3, C6′; 126.1, C5; 131.5, C7a″; 137.3, C3a″; 138.3, C4; 140.3, C3a′; 141.6, C7a′; 148.4, C2; 150.4, C5″; 150.7, C6; 151.3, 154.3, C2′, C2″; 157.7, O(C=O)N. MS (ESI+ve) m/z 510 (MH⁺, 100%). HRMS (ESI+ve) m/z 510.26192, C₂₉H₃₂N₇O₂ requires 510.26192 (Δ=1.4 ppm).

(D) Preparation of 2-(5′-(5″-(4′″-aminopiperidin-1′″-yl)benzimidazol-2″-yl)benzimidazol-2′-yl)pyridine To 2-(5′-(5″-(4′″-(N-BOC-amino)piperidin-1′″-yl)benzimidazol-2″-yl)benzimidazol-2′-yl)pyridine (200 mg, 0.39 mmol) was added dichloromethane (3 ml) followed by trifluoroacetic acid (3 ml) and the dark purple solution stirred at room temperature in a stoppered flask for 100 min. The solvents were then removed by rotary evaporator and the oily residue chilled in ice and carefully treated with dilute ammonia solution (2.7 M, 10 ml). The resultant heavy suspension was stirred for 45 min before being centrifuged and the supernatant removed. The residue was treated with water (3×10 ml), then acetonitrile (2×4 ml), with centrifugation and removal of the supernatant after each treatment. The remaining solid was dried under vacuum to give 2-(5′-(5″-(4′″-aminopiperidin-1′″-yl)benzimidazol-2″-yl)benzimidazol-2′-yl)pyridine as a yellow powder (116 mg, 72%), mp 270° C. (dec).

¹H nmr (400 MHz, d₄-MeOH+4 drops d-TFA) δ 1.86, app. dq (J=4.0, 12.4 Hz), 2H, H3′″/H5′″; 2.18, m, 2H, H3′″/5′″; 3.04, dt (J=1.8, 12.0 Hz), 2H, H2′″/6′″; 3.36, m, 1H, H4′″; 3.90, m, 2H, H2′″/6′″; 7.33, d (J=2.0 Hz), 1H, H4″; 7.42, dd (J=2.2, 9.0 Hz), 1H, H6″; 7.67, m, 1H, H5; 7.70, d (J=9.2 Hz), 1H, H7″; 8.05, d (J=8.4 Hz), 1H, H7′; 8.12, dt (J=1.2, 8.0 Hz), 1H, H4; 8.17, dd (J=1.8, 8.6 Hz), 1H, H6′; 8.40, d (J=8.0 Hz), 1H, H3; 8.56, d (J=0.8 Hz), 1H, H4′; 8.86, m, 1H, H6. ¹³C nmr (125 MHz, d₄-MeOH+4 drops HOAc) δ 31.2, C3′″/5′″; 49.7, C4′″; 50.5, C2′″/6′″; 102.2, C4″; 115.2, 116.0, 117.0, 117.4, C4′, C6″, C7′, C7″; 122.8, 123.0, C3, C6′; 123.8, C5′; 126.1, C5; 133.2, C7a″; 138.4, C4; 138.5, C3a″; 140.4, C3a′; 141.6, C7a′; 148.6, C2; 149.8, C5″; 150.8, C6; 152.3, 154.2, C2′, C2″. MS (ESI+ve) m/z 819 (M₂H⁺, 4%), 410 (MH⁺, 100). HRMS (ESI+ve) m/z 410.20870, C₂₄H₂₄N₇ requires 410.20877 (Δ=0.2 ppm).

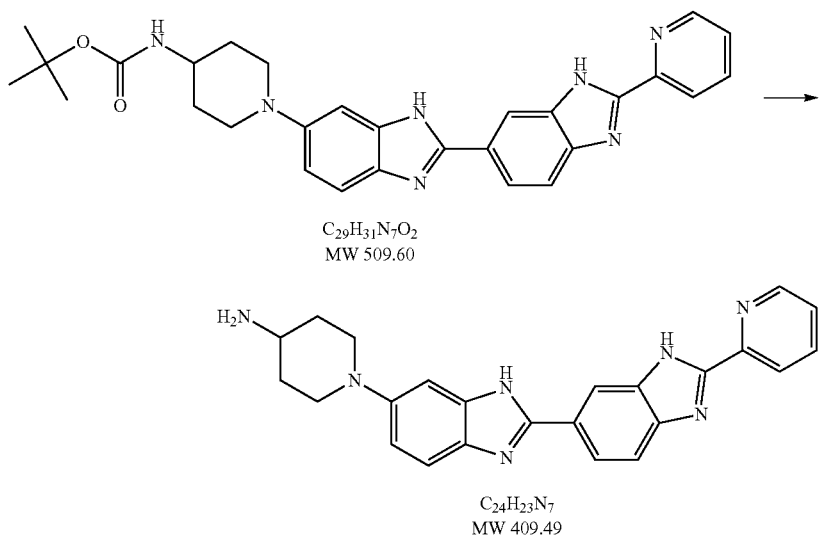

C₂₉H₃₁N₇O₂
MW 509.60

C₂₄H₂₃N₇
MW 409.49

81

(E) Preparation of 2-(5'-(5"-(4'"-(Dimethylamino) piperidin-1'"-yl)benzimidazol-2"-yl)benzimidazol-2'-yl)pyridine

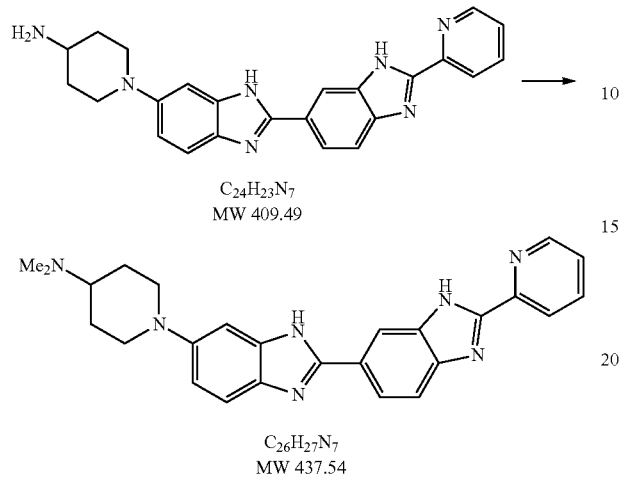

C₂₄H₂₃N₇
MW 409.49

C₂₆H₂₇N₇
MW 437.54

To a solution of 2-(5'-(5"-(4'"-aminopiperidin-1'"-yl)benzimidazol-2"-yl)benzimidazol-2'-yl)pyridine (42 mg, 0.10 mmol) and sodium cyanoborohydride (15 mg, 0.24 mmol, 2.4 eq) in methanol (1 ml) was added acetic acid (40 mg, 0.67 mmol, 6.7 eq) followed by 40% formaldehyde solution (30 μl, 0.40 mmol, 4.0 eq) and the mixture stirred at room temperature under nitrogen for 16 h. Potassium carbonate (50 mg, 0.36 mmol) was dissolved in the minimum volume of water and added to the reaction mixture before removal of the solvents by rotary evaporator. The residue was partitioned between n-butanol (5 ml) and water (5 ml), the butanol layer washed with water (2×4 ml) and evaporated to give the crude product as a light brown glass (44 mg). Trituration of the material with acetonitrile (2×2 ml) followed by drying under vacuum afforded 2-(5'-(5"-(4'"-(dimethylamino)piperidin-1'"-yl)benzimidazol-2"-yl)benzimidazol-2'-yl)pyridine as a light tan powder (36 mg, 80%), mp 198-205° C.

¹H nmr (500 MHz, d₄-MeOH+4 drops d-TFA) δ 1.94, app. dq (J=4.0, 12.0 Hz), 2H, H3'"/5'"; 2.25, m, 2H, H3'"/5'"; 2.93, s, 6H, 4'"-Me₂N; 2.98, m, 2H, H2'"/6'"; 3.43, m, 1H, H4'"; 4.00, m, 2H, H2'"/6'"; 7.30, d (J=2.0 Hz), 1H, H4"; 7.42, dd (J=2.0, 9.3 Hz), 1H, H6"; 7.71, m, 2H, H5, H7"; 8.08, d (J=8.5 Hz), 1H, H7'; 8.15, dt (J=1.5, 8.0 Hz), 1H, H4; 8.19, dd (J=1.5, 8.5 Hz), 1H, H6'; 8.42, d (J=7.5 Hz), 1H, H3; 8.59, d (J=1.5 Hz), 1H, H4'; 8.89, m, 1H, H6. ¹³C nmr (100 MHz, d₄-MeOH+5 drops HOAc) δ 27.5, C3'"/5'"; 40.3, 4'"-Me₂N; 50.9, C2'"/6'"; 64.7, C4'"; 102.3, C4"; 115.5, 116.1, 117.0, 117.6, C4', C6", C7', C7"; 122.9, 123.2, C3, C6'; 123.8, C5'; 126.3, C5; 133.2, C7a"; 138.6, C3a", C4 (overlap); 140.7, C3a'; 141.7, C7a'; 148.7, C2; 149.7, C5"; 150.9, C6; 152.5, 154.4, C2', C2". MS (ESI+ve) m/z 438 (MH⁺, 100%). HRMS (ESI+ve) m/z 438.23995, C₂₆H₂₈N₇ requires 438.24007 (Δ=0.3 ppm).

Cytotoxicity and Radioprotection Results
C50=46.9
PF=18.2
DMFm=1.76
DMF10=1.54

82

Example 30

2-(4'-Methoxy-6'-(5"-(4'"-methylpiperazin-1'"-yl) benzimidazol-2"-yl)benzimidazol-2'-yl)pyridine (A) Preparation of Ethyl 4-amino-3-methoxy-5-nitrobenzenecarboximidate hydrochloride

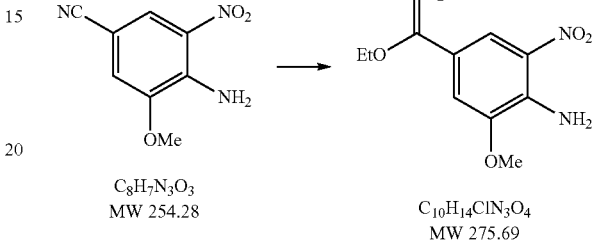

C₈H₇N₃O₃
MW 254.28

C₁₀H₁₄ClN₃O₄
MW 275.69

Anhydrous hydrogen chloride gas was bubbled through a suspension of 4-amino-3-methoxy-5-nitrobenzonitrile(11) (341 mg, 1.77 mmol) in dry ethanol (18 ml) at room temperature for 3 h, during which time the solid dissolved and re-precipitated. The gas inlet was then replaced with a calcium chloride drying tube and the stirring continued for 21 h. The heavy yellow suspension was tipped into dry diethyl ether (100 ml), stirred briefly then filtered. The filtered solid was washed carefully with diethyl ether (3×10 ml) and dried under vacuum to give ethyl 4-amino-3-methoxy-5-nitrobenzenecarboximidate hydrochloride (428 mg, 88%) as a yellow solid, mp 246-248° C.

¹H nmr (500 MHz, d₆-dmso) δ 1.47, t (J=7.0 Hz), 3H, OEt; 3.98, s, 3H, 3-Ome; 4.60, q (J=6.8 Hz), 2H, OEt; 7.92, d (J=1.5 Hz), 1H, H2; 7.97, br, 2H, 4-NH₂; 8.39, d (J=1.5 Hz), 1H, H6; 11.60, br, 2H, imidate H₂N⁺. ¹³C nmr (125 MHz, d₆-dmso) δ 13.5, OCH₂CH₃; 57.2, OMe; 69.2, OCH₂CH₃; 110.0, C1; 111.2, C2 or C6; 121.0, C6 or C2; 129.5, C4; 141.9, C5; 148.2, C3; 168.7, imidate. MS (ESI+ve) m/z 240 (M-Cl, 100%). HRMS (ESI+ve) m/z 240.09782, C₁₀H₁₄N₃O₄ requires 240.09788 (Δ=0.2 ppm).

(B) Preparation of 2-methoxy-4-(5'-(4"-methylpiperazin-1"-yl)benzimidazol-2'-yl)-6-nitroaniline

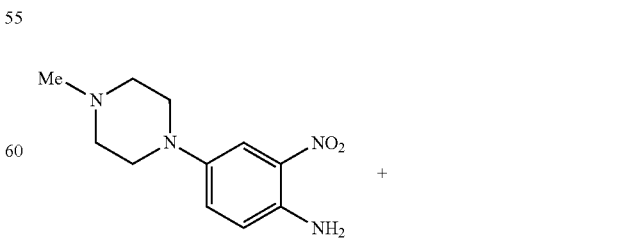

C₁₁H₁₆N₄O₂
MW 236.27

-continued

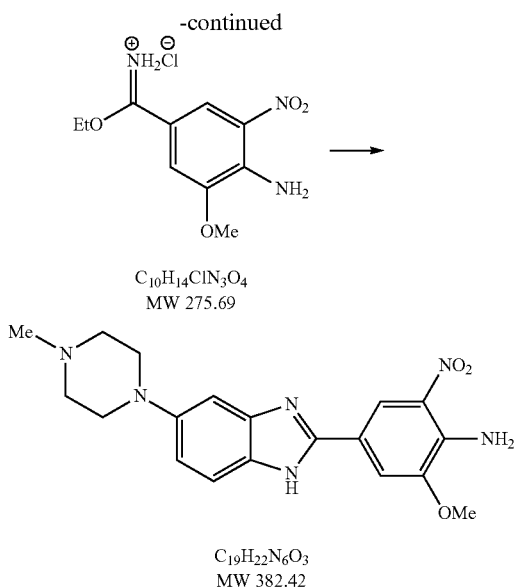

(i) Hydrogenation

To a suspension of 5-(4'-methylpiperazin-1'-yl)-2-nitroaniline(7) (294 mg, 1.24 mmol) in 4:1 ethyl acetate/methanol (20 ml) was added 5% palladium on carbon (62 mg) and the mixture stirred vigorously under an atmosphere of hydrogen at room temperature for 6 h. The reaction mixture was then filtered through celite to remove the catalyst and the residue washed with methanol. The combined filtrate and washings were evaporated to give the crude 2-amino-4-(4'-methylpiperazin-1'-yl)aniline which was reacted immediately in the next step.

(ii) Coupling Reaction

To a solution of the crude 2-amino-4-(4'-methylpiperazin-1'-yl)aniline (1.24 mmol, prepared above in (i)), in 2:1 ethanol/acetic acid (18 ml) was added ethyl 4-amino-3-methoxy-5-nitrobenzenecarboximidate hydrochloride (350 mg, 1.27 mmol) and the mixture refluxed under nitrogen for 17 h. The reaction mixture was cooled, the solid filtered off and washed carefully with dilute ammonia solution (2.7 M, 2×20 ml) before drying under vacuum over phosphorous pentoxide to give a dark red solid. The filtrate was evaporated and the residue dissolved in water (10 ml) and treated with dilute ammonia solution (2.7 M, ~15 ml) till strongly basic. The precipitate was filtered, washed with water then dried under vacuum to give an additional 55 mg of material. The combined material was dissolved in methanol (20 ml), applied to a plug of silica gel (50×50 mm) and eluted with methanol to give 2-methoxy-4-(5'-(4''-methylpiperazin-1''-yl)benzimidazol-2'-yl)-6-nitroaniline (405 mg, 85%) as a red glassy solid, mp 148° C. (dec).

$^1$H nmr (400 MHz, $d_4$-MeOH+3 drops d-TFA) δ 3.00, s, 3H, 4''-MeN; 3.17, t (J=12.4 Hz), 2H, NCH$_2$; 3.31, m (obscured), NCH$_2$; 3.67, d (J=11.6 Hz), 2H, NCH$_2$; 3.86, d (J=13.2 Hz), 2H, NCH$_2$; 4.01, s, 3H, 2-Ome; 7.07, d (J=2.0 Hz), 1H, H4'; 7.18, dd (J=9.2, 2.0 Hz), 1H, H6'; 7.44, d (J=9.2 Hz), 1H, H7'; 7.47, d (J=2.4 Hz), 1H, H3; 8.28, d (J=2.0 Hz), 1H, H5. $^{13}$C nmr (100 MHz, $d_4$-MeOH+3 drops HOAc) δ 43.6, 4''-MeN; 49.2, C2''/6''; 54.7, C3''/5''; 57.1, 2-Ome; 102.1, C4'; 111.2, C6'; 115.5, C4; 116.1, 116.4, 116.5, C3, C5, C7'; 131.5, C6; 134.4, C7a'; 139.0, C3a'; 140.1, C1; 148.3, C5'; 149.9, C2; 151.4, C2'. MS (ESI+ve) m/z 383 (MH$^+$, 100%). HRMS (ESI+ve) m/z 383.18251, C$_{19}$H$_{23}$N$_6$O$_3$ requires 383.18262 (Δ=0.3 ppm).

(C) Preparation of 2-(4'-methoxy-6'-(5''-(4'''-methylpiperazin-1'''-yl)benzimidazol-2''-yl)benzimidazol-2'-yl)pyridine

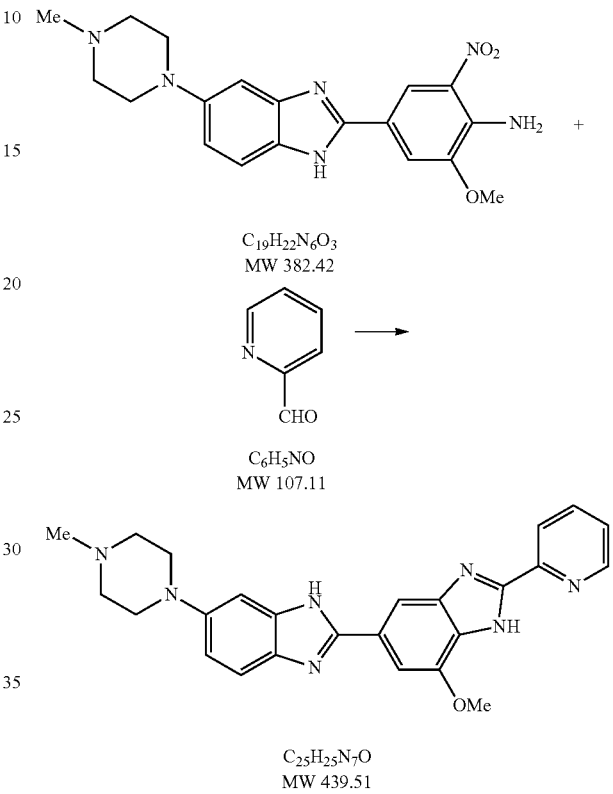

(i) Hydrogenation

To a solution of 2-methoxy-4-(5'-(4''-methylpiperazin-1''-yl)benzimidazol-2'-yl)-6-nitroaniline (274 mg, 0.72 mmol) in 4:1 ethyl acetate/methanol (20 ml) was added 5% palladium on carbon (60 mg) and the mixture stirred vigorously under an atmosphere of hydrogen at room temperature for 21 h. The reaction mixture was then filtered through celite to remove the catalyst and the residue washed with methanol. The combined filtrate and washings were evaporated to give 2-amino-3-methoxy-5-(5'-(4''-methylpiperazin-1''-yl)benzimidazol-2'-yl)aniline as a light orange solid, 238 mg (94%), used immediately in the next step.

$^1$H nmr (400 MHz, $d_4$-MeOH) δ 2.99, s, 3H, 4''-MeN; 3.18, t (J=11.8 Hz), 2H, NCH$_2$; 3.33, m (obscured), NCH$_2$; 3.66, d (J=12.0 Hz), 2H, NCH$_2$; 3.92, d (J=13.6 Hz), 2H, NCH$_2$; 4.05, s, 3H, 3-Ome; 7.30, d (J=2.0 Hz), 1H, H4'; 7.35, dd (J=8.6, 2.0 Hz), 1H, H6'; 7.56, d (J=2.0 Hz), 1H, H4 or H6; 7.61, d (J=2.0 Hz), 1H, H6 or H4; 7.66, d (J=8.8 Hz), 1H, H7'.

(ii) Coupling Reaction

A solution of pyridine-2-carboxaldehyde (78 mg, 0.728 mmol) in ethanol (5 ml) and a solution of sodium metabisulfite (151 mg, 0.794 mmol) in water (1 ml) were combined and added dropwise over 10 min to a solution of 2-amino-3-methoxy-5-(5'-(4''-methylpiperazin-1''-yl)benzimidazol-2'-yl)aniline (228 mg, 0.647 mmol) in ethanol (10 ml). Additional ethanol (2 ml) and water (1 ml) were used to complete the transfer. The mixture was then refluxed under nitrogen for 17 h before cooling and evaporation of the solvents. The residue was treated with dilute ammonia solution (6%, 30 ml), extracted with n-butanol (30 ml), the extract washed with water (30 ml), brine (30 ml), dried (MgSO$_4$) and evaporated to give a glassy orange solid. The material was subjected to column chromatography with alumina (neutral, 33×190 mm) eluting with 50:3:1 ethyl acetate/methanol/triethylamine to give 2-(4'-methoxy-6'-(5''-(4'''-methylpiperazin-1'''-yl)benzimidazol-2''-yl)benzimidazol-2'-yl)pyridine as a yellow powder (39 mg, 14%), mp 200° C. (dec).

$^1$H nmr (400 MHz, d$_4$-MeOH+4 drops d-TFA) δ 3.01, s, 3H, 4'''-MeN; 3.21, t (J=13.2 Hz), 2H, NCH$_2$; 3.35, m (obs), NCH$_2$; 3.68, d (J=12.0 Hz), 2H, NCH$_2$; 3.97, d (J=12.8 Hz), 2H, NCH$_2$; 4.26, s, 3H, 4'-MeO; 7.36, d (J=2.0 Hz), 1H, H4''; 7.44, dd (J=2.4, 9.2 Hz), 1H, H6''; 7.70, ddd (J=1.2, 4.8, 7.6 Hz), 1H, H5; 7.76, d (J=9.2 Hz), 1H, H7''; 7.78, d (J=1.2 Hz), 1H, H5'; 8.15, dt (J=1.6, 8.0 Hz), 1H, H4; 8.20, d (J=1.6 Hz), 1H, H7'; 8.43, dt (J=8.0, 1.0 Hz), 1H, H3; 8.89, ddd (J=0.8, 1.6, 4.8 Hz), 1H, H6. $^{13}$C nmr (100 MHz, d$_4$-MeOH+4 drops HOAc) δ 43.6, 4'''-MeN; 48.9, C2'''/6'''; 54.6, C3'''/5'''; 56.4, 4'-Ome; 101.8, 102.6, C4'' and C5' or C7'; 107.3, C7' or C5'; 116.0, 117.0, C6'', C7''; 122.7, C3; 123.4, C6'; 125.9, C5; 132.6, 133.6, C7a' and C7a''; 137.6, C3a' or C3a''; 138.3, C4; 139.9, C3a'' or C3a'; 148.3, 148.7; C2 and C5'', 150.6, C6; 150.9, C4'; 152.1, 153.0, C2' and C2''. MS (ESI+ve) m/z 440 (MH$^+$, 58%), 220.6 (MH$_2^{2+}$, 100). HRMS (ESI+ve) m/z 440.21942, C$_{25}$H$_{26}$N$_7$O requires 440.21933 (Δ=0.2 ppm).

Cytotoxicity and Radioprotection Results

C50=158.5
PF=13.3
DMFm=1.97
DMF10=1.78

Example 31

2-(6'-(5''-(4'''-Methylpiperazin-1'''-yl)benzimidazol-2''-yl)indol-2'-yl)pyridine (A) Preparation of (E)-2-(4'-cyano-2'-nitrostyryl)pyridine

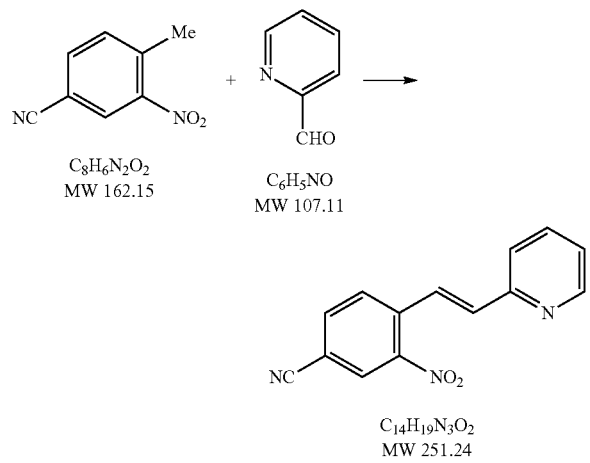

To 2-pyridinecarboxaldehyde (1.13 g, 10.5 mmol) was added 4-methyl-3-nitrobenzonitrile (1.62 g, 10.0 mmol) followed by piperidine (0.32 g, 3.8 mmol) and the mixture heated in a 120° oil-bath under nitrogen for 1 h. The viscous dark slurry was then stirred at room temperature for 23 h before ethyl acetate (10 ml) was added and the dark lumps broken up with a glass rod prior to filtering. The filtered solid was washed with ethyl acetate and dried under vacuum to give (E)-2-(4'-cyano-2'-nitrostyryl)pyridine as a light olive-green powder (1.43 g, 57%), mp 166-167° C.

$^1$H nmr (400 MHz, CDCl$_3$) δ 7.29, dt (J=1.2, 6.2 Hz), 1H, H5; 7.31, d (J=16.0 Hz), 1H, olefinic H; 7.53, d (J=7.6 Hz), 1H, H3; 7.77, dt (J=1.6, 7.6 Hz), 1H, H4; 7.88, ddd (J=0.6, 1.6, 8.2 Hz), 1H, H5'; 7.95, d (J=8.4 Hz), 1H, H6', 8.05, d (J=16.0 Hz), 1H, olefinic H; 8.27, d (J=2.0 Hz), 1H, H3'; 8.66, m, 1H, H6.

(B) Preparation of 6-cyano-2-(pyridin-2'-yl)indole

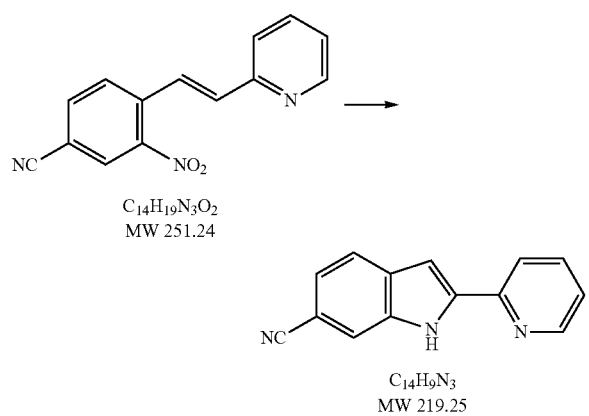

The (E)-2-(4'-cyano-2'-nitrostyryl)pyridine (1.20 g, 4.78 mmol) was treated with triethyl phosphite (26 ml) and heated in a 150-160° oil-bath under nitrogen for 21 h. After cooling, excess triethyl phosphite was removed by vacuum distillation using a short-path distillation apparatus. The dark residue was treated with water (100 ml), basified with sodium carbonate solution (0.5 M, 2.5 ml) then extracted with ethyl acetate (3×100 ml). The ethyl acetate extract was washed with water (100 ml), brine (100 ml), dried (MgSO$_4$) and evaporated to give a dark oil. Trituration with hexane (5×8 ml) removed traces of triethyl phosphite affording a viscous dark oil (0.97 g) that was taken up in dichloromethane (10 ml), applied to a plug of alumina (40×50 mm) and eluted with dichloromethane, then 99:1 dichloromethane/methanol. Appropriate fractions (TLC) were combined and the material recrystallized from methanol to give 6-cyano-2-(pyridin-2'-yl)indole (323 mg, 31%) as a light brown powder, mp 199-201° C. Additional material was obtained from the hexane supernatants, which precipitated on standing, as well as from the recrystallization filtrate after passage through silica gel and elution with chloroform, to give a total yield of 529 mg (50%).

$^1$H nmr (500 MHz, d$_6$-dmso) δ 7.30, dd (J=1.0, 2.5 Hz), 1H, H3; 7.33, dd (J=1.5, 8.5 Hz), 1H, H5; 7.39, ddd (J=1.0, 5.0, 7.5 Hz), 1H, H5'; 7.75, d (J=8.0 Hz), 1H, H4; 7.86, m, 1H, H7; 7.92, dt (J=2.0, 8.0 Hz), 1H, H4'; 8.08, dt (J=8.0, 1.0 Hz), 1H, H3'; 8.68, ddd (J=1.0, 2.0, 5.0 Hz), 1H, H6'; 12.22, s, 1H, 1-NH. $^{13}$C nmr (125 MHz, d$_6$-dmso) δ 101.2, C3; 103.6, C6; 116.9, C7; 120.8, CN; 120.9, C3'; 122.0, C4; 122.2, C5,; 123.5, C5; 131.8, C3a; 136.0, C7a; 137.5, C4'; 141.2, C2; 149.5, C2'; 149.6, C6'. MS (ESI+ve) m/z 220 (MH$^+$, 100%). HRMS (ESI+ve) m/z 220.08693, C$_{14}$H$_{10}$N$_3$ requires 220.08692 (Δ=0.1 ppm).

(C) Preparation of Ethyl 2-(pyridin-2'-yl)indole-6-carboximidate hydrochloride

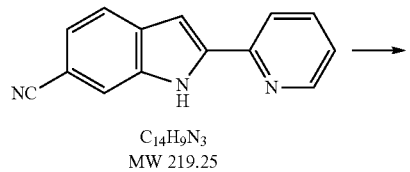

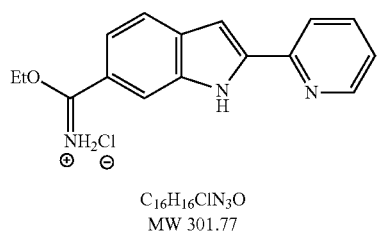

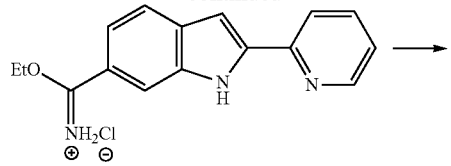

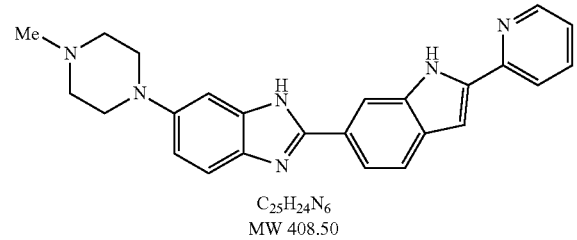

6-Cyano-2-(pyridin-2'-yl)indole (0.385 g, 1.76 mmol) was suspended in dry ethanol (50 ml) and a stream of dry HCl gas bubbled through the mixture with stirring. Shortly after the HCl was introduced the suspended solid dissolved prior to the formation of a new heavy precipitate, which was accompanied by a temperature rise in the reaction mixture to 35° C. After 3 h the gas inlet was replaced with a calcium chloride drying tube and the reaction mixture stirred overnight. The HCl gas stream was re-introduced into the reaction mixture for 3 h before again replacing the gas inlet with a drying tube and stirring overnight. Dry diethyl ether (50 ml) was then added to the mixture and stirring continued for 15 min before the solid was filtered under nitrogen. The collected solid was washed with dry diethyl ether (20 ml) and dried under vacuum to give ethyl 2-(pyridin-2'-yl)indole-6-carboximidate hydrochloride (0.525 g, 99%) as a yellow powder, mp 270° C. (dec).

$^1$H nmr (400 MHz, $d_6$-dmso) δ 1.51, t (J=7.0 Hz), 3H, OEt; 4.66, q (J=6.9 Hz), 2H, OEt; 7.41;,d (J=1.2 Hz), 1H, H3; 7.47, ddd (J=1.2, 4.8, 7.6 Hz), 1H, H5'; 7.77, dd (J=1.8, 8.6 Hz), 1H, H5; 7.81, d (J=8.4 Hz), 1H, H4; 8.01, dt (J=1.6, 7.8 Hz), 1H, H4'; 8.20, d (J=8.0 Hz), 1H, H3'; 8.25, br s, 1H, H7; 8.71, br d (J=4.0 Hz), 1H, H6'; 11.04, br, 1H, 1-NH or C=NH$_2$$^+$; 11.79, br, 1H, 1-NH or C=NH$_2$$^+$; 12.62, br, 1H, 1-NH or C=NH$_2$$^+$. MS (ESI+ve) m/z 266 (M-Cl$^+$, 100%). HRMS (ESI+ve) m/z 266.12878, $C_{16}H_{16}N_3O$ requires 266.12879 (Δ=0.04 ppm).

(D) Preparation of 2-(6'-(5''-(4'''-methylpiperazin-1'''-yl)benzimidazol-2''-yl)indol-2'-yl)pyridine

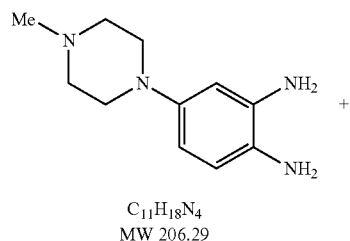

To a solution of the crude 2-amino-4-(4'-methylpiperazin-1'-yl)aniline (see Example 30B(i) for preparation) (61 mg, 0.29 mmol) in 2:1 ethanol/acetic acid (6 ml) was added ethyl 2-(pyridin-2'-yl)indole-6-carboximidate hydrochloride (91 mg, 0.30 mmol) and the red mixture heated under nitrogen in a 100° C. oil bath for 17 h. The reaction mixture was then cooled, the solvents removed by rotary evaporator and the residue treated with dilute ammonia solution (2.7 M, 10 ml). The resulting yellow suspension was centrifuged, the supernatant removed and the residue then treated with dilute ammonia (2.7 M, 5 ml), acetonitrile (2×5 ml) and diethyl ether (2×5 ml), with centrifugation and removal of the supernatant after each treatment. The resulting solid was dried under vacuum to give 2-(6'-(5''-(4'''-methylpiperazin-1'''-yl)benzimidazol-2''-yl)indol-2'-yl)pyridine (93 mg, 78%) as a light tan powder, mp 245-247° C.

$^1$H nmr (500 MHz, $d_4$-MeOH+5 drops d-TFA) δ 3.00, s, 3H, 4'''-MeN; 3.20, t (J=12.1 Hz), 2H, NCH$_2$; 3.33, m (obs), NCH$_2$; 3.68, d (J=12.2 Hz), 2H, NCH$_2$; 3.94, d (J=13.2 Hz), 2H, NCH$_2$; 7.30, d (J=2.0 Hz), 1H, H4''; 7.38, dd (J=2.3, 9.2 Hz), 1H, H6''; 7.52, d (J=0.7 Hz), 1H, H3'; 7.70, d (J=9.0 Hz), 1H, H7''; 7.76, ddd (J=1.2, 5.6, 7.6 Hz), 1H, H5; 7.79, dd (J=1.7, 8.6 Hz), 1H, H5'; 7.98, dd (J=0.6, 8.4 Hz), 1H, H4'; 8.32, m, 1H, H7'; 8.34, dt (J=8.1, 1.0 Hz), 1H, H3; 8.41, dt (J=1.6, 8.0 Hz), 1H, H4; 8.77, ddd (J=0.7, 1.7, 5.6 Hz), 1H, H6. $^{13}$C nmr (125 MHz, $d_4$-MeOH+4 drops HOAc) δ 43.6, 4'''-MeN; 49.2, C2'''/6'''; 54.6, C3'''/5'''; 102.2, C3' and C4'' (overlap); 111.8, C7'; 115.8, C7''; 117.3, C6''; 119.4, C5'; 121.6, C3; 121.8, C6'; 122.7, C4'; 123.8, C5; 132.65, 132.69; C3a' and C7a''; 138.0, C3a''; 138.4, C4 and C7a' (overlap); 141.3, C2'; 149.0, C5''; 150.4, C6; 151.4, C2; 153.4, C2''. MS (ESI+ve) m/z 817 (M$_2$H$^+$, 12%), 409 (MH$^+$, 100). HRMS (ESI+ve) m/z 409.21387, $C_{25}H_{25}N_6$ requires 409.21352 (Δ=0.9 ppm).

Cytotoxicity and Radioprotection Results

C50=19.8

PF=22.8

DMFm=2.20

DMF10=2.09

Example 32

Preparation of 2-(5'-methoxy-6'-(5"-(4"'-methylpiperazin-1"'-yl)benzimidazol-2"-yl)benzimidazol-2'-yl)pyridine

(A) Preparation of Methyl 4-acetamido-2-methoxybenzoate

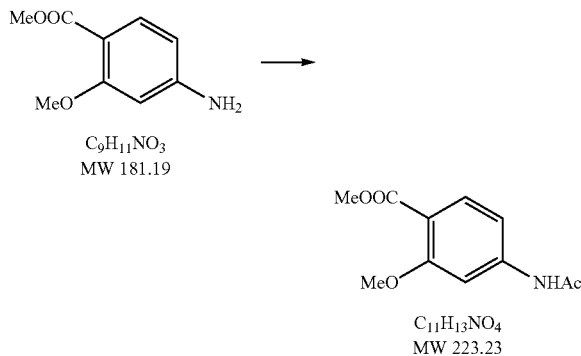

To a solution of methyl 4-amino-2-methoxybenzoate (501 mg, 2.77 mmol) in ethanol (8 ml) was added acetic anhydride (0.42 ml, 4.44 mmol, 1.6 eq) and the clear solution heated at 60-65° C. for 2 h. After cooling to room temperature the solvent was removed by rotary evaporator and the residue treated with water (10 ml) and saturated sodium bicarbonate solution (10 ml) before extracting with ethyl acetate (20 ml, 2×10 ml). The combined ethyl acetate extract was washed with water, then brine, dried (MgSO$_4$) and evaporated to give methyl 4-acetamido-2-methoxybenzoate (545 mg, 88%) as a white solid.

$^1$H nmr$^1$ (400 MHz, d$_6$-dmso) δ 2.07, s, 3H, 4-AcNH; 3.74, s, 3H, 2-OMe or COOMe; 3.77, s, 3H, COOMe or 2-Ome; 7.19, br d (J=8.8 Hz), 1H, H5; 10.22, s, 1H, NH.
Ref. 17: *J. Med. Chem.* 2007, 50(15), 3561-3572.

(B) Preparation of Methyl 4-acetamido-2-methoxy-5-nitrobenzoate

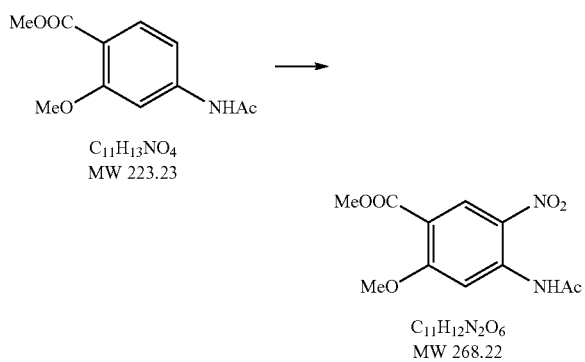

To methyl 4-acetamido-2-methoxybenzoate (299 mg, 1.34 mmol) in acetic anhydride (3 ml) stirred under nitrogen at −10° C. was added concentrated nitric acid (0.35 ml) dropwise. After then stirring at 0° C. for 10 min the reaction mixture was partitioned between ethyl acetate (20 ml) and water (20 ml). The aqueous layer was further extracted with ethyl acetate (2×10 ml) and the combined organic extract washed with saturated sodium bicarbonate solution (2×10 ml), brine (2×10 ml), dried (MgSO$_4$) and evaporated to give methyl 4-acetamido-2-methoxy-5-nitrobenzoate (301 mg, 84%) as a dull orange powder.

$^1$H nmr (400 MHz, CDCl$_3$) δ 2.33, s, 3H, AcNH; 3.91, s, 3H, 2-MeO or COOMe; 4.03, s, 3H, COOMe or 2-MeO; 8.63, s, 1H, H3 or H6; 8.84, s, 1H, H6 or H3; 10.89, br, NH.

(C) Preparation of Ethyl 4-amino-2-methoxy-5-nitrobenzoate

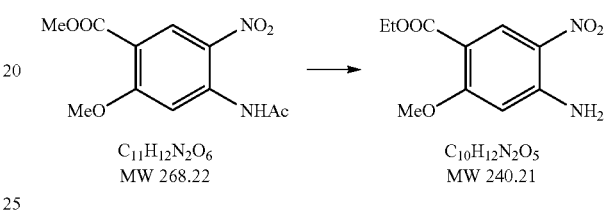

To a solution of methyl 4-acetamido-2-methoxy-5-nitrobenzoate (135 mg, 0.50 mmol) in ethanol 10 ml) was added concentrated hydrochloric acid (0.5 ml) dropwise and the mixture refluxed under nitrogen overnight. The reaction mixture was then cooled, the solvents removed and the residue purified by column chromatography (silica gel), eluting with 1:1 ethyl acetate/hexane to give ethyl 4-amino-2-methoxy-5-nitrobenzoate as a yellow solid (110 mg, 91%).

$^1$H nmr (500 MHz, d$_6$-dmso) δ 1.27, t (J=7.0 Hz), 3H, COOEt; 3.82, s, 3H, 2-MeO; 4.21, q (J=7.0 Hz), 2H, COOEt; 6.53, s, 1H, H3; 7.83, br s, 2H, 4-NH$_2$; 8.47, s, 1H, H6. $^{13}$C nmr (125 MHz, d$_6$-dmso) δ 14.2, OEt; 56.1, 2-MeO; 60.2, OEt; 98.7, C3; 108.8, C1; 124.2, 131.2, C5, C6; 150.1, C4; 163.2, 163.4, C2, C=O. MS (ESI+ve) m/z 263 (MNa$^+$, 100%). HRMS (ESI+ve) m/z 263.0638, C$_{10}$H$_{12}$N$_2$NaO$_5$ requires 263.0638 (Δ=0 ppm).

(D) Preparation of Ethyl 4,5-diamino-2-methoxybenzoate

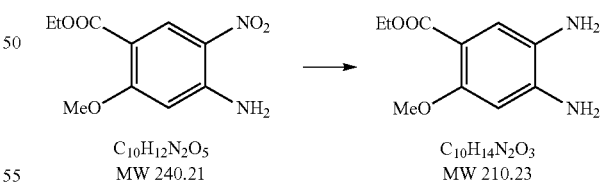

To a solution of ethyl 4-amino-2-methoxy-5-nitrobenzoate (248 mg, 1.03 mmol) in methanol (20 ml) was added 5% palladium on activated carbon (85 mg) and the mixture stirred vigorously at room temperature under a hydrogen atmosphere for 18 h. The reaction mixture was then filtered through celite, the catalyst/residue washed with methanol and the combined filtrate and washings concentrated to give crude ethyl 4,5-diamino-2-methoxybenzoate (220 mg, 100%) as a dark-brown material, which was used in the next step without further purification.

¹H nmr (400 MHz, CDCl₃) δ 1.35, t (J=7.0 Hz), 3H, COOEt; 3.82, s, 3H, 2-MeO; 4.29, q (J=7.1 Hz), 2H, COOEt; 6.29, s, 1H, H3; 7.33, s, 1H, H6.

(E) Preparation of Ethyl 6-methoxy-2-(pyridin-2'-yl)benzimidazole-5-carboxylate

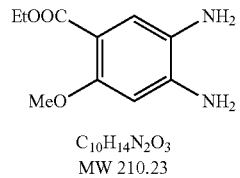

C₁₀H₁₄N₂O₃
MW 210.23

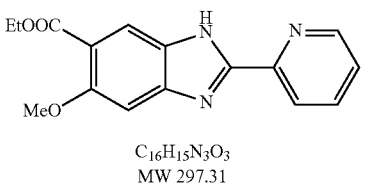

C₁₆H₁₅N₃O₃
MW 297.31

2-Cyanopyridine (161 mg, 1.55 mmol) was treated with methanolic sodium methoxide solution (0.09 M, 1.7 ml, 0.15 mmol) and stirred under nitrogen in a 50-60° C. oil-bath for 90 min. A solution of the crude diamine (220 mg, 1.03 mmol) in methanol (15 ml) and acetic acid (0.2 ml) was added and the resulting dark solution was refluxed under nitrogen for 20 h. The solvents were then removed and the residue treated with dilute ammonia solution (3 M, 10 ml) before extracting with n-butanol (2×20 ml). The organic extract was concentrated and the residue purified using column chromatography (silica gel) eluting with ethyl acetate to give ethyl 6-methoxy-2-(pyridin-2'-yl)benzimidazole-5-carboxylate (268 mg, 87%) as a light brown solid.

¹H nmr (400 MHz, d₄-MeOH+4 drops d-TFA) δ 1.33, t (J=7.2 Hz), 3H, COOEt; 3.99, s, 3H, 6-MeO; 4.36, q (J=7.2 Hz), 2H, COOEt; 7.39, s, 1H, H7; 7.70, ddd (J=0.8, 4.8, 7.6 Hz), 1H, H5'; 8.12, s, 1H, H4; 8.14, m (obs), H4'; 8.27, dt (J=8.0, 1.0 Hz), 1H, H3'; 8.88, ddd (J=1.2, 1.6, 4.6 Hz), 1H, H6'. ¹³C nmr (125 MHz, d₄-MeOH+3 drops HOAc) δ 14.6, OEt; 56.8, 6-MeO; 62.0, OEt; 97.8, br, C7; 118.3, C5; 120.8, br, C4; 122.4, 126.0, C3', C5'; 135.1, br, C3a; 138.5, C4'; 142.2, br, C7a; 148.9, C2, C2' or C6; 150.9, C6'; 154.1, 158.1, C2, C2' or C6; 168.2, C=O. MS (ESI+ve) m/z 298 (MH⁺, 100%). HRMS (ESI+ve) m/z 298.1186, C₁₆H₁₆N₃O₃ requires 298.1186 (Δ=0 ppm).

(F) Preparation of 6-methoxy-2-(pyridin-2'-yl)benzimidazole-5-carboxylic Acid

C₁₆H₁₅N₃O₃
MW 297.31

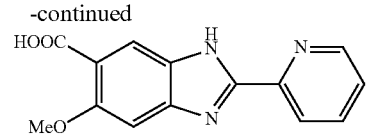

C₁₄H₁₁N₃O₃
MW 269.26

To a solution of ethyl ester (248 mg, 0.834 mmol) in ethanol (10 ml) at was added a solution of potassium hydroxide (185 mg, 3.3 mmol) in water (5 ml) and the mixture refluxed for 2 h. The ethanol was then removed under reduced pressure and the aqueous layer carefully acidified (~pH 4) with 1 M hydrochloric acid solution. The mixture was then extracted with ethyl acetate (2×20 ml), the organic extract washed with brine, dried (MgSO₄) and evaporated to give 6-methoxy-2-(pyridin-2'-yl)benzimidazole-5-carboxylic acid (167 mg, 74%) as a light orange solid.

¹H nmr (500 MHz, d₄-MeOH+4 drops d-TFA) δ 4.02, s, 3H, 6-MeO; 7.42, s, 1H, H7; 7.72, dd (J=4.5, 7.5 Hz), 1H, H5'; 8.16, dt (J=1.5, 7.8 Hz), 1H, H4', 8.23, s, 1H, H4; 8.29, dd (J=0.8, 7.8 Hz), 1H, H3'; 8.90, m, 1H, H6'.

(G) Preparation of 2-(5'-methoxy-6'-(5"-(4'''-methylpiperazin-1'''-yl)benzimidazol-2"-yl)benzimidazol-2'-yl)pyridine

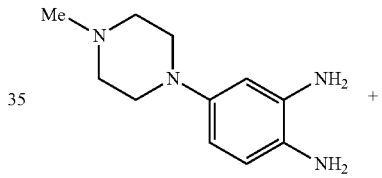

C₁₁H₁₈N₄
MW 206.29

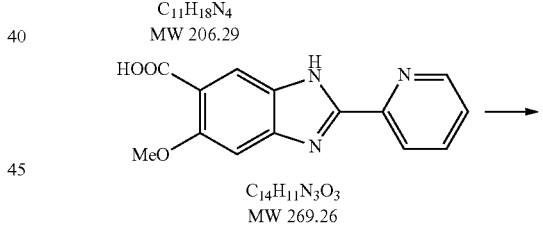

C₁₄H₁₁N₃O₃
MW 269.26

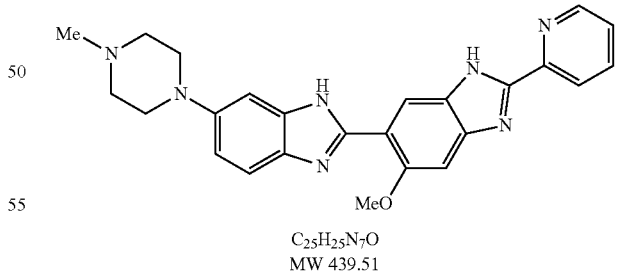

C₂₅H₂₅N₇O
MW 439.51

To 2-amino-4-(4'-methylpiperazin-1'-yl)aniline (64 mg, 0.31 mmol) was added 6-methoxy-2-(pyridin-2'-yl)benzimidazole-5-carboxylic acid (125 mg, 0.46 mmol, 1.5 eq) and the two solids intimately mixed. Polyphosphoric acid (5 g) followed by phosphorous pentoxide (0.8 g) were then added and the mixture heated under nitrogen at 180° C. for 9 h. After cooling to room temperature, water (30 ml) was added and the dark olive suspension basified to pH 8-9 using 3 M ammonia solution. The brown suspension was extracted with n-butanol (2×50 ml), the extract washed with water (2×50 ml) and evaporated to give a brown glass (101 mg). The material was subjected to column chromatography using alumina (basic, Act I, 25×200 mm) eluting with 50:3:1 ethyl acetate/methanol/triethylamine. All fractions containing significant UV absorption were combined, evaporated and the material (82 mg) applied to a short silica gel column (25×130 mm). Elution with methanol afforded 2-(5'-methoxy-6'-(5'''-(4''''-methylpiperazin-1'''-yl)benzimidazol-2''-yl)benzimidazol-2'-yl)pyridine (37 mg, 27%) as a yellow powder, mp 190-195° C.

$^1$H nmr (400 MHz, d$_4$-MeOH+4 drops d-TFA) δ 3.01, s, 3H, 4''''-MeN; 3.21, t (J=12.0 Hz), 2H, NCH$_2$; 3.35, m (obs), NCH$_2$; 3.68, d (J=12.4 Hz), 2H, NCH$_2$; 3.96, d (J=13.6 Hz), 2H, NCH$_2$; 4.23, s, 3H, 5'-MeO; 7.35, d (J=2.0 Hz), 1H, H4''; 7.44, dd (J=2.0, 9.2 Hz), 1H, H6''; 7.63, s, 1H, H4'; 7.70, ddd (J=1.2, 4.8, 7.6 Hz), 1H, H5; 7.77, d (J=9.2 Hz), 1H, H7''; 8.15, dt (J=1.6, 7.8 Hz), 1H, H4; 8.39, br d (J=8.0 Hz), 1H, H3; 8.52, s, 1H, H7'; 8.88, br d (J=4.0 Hz), 1H, H6. $^{13}$C nmr (125 MHz, d$_4$-MeOH+3 drops HOAc) δ 43.7, 4''''-MeN; 49.4, C2'''/6'''; 54.8, C3'''/5'''; 56.8, 5'-Ome; 97.9, C4'; 102.5, C4''; 113.4, C6'; 116.1, 117.6, C6'', C7''; 118.5, C7'; 122.7, C3; 126.2, C5; 132.3, C7a''; 135.8, C7a'; 137.7, C3a''; 138.6, C4; 142.3, C3a'; 148.9, 149.0; C2 and C5''; 150.3, C2', C2'' or C5'; 150.9, C6; 154.4, 156.5, C2', C2'' or C5'. MS (ESI+ve) m/z 440 (MH$^+$, 100%). HRMS (ESI+ve) m/z 440.21927, C$_{25}$H$_{26}$N$_7$O requires 440.21933 (Δ=0.1 ppm).

Cytotoxicity and Radioprotection Results
C50=112.0
PF=23.6
DMFm=1.56
DMF10=1.32

Example 33

2-(5'-(5''-(4'''-Isopropylpiperazin-1'''-yl)benzimidazol-2''-yl)benzimidazol-2'-yl)pyridine (A) Preparation of 5-(4-isopropyl-piperazin-1-yl)-2-nitro-phenylamine

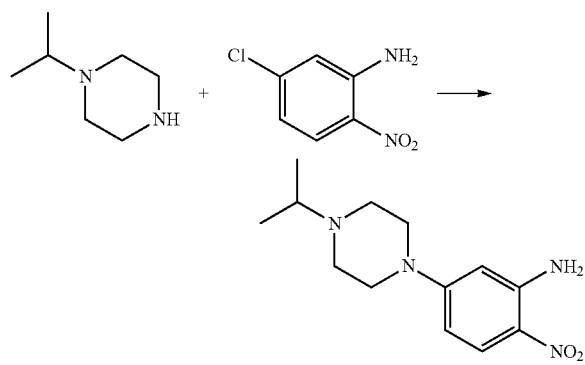

A mixture of 5-chloro-2-nitroaniline (1.35 g, 7.8 mmol), 1-isopropyl-piperazine (2.0 g, 15.6 mmol) and anhydrous potassium carbonate (1.18 g, 8.6 mmol) in N,N-dimethylacetamide (2.5 ml) was stirred at 130° C. under nitrogen for 1 day. Sample NMR analysis showed complete conversion of the starting material. The resultant mixture was then cooled to room temperature, poured onto cold water and stirred vigorously for 3 h. The resulting brown precipitate was collected by filtration, washed well with water then dried on the filter funnel. The resulting brown solid was slurried in diethyl ether, filtered, washed with additional diethyl ether, dried to afford 5-(4-Isopropyl-piperazin-1-yl)-2-nitro-phenylamine (1.1 g, 53%) and used in the next step without further purification.

$^1$H NMR (400 MHz, CDCl$_3$) δ 1.0, d (J=6.6 Hz), 6H; 2.6, m, 4H; 2.17, m, 1H; 3.3, m, 4H; 5.9, d, (J=3.54 Hz), 1H; 6.1, s (broad), 2H; 6.24, dd (J=2.3, 7.4 Hz), 1H; 7.96, d (J=10.8 Hz)

(B) Preparation of 4-[5-(4-isopropyl-piperazin-1-yl)-1H-benzoimidazol-2-yl]-2-nitro-phenylamine

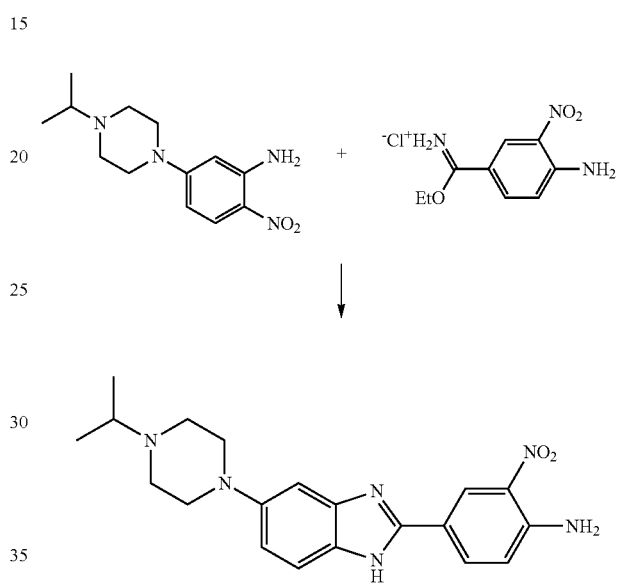

(i) Hydrogenation

To a solution of 5-(4-isopropyl-piperazin-1-yl)-2-nitrophenylamine (1.1 g, 4.2 mmol) in 1:1 acetic acid/ethanol (100 ml), under nitrogen, was added 5% palladium on activated carbon (0.32 g). The resulting mixture was evacuated and next, stirred at room temperature under an atmosphere of hydrogen for one day. The reaction mixture was then directly filtered through celite into a round bottom flask under a nitrogen atmosphere containing ethyl 4-amino-3-nitrobenzenecarboximidate hydrochloride(7) (1.02 g, 4.2 mmol), and proceeded to the coupling step.

(ii) Coupling Reaction

The resulting slurry from step (i) was heated at 80-90° C. under nitrogen for 17 h, then cooled to room temperature and the solvents removed by rotary evaporator. The resulting thick dark reddish oil was treated with dilute aqueous ammonia solution (5% in water, 20 ml), mixed vigorously and was kept overnight at 4° C. Next supernatant water was decanted and the residue was washed with additional water. The resulting solid was filtered, dried on the filter funnel, then washed with diethyl ether. This yielded the crude product as a brick red powder, 1 g (62% crude yield). This material was directly used in next step without further purification.

$^1$H NMR (400 MHz, DMSO-d6+TFA 1 drop) δ 1.25, d (J=6.6 Hz), 6H; 3.1, m, 2H; 3.19, m, 2H; 3.5, m, 3H; 3.90, m, 2H; 7.12, d (J=1.95 Hz); 7.19, d (J=8.99 Hz) 1H, 7.28, dd, (J=1.95, 7.7 Hz), 1H; 7.62, d (J=8.99 Hz), 8.3 dd (J=1.15, 7.03 Hz), 1H; 8.9 d (J=2.15 Hz), 1H.

(C) Preparation of 2-(5'-(5"-(4'''-isopropylpiperazin-1'''-yl)benzimidazol-2"-yl)benzimidazol-2'-yl)pyridine

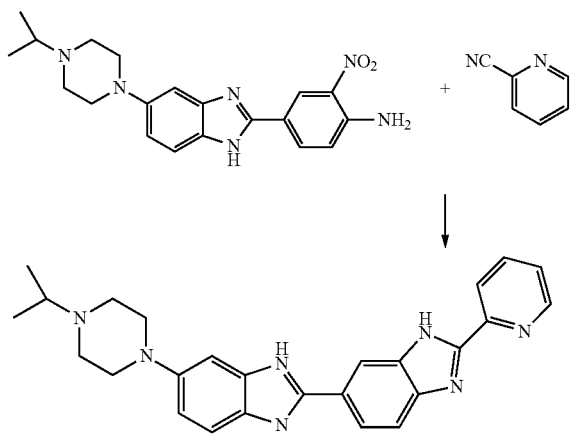

(i) Hydrogenation

To a solution of 4-[5-(4-isopropyl-piperazin-1-yl)-1H-benzoimidazol-2-yl]-2-nitro-phenylamine (500 mg, 1.3 mmol) in 4:1 ethyl acetate/methanol (50 ml) was added 5% palladium on carbon (120 mg) and the mixture was first evacuated and then stirred at room temperature under an atmosphere of hydrogen for 1 day. The reaction mixture was filtered through Celite, washed with methanol, and the combined filtrate and washings were concentrated to give the crude 4-[5-(4-isopropyl-piperazin-1-yl)-1H-benzoimidazol-2-yl]-benzene-1,2-diamine as an orange solid that was used in the next step without any purification.

(ii) Coupling Reaction

The crude 4-[5-(4-isopropyl-piperazin-1-yl)-1H-benzoimidazol-2-yl]-benzene-1,2-diamine (1.3 mmol, prepared as mentioned in (i)) was dissolved in methanol (20 ml). To this was added a solution of 2-cyanopyridine (203 mg, 1.95 mmol) that had been treated (immediately before) with sodium methoxide (0.195 mmol) in methanol (2 mL) at 40° C. for 1 hour under nitrogen. To this mixture, acetic acid (0.28 ml, 4.9 mmol) was added next.

This mixture was heated at 80° C. for a day under nitrogen followed by cooling to room temperature, and removing the solvents under reduced pressure. Next the residue treated with a 5% aqueous ammonia solution, incubated at 5° C. over two days, decanted the aqueous layer, and washed well with water. Resulting solid was filtered, washing well with water, drying on the filter funnel and then washing with acetonitrile. This yielded the product as a dark red powder 400 mg (70% yield)

MP: 188-191° C.

$^1$H NMR (400 MHz, CD$_3$OD+TFA 2 drops) δ 1.4, d (J=6.6 Hz), 6H, C(C$\underline{H}_3$)$_2$; 3.18, m, 2H, NCH$_2$; 3.34, m, 2H, NCH$_2$; 3.6, m, 3H, NCH$_2$, $\underline{H}$C(CH$_3$)$_2$; 4.0, m, 2H, NCH$_2$; 7.30, d (J=2.15 Hz), 1H; 7.4, dd (J=2.15, 6.84 Hz), 1H; 7.61, m, 1H; 7.72, d (J=9.18 Hz), 1H; 8.00, d (J=8.6 Hz), 1H; 8.04-8.14, m, 2H; 8.39, d (J=8.0 Hz), 1H; 8.52, d (J=1.5 Hz), 1H; 8.82, d (J=4.7 Hz), 1H.

$^{13}$C NMR (100 MHz, CD$_3$OD+HOAc 1 drop)

δ 15.9, 48.2, 48.4, 57.8, 101.7, 113.9, 115.3, 115.4, 115.7, 121.6, 122.0, 124.1, 124.9, 134. 2, 137.2, 138.6, 139.4, 140.3, 147.1, 147.7, 149.7, 152.3, 153.0.

Cytotoxicity and Radioprotection Results

C50=100.8

PF=17.4

DMFm=2.04

DMF10=1.87

Example 34

2-(5'-(5"-(4'''-Butylpiperazin-1'''-yl)benzimidazol-2"-yl)benzimidazol-2'-yl)pyridine (A) Preparation of 5-(4-butyl-piperazin-1-yl)-2-nitrophenylamine

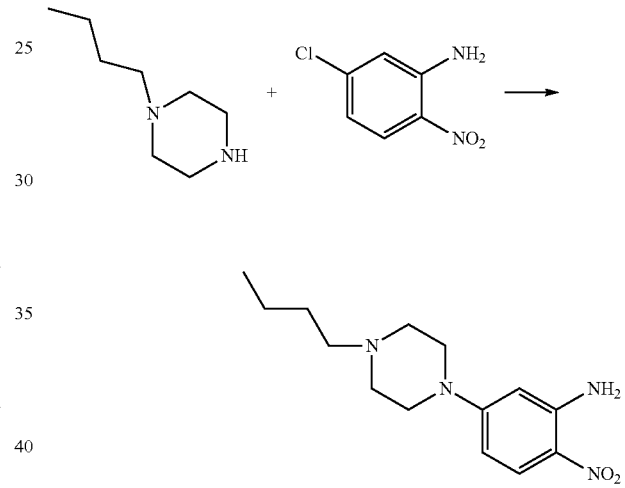

A mixture of 5-chloro-2-nitroaniline (4.05 g, 23.5 mmol), 1-n-butyl-piperazine (10.0 g, 70 mmol) and anhydrous potassium carbonate (3.6 g, 26 mmol) in N,N-dimethylacetamide (10 ml) was stirred at 130° C. under nitrogen for 1 day. Sample NMR analysis showed complete conversion of the starting material. The resultant mixture was then cooled to room temperature, poured into cold water and stirred vigorously for 3 hours. The resulting yellow brown precipitate was collected by filtration, washed well with water then dried on the filter funnel. The resulting yellow brown solid was slurried in diethyl ether, filtered, washed with additional diethyl ether, dried to afford 5-(4-butyl-piperazin-1-yl)-2-nitro-phenylamine (4.4 g, 67%) as a yellow powder, and used in the next step without further purification.

$^1$H NMR (400 MHz, CDCl$_3$) δ 0.9, t (J=7.43 Hz), 3H, C$\underline{H}_3$CH$_2$CH$_2$CH$_2$; 1.3, m, 2H, CH$_3$C$\underline{H}_2$CH$_2$CH$_2$; 1.5, m, 2H, CH$_3$CH$_2$C$\underline{H}_2$CH$_2$; 2.3, t (J=7.62 Hz), 2H, CH$_3$CH$_2$CH$_2$C$\underline{H}_2$; 3.0-3.4, m, 6H, CH$_3$CH$_2$CH$_2$C$\underline{H}_2$+2(NCH$_2$); 2.5, m, 4H, 2(NCH$_2$); 3.5, m, 4H, 2(NCH$_2$)

(B) Preparation of 4-[5-(4-butyl-piperazin-1-yl)-1H-benzoimidazol-2-yl]-2-nitro-phenylamine

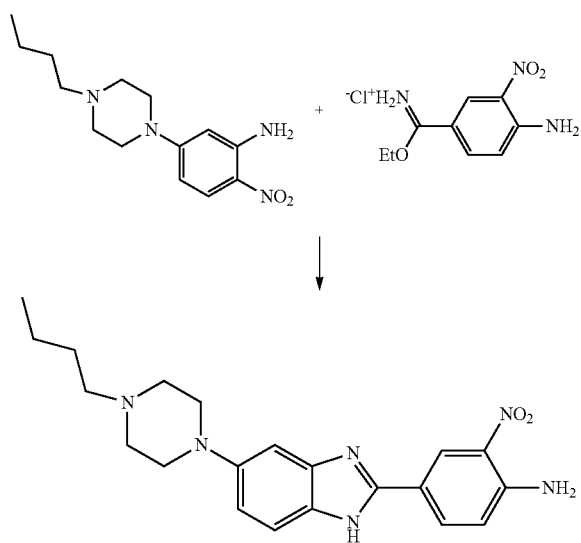

(i) Hydrogenation

To a solution of 5-(4-butyl-piperazin-1-yl)-2-nitro-phenylamine (2.0 g, 7.1 mmol) in 1:1 acetic acid/ethanol (100 ml), under nitrogen, was added 5% palladium on activated carbon (0.32 g). The resulting mixture was evacuated and next stirred at room temperature under an atmosphere of hydrogen for one day. The reaction mixture was then directly filtered through celite into a round bottom flask under a nitrogen atmosphere containing ethyl 4-amino-3-nitrobenzenecarboximidate hydrochloride(7) (1.77 g, 7.1 mmol), and proceeded to the coupling step.

(ii) Coupling Reaction

The resulting slurry from step (i) was heated at 90° C. under nitrogen for 17 h, then cooled to room temperature and the solvents removed by rotary evaporator. The resulting thick dark reddish gum was treated with dilute aqueous ammonia solution (5% in water, 20 ml), mixed vigorously and was kept over two days at 4° C. Next, supernatant water was decanted and the residue was washed with additional water. The resulting solid was filtered, dried on the filter funnel and then washed with diethyl ether. This yielded the crude product as a brick red powder, 2.45 g (87.5% crude yield). This material was directly used in next step without further purification.

$^1$H NMR (400 MHz, DMSO-d6+TFA 1 drop) δ 0.9, t (J=7.43 Hz), 3H, C$\underline{H}_3$CH$_2$CH$_2$CH$_2$; 1.3, m, 2H, CH$_3$C$\underline{H}_2$CH$_2$CH$_2$; 1.6, m, 2H, CH$_3$CH$_2$C$\underline{H}_2$CH$_2$; 3.0-3.4, m, 6H, CH$_3$CH$_2$CH$_2$C$\underline{H}_2$+N(CH$_2$)$_2$; 3.55, m, 2H, NCH$_2$; 3.85, m, 2H, NC$\underline{H}_2$; 7.1, s, 1H; 7.19, d (J=8.99 Hz) 1H; 7.26, crude dd, 1H; 7.61, d (J=8.99 Hz); 8.1 crude d, 1H; 8.9 d (J=2.15 Hz), 1H.

(C) Preparation of 2-(5'-(5''-(4'''-butylpiperazin-1'''-yl)benzimidazol-2''-yl)benzimidazol-2'-yl)pyridine

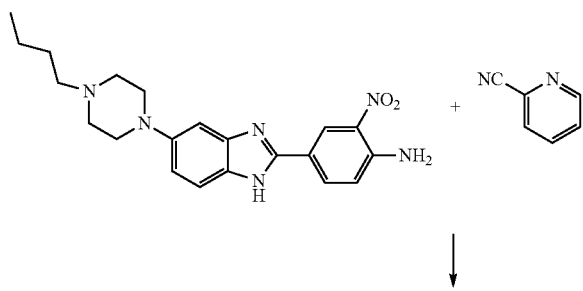

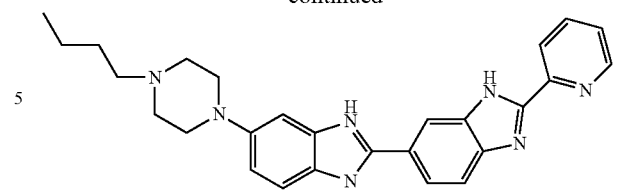

(i) Hydrogenation

To a solution of 4-[5-(4-butyl-piperazin-1-yl)-1H-benzoimidazol-2-yl]-2-nitro-phenylamine (1.0 g, 2.5 mmol) in 4:1 ethyl acetate/methanol (100 ml) under nitrogen, was added 5% palladium on carbon (120 mg) and the mixture was first evacuated and then stirred at room temperature under an atmosphere of hydrogen for 1 day. The reaction mixture was then filtered through Celite, washed with 1:1 ethyl acetate/methanol (10 mL) and the combined filtrate and washings were concentrated to give the crude 4-[5-(4-butyl-piperazin-1-yl)-1H-benzoimidazol-2-yl]-benzene-1,2-diamine as an orange solid that was used in the next step without any purification.

(ii) Coupling Reaction

The crude 4-[5-(4-butyl-piperazin-1-yl)-1H-benzoimidazol-2-yl]-benzene-1,2-diamine (2.5 mmol, prepared as mentioned in (i)) was dissolved in methanol (40 ml). To this was added a solution of 2-cyanopyridine (390 mg, 3.75 mmol) that had been treated (immediately before) with sodium methoxide (0.375 mmol) in methanol (4 mL) at 40° C. for 1 hour under nitrogen. To this mixture, acetic acid (0.537 ml, 9.4 mmol) was added.

This mixture was heated at 80° C. overnight under nitrogen followed by cooling to room temperature, and removing the solvents under reduced pressure. Next the residue treated with a 5% aqueous ammonia solution, incubated at 5° C. over two days, decanted the aqueous layer, washed well with water. Resulting red solid was filtered, washing well with water, drying on the filter funnel and then washing extensively with acetonitrile. This yielded the crude product as a brick orange powder. This was then slurried in acetonitrile (20 mL) over two days, filtered and dried to give the product as a brick orange powder 500 mg (44.6% yield).

MP (impure): 142-145° C. (dec)

$^1$H NMR (400 MHz, CD$_3$OD+TFA 2 drops) δ 1.0, t, 3H, C$\underline{H}_3$CH$_2$CH$_2$CH$_2$; 1.4, m, 2H, CH$_3$C$\underline{H}_2$CH$_2$CH$_2$; 1.8, m, 2H, CH$_3$CH$_2$C$\underline{H}_2$CH$_2$; 3.2-3.3, m, 6H, CH$_3$CH$_2$CH$_2$C$\underline{H}_2$+N(CH$_2$)$_2$; 3.7, m, 2H, NCH$_2$; 3.9, m, 2H, NCH$_2$; 7.30, d (J=2.15 Hz), 1H; 7.4, dd (J=2.35, 6.84 Hz), 1H; 7.69-7.74, m, 2H; 8.10, d (J=8.8 Hz), 1H; 8.15 dt (J=1.76 Hz, 6.25 Hz), 1H; 8.24, dd (J=1.6, 7.04 Hz), 1H; 8.4, d (J=7.82 Hz), 1H; 8.63, m, 1H; 8.88, d (J=4.9 Hz), 1H.

$^{13}$C NMR (100 MHz, CD$_3$OD+HOAc 1 drop): δ 12.7, 19.7, 26.0, 52.1, 56.7, 102.1, 114.4, 115.3, 115.5, 119.7, 121.6, 122.1, 123.9, 124.6, 125.0, 132.9, 134.5, 137.4, 139.3, 147.2, 147.8, 149.7, 152.7, 153.1

Cytotoxicity and Radioprotection Results

C50=47.0

PF=27.6

DMFm=2.27

DMF10=2.05

Example 35

2-(5'-(5''-(2'''-methoxyethylamino)benzimidazol-2''-yl)benzimidazol-2'-yl)pyridine (A) Preparation of N¹-(2-methoxy-ethyl)-4-nitro-benzene-1,3-diamine

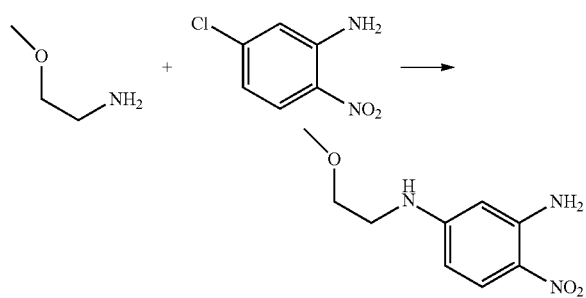

A mixture of 5-chloro-2-nitroaniline (21.6 g, 125 mmol), 2-Methoxy-ethylamine (28.1 g, 375 mmol) and anhydrous potassium carbonate (18.9 g, 137 mmol) in N,N-dimethylacetamide (40 ml) was stirred at 135° C. under nitrogen for 2 days. Sample NMR analysis showed complete conversion of the starting material. The resultant mixture was then cooled to room temperature, poured into cold water and stirred vigorously for 30 minutes The resulting precipitate was collected by filtration, washed well with water then dried on the filter funnel. The resulting solid was slurried in diethyl ether, filtered, washed with additional diethyl ether, dried to afford N¹-(2-methoxy-ethyl)-4-nitro-benzene-1,3-diamine (16 g, 61%) as a yellow-orange powder, and used in the next step without further purification.

¹H NMR (400 MHz, CDCl₃) δ 3.27, dd (J=5.3, 5.3 Hz), 2H; 3.56, t (J=5.1 Hz), 2H; 5.65, d, (J=2.35 Hz), 1H; 5.92, dd (J=2.4, 7.0 Hz), 1H; 6.1, s (broad), 2H; 7.91, d (J=9.4 Hz)

(B) Preparation of [2-(4-amino-3-nitro-phenyl)-1H-benzoimidazol-5-yl]-(2-methoxy-ethyl)-amine

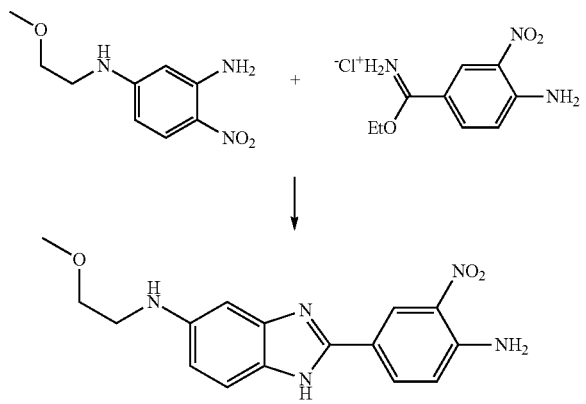

(i) Hydrogenation

To a solution of N¹-(2-methoxy-ethyl)-4-nitro-benzene-1,3-diamine (1.25 g, 5.9 mmol) in 1:2 acetic acid/ethanol (50 ml), under nitrogen, was added 5% palladium on activated carbon (0.20 g). The resulting mixture was evacuated and next stirred at room temperature under an atmosphere of hydrogen for one day. The reaction mixture was then directly filtered through celite into a round bottom flask. Of this solution, 40 mL (containing approximately 4.7 mmol of the reduced material) was transferred under a nitrogen atmosphere to a flask containing ethyl 4-amino-3-nitrobenzenecarboximidate hydrochloride(7) (1.16 g, 4.7 mmol), and proceeded to the coupling step.

(ii) Coupling Reaction

The resulting slurry from step (i) was heated at 90° C. under nitrogen for 17 h, then cooled to room temperature and the solvents removed by rotary evaporator. The resulting thick dark reddish gum was treated with dilute aqueous ammonia solution (5% in water, 50 ml), mixed vigorously and was kept over two days at 4° C. Next, supernatant water was decanted and the residue was washed with additional water. The resulting solid was filtered, dried on the filter funnel and then washed with diethyl ether. This yielded the crude product as a dark red powder, 1.1 g (72% crude yield). This material was directly used in next step without further purification.

¹H NMR (400 MHz, DMSO-d6+TFA 1 drop) δ 3.3, crude t, 2H; 3.48, crude t, 2H; 7.03, s 1H; 7.06, d (J=8.8 Hz), 1H; 7.16, d, (J=8.9 Hz), 1H; 7.52, d (J=8.8 Hz), 8.0 dd (J=1.6, 7.4 Hz), 1H; 8.85 d (J=1.8 Hz), 1H.

(C) Preparation of 2-(5'-(5''-(2'''-methoxyethylamino)benzimidazol-2''-yl)benzimidazol-2'-yl)pyridine

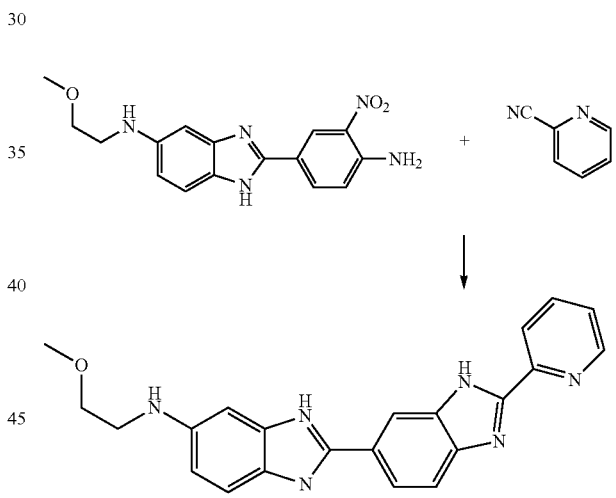

(i) Hydrogenation

To a solution of [2-(4-amino-3-nitro-phenyl)-1H-benzoimidazol-5-yl]-(2-methoxy-ethyl)-amine (0.5 g, 1.5 mmol) in 4:1 ethyl acetate/methanol (50 ml) under nitrogen, was added 5% palladium on carbon (120 mg) and the mixture was first evacuated and then stirred at room temperature under an atmosphere of hydrogen for 1 day. The reaction mixture was then filtered through Celite, washed with 1:1 ethyl acetate/methanol (10 mL), and the combined filtrate and washings were concentrated to give the crude 4-[5-(2-methoxy-ethylamino)-1H-benzoimidazol-2-yl]-benzene-1,2-diamine which was used in the next step without any purification.

(ii) Coupling Reaction

The crude 4-[5-(2-methoxy-ethylamino)-1H-benzoimidazol-2-yl]-benzene-1,2-diamine (1.5 mmol, prepared as mentioned in (i)) was dissolved in methanol (20 ml). To this was added a solution of 2-cyanopyridine (238 mg, 2.29 mmol)

that had been treated (immediately before) with sodium methoxide (0.229 mmol) in methanol (3 mL) at 40° C. for 1 hour under nitrogen. To this mixture, acetic acid (0.327 ml, 5.7 mmol) was added.

This mixture was heated at 80° C. overnight under nitrogen followed by cooling to room temperature, and removing the solvents under reduced pressure. Next the residue treated with a 5% aqueous ammonia solution, decanted the aqueous layer, washed well with water through decantation. Resulting black semi-solid was dried under reduced pressure, stirred with acetonitrile (5 mL) and filtered the resulting solid. This solid was again slurried in acetonitrile (10 mL) overnight, filtered and dried to the product as a brown powder, 200 mg (34% isolated yield).

MP: 220-225° C.

$^1$H NMR (400 MHz, CD$_3$OD+TFA 2 drops) δ 3.31, t (J=5.47 Hz), 2H, NCH$_2$; 3.57, t (J=5.47 Hz), 2H, OCH$_2$; 6.86, d (J=1.76 Hz), 1H; 6.96, dd (J=2.15, 6.84 Hz), 1H; 7.46, d (J=8.8 Hz), 1H; 7.5, crude dd, 1H; 7.87, d (J=8.6 Hz), 1H; 7.9-7.96, m, 2H; 8.24, d (J=5.9 Hz), 1H; 8.28, d (J=1.4 Hz), 1H; 8.7, d (J=8.0 Hz), 1H.

$^{13}$C NMR (100 MHz, CD$_3$OD+HOAc 1 drop): δ 44.0, 48.0, 70.9, 94.4, 113.4, 114.0, 115.2, 115.8, 121.6, 121.8, 122.6, 125.1, 128.5, 130.1, 137.3, 138.2, 146.7, 147.4, 149.7, 150.2, 153.3 (one aromatic peak overlapping or too weak).

Cytotoxicity and Radioprotection Results

C50=125.7
PF=21.9
DMFm=2.19
DMF10=1.66

Example 36

2-(5'-(5''-thiomorpholinobenzimidazol-2''-yl)benzimidazol-2'-yl)pyridine (A) Preparation of 2-nitro-5-thiomorpholin-4-yl-phenylamine

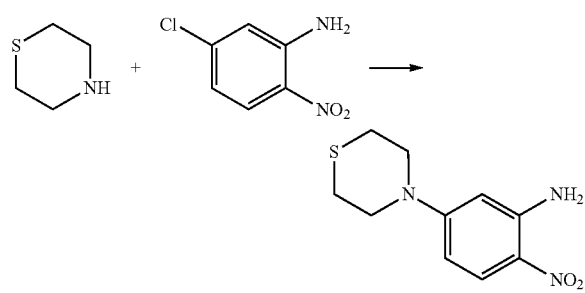

A mixture of 5-chloro-2-nitroaniline (5.6 g, 32 mmol), thiomorpholine (10.0 g, 97 mmol) and anhydrous potassium carbonate (4.98 g, 36 mmol) in N,N-dimethylacetamide (10 ml) was stirred at 135° C. under nitrogen for 1 day. Sample NMR analysis showed complete conversion of the starting material. The resultant mixture was then cooled to room temperature, poured into cold water and stirred vigorously for 3 hours. The resulting brown precipitate was collected by filtration, washed well with water then dried on the filter funnel. The resulting brown solid was washed with diethyl ether, filtered, washed with additional diethyl ether, dried to afford 2-Nitro-5-thiomorpholin-4-yl-phenylamine (7.0 g, 91.5%) as a brown powder, and used in the next step without further purification.

$^1$H NMR (400 MHz, CDCl$_3$) δ 2.6, m, 4H; 3.75 m, 4H; 5.95, d, (J=2.34 Hz), 1H; 6.1, s (broad), 2H; 6.18, dd (J=2.3, 7.3 Hz), 1H; 7.98, d (J=9.6 Hz)

(B) Preparation of 2-Nitro-4-(5-thiomorpholin-4-yl-1H-benzoimidazol-2-yl)-phenylamine

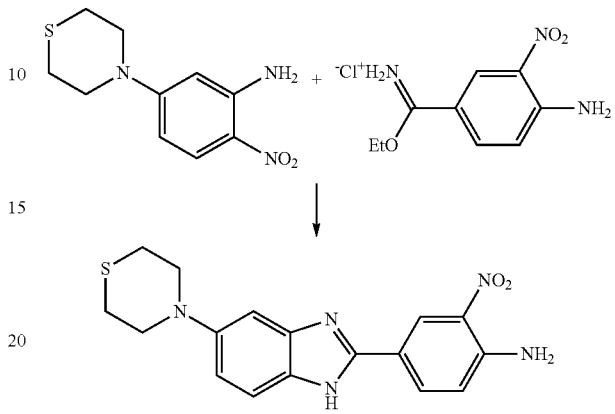

(i) Hydrogenation

To a solution of 2-Nitro-5-thiomorpholin-4-yl-phenylamine (2.0 g, 8.4 mmol) in 1:1 acetic acid/ethanol (100 ml), under nitrogen, was added 5% palladium on activated carbon (0.32 g). The resulting mixture was evacuated and next stirred at room temperature under an atmosphere of hydrogen for one day. The reaction mixture was then directly filtered through celite into a round bottom flask under a nitrogen atmosphere containing ethyl 4-amino-3-nitrobenzenecarboximidate hydrochloride (7) (2.0 g, 8.1 mmol), and proceeded to the coupling step.

(ii) Coupling Reaction

The resulting slurry from step (i) was heated at 90° C. under nitrogen for 17 h, then cooled to room temperature and the solvents removed by rotary evaporator. The resulting thick dark reddish oil was treated with dilute aqueous ammonia solution (5% in water, 20 ml), mixed vigorously and was kept over two days at 4° C. Next, supernatant water was decanted and the residue was washed with additional water. The resulting solid was filtered, dried on the filter funnel and then washed with diethyl ether. This yielded the crude product as a dark red powder, 2.0 g (66.9% crude yield). This material was directly used in next step without further purification.

$^1$H NMR (400 MHz, DMSO+TFA 1 drop) δ 3.15, m, 4H; 3.5, m, 4H; 7.04, s 1H; 7.18, d (J=9.2 Hz), 1H; 7.23, dd (J=1.85, 7.2 Hz), 1H; 7.57, d (J=8.9 Hz), 8.0 dd (J=2.1, 7.0 Hz), 1H; 8.89 d (J=2.15 Hz), 1H.

(C) Preparation of 2-(5'-(5''-thiomorpholinobenzimidazol-2''-yl)benzimidazol-2'-yl)pyridine

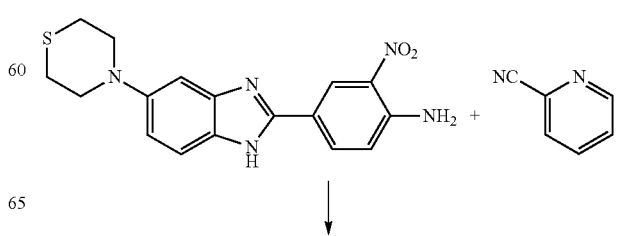

-continued

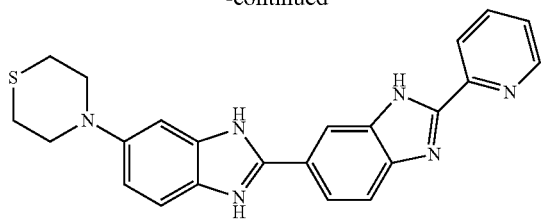

(i) Hydrogenation

To a solution of 2-nitro-4-(5-thiomorpholin-4-yl-1H-benzoimidazol-2-yl)-phenylamine (1.0 g, 2.8 mmol) in 4:1 ethyl acetate/methanol (80 ml) under nitrogen, was added 5% palladium on carbon (240 mg) and the mixture was first evacuated and then stirred at room temperature under an atmosphere of hydrogen for 1 day. The reaction mixture was then filtered through Celite, washed with 1:1 ethyl acetate/methanol (10 mL), and the combined filtrate and washings were concentrated to give the crude 4-(5-thiomorpholin-4-yl-1H-benzoimidazol-2-yl)-benzene-1,2-diamine as a red oil that was used in the next step without any purification.

(ii) Coupling Reaction

The crude 4-(5-thiomorpholin-4-yl-1H-benzoimidazol-2-yl)-benzene-1,2-diamine (2.5 mmol, prepared as mentioned in (i)) was dissolved in methanol (40 ml). To this was added a solution of 2-cyanopyridine (427 mg, 4.2 mmol) that had been treated (immediately before) with sodium methoxide (0.42 mmol) in methanol (4 mL) at 40° C. for 1 hour under nitrogen. To this mixture acetic acid (0.6 ml, 10.5 mmol) was added.

This mixture was heated at 80° C. overnight under nitrogen followed by cooling to room temperature, and removing the solvents under reduced pressure. Next the residue treated with a 5% aqueous ammonia solution (60 mL), and after 30 minute decanted the aqueous layer as the oil solidified.

This solid was washed well with water, filtered, washing well with water, drying on the filter funnel and then washing extensively with acetonitrile. Drying this yielded the product as a brick orange powder, 900 mg (77.6% yield)

MP: 187-193° C.

$^1$H NMR (400 MHz, CD$_3$OD+TFA 2 drops) δ 2.9, m, 4H, S(CH$_2$)$_2$; 3.7, m, 4H, N(CH$_2$)$_2$; 7.48-7.54, m, 2H; 7.70, m, 1H; 7.77, dd (J=0.58, 8.4 Hz), 1H; 8.00, dd (J=0.58, 8.0 Hz), 1H; 8.15, dt (J=1.76, 7.25 Hz), 1H; 8.24 dd (J=1.56, 7.03 Hz), 1H; 8.4, d (J=7.81 Hz), 1H; 8.61, m, 1H; 8.89, m, 1H.

$^{13}$C NMR (100 MHz, CD$_3$OD+HOAc 1 drop): δ 27.0, 54.0, 101.9, 113.9, 115.1, 115.7, 116.7, 121.6, 121.9, 123.7, 124.9, 128.8, 133.3, 137.3, 138.1, 139.5, 140.4, 147.7, 149.7, 151.7, 153.1

Cytotoxicity and Radioprotection Results

C50=31.3

PF=16.4

DMFm=1.53

DMF10=1.49

Example 37

2-(5'-(5"-(4'''-(dimethylcarbamoyl)piperazin-1'''-yl)benzimidazol-2"-yl)benzimidazol-2'-yl)pyridine (A) Preparation of 4-(3-amino-4-nitro-phenyl)-piperazine-1-carboxylic acid tert-butyl ester

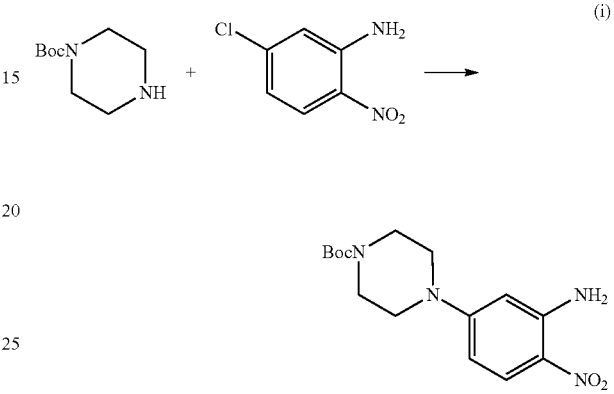

A mixture of 5-chloro-2-nitroaniline (5.0 g, 29 mmol), piperazine-1-carboxylic acid tert-butyl ester (17 g, 9.1 mmol) and anhydrous potassium carbonate (4.4 g, 32 mmol) in N,N-dimethylacetamide (20 ml) was stirred at 120° C. under nitrogen for 2 days. Sample NMR analysis showed almost complete conversion of the starting material. The resultant mixture was then cooled to room temperature, poured into cold water (50 mL) and stirred vigorously for 2 hours. The resulting yellow precipitate was collected by filtration, washed well with water then dried on the filter funnel. The resulting yellow brown solid was slurried in diethyl ether, filtered, washed with additional diethylether, dried to afford 4-(3-Amino-4-nitro-phenyl)-piperazine-1-carboxylic acid tert-butyl ester (8.0 g, 85.7%) as a yellow powder, and used in the next step without further purification.

$^1$H NMR (400 MHz, CDCl$_3$) δ 1.4, s, 9H; 3.3, m, 4H; 3.45, m, 4H; 5.9, d (J=2.35 Hz), 1H; 6.15, s (broad), 2H; 6.22, dd (J=2.54, 7.23 Hz), 1H; 8.0, d (J=9.57 Hz), 1H

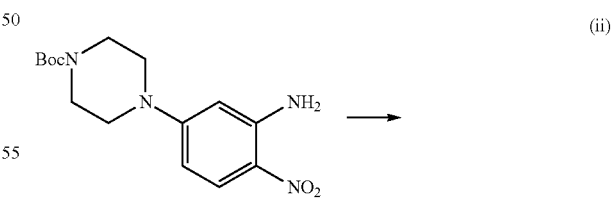

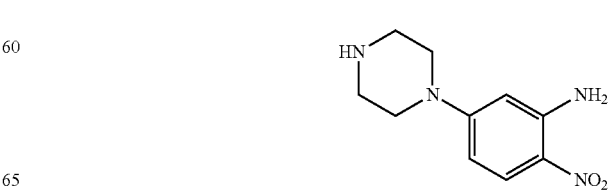

4-(3-Amino-4-nitro-phenyl)-piperazine-1-carboxylic acid tert-butyl ester (40.0 g, 120 mmol) was dissolved in dichloromethane (500 mL) and to this was added trifluoroacetic acid (123 g, 1.08 mol) slowly. Following overnight stirring, the mixture was poured into a beaker, cooled in ice and was treated with sodium hydroxide (43.2 g, 1.08 mol) dissolved in water (100 mL) slowly resulting in the precipitating out of some of the product. The mixture was stirred for 30 minutes. Filtering and drying the solid yieldede 13 g of product.

From the mother liquor, organic layer was separated and the aqueous layer was extracted with dichloromethane (3×100 mL). The combined organic layers were dried and evaporated to give 9 g of additional product. Combined solids gave the product, 2-nitro-5-piperazin-1-yl-phenylamine, 22 g, 82.5% yield.

$^1$H NMR (400 MHz, CDCl$_3$) δ 2.6, m, 4H; 3.1, m, 4H; 6.1, s, 1H; 6.25, d (J=8.99 Hz), 1H; 6.12, s (broad), 2H; 8.0, d (J=9.57 Hz), 1H

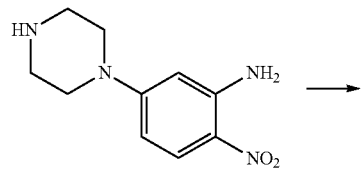

(iii)

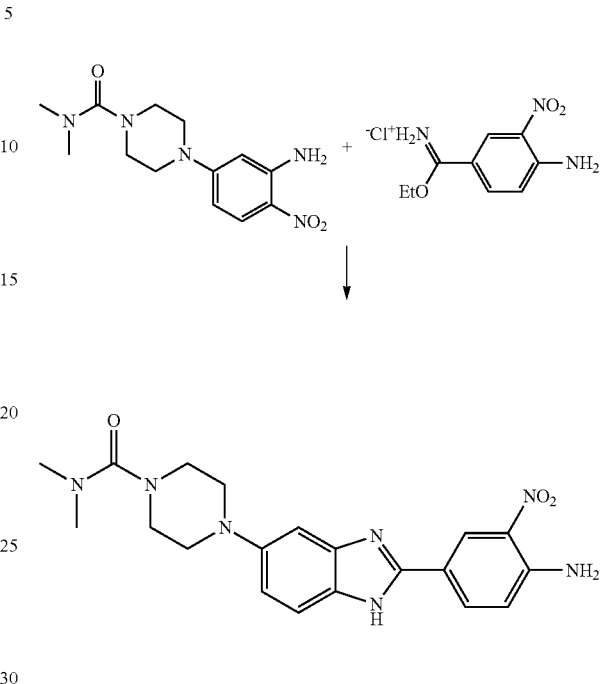

Under a nitrogen atmosphere, triethylamine (0.546 g, 5.4 mmol) was added to 2-nitro-5-piperazin-1-yl-phenylamine (1.0 g, 4.5 mmol) in dry DMF (8 mL) and the mixture was cooled in an ice water bath. Dimethylcarbamyl chloride (0.581 g, 5.4 mmol) was added slowly to this reaction mixture via syringe and the mixture was brought up to room temperature and stirred overnight. After overnight stirring, the reaction mixture was slowly poured into cold water (100 mL) and stirred for 1 hour resulting in the solidification of the product. This was filtered, dried give the product, 4-(3-Amino-4-nitro-phenyl)-piperazine-1-carboxylic acid dimethylamide, as a yellow solid, 1.2 g (92.4% yield), which was used without any further purification.

$^1$H NMR (400 MHz, CDCl$_3$) δ 2.8, s, 6H; 3.35, s, 8H; 5.9, d (J=2.74 Hz), 1H; 6.12, s (broad), 2H; 6.22, dd (J=2.54, 7.03 Hz), 1H; 8.0, d (J=9.57 Hz), 1H (B) Preparation of 4-[2-(4-Amino-3-nitro-phenyl)-1H-benzoimidazol-5-yl]-piperazine-1-carboxylic Acid Dimethylamide (i) Hydrogenation To a solution of 4-(3-Amino-4-nitro-phenyl)-piperazine-1-carboxylic acid dimethylamide (1.2 g, 4.1 mmol) in 1:1 acetic acid/ethanol (60 ml), under nitrogen, was added 5% palladium on activated carbon (0.175 g). The resulting mixture was evacuated and next stirred at room temperature under an atmosphere of hydrogen for one day. The reaction mixture was then directly filtered through celite into a round bottom flask under a nitrogen atmosphere containing ethyl 4-amino-3-nitrobenzenecarboximidate hydrochloride(7) (1.0 g, 4.1 mmol), and proceeded to the coupling step.

(ii) Coupling Reaction

The resulting slurry from step (i) was heated at 90° C. under nitrogen for 24 h, then cooled to room temperature and the solvents removed by rotary evaporator. The resulting thick dark blackish gum was treated with dilute aqueous ammonia solution (5% in water, 25 ml), mixed vigorously and was kept for 1 day at 4° C. Next, supernatant water was decanted and the residue was washed with additional water. The resulting solid was filtered, dried under reduced pressure, then washed and slurried in diethyl ether (20 mL) for two days. This yielded the product, 4-[2-(4-Amino-3-nitro-phenyl)-1H-benzoimidazol-5-yl]-piperazine-1-carboxylic acid dimethylamide as an orange powder, 1.5 g (89.8% crude yield). This material was directly used in next step without further purification.

$^1$H NMR (400 MHz, DMSO-d6) δ 2.7, s, 6H; 3.05, m, 4H; 3.21, m, 4H; 6.87, dd (J=2.15, 6.6 Hz) 1H; 6.92 s, 1H; 7.09, d (J=9.0 Hz), 1H; 7.36, d (J=8.8 Hz), 1H; 7.7, s (broad), 2H; 8.1, dd (J=2.15, 6.84 Hz), 1H; 8.7, d (J=2.15 Hz), 1H.

(C) Preparation of 2-(5'-(5''-(4'''-(dimethylcarbamoyl)piperazin-1'''-yl)benzimidazol-2''-yl)benzimidazol-2'-yl)pyridine

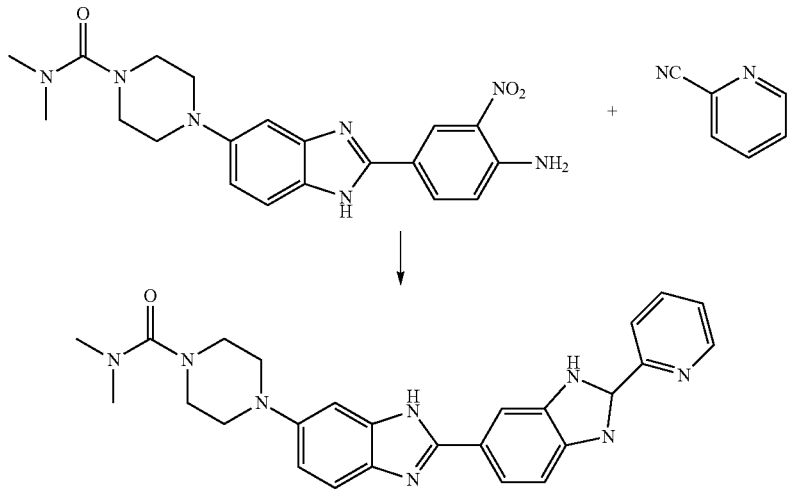

(i) Hydrogenation

To a solution of 4-[2-(4-amino-3-nitro-phenyl)-1H-benzoimidazol-5-yl]-piperazine-1-carboxylic acid dimethylamide (1.0 g, 2.4 mmol) in 4:1 ethyl acetate/methanol (100 ml) under nitrogen, was added 5% palladium on carbon (240 mg) and the mixture was first evacuated and then stirred at room temperature under an atmosphere of hydrogen for 1 day. The reaction mixture was then filtered through celite, washed with 1:1 ethyl acetate/methanol (10 mL) and the combined filtrate and washings were concentrated to give the crude 4-[2-(3,4-diamino-phenyl)-1H-benzoimidazol-5-yl]-piperazine-1-carboxylic acid dimethylamide as an orange solid that was used in the next step without any purification.

(ii) Coupling Reaction

The crude 4-[2-(3,4-diamino-phenyl)-1H-benzoimidazol-5-yl]-piperazine-1-carboxylic acid dimethylamide (2.5 mmol, prepared as mentioned in (i)) was dissolved in methanol (40 ml). To this was added a solution of 2-cyanopyridine (380 mg, 3.66 mmol) that had been treated (immediately before) with sodium methoxide (0.366 mmol) in methanol (3.7 mL) at 40° C. for 1 hour under nitrogen. To this mixture acetic acid (0.52 ml, 9.0 mmol) was added next.

This mixture was heated at 80° C. for 1 day under nitrogen followed by cooling to room temperature, and removing the solvents under reduced pressure. Next the residue treated with a 5% aqueous ammonia solution (60 mL), incubated at 5° C. over two hours, decanted the aqueous layer, washed well with water. Resulting sticky solid was dried under reduced pressure and slurried in acetonitrile for two days. Filtering this gave 450 mg of slightly impure material as a brown solid (40.5% crude yield).

150 mg of this material was eluted through silica gel plug (6 cm×3.5 cm) on a sinter funnel using suction. (The silica gel was first treated methanolic ammonia and the product eluted with ethanol). This yielded the product 2-(5'-(5''-(4'''-(dimethylcarbamoyl)piperazin-1'''-yl)benzimidazol-2''-yl)benzimidazol-2'-yl)pyridine as a brown powder, 75 mg. MP: >230° C.

$^1$H NMR (400 MHz, CD$_3$OD+HOAc 1 drop) δ 2.85, s, 6H; 2 (CH$_3$); 3.19, m, 4H, N(CH$_2$)$_2$; 3.41, m, 4H, N(CH$_2$)$_2$; 7.04-7.12, m, 2H; 7.46, m, 1H 7.77, dd (J=0.39, 9.2 Hz), 1H; 8.00, dd (J=0.58, 8.9 Hz), 1H; 7.9-7.98, m, 2H; 8.26-8.3, m, 2H; 8.7, m, 1H.

$^{13}$C NMR (100 MHz), CD$_3$OD+HOAc: δ 37.5, 50.7, 100.8, 114.2, 115.1, 115.6, 115.9, 121.6, 122.0, 123.6, 125.9, 137.4, 137.9, 147.8, 149.1, 149.8, 151.7, 153.3, 165.0 (three aromatic peaks overlapping or too weak).

Cytotoxicity and Radioprotection Results
C50=119.9
PF=34.6
DMFm=1.82
DMF10=1.49

Example 38

2-(5'-(5''-((2'''-Methoxyethyl)(methyl)amino)benzimidazol-2''-yl)benzimidazol-2'-yl)pyridine (A) Preparation of N$^1$-(2-methoxy-ethyl)-N1-methyl-4-nitro-benzene-1,3-diamine

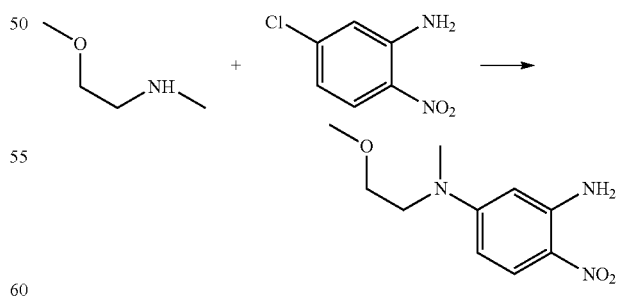

A mixture of 5-chloro-2-nitroaniline (2.2 g, 12.7 mmol), (2-methoxy-ethyl)-methyl-amine (3.0 g, 33.7 mmol) and anhydrous potassium carbonate (1.93 g, 14 mmol) in N,N-dimethylacetamide (5 ml) was stirred at 115-120° C. under nitrogen for 2 days. Sample NMR analysis showed complete conversion of the starting material. The resultant mixture was then cooled to room temperature, poured into cold water (20 ml) and stirred vigorously and cooled at 5° C. overnight. The resulting yellow brown precipitate was collected by filtration, washed well with water then dried on the filter funnel. The resulting yellow brown solid was slurried in diethyl ether (20 mL), filtered, washed with additional diethyl ether, dried to afford $N^1$-(2-methoxy-ethyl)-N1-methyl-4-nitro-benzene-1,3-diamine (2.1 g, 72%) as a yellow brown powder.

$^1$H NMR (400 MHz, CDCl$_3$) δ 3.0, s, 3H; 3.35, s, 3H; 3.9, m, 4H; 5.7, d (J=2.54 Hz), 1H; 6.0-6.3 and 6.22, d+broad s, overlapping, 3H; 8.0, d (J=9.5 Hz), 1H (B) Preparation of [2-(4-amino-3-nitro-phenyl)-1H-benzoimidazol-5-yl]-(2-methoxy-ethyl)-methyl-amine

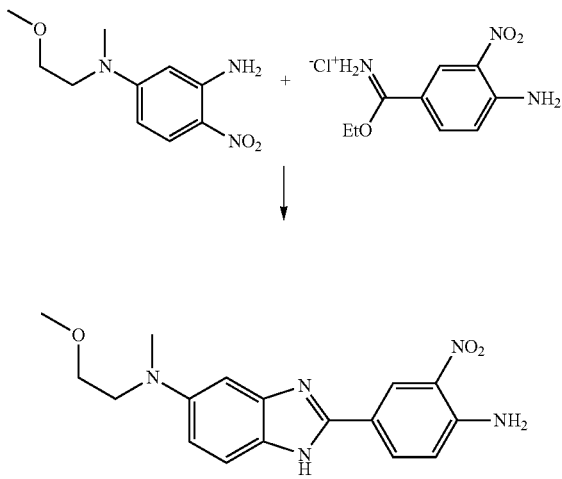

(i) Hydrogenation

To a solution of $N^1$-(2-methoxy-ethyl)-N1-methyl-4-nitro-benzene-1,3-diamine (1.0 g, 4.4 mmol) in 1:1 acetic acid/ethanol (60 ml), under nitrogen, was added 5% palladium on activated carbon (0.075 g). The resulting mixture was evacuated and next stirred at room temperature under an atmosphere of hydrogen for one day. The reaction mixture was then directly filtered through celite into a round bottom flask under a nitrogen atmosphere containing ethyl 4-amino-3-nitrobenzenecarboximidate hydrochloride (7) (1.09 g, 4.4 mmol), and proceeded to the coupling step.

(ii) Coupling Reaction

The resulting slurry from step (i) was heated at 80° C. under nitrogen for 36 h, then cooled to room temperature and the solvents removed by rotary evaporator. The resulting thick gum was treated with dilute aqueous ammonia solution (5% in water, 30 ml), mixed vigorously and was kept over two days at 4° C. Next, supernatant water was decanted and the residue was washed with additional water. The resulting solid was filtered, dried on the filter funnel, then slurried in diethyl ether. This yielded the crude product as a powder, 1.0 g (66.6% crude yield). This impure material was directly used in next step without purification.

$^1$H NMR (400 MHz, DMSO-d6) δ 2.96, s, 3H; 3.32, s, 3H; 3.42-3.58 two crude m (6H); 6.8, m, 2H; 7.07, d (J=8.6 Hz) 1H; 7.39, d (J=9.2 Hz) 1H; 8.0, d (J=9.77 Hz), 1H; 8.7, s 1H (C) Preparation of 2-(5'-(5''-((2'''-Methoxyethyl)(methyl)amino)benzimidazol-2''-yl)benzimidazol-2'-yl)pyridine

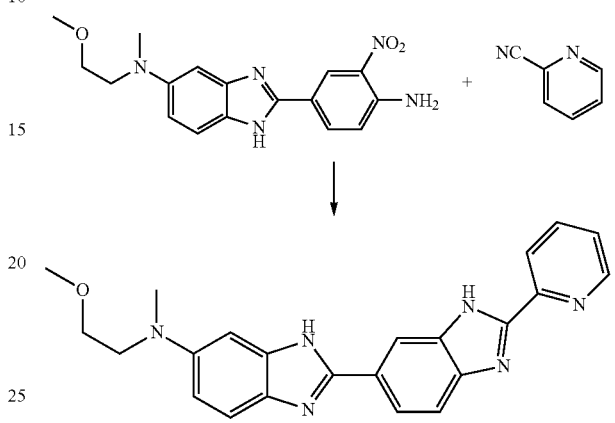

(i) Hydrogenation

To a solution of [2-(4-amino-3-nitro-phenyl)-1H-benzoimidazol-5-yl]-(2-methoxy-ethyl)-methyl-amine (0.65 g, 1.9 mmol) in 4:1 ethyl acetate/methanol (50 ml) under nitrogen, was added 5% palladium on carbon (100 mg) and the mixture was first evacuated and then stirred at room temperature under an atmosphere of hydrogen for 1 day. The reaction mixture was then filtered through celite, washed with 1:1 ethyl acetate/methanol (10 mL) and the combined filtrate and washings were concentrated to give the crude 4-{5-[(2-methoxy-ethyl)-methyl-amino]-1H-benzoimidazol-2-yl}-benzene-1,2-diamine as a thick oil that was used in the next step without any purification.

(ii) Coupling Reaction

The crude 4-{5-[(2-methoxy-ethyl)-methyl-amino]-1H-benzoimidazol-2-yl}-benzene-1,2-diamine (1.9 mmol, prepared as mentioned in (i)) was dissolved in methanol (20 ml). To this was added a solution of 2-cyanopyridine (297 mg, 2.9 mmol) that had been treated (immediately before) with sodium methoxide (0.29 mmol) in methanol (2.9 mL) at 40° C. for 1 hour under nitrogen. To this mixture, acetic acid (0.415 ml, 7.25 mmol) was added next.

This mixture was heated at 80° C. for 1 day under nitrogen followed by cooling to room temperature, and removing the solvents under reduced pressure. Next the residue treated with a 5% aqueous ammonia solution, incubated at 5° C. overnight. Next the aqueous layer was decanted, and the residue washed with water and dried under reduced pressure. Resulting semi solid was slurried in acetonitrile overnight giving a brown powder. Filtering this gave 250 mg of slightly impure material as a brown solid (38.6% crude yield).

100 mg of this material was eluted through a silica gel plug (6 cm×3.5 cm) on a sinter funnel using suction. (The silica gel was first treated methanolic ammonia and the product gradient eluted with 5% ethanol in dichloromethane to 10% ethanol in dichloromethane). This yielded the product 2-(5'-(5''-((2'''-methoxyethyl)(methyl)amino)benzimidazol-2''-yl)benzimidazol-2'-yl)pyridine as a dark reddish brown powder, 59 mg. MP: 150-155° C.

$^1$H NMR (400 MHz, CD$_3$OD) δ 2.99, s, 3H(NCH$_3$); 3.37, s, 3H(OCH$_3$); 3.51, t, (J=5.66 Hz) (3H) (CH$_2$); 3.58, t, (J=5.47 Hz) (3H) (CH$_2$); 6.8-6.9, m, 2H; 7.4-7.5, m, 2H; 7.7, d (J=8.2 Hz), 1H; 7.9-8.0, m, 2H; 8.2-8.3, m, 2H; 8.7, d (J=4.7 Hz), 1H.

$^{13}$C NMR (100 MHz, CD$_3$OD+HOAc 1 drop): δ 38.8, 53.3, 57.9, 70.2, 95.5, 112.1, 113.9, 114.99, 115.7, 121.6, 121.7, 122.3, 124.9, 130.0, 136.9, 137.2, 140.4, 147.6, 147.7, 149.7, 149.8, 153.2 (one aromatic peaks overlapping or too weak)

Cytotoxicity and Radioprotection Results

C50=41.2
PF=8.8
DMFm=1.55
DMF10=1.32

Example 39

2-(5'-(5''-(2'''-(2''''-methoxyethoxy)ethylamino)benz-imidazol-2''-yl)benzimidazol-2'-yl)pyridine (A) Preparation of N$^1$-[2-(2-methoxy-ethoxy)-ethyl]-4-nitro-benzene-1,3-diamine

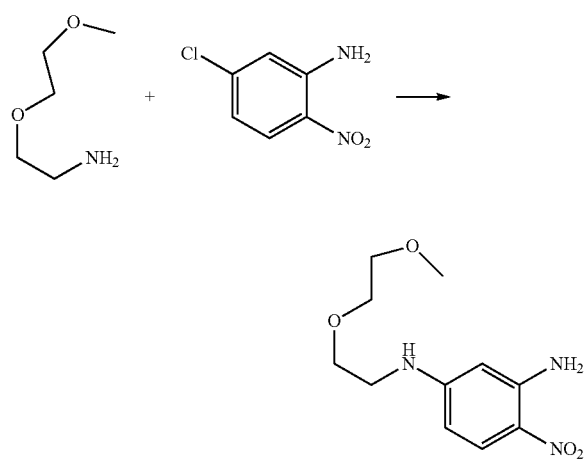

A mixture of 5-chloro-2-nitroaniline (1.6 g, 9.3 mmol), 2-(2-methoxy-ethoxy)-ethylamine (2.0 g, 16.8 mmol) and anhydrous potassium carbonate (1.38 g, 10 mmol) in N,N-dimethylacetamide (3 ml) was stirred at 120° C. under nitrogen for 3 days. Sample NMR analysis showed 80% conversion of the starting material. The resultant mixture was then cooled to room temperature, poured into cold water (30 ml) and extracted with ethyl acetate. The organic extract was washed with brine, dried and evaporated. The resulting orange yellow oil was subjected to a silica gel filtration on a 5 cm×6 cm silica gel plug, eluting first with 50% ethyl acetate/petroleum spirits (40-60° C.), followed by 100% ethyl acetate. Evaporation yielded an orange-red liquid, 1.1 g (45.8% yields).

$^1$H NMR (400 MHz, CDCl3) δ 3.2, q (J=5.28 Hz), 2H; 3.34, s, 3H; 3.5, m, 2H; 3.6, m, 2H; 3.65, t (J=5.1 Hz), 2H; 5.6, d (J=2.54 Hz), 1H; 5.9, dd (J=2.35, 7.03 Hz), 1H, 6.20 broad s, 2H; 7.87, d (J=9.4 Hz), 1H (B) Preparation of [2-(4-amino-3-nitro-phenyl)-1H-benzoimidazol-5-yl]-[2-(2-methoxy-ethoxy)-ethyl]-amine

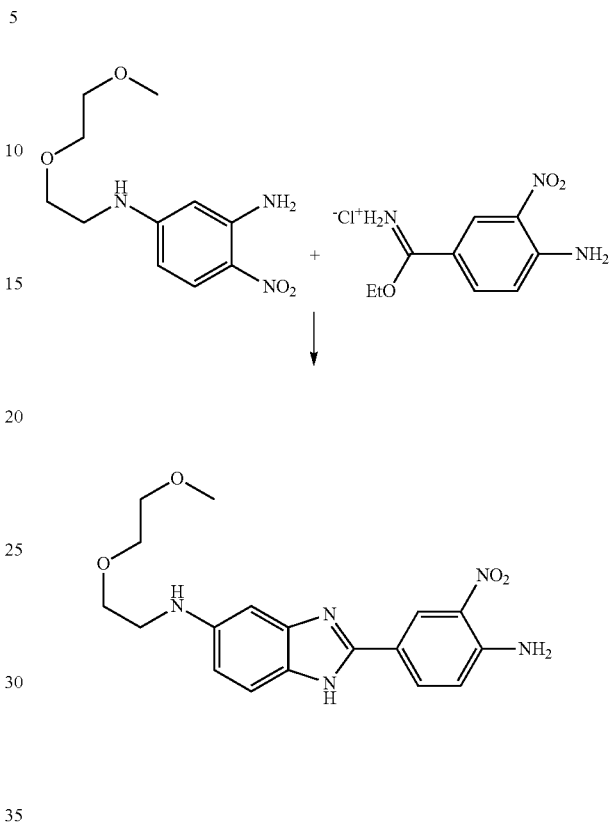

(i) Hydrogenation

To a solution of N$^1$-[2-(2-methoxy-ethoxy)-ethyl]-4-nitro-benzene-1,3-diamine (1.1 g, 4.3 mmol) in 1:1 acetic acid/ethanol (60 ml), under nitrogen, was added 5% palladium on activated carbon (0.075 g). The resulting mixture was evacuated and next stirred at room temperature under an atmosphere of hydrogen for one day. The reaction mixture was then directly filtered through celite into a round bottom flask under a nitrogen atmosphere containing ethyl 4-amino-3-nitrobenzenecarboximidate hydrochloride(7) (1.00 g, 4.1 mmol), and proceeded to the coupling step.

(ii) Coupling Reaction

The resulting slurry from step (i) was heated at 80° C. under nitrogen for 17 h, then cooled to room temperature and the solvents removed by rotary evaporator. The resulting thick oil was treated with dilute aqueous ammonia solution (5% in water, 30 ml), mixed vigorously and was kept overnight at 4° C. Next, supernatant water was decanted and the residue was washed with additional water. The resulting semi solid was dried under reduced pressure, then slurried in diethyl ether (150 mL) for 1 hour and the ether layer decanted. As the product still remained in the semi-solid form (1.4 g, 88% crude yield), this was directly carried over to the next step without further attempts at purification.

$^1$H NMR (400 MHz, CDCl$_3$) δ 3.17 t (J=5.7 Hz), 2H; 3.2, s, 3H; 3.4, m, 2H; 3.5, m, 2H; 3.56, t (J=6.1 Hz), 2H; 6.55, m, 2H; 7.1, d (J=8.8 Hz), 1H; 7.24, d (J=9.18 Hz), 8.64, d (J=2.14 Hz), 1H

113

(C) Preparation of 2-(5'-(5"-(2'"-(2""-methoxy-ethoxy)ethylamino)benzimidazol-2"-yl)benzimidazol-2'-yl)pyridine

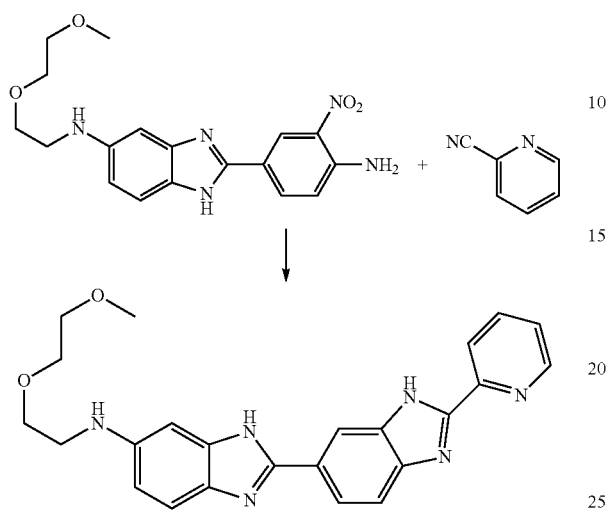

(i) Hydrogenation

To a solution of [2-(4-amino-3-nitro-phenyl)-1H-benzoimidazol-5-yl]-(2-methoxy-ethyl)-methyl-amine (0.8 g, 2.1 mmol) in 4:1 ethyl acetate/methanol (50 ml) under nitrogen, was added 5% palladium on carbon (100 mg) and the mixture was first evacuated and then stirred at room temperature under an atmosphere of hydrogen for 1 day. The reaction mixture was then filtered through Celite, washed with 1:1 ethyl acetate/methanol (10 mL) and the combined filtrate and washings were concentrated to give the crude 4-{5-[2-(2-methoxy-ethoxy)-ethylamino]-1H-benzoimidazol-2-yl}-benzene-1,2-diamine as a thick oil that was used in the next step without any purification.

(ii) Coupling Reaction

The crude 4-{5-[2-(2-methoxy-ethoxy)-ethylamino]-1H-benzoimidazol-2-yl}-benzene-1,2-diamine (2.1 mmol, prepared as mentioned in (i)) was dissolved in methanol (25 ml). To this was added a solution of 2-cyanopyridine (336 mg, 3.2 mmol) that had been treated (immediately before) with sodium methoxide (0.32 mmol) in methanol (2.9 mL) at 40° C. for 1 hour under nitrogen. To this mixture, acetic acid (0.46 ml, 8.0 mmol) was added next.

This mixture was heated at 80° C. for 1 day under nitrogen followed by cooling to room temperature, and removing the solvents under reduced pressure. Next the residue treated with a 5% aqueous ammonia solution, incubated at 5° C. for 3 hours. Next the aqueous layer was decanted, and the residue washed with water and dried under reduced pressure. Resulting semi solid was slurried first in diethyl ether and then in acetonitrile overnight. Filtering this gave 400 mg of slightly impure material as a brown solid (49% crude yield).

100 mg of this material was eluted through a silica gel plug (6 cm×3.5 cm) on a sinter funnel using suction. (The product was gradient eluted with 2% ethanol in dichloromethane to 20% ethanol in dichloromethane). This yielded the product 2-(5'-(5"-(2'"-(2""-methoxyethoxy)ethylamino)benzimidazol-2"-yl)benzimidazol-2'-yl)pyridine as a dark reddish brown powder, 25 mg.

MP: 183-186° C.

114

$^1$H NMR (400 MHz, CD$_3$OD) δ 3.3, m, 2H, (CH$_2$); 3.39, s, 3H, (CH$_3$); 3.59, m, 2H; (CH$_2$); 3.6, m, 2H, (CH$_2$); 3.7, t (J=5.5 Hz), 2H, (CH$_2$); 6.7, dd (J=1.56, 7.2 Hz), 1H; 6.8, s, 1H; 7.4, d (J=8.6 Hz), 1H; 7.44, crude t, 1H; 7.72, d (J=8.4 Hz), 1H; 7.88-7.98, m, 2H; 8.2-8.3, m, 2H; 8.7, crude d, 1H.

$^{13}$C NMR (100 MHz, CD$_3$OD+5 drop HOAc):

δ 44.0, 57.9, 69.4, 69.9, 71.8, 94.3, 113.1, 113.6, 115.1, 115.7, 121.5, 122.5, 124.8, 128.4, 137.0, 138.2, 139.1, 140.3, 143.8, 146.4, 147.4, 149.5, 150.1, 152.9

Cytotoxicity and Radioprotection Results

C50=173.0

PF=171.5

DMFm=2.70

DMF10=1.50

Example 40

2-(5'-(5"-(4'"-(2""-methoxyethyl)piperazin-1'"-yl)benzimidazol-2"-yl)benzimidazol-2'-yl)pyridine (A) Preparation of 5-[4-(2-methoxy-ethyl)-piperazin-1-yl]-2-nitro-phenylamine

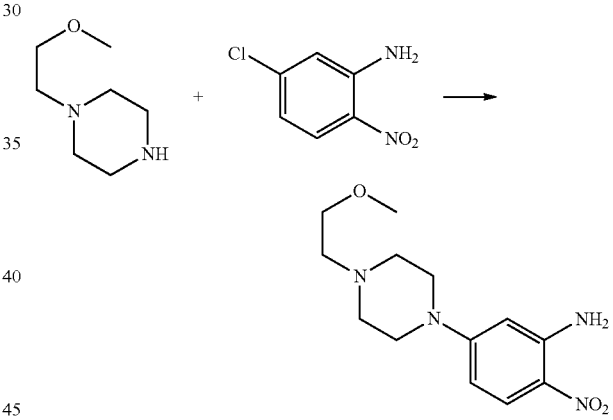

A mixture of 5-chloro-2-nitroaniline (1.4 g, 8.1 mmol), 1-(2-methoxy-ethyl)-piperazine (2.0 g, 14.0 mmol) and anhydrous potassium carbonate (1.38 g, 10.0 mmol) in N,N-dimethylacetamide (3 ml) was stirred at 120-130° C. under nitrogen for 1 day. Sample NMR analysis showed complete conversion of the starting material. The resultant mixture was then cooled to room temperature, poured into cold water (15 ml) and stirred vigorously. The resulting yellow brown precipitate was collected by filtration, washed well with water then dried on the filter funnel. The resulting yellow brown solid was slurried in diethyl ether (20 mL), filtered, washed with additional diethyl ether, dried to afford 5-[4-(2-methoxy-ethyl)-piperazin-1-yl]-2-nitro-phenylamine (1.7 g, 75%) as a yellow brown powder.

$^1$H NMR (400 MHz, DMSO-d6) δ 2.40-2.50, m, 6H; 3.19, s, 3H; 3.25, m, 4H; 3.41, t (J=5.9 Hz), 2H; 6.16, d (J=2.7 Hz), 1H; 6.34, dd (J=2.54, 7.23 Hz), 1H; 7.20 broad 2H; 7.76, d (J=9.8 Hz), 1H

(B) Preparation of 4-{5-[4-(2-methoxy-ethyl)-piperazin-1-yl]-1H-benzoimidazol-2-yl}-2-nitro-phenylamine

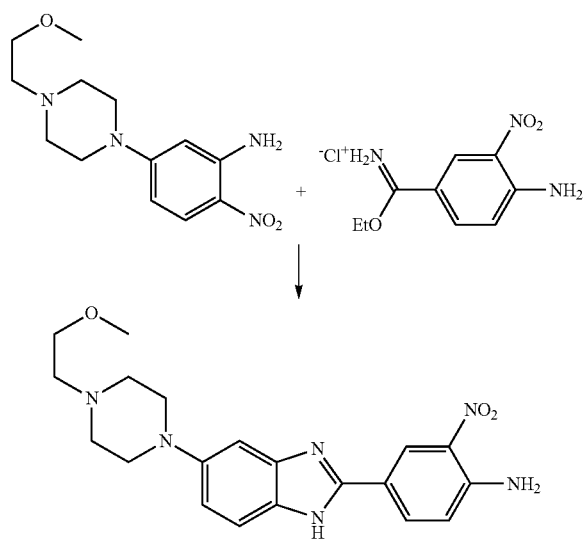

(i) Hydrogenation

To a solution of 5-[4-(2-methoxy-ethyl)-piperazin-1-yl]-2-nitro-phenylamine (1.0 g, 3.6 mmol) in 1:1 acetic acid/ethanol (60 ml), under nitrogen, was added 5% palladium on activated carbon (0.075 g). The resulting mixture was evacuated and next stirred at room temperature under an atmosphere of hydrogen for one day. The reaction mixture was then directly filtered through celite into a round bottom flask under a nitrogen atmosphere containing ethyl 4-amino-3-nitrobenzenecarboximidate hydrochloride(7) (0.83 g, 3.4 mmol), and proceeded to the coupling step.

(ii) Coupling Reaction

The resulting slurry from step (i) was heated at 80° C. under nitrogen for 24 h, then cooled to room temperature and the solvents removed by rotary evaporator. The resulting thick gum was treated with dilute aqueous ammonia solution (5% in water, 30 ml), mixed vigorously and was kept for 1 day at 4° C. Next, supernatant water was decanted and the residue was washed with additional water. The resulting solid was filtered, dried on the filter funnel, then slurried in diethyl ether. This yielded the crude product as an orange powder, 1.0 g (74.6% crude yield). This material was directly used in next step without further purification.

$^1$H NMR (400 MHz, DMSO-d6) δ 2.40-2.60, m, 6H; 3.0-3.10, m, 4H; 3.20, s, 3H; 3.42, t (J=5.9 Hz), 2H; 8.7, m, 1H; 8.1, d (J=9.18 Hz), 1H; 7.4, d (J=8.6 Hz), 1H; 7.1 (d (J=8.9 Hz), 6.8-6.9, m, 2H

(C) Preparation of 2-(5'-(5''-(4'''-(2''''methoxyethyl)piperazin-1'''-yl)benzimidazol-2''-yl)benzimidazol-2'-yl)pyridine

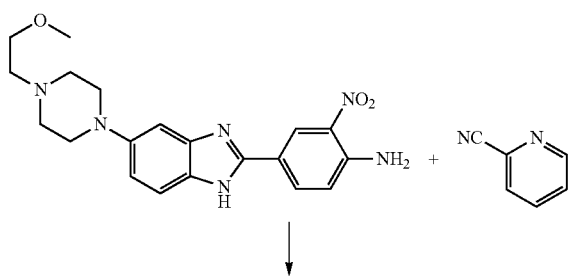

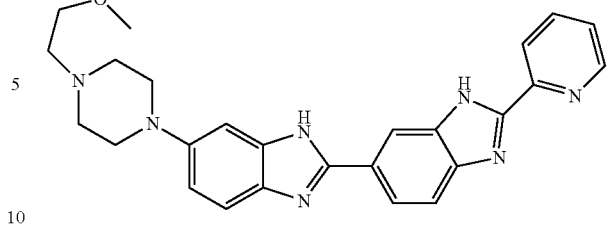

(i) Hydrogenation

To a solution of 4-{5-[4-(2-methoxy-ethyl)-piperazin-1-yl]-1H-benzoimidazol-2-yl}-2-nitro-phenylamine (0.5 g, 1.2 mmol) in 4:1 ethyl acetate/methanol (60 ml) under nitrogen, was added 5% palladium on carbon (100 mg) and the mixture was first evacuated and then stirred at room temperature under an atmosphere of hydrogen for 1 day. The reaction mixture was then filtered through Celite, washed with 1:1 ethyl acetate/methanol (10 mL) and the combined filtrate and washings were concentrated to give the crude 4-{5-[4-(2-methoxy-ethyl)-piperazin-1-yl]-1H-benzoimidazol-2-yl}-benzene-1,2-diamine as a thick oil that was used in the next step without any purification.

(ii) Coupling Reaction

The crude 4-{5-[4-(2-methoxy-ethyl)-piperazin-1-yl]-1H-benzoimidazol-2-yl}-benzene-1,2-diamine (1.2 mmol, prepared as mentioned in (i)) was dissolved in methanol (20 ml). To this was added a solution of 2-cyanopyridine (190 mg, 1.8 mmol) that had been treated (immediately before) with sodium methoxide (0.18 mmol) in methanol (1.8 mL) at 40° C. for 1 hour under nitrogen. To this mixture, acetic acid (0.26 ml, 4.6 mmol) was added next.

This mixture was heated at 80° C. for 1 day under nitrogen followed by cooling to room temperature, and removing the solvents under reduced pressure. Next the residue treated with a 5% aqueous ammonia solution, incubated at 5° C. overnight. Next the aqueous layer was decanted, and the residue washed with water and dried under reduced pressure. Resulting semi solid was slurried in acetonitrile over two days giving a light tan powder. Filtering this and washing with acetonitrile gave the product 2-(5'-(5''-(4'''-(2''''-methoxyethyl)piperazin-1'''-yl)benzimidazol-2''-yl)benzimidazol-2'-yl)pyridine as a light tan powder, 300 mg (55.1% yield). MP: 164-166° C.

$^1$H NMR (400 MHz, CD$_3$OD) δ 2.62, t (J=5.7 Hz), 2H, CH$_2$; 2.70, m, 4H, N(CH$_2$)$_2$; 3.0-3.10, m, 4H, N(CH$_2$)$_2$; 3.20, s, 3H; 3.42, t (J=5.4 Hz), 2H; 7.0, dd (J=2.15, 6.64 Hz), 1H; 7.08, s, 1H; 7.4-7.5, m, 2H; 7.7, d (J=8.0 Hz), 1H; 7.9-8.0, m, 2H; 8.2-8.3, m, 2H; 8.69, crude d, 1H.

$^{13}$C NMR (100 MHz, CD$_3$OD+5 drop HOAc):

δ 49.3, 52.9, 56.8, 57.9, 68.2, 101.1, 113.7, 115.1, 115.4, 115.7, 121.5, 121.9, 124.8, 134.4, 137.1, 138.7, 139.3, 140.2, 147.7, 147.8, 149.6, 152.1, 152.8 (one aromatic peak overlapping or too weak)

Cytotoxicity and Radioprotection Results

C50=80.7

PF=20.2

DMFm=1.98

DMF10=1.77

Example 41

2-(5'-(5''-(4'''-(2''''-hydroxyethyl)piperazin-1'''-yl)benzimidazol-2''-yl)benzimidazol-2'-yl)pyridine (A) Preparation of 2-[4-(3-amino-4-nitro-phenyl)-piperazin-1-yl]ethanol

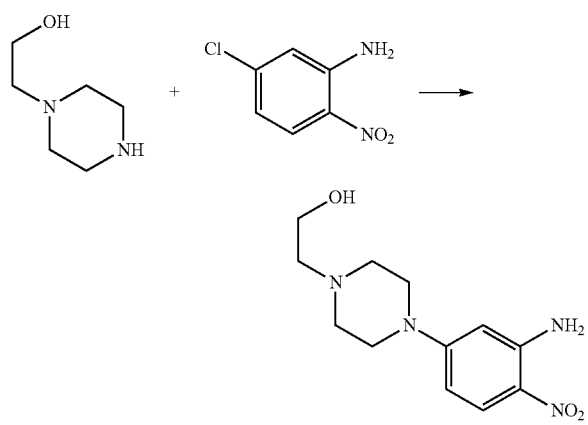

A mixture of 5-chloro-2-nitroaniline (5.0 g, 29.0 mmol), 2-piperazin-1-yl-ethanol (11.3 g, 87.0 mmol) and anhydrous potassium carbonate (4.4 g, 31 mmol) in N,N-dimethylacetamide (10 ml) was stirred at 120-125° C. under nitrogen for 1 day. Sample NMR analysis showed complete conversion of the starting material. The resultant mixture was then cooled to room temperature, poured into cold water (30 ml) and stirred vigorously and cooled at 5° C. overnight. The resulting yellow precipitate was collected by filtration, washed well with water then dried on the filter funnel. The resulting yellow brown solid was slurried in diethyl ether (30 mL), filtered, washed with additional diethyl ether, dried to afford 2-[4-(3-Amino-4-nitro-phenyl)-piperazin-1-yl]-ethanol (6.0 g, 77%) as a yellow powder.

$^1$H NMR (400 MHz, CDCl$_3$) δ 2.50-2.60, m, 6H, 3.30, m, 4H; 3.60, m, 2H; 5.9, crude d (J=2.15 Hz), 1H; 6.1 broad s, 2H; 6.25, crude dd (not resolved), 1H; 7.76, d (J=9.77 Hz), 1H (B) Preparation of 2-{4-[2-(4-amino-3-nitro-phenyl)-1H-benzoimidazol-5-yl]-piperazin-1-yl}-ethanol

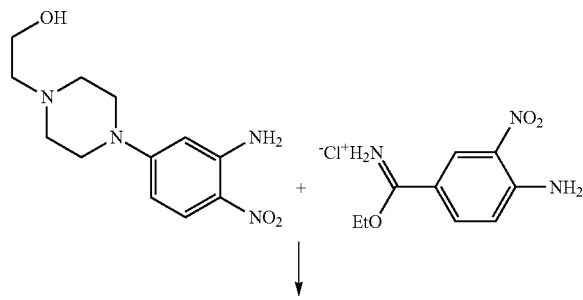

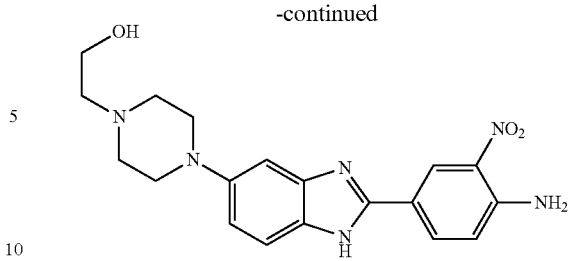

(i) Hydrogenation

To a solution of 2-[4-(3-amino-4-nitro-phenyl)-piperazin-1-yl]-ethanol (1.75 g, 6.6 mmol) in 1:1 acetic acid/ethanol (100 ml), under nitrogen, was added 5% palladium on activated carbon (0.150 g). The resulting mixture was evacuated and next stirred at room temperature under an atmosphere of hydrogen for one day. The reaction mixture was then directly filtered through celite into a round bottom flask under a nitrogen atmosphere containing ethyl 4-amino-3-nitrobenzenecarboximidate hydrochloride(7) (1.50 g, 6.3 mmol), and proceeded to the coupling step.

(ii) Coupling Reaction

The resulting slurry from step (i) was heated at 80° C. under nitrogen for 1 day, then cooled to room temperature and the solvents removed by rotary evaporator. The resulting thick semi solid was treated with dilute aqueous ammonia solution (5% in water, 30 ml), mixed vigorously and was kept 1 day at 4° C. Next, supernatant water was decanted and the residue was washed with additional water. The resulting solid was filtered, dried on the filter funnel, then washed with diethyl ether. This yielded the crude product as a brick orange powder, 1.9 g (79.2% crude yield). This material was directly used in next step without further purification.

$^1$H NMR (400 MHz, DMSO-d6+TFA) δ 3.1, crude t, 2H; 3.20, broad m, 4H; 3.60, broad d, 2H; 3.7 broad m, 2H; 3.85, broad d, 2H; 7.6, s, 1H; 7.2, d (J=9.18 Hz), 1H; 7.27;,d (d=7.62 Hz), 1H; 8.04, d (J=8.8 Hz), 1H; 8.9, s, 1H (C) Preparation of 2-(5'-(5''-(4'''-(2''''-hydroxyethyl)piperazin-1'''-yl)benzimidazol-2''-yl)benzimidazol-2'-yl)pyridine

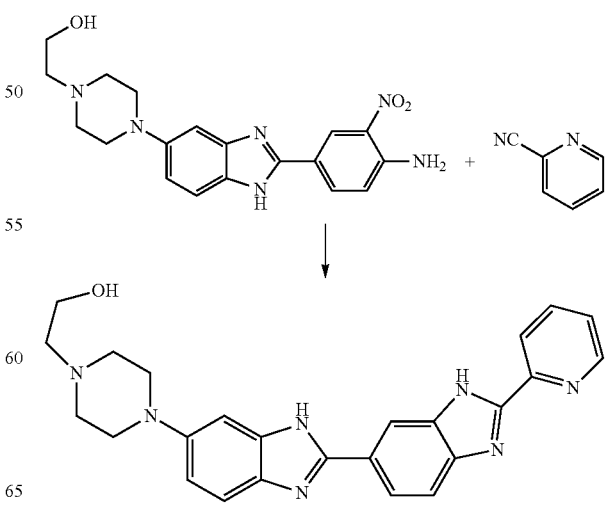

(i) Hydrogenation

To a solution of 2-{4-[2-(4-amino-3-nitro-phenyl)-1H-benzoimidazol-5-yl]-piperazin-1-yl}-ethanol (1.0 g, 2.6 mmol) in 4:1 ethyl acetate/methanol (100 ml) under nitrogen, was added 5% palladium on carbon (200 mg) and the mixture was first evacuated and then stirred at room temperature under an atmosphere of hydrogen for 1 day. The reaction mixture was then filtered through Celite, washed with 1:1 ethyl acetate/methanol (10 mL) and the combined filtrate and washings were concentrated to give the crude 2-{4-[2-(3,4-diamino-phenyl)-1H-benzoimidazol-5-yl]-piperazin-1-yl}-ethanol as a reddish solid that was used in the next step without any purification.

(ii) Coupling Reaction

The crude 2-{4-[2-(3,4-diamino-phenyl)-1H-benzoimidazol-5-yl]-piperazin-1-yl}-ethanol (2.6 mmol, prepared as mentioned in (i)) was dissolved in methanol (40 ml). To this was added a solution of 2-cyanopyridine (408 mg, 3.9 mmol) that had been treated (immediately before) with sodium methoxide (0.39 mmol) in methanol (4.0 mL) at 40° C. for 1 hour under nitrogen. To this mixture, acetic acid (0.55 ml, 9.83 mmol) was added next.

This mixture was heated at 80° C. for 1 day under nitrogen followed by cooling to room temperature, and removing the solvents under reduced pressure. Next the residue treated with a 5% aqueous ammonia solution, incubated at 5° C. overnight. Next the aqueous layer was decanted, and the residue washed with water and dried under reduced pressure. Resulting semi solid was slurried in acetonitrile overnight giving a red-brown powder. Filtering this gave 800 mg of slightly impure material as a brown solid (52.6% crude yield).

100 mg of this material was eluted through a silica gel plug (6 cm×3.5 cm) on a sinter funnel using suction. (The silica gel was first treated methanolic ammonia and the product gradient eluted with ethanol to 10% methanolic ammonia in ethanol in dichloromethane). This yielded the product 2-(5'-(5''-(4'''-(2''''-hydroxyethyl)piperazin-1'''-yl)benzimidazol-2''-yl)benzimidazol-2'-yl)pyridine as a dark reddish brown powder, 44 mg. MP: 218-221° C.

$^1$H NMR (400 MHz, CD$_3$OD) δ 2.5, t (J=5.7 Hz), 2H, CH$_2$; 2.70, m, 4H, N(CH$_2$)$_2$; 3.10, m, 4H N(CH$_2$)$_2$; 3.62, t (J=5.4 Hz), 2H, CH$_2$; 6.94, dd (J=2.15, 6.64 Hz), 1H; 7.03, broad s, 1H; 7.34-7.42, m, 2H; 7.66, broad d, 1H; 7.82-7.9, m, 2H; 8.20-8.25, m, 2H; 8.63, crude d, 1H.

$^{13}$C NMR (100 MHz), CD$_3$OD+HOAc: δ 52.4, 55.5, 58.5, 102.0, 114.3, 115.1, 115.7 121.7, 122.1, 124.0, 125.1, 133.8, 137.4, 138.8, 139.7, 142.4, 147.4, 147.8, 149.8, 152.5, 153.5 (one aromatic peak overlapping or too weak).

Cytotoxicity and Radioprotection Results

C50=90.6
PF=19.6
DMFm=1.95
DMF10=1.44

Example 42

2-(5'-(5''-(morpholinoamino)benzimidazol-2''-yl)benzimidazol-2'-yl)pyridine (A) Preparation of N$^1$-morpholin-4-yl-4-nitro-benzene-1,3-diamine

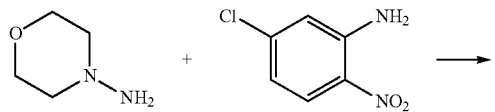

+

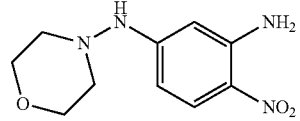

→

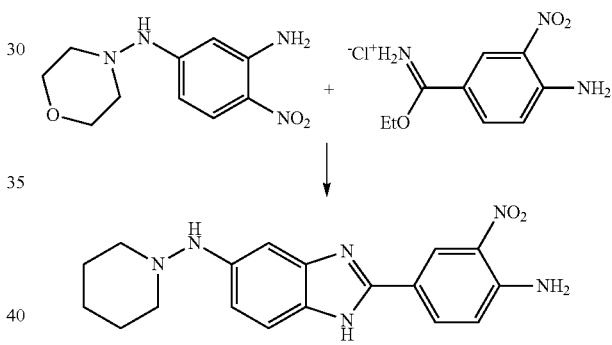

A mixture of 5-chloro-2-nitroaniline (6.7 g, 40 mmol), morpholin-4-ylamine (10.0 g, 9.8 mmol) and anhydrous potassium carbonate (6.1 g, 44 mmol) in N,N-dimethylacetamide (10 ml) was stirred at 120° C. under nitrogen for 2 days. Sample NMR analysis showed almost complete conversion of the starting material. The resultant mixture was then cooled to room temperature, poured into cold water (100 ml) and stirred vigorously and cooled at 5° C. overnight. The resulting precipitate was collected by filtration, washed well with water then dried on the filter funnel. The resulting solid was slurried in diethyl ether, filtered, washed with additional diethyl ether, dried to afford N$^1$-Morpholin-4-yl-4-nitro-benzene-1,3-diamine (6.0 g, 63%).

$^1$H NMR (400 MHz, CDCl$_3$) δ 3.30, m, 4H, N(CH$_2$)$_2$; 3.80, m, 4H, O(CH$_2$)$_2$; 5.9, d (J=2.55 Hz), 1H; 6.1 broad s, 2H; 6.25, dd (J=2.54, 7.03 Hz), 1H; 8.0, d (J=9.8 Hz), 1H (B) Preparation of [2-(4-amino-3-nitro-phenyl)-1H-benzoimidazol-5-yl]-morpholin-4-yl-amine (i) Hydrogenation To a solution of N$^1$-morpholin-4-yl-4-nitro-benzene-1,3-diamine (1.0 g, 4.2 mmol) in 1:1 acetic acid/ethanol (50 ml), under nitrogen, was added 5% palladium on activated carbon (0.075 g). The resulting mixture was evacuated and next stirred at room temperature under an atmosphere of hydrogen for one day. The reaction mixture was then directly filtered through celite into a round bottom flask under a nitrogen atmosphere containing ethyl 4-amino-3-nitrobenzenecarboximidate hydrochloride (7) (0.98 g, 4.0 mmol), and proceeded to the coupling step.

(ii) Coupling Reaction

The resulting slurry from step (i) was heated at 80° C. under nitrogen for 24 h, then cooled to room temperature and the solvents removed by rotary evaporator. The resulting thick gum was treated with dilute aqueous ammonia solution (5% in water, 30 ml), mixed vigorously and was kept overnight at 4° C. Next, supernatant water was decanted and the residue was washed with additional water. The resulting solid was filtered, dried on the filter funnel, then slurried in diethyl ether. This yielded the crude product as a dark red powder, 1.0 g (70.9% crude yield). This material was directly used in next step without further purification.

$^1$H NMR (400 MHz, DMSO-d6+TFA 1 drop) δ 3.10, m, 4H; 3.70, m, 4H; 7.0, s, 1H; 7.3, m, 2H; 7.55, d, (J=8.4 Hz) 1H; 8.0, d (J=8.4 Hz), 1H; 8.1 (broad s), 2H; 8.85, s, 1H (C) Preparation of 2-(5'-(5"-(morpholinoamino)benzimidazol-2"-yl)benzimidazol-2'-yl)pyridine

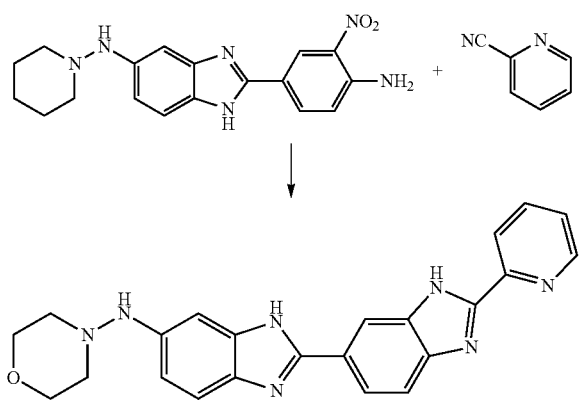

(i) Hydrogenation

To a solution of [2-(4-amino-3-nitro-phenyl)-1H-benzoimidazol-5-yl]-morpholin-4-yl-amine (0.5 g, 1.4 mmol) in 4:1 ethyl acetate/methanol (50 ml) under nitrogen, was added 5% palladium on carbon (100 mg) and the mixture was first evacuated and then stirred at room temperature under an atmosphere of hydrogen for 1 day. The reaction mixture was then filtered through Celite, washed with 1:1 ethyl acetate/methanol (10 mL) and the combined filtrate and washings were concentrated to give the crude 4-[5-(morpholin-4-ylamino)-1H-benzoimidazol-2-yl]-benzene-1,2-diamine, as a thick oil that was used in the next step without any purification.

(ii) Coupling Reaction

The crude 4-[5-(morpholin-4-ylamino)-1H-benzoimidazol-2-yl]-benzene-1,2-diamine (1.4 mmol, prepared as mentioned in (i)) was dissolved in methanol (20 ml). To this was added a solution of 2-cyanopyridine (219 mg, 2.1 mmol) that had been treated (immediately before) with sodium methoxide (0.21 mmol) in methanol (2.1 mL) at 40° C. for 1 hour under nitrogen. To this mixture, acetic acid (0.300 ml, 5.25 mmol) was added next.

This mixture was heated at 80° C. for 36 hours under nitrogen followed by cooling to room temperature, and removing the solvents under reduced pressure. Next the residue treated with a 5% aqueous ammonia solution, incubated at 5° C. for 5 hours. Next the aqueous layer was decanted, and the residue washed with water and dried under reduced pressure. Resulting semi solid was slurried in acetonitrile for 36 hours giving a brown solid. Filtering this gave 200 mg of slightly impure material as a brown solid (35.1% crude yield).

100 mg of this material was chromatographed through a silica gel column (2 cm×14 cm). (The material was gradient eluted with 5% ethanol in dichloromethane to 100% ethanol). This yielded the product 2-(5'-(5"-(morpholinoamino)benzimidazol-2"-yl)benzimidazol-2'-yl)pyridine as a dark reddish brown powder, 40 mg.

MP: 198-205° C.

$^1$H NMR (400 MHz, CD$_3$OD) δ 3.10, m, 4H, N(CH$_2$)$_2$; 3.80, m, 4H, O(CH$_2$)$_2$; 6.98, dd (J=2.15, 6.64 Hz), 1H; 7.03, s, 1H; 7.40-7.48, m, 2H; 7.68, d (J=8.4 Hz), 1H; 7.82-7.94, m, 2H; 8.20-8.25, m, 2H; 8.63, broad d (J=4.3 Hz), 1H.

$^{13}$C NMR (100 MHz, CD$_3$OD+HOAc 1 drop): δ 50.7, 66.7, 99.7, 114.1, 114.9, 115.2, 115.7, 121.6, 121.8, 122.7, 125.0, 132.1, 137.3, 139.9, 147.6, 149.2, 149.3, 149.7, 151.1, 153.2 (one aromatic peak overlapping or too weak).

Cytotoxicity and Radioprotection Results

C50=206.4
PF=17.8
DMFm=1.86
DMF10=1.38

Example 43

2-(5'-(5"-(2'''-(dimethylamino)ethylamino)benzimidazol-2"-yl)benzimidazol-2'-yl)pyridine

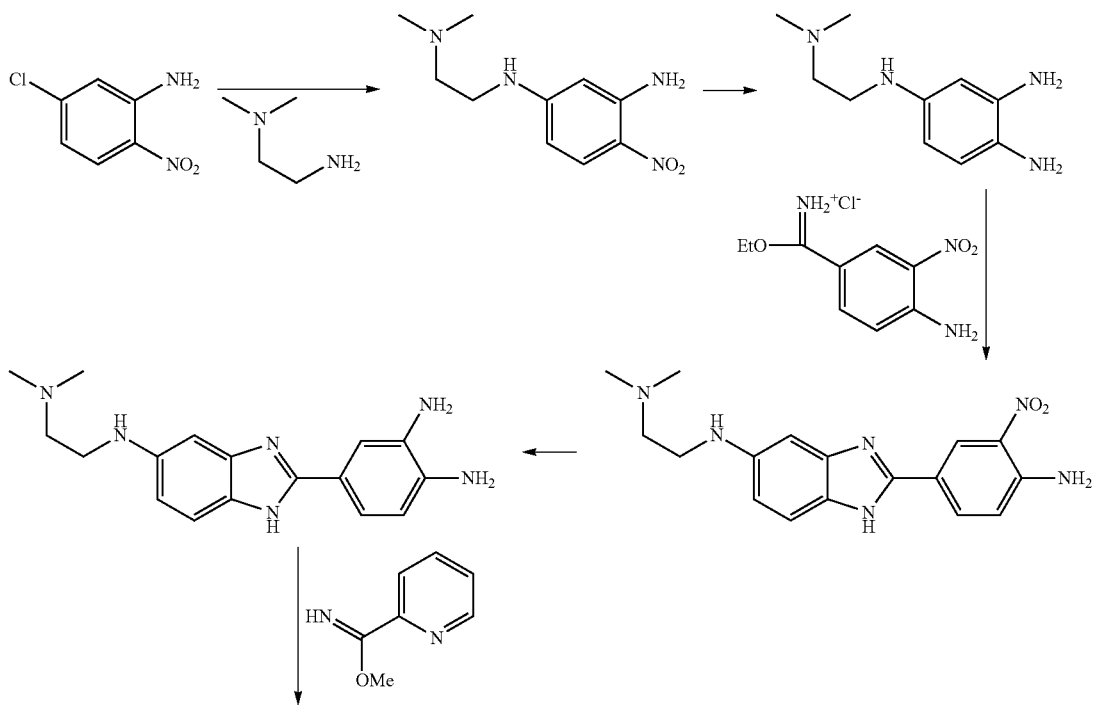

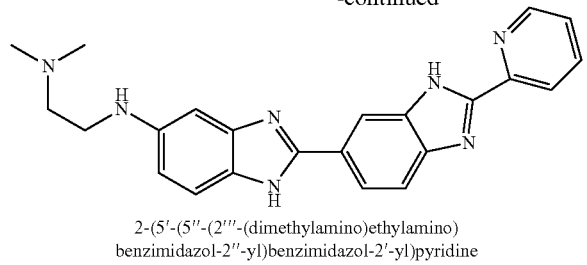

2-(5'-(5''-(2'''-(dimethylamino)ethylamino)
benzimidazol-2''-yl)benzimidazol-2'-yl)pyridine 2-(5'-(5''-(2'''-(Dimethylamino)ethylamino)benzimidazol-2''-yl)benzimidazol-2'-yl)pyridine was synthesized in a manner similar to 2-(5'-(5''-(morpholinoamino)benzimidazol-2''-yl)benzimidazol-2'-yl)pyridine previously mentioned, following the scheme above. The nucleophile used for the first step was $N^1,N^1$-dimethyl-ethane-1,2-diamine. The final product (2-(5'-(5''-(2''''-(dimethylamino)ethylamino)benzimidazol-2''-yl)benzimidazol-2'-yl)pyridine) was isolated as a dark red liquid, and evaporated to a solid/powder.

$^1$H NMR (400 MHz, CD$_3$OD+TFA) δ 2.94, s, 6H, N(CH$_3$)$_2$; 3.40, t (J=5.9 Hz), 2H, NCH$_2$; 3.60, t (J=5.9 Hz), 2H, NCH$_2$; 6.95, d (J=1.76 Hz), 1H; 7.02, dd (J=2.15, 6.80 Hz), 1H; 7.56, d (J=8.8 Hz), 1H; 7.70, dq (J=0.98, 3.91, 1.95 Hz), 1H; 8.06-8.22, m, 3H; 8.4, m, 1H, H3; 8.56, m, 1H; 8.86, m, 1H.

Cytotoxicity and Radioprotection Results
C50=117.7
PF=11.2
DMFm=1.61
DMF10=1.28

Example 44

2-(5'-(5''-(2'''-(dimethylamino)ethoxy)benzimidazol-2''-yl)benzimidazol-2'-yl)pyridine

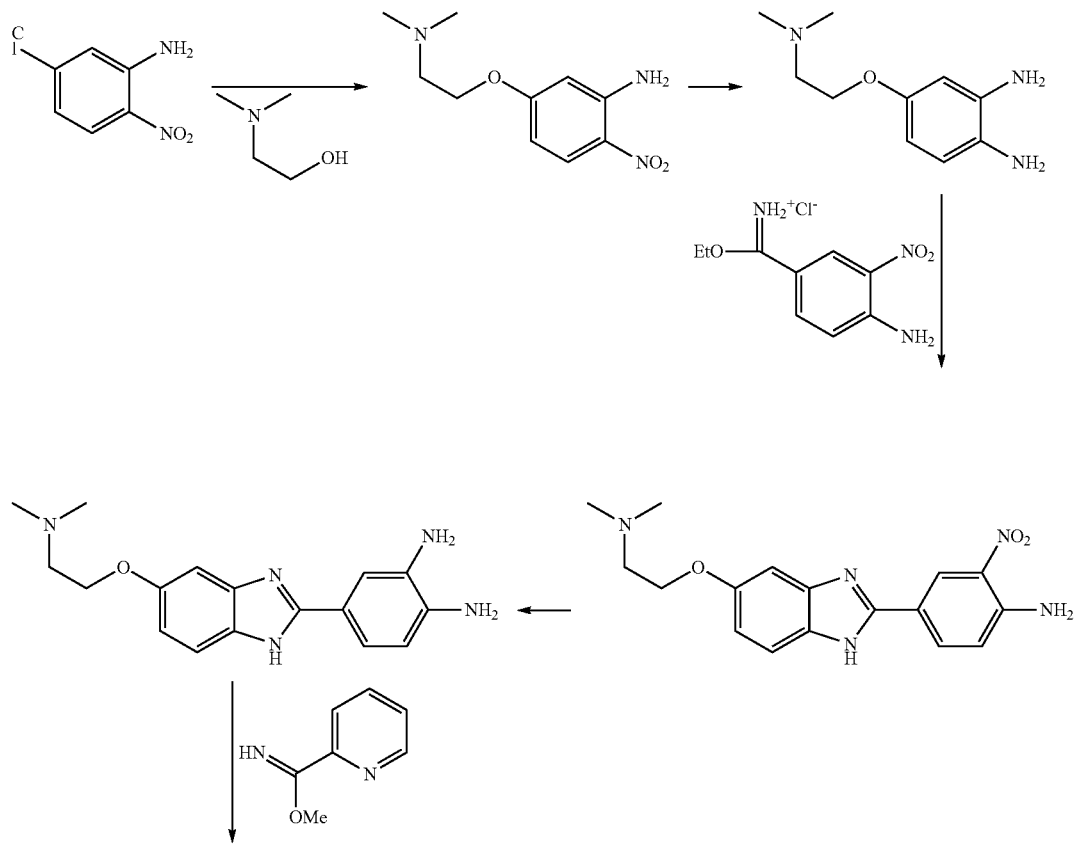

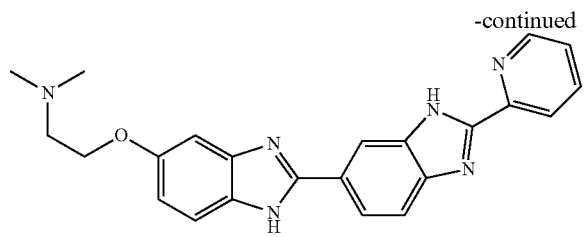

2-(5'-(5''-(2''''-(dimethylamino)ethoxy)benzimidazol-2''-yl)
benzimidazol-2'-yl)pyridine 2-(5'-(5''-(2''''-(Dimethylamino)ethoxy)benzimidazol-2''-yl)benzimidazol-2'-yl)pyridine was synthesized in a manner similar to 2-(5'-(5''-(morpholinoamino)benzimidazol-2''-yl)benzimidazol-2'-yl)pyridine previously mentioned, following the scheme above. The nucleophile used for the first step was 2-dimethylamino-ethanol. The final product 2-(5'-(5''-(2''''-(dimethylamino)ethoxy)benzimidazol-2''-yl)benzimidazol-2'-yl)pyridine was isolated as a yellow brown solid.

$^1$H NMR (400 MHz, CD$_3$OD+TFA) δ 3.00, s, 6H, N(CH$_3$)$_2$; 3.70, t (J=4.9 Hz), 2H, NCH$_2$; 4.5, t (J=4.9 Hz), 2H, OCH$_2$; 7.30, dd (J=2.35, 6.60 Hz), 1H; 7.40, d (J=1.95 Hz), 1H; 7.60, broad m, 1H; 7.74, d (J=8.99 Hz), 1H; 8.00-8.20, m, 3H; 8.4, d (J=7.82 Hz), 1H; 8.56, broad s, 1H; 8.80, broad m, 1H.

Cytotoxicity and Radioprotection Results
C50=145.6
PF=17.6
DMFm=1.88
DMF10=1.50

Example 45

Synthesis of 2-(5'-(5''-(tetrahydropyridazin-1'''-yl)benzimidazol-2''-yl)benzimidazol-2'-yl)pyridine (A) Preparation of 2-Nitro-5-(tetrahydro-pyridazin-1-yl)-phenylamine

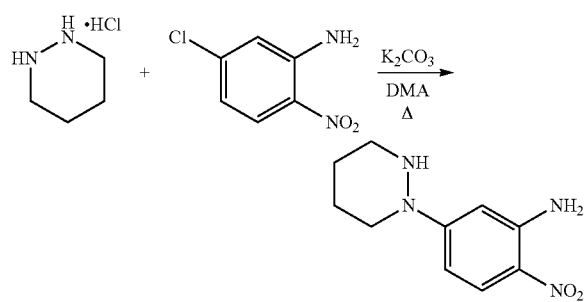

A mixture of 5-chloro-2-nitroaniline (2.36 g, 13.6 mmol), the hydrochloride salt of the hexahydro-pyridazine (5.0 g, 41 mmol) and anhydrous potassium carbonate (11.3 g, 82 mmol) in N,N-dimethylacetamide (20 ml) was stirred at 115-120° C. under nitrogen for 3 days. A sample was analyzed by NMR showed complete conversion of the starting material. The resultant mixture was cooled to room temperature, poured onto cold water (200 mL), stirred vigorously and incubated at 4° C. overnight. The resulting brown precipitate was collected by filtration, washed well with water and dried on the filter funnel. This was then slurried in diethyl ether, filtered, washed with additional diethyl ether, dried to afford 2-Nitro-5-(tetrahydro-pyridazin-1-yl)-phenylamine (1.9 g, 62.5%). The crude product was used in the next step without further purification.

$^1$H NMR (400 MHz, CDCl$_3$) δ 1.8 (m, 4H); 3.1 (m, 2H); 3.5 (m, 2H); 6.37, (dd, 1H); 6.41, (d, 1H); 7.95, (d, 1H)

(B) Preparation of 2-Nitro-4-[5-(tetrahydro-pyridazin-1-yl)-1H-benzoimidazol-2-yl]-phenylamine

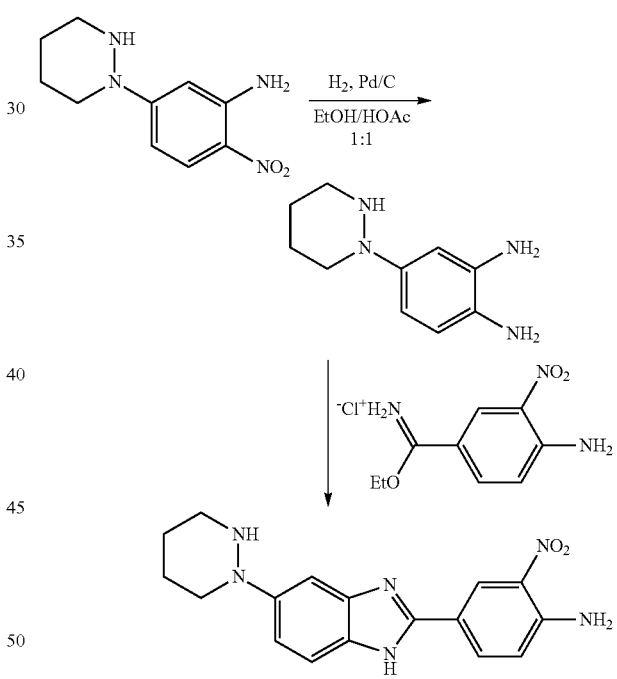

(i) Hydrogenation

To a solution of 2-Nitro-5-(tetrahydro-pyridazin-1-yl)-phenylamine (1.6 g, 7.2 mmol) in 1:1 acetic acid/ethanol (100 ml), under nitrogen, was added 5% palladium on activated carbon (0.20 g). The resulting mixture was evacuated and, stirred at room temperature under an atmosphere of hydrogen (balloon) for one day. The reaction mixture was then directly filtered through celite into a round bottom flask under a nitrogen atmosphere containing ethyl 4-amino-3-nitrobenzenecarboximidate hydrochloride (1.9 g, 7.9 mmol), and proceeded to the coupling step.

(ii) Coupling Reaction

The resulting slurry from step (i) was heated at 80-90° C. under nitrogen for 36 h, then cooled to room temperature and the solvents removed by rotary evaporation. The resulting violet oil was treated with dilute aqueous ammonia solution (3% in water, 50 ml), mixed vigorously and was kept overnight at 4° C. As there was no proper precipitation (just small amounts of thickened semisolids at the bottom), the solution was decanted and both portions (thickened semisolids and the aqueous fractions) were evaporated separately to remove water. The resulting thick liquids were then co-evaporated with absolute EtOH (5×100 mL) to remove residual water azeotropically. Both fractions contained product. The semisolid fraction was cleaner whereas the aqueous fraction gave 1.7 g however it was not as clean. Total crude yield was 83.3%. The crude product was used in the next step without further purification.

$^1$H NMR (400 MHz, DMSO-d6) δ 1.6 (m, 4H); 2.8 (m, 2H); 3.0 (m, 2H); 7.02, (d, 1H); 7.08, (d, 1H); 7.8, (dd, 1H); 7.9, (broad peak, 1H); 8.08 (dd, 1H); 8.5 (d, 1H).

(C) Preparation of 2-(5'-(5''-(tetrahydropyridazin-1'''-yl)benzimidazol-2''-yl)benzimidazol-2'-yl)pyridine

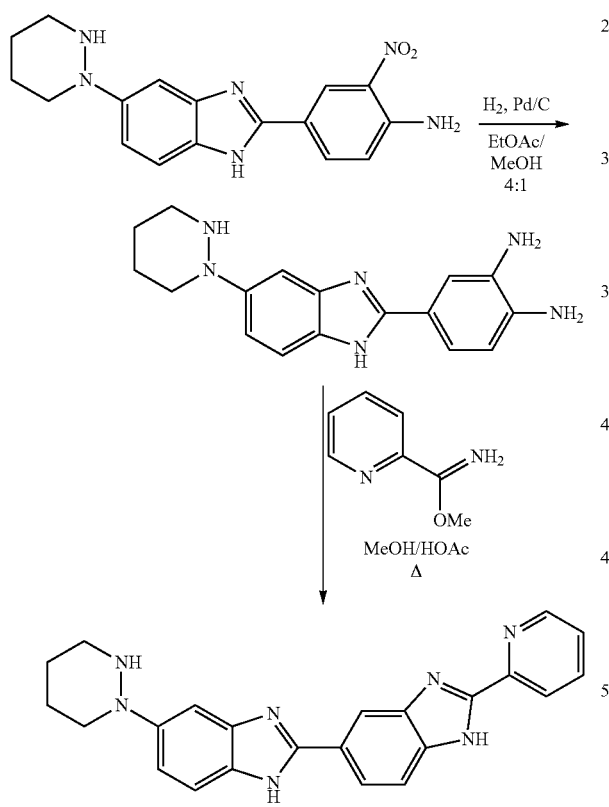

(i) Hydrogenation

To a solution of crude 2-Nitro-4-[5-(tetrahydro-pyridazin-1-yl)-1H-benzoimidazol-2-yl]-phenylamine (1.99 g, 5.9 mmol) in 2:1 ethyl acetate/methanol (150 ml), under nitrogen was added 5% palladium on carbon (240 mg) and the mixture was first evacuated and then stirred at room temperature under an atmosphere of hydrogen (balloon) for 1 day. The reaction mixture was next filtered through celite, washed with methanol, and the combined filtrate and washings were concentrated to give the crude diamine as a violet oil that was used in the next step without any purification.

(ii) Coupling Reaction

The crude diamine (prepared as above) was dissolved in methanol (125 ml). To this was added a solution of 2-cyanopyridine (884 mg, 8.5 mmol) that had been treated (immediately before) with sodium methoxide (0.85 mmol) in methanol (12 mL) at 40° C. for 1 hour under nitrogen. To this total mixture, acetic acid (1.2 ml, 21 mmol) was added.

This mixture was heated at 80° C. for a day under nitrogen followed by cooling to room temperature, and removing the solvents under reduced pressure. The resulting maroon residue was treated with a 5% aqueous ammonia solution (30 ml), incubated at 5° C. for one day. Next the aqueous layer was decanted, and residue was washed well with water via decantation. The resulting residue was co-evaporated with absolute ethanol to remove water and slurried overnight in acetonitrile. The acetonitrile was decanted and the resulting semisolid was dried. This yielded the product as a dark red semisolid, 1 g, however impure. (43.4% crude yield).

0.4 g of this material was then pre-absorbed into 1.2 g of silicagel pre-treated with 1% triethylamine in methanol. This was then loaded into a 2×10 cm silicagel column, (equilibrated with 20% methanol in dichloromethane+1% triethylamine), gradient eluted with 20% methanol in dichloromethane (+1% triethylamine) to 100% methanol (+1% triethylamine), and finally 10% methanolic ammonia in methanol. The product mainly eluted with 10% methanolic ammonia in methanol. Some 240 mg product was obtained on removal of the solvent.

$^1$H NMR (400 MHz, CD$_3$OD) δ 1.8 (m, 4H); 3.15 (m, 2H); 3.4 (m, 2H); 6.68 (m, 1H); 6.72 (unresolved, 1H); 7.3-7.4 (m, 2H); 7.8 (m, 1H); 7.9 (m, 2H), 8.25 (m, 1H); 8.3 (d, 1H), 8.7 (d, 1H).

Example 46

Synthesis of 2-(5'-(5''-(2''',2'''-dimethylhydrazinyl) benzimidazol-2''-yl)benzimidazol-2'-yl)pyridine (A) Preparation of 5-(N',N'-Dimethyl-hydrazino)-2-nitro-phenylamine

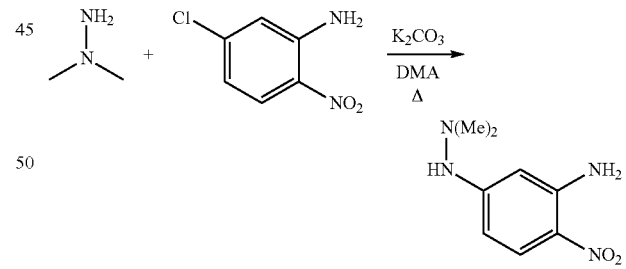

A mixture of 5-chloro-2-nitroaniline (20 g, 116 mmol), N,N-dimethyl-hydrazine (44 mL, 580 mmol) and anhydrous potassium carbonate (17.6 g, 128 mmol) in N,N-dimethylacetamide (50 ml) were stirred at 125° C. under nitrogen for 3 days Sample NMR analysis showed complete conversion of the starting material. The resultant mixture was then cooled to room temperature, poured onto cold water (400 mL), stirred vigorously and incubated at 4° C. overnight. The resulting brown precipitate was collected by filtration, washed well with water then dried on the filter funnel. This was then slurried in diethyl ether, filtered, washed with additional diethyl ether, dried to afford 5-(N',N'-Dimethyl-hydrazino)-

2-nitro-phenylamine (10.7 g, 47% yield) as a yellow solid. The crude product was used in the next step without further purification.

$^1$H NMR (400 MHz, CDCl$_3$): δ 3.0 (s, 6H); 5.7, (d, 1H); 6.1, (dd, 1H); 7.95, (d, 1H)

(B) Preparation of 4-[5-(N',N'-Dimethyl-hydrazino)-1H-benzoimidazol-2-yl]-2-nitro-phenylamine

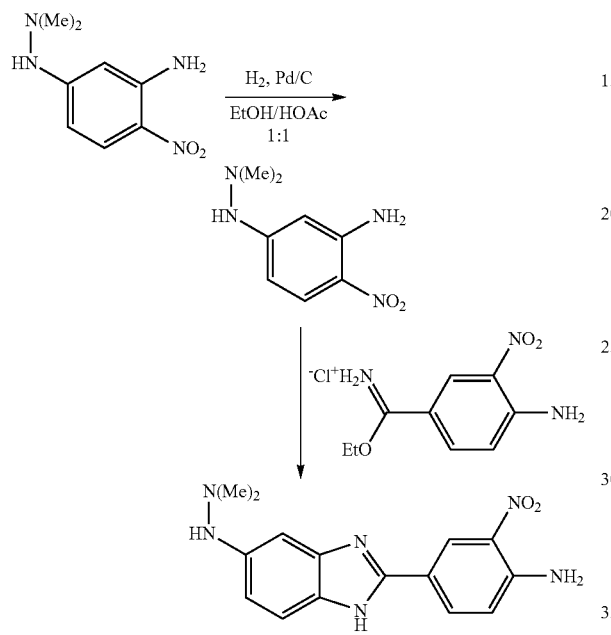

(i) Hydrogenation

To a solution of 5-(N',N'-Dimethyl-hydrazino)-2-nitro-phenylamine (1.56 g, 8.0 mmol) in 1:1 acetic acid/ethanol (100 ml), under nitrogen, was added 5% palladium on activated carbon (0.20 g). The resulting mixture was evacuated and next, stirred at room temperature under an atmosphere of hydrogen (balloon) for one day. The reaction mixture was then directly filtered through celite into a round bottom flask under a nitrogen atmosphere containing ethyl 4-amino-3-nitrobenzenecarboximidate hydrochloride (2.0 g, 8.0 mmol), and proceeded to the coupling step. The reduction product appears to be unstable-darkening rapidly.

(ii) Coupling Reaction

The resulting slurry from step (i) was heated at 80-90° C. under nitrogen for 72 h, then cooled to room temperature and solvents removed by rotary evaporator. The resulting violet oil was treated with dilute aqueous ammonia solution (3% in water, 60 ml), mixed vigorously and was kept overnight at 4° C. The supernatant liquid was decanted and the precipitated solid was washed with water again and decanted and the residual water was removed by evaporation.

Resulting solid was slurried in ether (100 mL) overnight and filtered, giving 1.9 g brown solid (76% crude yield).

The crude product was used in the next step without further purification.

$^1$H NMR (400 MHz, DMSO-d6) δ 3.0 (s, 6H); 6.7, (d, 1H); 7.08, (d, 1H); 7.3, (d, 1H); 7.7, (s, 1H); 8.1 (dd, 1H); 8.65 (d, 1H).

(C) Synthesis of 2-(5'-(5"-(2''',2'''-dimethylhydrazinyl)benzimidazol-2"-yl)benzimidazol-2"-yl)pyridine

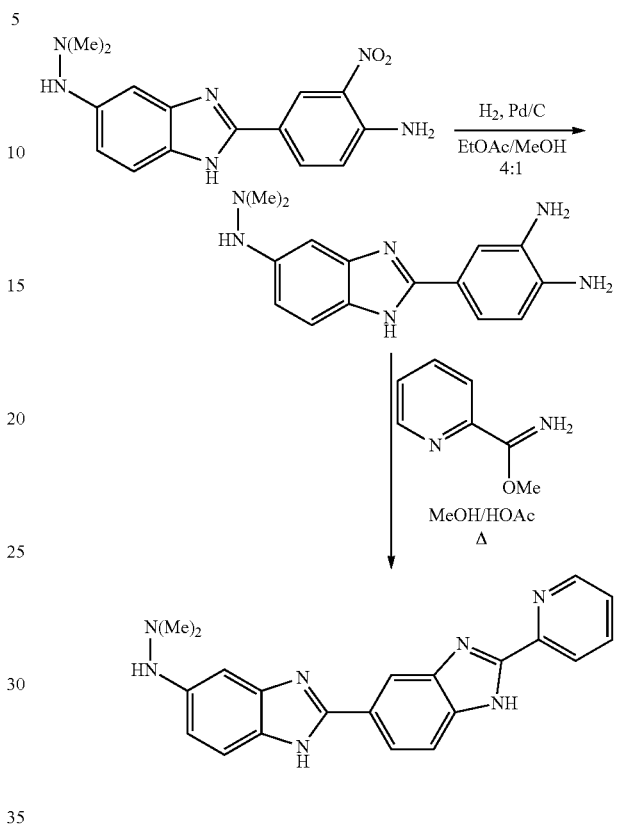

(i) Hydrogenation

To a solution of crude 2-Nitro-4-[5-(tetrahydro-pyridazin-1-yl)-1H-benzoimidazol-2-yl]-phenylamine (1.0 g, 3.2 mmol) in 4:1 ethyl acetate/methanol (100 ml) was added 5% palladium on carbon (200 mg) and the mixture was first evacuated and then stirred at room temperature under an atmosphere of hydrogen (balloon) for 1 day. The reaction mixture was next filtered through celite, washed with methanol, and the combined filtrate and washings were concentrated to give the crude diamine as a dark brown oil that was used in the next step without any purification.

(ii) Coupling Reaction

The crude diamine (prepared as above) was dissolved in methanol (50 ml). To this was added a solution of 2-cyanopyridine (499 mg, 4.8 mmol) that had been treated (immediately before) with sodium methoxide (0.48 mmol) in methanol (5 mL) at 40° C. for 1 hour under nitrogen. To this total mixture, acetic acid (0.67 ml, 12 mmol) was added.

This mixture was heated at 80° C. for a day under nitrogen followed by cooling to room temperature, and removing the solvents under reduced pressure. The resulting dark red-brown residue was treated with a 5% aqueous ammonia solution (20 ml), incubated at 5° C. for one day. No solid formed however the crude product separated as a thick oil at the bottom of the vessel. Next the aqueous layer was decanted, and residue was washed well with water via decantation. The resulting residue was evaporated to remove water and the resulting dark red film was stirred with acetonitrile to give a crude solid 0.5 g (42% crude yield). 0.25 g of this was chromatographed on a 2×9 silicagel column equilibrated with 1% triethylamine in ethyl acetate, eluting with 1-10% methanol in ethyl acetate. The product was isolated as a dark red-brown solid, 65 mg.

$^1$H NMR (400 MHz, CD$_3$OD) δ 3.0 (s, 6H); 6.9 (m, 2H); 7.44 (m, 2H); 7.7 (unresolved d, 1H); 7.9 (m, 2H); 8.26 (m, 2H), 8.68 (d, 1H).

Cytotoxicity and Radioprotection Results
  C50=74.6
  PF=27.9
  DMFm=1.71
  DMF10=1.29

Example 47

Preparation of 5-fluoro-2-(5'-(5"-(4'''-methylpiperazin-1'''-yl)benzimidazol-2"-yl)benzimidazol-2'-yl)pyridine

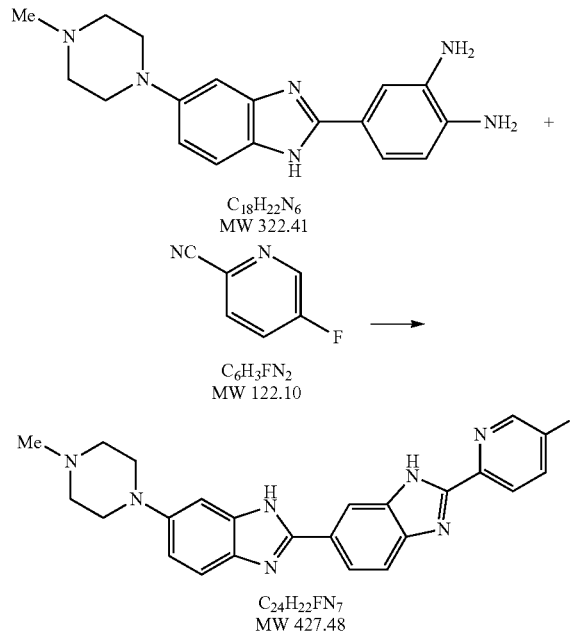

To 5-fluoropyridine-2-carbonitrile (200 mg, 1.64 mmol) was added a solution of sodium methoxide in methanol (0.1 M, 1.7 ml, 0.1 eq.) and the solution heated under nitrogen in a 40-45° C. oil-bath for 100 min. A solution of 2-amino-4-(5'-(4"-methylpiperazin-1"-yl)benzimidazol-2'-yl)aniline (277 mg, 0.86 mmol) in dry methanol (15 ml) and glacial acetic acid (0.19 ml, 3.3 mmol) was then added and the mixture gently refluxed under nitrogen overnight. After cooling the solvents were removed by rotary evaporator, the residue dissolved in water (10 ml) and basified to pH 8 with dilute ammonia solution (3.0 M). After stirring for 40 min the light brown suspension was centrifuged and the supernatant removed. Then solid was then treated with water (3×5 ml), followed by acetonitrile (4×3 ml) with centrifuging and removal of the supernatant between treatments. The remaining solid was dried under vacuum to give a brown glassy solid (270 mg). The material was then dissolved in methanol (2 ml) and applied to a silica cartridge (KP-Sil 25 g) and eluted with methanol to give 5-fluoro-2-(5'-(5"-(4'''-methylpiperazin-1'''-yl)benzimidazol-2"-yl)benzimidazol-2'-yl)pyridine as a dull light yellow powder (235 mg, 64%), mp 196-199° C.

$^1$H nmr (500 MHz, d$_4$-MeOH+5 drops d-TFA) δ 3.00, s, 3H, 4'''-MeN; 3.21, t (J=12.0 Hz), 2H, NCH$_2$; 3.34, m (obs), NCH$_2$; 3.69, d (J=12.0 Hz), 2H, NCH$_2$; 3.96, d (J=13.5 Hz), 2H, NCH$_2$; 7.32, d (J=1.5 Hz), 1H, H4"; 7.41, dd (J=2.5, 9.0 Hz), 1H, H6"; 7.73, d (J=9.0 Hz), 1H, H7"; 7.90, ddd (J=3.0, 8.5, 8.5 Hz), 1H, H4; 8.02, dd (J=0.5, 8.5 Hz), 1H, H7'; 8.14, dd (J=1.8, 8.8 Hz), 1H, H6'; 8.46, dd (J=4.0, 8.5 Hz), 1H, H3; 8.53, dd (J=0.5, 1.5 Hz), 1H, H4'; 8.74, d (J=3.0 Hz), 1H, H6. $^{13}$C nmr (125 MHz, d$_4$-MeOH+5 drops HOAc) δ 43.6, 4'''-MeN; 49.3, C2'''/6'''; 54.6, C3'''/5'''; 102.5, C4"; 115.0, 116.3, 116.8 (overlap), C4', C6", C7', C7"; 122.9, C6'; 124.0, C5'; 124.2, d ($^3$J$_{CF}$=5 Hz), C3; 125.0, d ($^2$J$_{CF}$=19 Hz), C4; 134.1, C7a"; 138.8, C3a' or C3a"; 139.0, d ($^2$J$_{CF}$=25 Hz), C6; 140.3, C3a" or C3a'; 141.5, C7a'; 145.0, C2; 148.5, C5"; 152.7, 153.1, C2', C2"; 161.4, d ($^1$J$_{CF}$=258 Hz), C5. MS (ESI+ve) m/z 428 (MH$^+$, 100%). HRMS (ESI+ve) m/z 428.19934, C$_{24}$H$_{23}$FN$_7$ requires 428.19935 (Δ=0.0 ppm).

Cytotoxicity and Radioprotection Results
  C50=537.5
  PF=40.0
  DMFm=2.46
  DMF10=2.20

Example 48

Preparation of 2-(5'-(5"-(4'''-methylpiperazin-1'''-yl) benzimidazol-2"-yl)benzimidazol-2'-yl)-4-(trifluoromethyl)pyridine

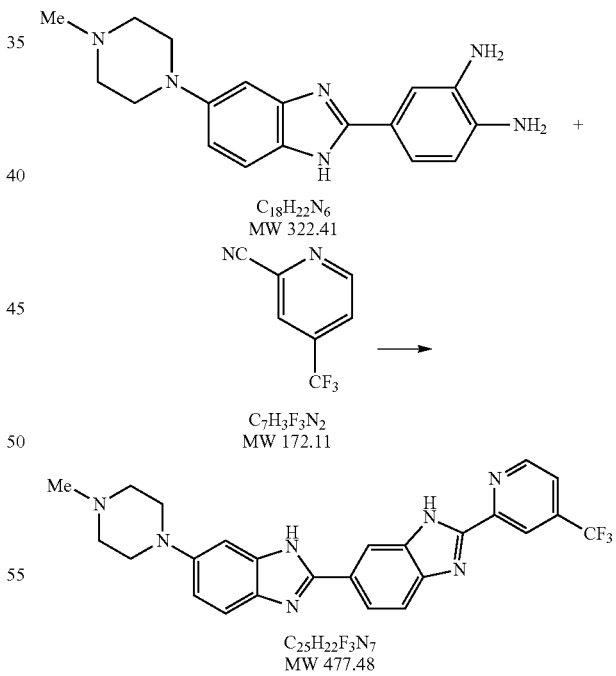

To 4-trifluoromethyl-2-pyridinecarbonitrile (262 mg, 1.52 mmol) was added a solution of sodium methoxide in methanol (0.1 M, 1.5 ml, 0.1 eq.) and the solution heated under nitrogen in a 40-45° C. oil-bath for 105 min. A solution of 2-amino-4-(5'-(4"-methylpiperazin-1"-yl)benzimidazol-2'-yl)aniline (295 mg, 0.92 mmol) in dry methanol (15 ml) and glacial acetic acid (0.18 ml, 3.1 mmol) was then added and the mixture gently refluxed under nitrogen for 19 h. After cooling the solvents were removed by rotary evaporator, the residue dissolved in water (10 ml) and basified to pH 8 with dilute ammonia solution (3.0 M). The oily precipitate was stirred for 40 min to give a friable light brown suspension that was centrifuged and the supernatant removed. Then solid was then treated with water (3×8 ml), followed by acetonitrile (3×4 ml) with centrifuging and removal of the supernatant between treatments. The remaining solid was dried under vacuum to give a dull yellow powder (358 mg). A portion of this material (250 mg) was dissolved in methanol (1-2 ml) and applied to a silica cartridge (KP-Sil 25 g) and eluted with methanol to give 2-(5'-(5''-(4'''-methylpiperazin-1'''-yl)benzimidazol-2''-yl)benzimidazol-2'-yl)-4-(trifluoromethyl)pyridine as a yellow powder (236 mg, 77%), mp 203-208° C.

$^1$H nmr (400 MHz, d$_4$-MeOH+5 drops d-TFA) δ 3.01, s, 3H, 4'''-MeN; 3.21, t (J=12.0 Hz), 2H, NCH$_2$; 3.35, m (obs), NCH$_2$; 3.68, d (J=12.0 Hz), 2H, NCH$_2$; 3.96, d (J=13.6 Hz), 2H, NCH$_2$; 7.32, d (J=2.0 Hz), 1H, H4''; 7.41, dd (J=2.5, 9.2 Hz), 1H, H6''; 7.73; d (J=8.8 Hz), 1H, H7''; 7.88, m, 1H, H5; 8.01, dd (J=0.6, 8.6 Hz), 1H, H7'; 8.09, dd (J=2.5, 8.8 Hz), 1H, H6'; 8.52, m, 1H, H4'; 8.66, s, 1H, H3; 9.05, d (J=4.8 Hz), 1H, H6. $^{13}$C nmr (125 MHz, d$_4$-MeOH+5 drops HOAc) δ 43.6, 4'''-MeN; 49.4, C2'''/6'''; 54.7, C3'''/5'''; 102.7, C4''; 115.4, 116.4, 116.8, 117.1, C4', C6'', C7', C7''; 118.0, 121.2, C3, C5; 123.4, C6'; 124.1, q ($^1J_{CF}$=273 Hz), 4-F$_3$C; 124.9, C5'; 134.6, C7a''; 139.2, C3a' or C3a''; 140.3, d ($^2J_{CF}$=34 Hz), C4; 140.5, C3a'' or C3a'; 141.4, C7a'; 148.5, C5''; 150.2, C2; 152.2, C6; 152.7, 152.9, C2', C2''. MS (ESI+ve) m/z 478 (MH$^+$, 100%). HRMS (ESI+ve) m/z 478.19599, C$_{25}$H$_{23}$F$_3$N$_7$ requires 478.19615 (Δ=0.3 ppm).

Cytotoxicity and Radioprotection Results

C50=23.3

PF=63.8

DMFm=2.75

DMF10=2.58

Example 49

Preparation of 2-(5'-(5''-(4'''-methylpiperazin-1'''-yl)benzimidazol-2''-yl)benzimidazol-2'-yl)-5-(trifluoromethyl)pyridine

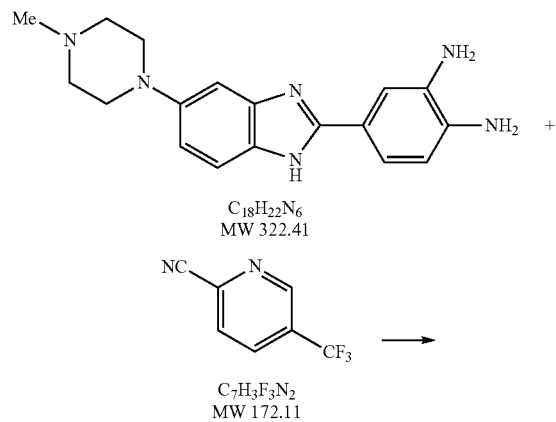

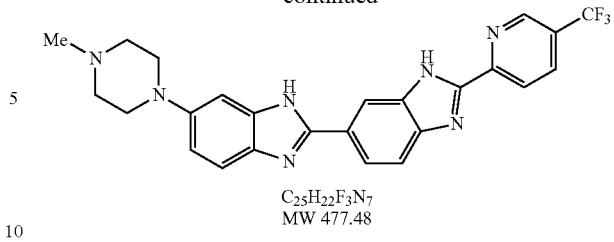

To 5-(trifluoromethyl)pyridine-2-carbonitrile (261 mg, 1.52 mmol) was added a solution of sodium methoxide in methanol (0.1 M, 1.5 ml, 0.15 mmol) and the solution heated under nitrogen in a 40-45° C. oil-bath for 90 min. A solution of 2-amino-4-(5'-(4''-methylpiperazin-1''-yl)benzimidazol-2'-yl)aniline (295 mg, 0.92 mmol) in dry methanol (15 ml) and glacial acetic acid (0.18 ml, 3.1 mmol) was then added and the mixture gently refluxed under nitrogen for 19 h. After cooling, the solvents were removed by rotary evaporator, the residue dissolved in water (10 ml) and basified to pH 9 with dilute ammonia solution (3.0 M), resulting in an oily-solid being deposited on the glass surface. The aqueous liquid was removed and the material treated with water (10 ml) with vigorous scratching until a friable solid was obtained. After stirring for 40 min the suspension was centrifuged and the supernatant removed. Then solid was then treated with water (2×8 ml), followed by acetonitrile (2×5 ml) with centrifuging and removal of the supernatant between treatments. The solid was then dried under vacuum to give a dull yellow powder (328 mg). A portion of the material (250 mg) was dissolved in methanol (3-4 ml) and applied to a silica cartridge (KP-Sil 25 g) and eluted with methanol to give 2-(5'-(5''-(4'''-methylpiperazin-1'''-yl)benzimidazol-2''-yl)benzimidazol-2'-yl)-5-(trifluoromethyl)pyridine as a yellow powder (228 mg, 68%), mp 320° C. (dec).

$^1$H nmr (400 MHz, d$_4$-MeOH+5 drops d-TFA) δ 3.00, s, 3H, 4'''-MeN; 3.21, t (J=12.0 Hz), 2H, NCH$_2$; 3.34, m (obs), NCH$_2$; 3.68, d (J=12.4 Hz), 2H, NCH$_2$; 3.97, d (J=12.8 Hz), 2H, NCH$_2$; 7.32, d (J=2.0 Hz), 1H, H4''; 7.41, dd (J=2.2, 9.0 Hz), 1H, H6''; 7.73, d (J=9.2 Hz), 1H, H7''; 8.02, d (J=8.8 Hz), 1H, H7'; 8.09, dd (J=1.8, 8.6 Hz), 1H, H6'; 8.38, dd (J=1.6, 8.4 Hz), 1H, H4; 8.53, d (J=1.2 Hz), 1H, H4'; 8.56, d (J=8.4 Hz), 1H, H3; 9.11, s, 1H, H6. $^{13}$C nmr (125 MHz, d$_4$-MeOH+5 drops HOAc) δ 43.6, 4'''-MeN; 49.4, C2'''/6'''; 54.7, C3'''/5'''; 102.7, C4''; 115.3, 116.4, 116.8, 117.2, C4', C6'', C7', C7''; 122.4, C3; 123.4, C6'; 124.8, q ($^1J_{CF}$=271 Hz), 5-CF$_3$; 125.1, C5'; 127.9, q ($^2J_{CF}$=33 Hz), C5; 134.8, C7a''; 135.7, C4; 139.4, 140.5, C3a', C3a''; 141.5, C7a'; 147.5; C6; 148.5, C5''; 152.0, 152.5, 152.9, C2, C2', C2''. MS (ESI+ve) m/z 478 (MH$^+$, 100%). HRMS (ESI+ve) m/z 478.19601, C$_{25}$H$_{23}$F$_3$N$_7$ requires 478.19615 (Δ=0.1 ppm).

Cytotoxicity and Radioprotection Results

C50=12.2

PF=33.1

DMFm=2.38

DMF10=2.21

Example 50

Preparation of 2-(5'-(5"-(4'''-hydroxypiperidin-1'''-yl)benzimidazol-2"-yl)benzimidazol-2'-yl)-4-methylpyridine

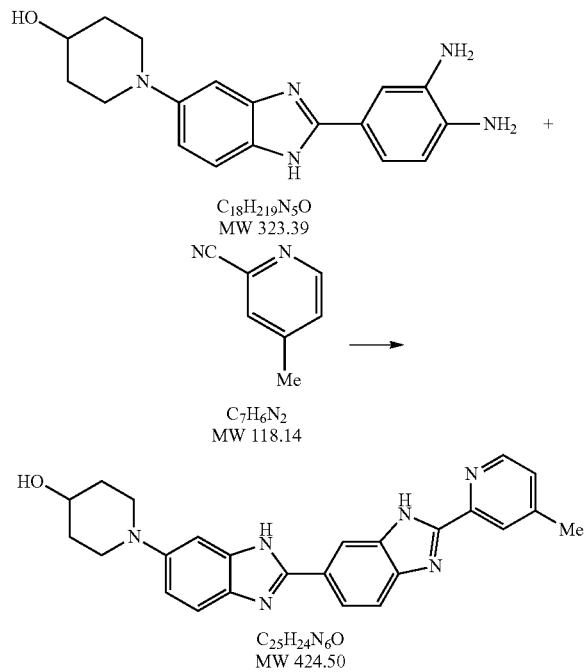

To 4-methylpyridine-2-carbonitrile (135 mg, 1.14 mmol) was added a solution of sodium methoxide in methanol (0.1 M, 1.1 ml, 0.11 mmol) and the solution heated under nitrogen in a 40-45° C. oil-bath for 110 min. A solution of 2-amino-4-(5'-(4"-hydroxypiperidin-1"-yl)benzimidazol-2'-yl)aniline (0.60 mmol) in dry methanol (10 ml) and glacial acetic acid (0.12 ml, 2.1 mmol) was added and the mixture gently refluxed under nitrogen for 19 h. After cooling the solvents were removed by rotary evaporator and the residue dissolved in water (9 ml) and basified to pH 8-9 with 3 M ammonia solution. Additional water was added (~10 ml) and the oily suspension extracted with n-butanol (20 ml). The butanol extract was washed with water (20 ml) and evaporated to give a brown oil. The oil was treated with acetonitrile (2 ml) and stirred for 40 min to give a friable olive solid that was further triturated with acetonitrile (2×2 ml). The solid was dissolved in methanol (3 ml) with heating and applied to a silica gel cartridge (Reveleris 12 g) and eluted with a ethyl acetate/methanol gradient to give 2-(5'-(5"-(4'''-hydroxypiperidin-1'''-yl)benzimidazol-2"-yl)benzimidazol-2'-yl)-4-methylpyridine as a yellow powder (155 mg, 61%), mp 204-209° C.

$^1$H nmr (500 MHz, d$_4$-MeOH+4 drops d-TFA) δ 2.00, m, 2H, H3'''/H5'''; 2.25, m, 2H, H3'''/5'''; 2.58, s, 3H, 4-Me; 3.61, m, 2H, H2'''/6'''; 3.91, m, 2H, H2'''/6'''; 4.09, tt (J=3.5, 7.0 Hz), 1H, H4'''; 7.58, dq (J=5.0, 0.7 Hz), 1H, H5; 7.74, dd (J=2.2, 8.8 Hz), 1H, H6'; 7.92, d (J=8.5 Hz), 1H, H7"; 7.99, d (J=2.0 Hz), 1H, H4"; 8.07, dd (J=0.8, 8.8 Hz), 1H, H7'; 8.27, m, 2H, H3, H6'; 8.64, dd (J=0.5, 1.5 Hz), 1H, H4'; 8.73, d (J=5.0 Hz), 1H, H6. $^{13}$C nmr (125 MHz, d$_4$-MeOH+5 drops HOAc) δ 21.1, 4-Me; 34.8, C3'''/5'''; 49.7, C2'''/6'''; 68.0, C4'''; 101.0, C4"; 115.1, 115.5, 116.9, 117.6, C4', C6", C7', C7"; 121.5, C5'; 122.6, 123.4, 126.9, C3, C5, C6'; 130.9, C7a"; 136.9, C3a"; 140.0, C3a'; 141.6, C7a'; 148.0, C2; 149.9, 150.1, C4, C5", 150.4; C6, 150.9; 154.3; C2', C2". MS (ESI+ve) m/z 425 (MH$^+$, 100%). HRMS (ESI+ve) m/z 425.20844, C$_{25}$H$_{25}$N$_6$O requires 425.20844 (Δ=0.0 ppm).

Cytotoxicity and Radioprotection Results
C50=134.3
PF=23.5
DMFm=1.79
DMF10=1.33

Example 51

Preparation of 2-(5'-(5"-(4'''-hydroxypiperidin-1'''-yl)benzimidazol-2"-yl)benzimidazol-2'-yl)-5-methylpyridine

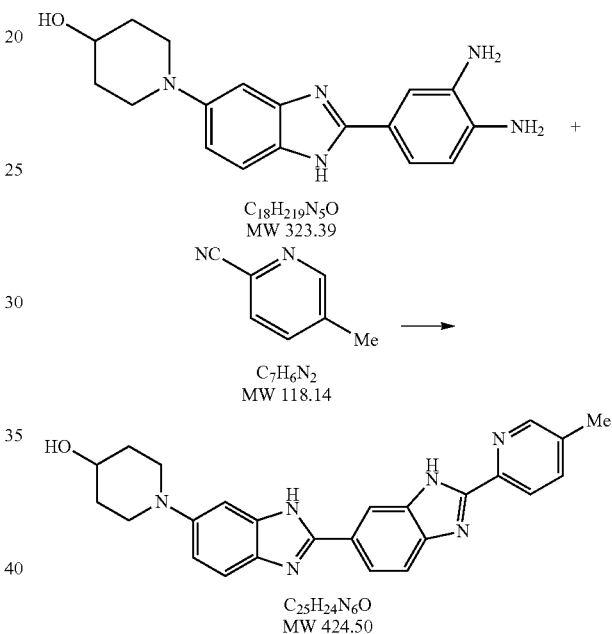

To 5-methylpyridine-2-carbonitrile (135 mg, 1.14 mmol) was added a solution of sodium methoxide in methanol (0.1 M, 1.1 ml, 0.11 mmol) and the solution heated under nitrogen in a 40-45° C. oil-bath for 110 min. A solution of 2-amino-4-(5'-(4"-hydroxypiperidin-1"-yl)benzimidazol-2'-yl)aniline (0.60 mmol) in dry methanol (10 ml) and glacial acetic acid (0.12 ml, 2.1 mmol) was added and the mixture gently refluxed under nitrogen for 19 h. After cooling the solvents were removed by rotary evaporator and the residue dissolved in water (10 ml) and basified to pH 8-9 with 3 M ammonia solution. The mixture was stirred for 40 min resulting in an even suspension of a friable grey solid, which was centrifuged and the supernatant removed. The residue was treated with water (10 ml), then acetonitrile (3×2 ml), with centrifugation and removal of the supernatant after each treatment. The remaining solid was dissolved in methanol (2 ml) and applied to a silica gel cartridge (Reveleris 12 g) and eluted with methanol to give 2-(5'-(5"-(4'''-hydroxypiperidin-1'''-yl)benzimidazol-2"-yl)benzimidazol-2'-yl)-5-methylpyridine as a yellow powder (112 mg, 44%), mp 208-213° C.

$^1$H nmr (500 MHz, d$_4$-MeOH+4 drops d-TFA) δ 2.00, m, 2H, H3'''/H5'''; 2.24, m, 2H, H3'''/5'''; 2.51, s, 3H, 5-Me; 3.60, m, 2H, H2'''/6'''; 3.91, m, 2H, H2'''/6'''; 4.09, tt (J=3.5, 7.0 Hz), 1H, H4'''; 7.72, dd (J=2.5, 9.0 Hz), 1H, H6''; 7.91, d (J=8.5 Hz), 1H, H7''; 7.97, m, 2H, H4, H4''; 8.06, d (J=8.8 Hz), 1H, H7'; 8.28, m, 2H, H3, H6'; 8.62, d (J=1.5 Hz), 1H, H4'; 8.75, m, 1H, H6. $^{13}C$ nmr (125 MHz, $d_4$-MeOH+5 drops HOAc) δ 18.4, 5-Me; 34.9, C3'''/5'''; 49.7, C2'''/6'''; 68.0, C4'''; 100.9, C4''; 115.0, 115.4, 116.7, 117.5, C4', C6'', C7', C7''; 121.2, C5'; 122.2, 122.4, C3, C6'; 130.7, C7a''; 136.5, C5; 136.8, C3a''; 138.4, C4; 139.9, C3a'; 141.5, C7a'; 145.5, C2; 150.0, C5''; 150.8, C2' or C2''; 151.0, C6; 154.3, C2'' or C2'. MS (ESI+ve) m/z 425 ($MH^+$, 100%). HRMS (ESI+ve) m/z 425.20846, $C_{25}H_{25}N_6O$ requires 425.20844 (Δ=0.1 ppm).

Cytotoxicity and Radioprotection Results

C50=123.9
PF=58.7
DMFm=2.07
DMF10=1.90

Example 52

Preparation of 2-(5'-(5''-(cis-2''',6'''-dimethylmorpholino)benzimidazol-2''-yl)benzimidazol-2'-yl)pyridine (A) Preparation of 5-(cis-2',6'-dimethylmorpholino)-2-nitroaniline

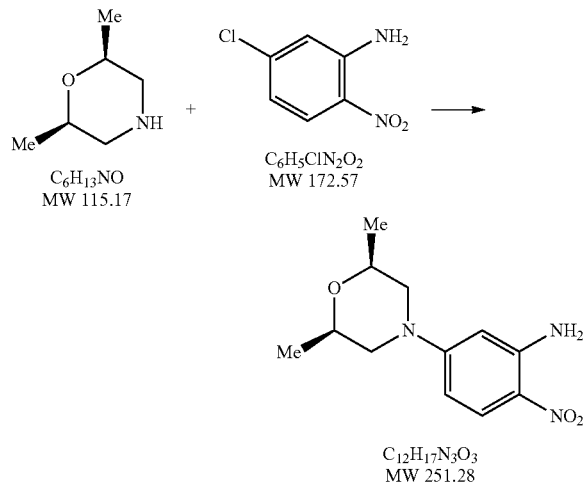

To a solution of cis-2,6-dimethylmorpholine (4.15 g, 36.0 mmol, 1.8 eq) in dry N,N-dimethylacetamide (35 ml) was added potassium carbonate (2.94 g, 21.2 mmol, 1.05 eq) followed by 5-chloro-2-nitroaniline (3.44 g, 19.9 mmol) and the mixture heated in a 120° C. oil-bath under nitrogen for 46 h. The reaction mixture was then cooled to room temperature, poured into water (200 ml) and stirred for 1 h. The suspension was filtered and the collected solid washed carefully with water (3×30 ml), then diethyl ether (2×20 ml) before drying under vacuum over $P_2O_5$ to give 5-(cis-2',6'-dimethylmorpholino)-2-nitroaniline (3.67 g, 73%) as a light ochre powder.

$^1H$ nmr$^1$ (400 MHz, $CDCl_3$) δ 1.26, d (J=6.4 Hz), 6H, 2',6'-diMe; 2.56, dd (J=10.8, 12.4 Hz), 2H, H3'/5'; 3.58, m, 2H, H3'/5'; 3.72, m, 2H, H2'/6'; 5.94, d (J=2.8 Hz), 1H, H6; 6.14, br, 2H, 1-$NH_2$; 6.27, dd (J=2.8, 9.6 Hz), 1H, H4; 8.02, d (J=9.6 Hz), 1H, H3.

Ref 10: WO 02/20500A2.

(B) Preparation of 4-(5'-(cis-2'',6''-dimethylmorpholino)benzimidazol-2'-yl-2-nitroaniline

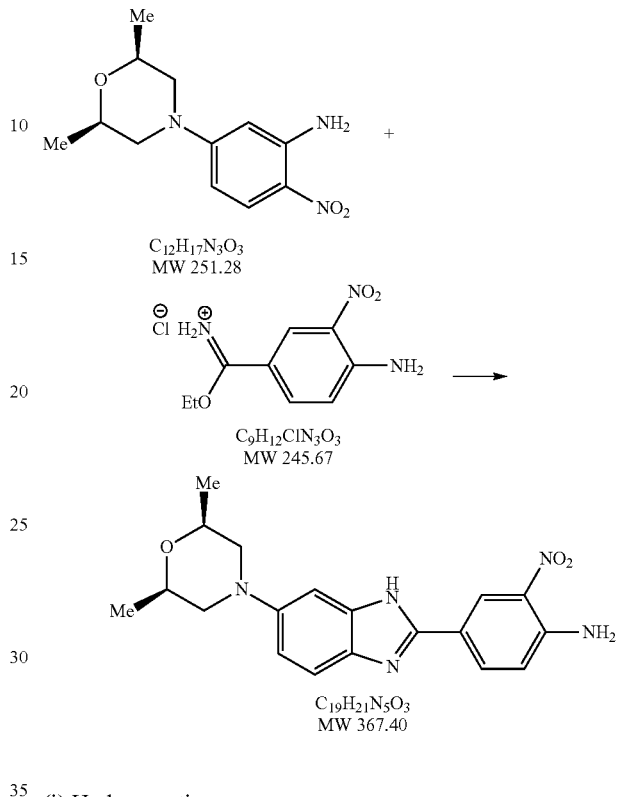

(i) Hydrogenation

To a solution of 5-(cis-2',6'-dimethylmorpholino)-2-nitroaniline (1.26 g, 5.03 mmol) in 4:1 ethyl acetate/methanol (75 ml) was added 5% palladium on carbon (0.24 g) and the reaction mixture stirred under an atmosphere of hydrogen for 25 h. The reaction mixture was then filtered through celite, the filtered solid washed with methanol, and the combined filtrate and washings concentrated in vacuo to give crude 2-amino-4-(cis-2',6'-dimethylmorpholino)aniline (1.08 g, 97%) which was used immediately in the next step.

(ii) Coupling Reaction

The crude 2-amino-4-(cis-2',6'-dimethylmorpholino)aniline (1.08 g, 4.9 mmol, prepared above in (i)) and ethyl 4-amino-3-nitrobenzenecarboximidate hydrochloride (1.27 g, 5.2 mmol) were refluxed in dry ethanol (25 ml) and glacial acetic acid (12.5 ml) under nitrogen for 19 h. The reaction mixture was cooled to room temperature, the solvents removed by rotary evaporator and the residue suspended in water (100 ml) and basified to ~pH 11 with concentrated ammonia solution. After stirring for 2-3 h, a fine red precipitate had developed which was collected (por 3 sinter), washed carefully with water before drying under vacuum over $P_2O_5$ overnight, to give 4-(5'-(cis-2'',6''-dimethylmorpholino)benzimidazol-2'-yl)-2-nitroaniline (1.62 g, 90%) as a dark red powder, mp 147° C. (dec).

$^1H$ nmr (400 MHz, $d_4$-MeOH+4 drops d-TFA) δ 1.26, d (J=6.4 Hz), 6H, 2'',6''-diMe; 2.54, dd (J=11.2, 11.6 Hz), 2H, H3''/5''; 3.62, d (J=10.8 Hz), 2H, H3''/5''; 3.86, m, 2H, H2''/6''; 7.21, d (J=2.0 Hz), 1H, H4'; 7.23, d (J=9.2 Hz), 1H, H6; 7.37, dd (J=2.0, 9.2 Hz), 1H, H6'; 7.62, d (J=9.2 Hz), 1H, H7'; 7.96, dd (J=2.2, 9.0 Hz), 1H, H5; 8.92, d (J=2.4 Hz), 1H, H3.

¹³C nmr (100 MHz, d₄-MeOH+15 drops HOAc) δ 19.2, 2",6"-diMe; 56.4, C3"/5"; 73.0, C2"/6"; 99.6, C4'; 113.1, C4; 115.3, 117.0, 121.2, 126.4, C3, C6, C6' and C7'; 129.1, C2; 132.0, C3a' or C7a'; 133.5, C5; 135.8, C7a' or C3a'; 148.9, 149.1, 150.7, C1, C2' and C5'. MS (ESI+ve) m/z 735 (M₂H⁺, 6%), 368 (MH⁺, 100). HRMS (ESI+ve) m/z 368.17163, C₁₉H₂₂N₅O₃ requires 368.17172 (Δ=0.2 ppm).

(C) Preparation of 2-(5'-(5"-(cis-2''',6'''-dimethylmorpholino)benzimidazol-2"-yl) benzimidazol-2'-yl) pyridine

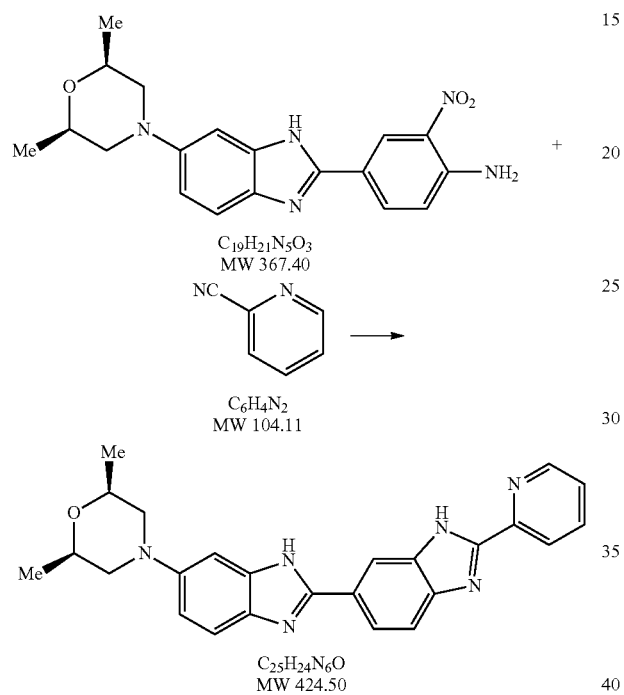

(i) Hydrogenation

To a solution of 4-(5'-(cis-2",6"-dimethylmorpholino)benzimidazol-2'-yl)-2-nitroaniline (0.38 g, 1.03 mmol) in 4:1 ethyl acetate/methanol (40 ml) was added 5% palladium on carbon (100 mg) and the reaction mixture stirred under an atmosphere of hydrogen for 21 h. The reaction mixture was then filtered through celite, the filtered solid washed with methanol, and the combined filtrate and washings concentrated in vacuo to give the crude 2-amino-4-(5'-(cis-2",6"-dimethylmorpholino)benzimidazol-2'-yl)aniline (350 mg, 100%) which was used immediately in the next step.

(ii) Coupling Reaction

2-Cyanopyridine (207 mg, 1.99 mmol) was treated with methanolic sodium methoxide solution (0.07 M, 2.9 ml, 0.20 mmol) and heated in a 40-45° C. oil-bath for 2 h under nitrogen. Heating was then stopped and a solution of 2-amino-4-(5'-(cis-2",6"-dimethylmorpholino)benzimidazol-2'-yl)aniline (350 mg, 1.03 mmol) in dry methanol (15 ml) and glacial acetic acid (0.23 ml, 4.0 mmol) was then added, and the mixture gently refluxed under nitrogen for 19 h. The reaction mixture was cooled to room temperature, the solvent removed by rotary evaporator and the residue treated with dilute ammonia solution (3.0 M, 15 ml) and stirred for 1 h. The tan suspension was centrifuged, the supernatant removed and the residue treated with water (2×10 ml), then acetonitrile (3×3 ml), with centrifuging and removal of the supernatant between treatments. The residue was dissolved in methanol (~3 ml) and applied to a silica gel column (32×170 mm) and eluted with 4:1 ethyl acetate/methanol to give 2-(5'-(5"-(cis-2''',6'''-dimethylmorpholino)benzimidazol-2"-yl) benzimidazol-2'-yl)pyridine (246 mg, 56%) as an orange glassy solid, mp 195-197° C.

¹H nmr (500 MHz, d₄-MeOH+4 drops d-TFA) δ 1.27, d (J=6.5 Hz), 6H, 2''',6'''-diMe; 2.52, dd (J=10.5, 12.0 Hz), 2H, H3'''/5'''; 3.64, app. d (J=10.5 Hz), 2H, H3'''/5'''; 3.86, m, 2H, H2'''/6'''; 7.23, d (J=2.0 Hz), 1H, H4"; 7.40, dd (J=2.5, 9.0 Hz), 1H, H6"; 7.65, ddd (J=1.0, 4.5, 7.5 Hz), 1H, H5; 7.69, d (J=9.0 Hz), 1H, H7"; 8.03, d (J=9.0 Hz), 1H, H7'; 8.11, m, 2H, H4, H6'; 8.40, br d (J=8.0 Hz), 1H, H3; 8.51, d (J=1.0 Hz), 1H, H4'; 8.85, m, 1H, H6. ¹³C nmr (125 MHz, d₄-MeOH+4 drops HOAc) δ 19.2, 2'''/6'''-Me; 56.6, C3'''/5'''; 72.9, C2'''/6'''; 99.9, C4"; 115.1, 115.7, 116.3, 116.9, C4', C6", C7', C7"; 122.1, C5'; 122.6, 122.8, C3 and C6'; 126.1, C5; 131.2, C7a"; 137.2, C3a', C3a" or C7a'; 138.3, C4; 140.2, 141.6, C3a', C3a" or C7a'; 148.5, 150.0, C2, C5" and C2' or C2"; 150.7, C6; 151.0, C2, C5" and C2' or C2"; 154.2, C2" or C2'. MS (ESI+ve) m/z 849 (M₂H⁺7%), 397 (MH⁺, 100). HRMS (ESI+ve) m/z 425.20831, C₂₅H₂₅N₆O requires 425.20844 (Δ=0.3 ppm).

Cytotoxicity and Radioprotection Results
C50=133.5
PF=55.9
DMFm=1.75
DMF10=1.40

Example 53

Synthesis of 2-(5'-(5"-(4'''-methylpiperazin-1'''-yl)-1H-indol-2"-yl)benzimidazol-2'-yl)pyridine (A) Synthesis of 6-(4-Methyl-piperazin-1-yl)-1-(toluene-4-sulfonyl)-1H-indole

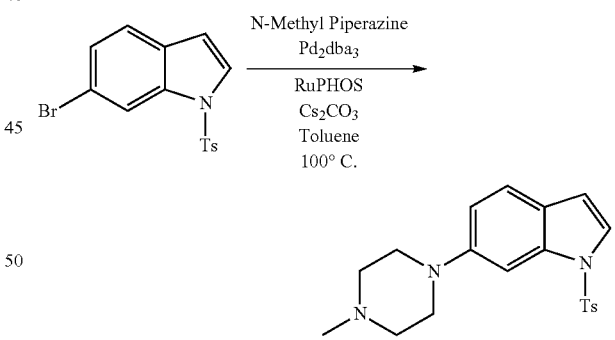

A 250 mL round bottom flask was loaded with 6-Bromo-1-(toluene-4-sulfonyl)-1H-indole (4 g, 11.4 mmol), Cs₂CO₃ (7.4 g, 22.8 mmol), Pd₂dba₃ (0.104 g, 0.114 mmol), RuPHOS (0.106 g, 0.23 mmol), Toluene (150 mL), N-Methyl piperazine (1.9 mL, 17.2 mol), evacuated and flushed with nitrogen. Next the reaction flask was heated at 100° C., over the weekend. Analysis at this point showed that most of the starting material had converted to the product. After cooling to room temperature, the solution was diluted with EtOAc (150 mL), filtered through a pad of celite, washed with additional EtOAc (150 mL) and was evaporated. The resulting oil was chromatographed on silica gel to give the product as a thick brown oil (which crystallized on standing), 3.1 g, (73.8% yield).

$^1$H NMR (CDCl$_3$, 400 MHz): δ 7.7 (d, 2H), 7.48 (d, 1H), 7.38 (d, 1H), 7.33 (d, 1H), 7.16 (d, 2H), 6.9 (dd, 1H), 6.5 (dd, 1H), 3.2 (m, 4H), 2.6 (m, 4H), 2.33 (s, 3H), 2.3 (s, 3H)

(B) Synthesis of 6-(4-Methyl-piperazin-1-yl)-1-(toluene-4-sulfonyl)-2-tributylstannanyl-1H-indole

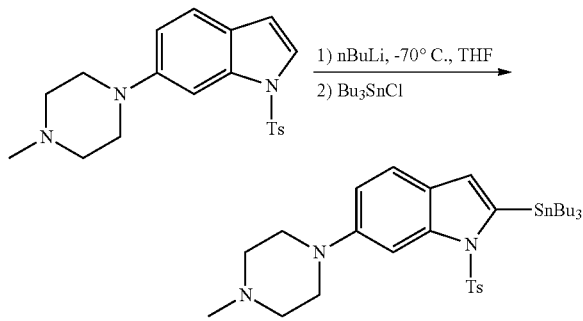

6-(4-Methyl-piperazin-1-yl)-1-(toluene-4-sulfonyl)-1H-indole (3.43 g, 9.3 mmol) was first thoroughly dried and then dissolved in dry THF (50 mL) and cooled to −70° C. Next, nBuLi (2.5 M in Hexanes, 5 mL, 12.5 mmol) was added dropwise, maintaining the same internal temperature. The mixture was stirred at −70° C. and tributyltin chloride (3.4 mL, 12.5 mmol) in 15 mL THF was added to this dropwise. After stirring for 1 hour at this temperature, the reaction mixture was warmed to room temperature and stirred overnight. The reaction was quenched by the addition of water (50 mL), extracted with EtOAc (150 mL) and the extracts were repeatedly washed with water (5×100 mL). Organic layer was dried with MgSO$_4$, evaporated to give the crude product, 7.8 g. This was next chromatographed on silicagel to isolate the product (still contaminated with some tributyltin impurities) as a brownish viscous oil 4.7 g (77% yield).

$^1$H NMR (CDCl$_3$, 400 MHz): δ 7.5 (d, 2H), 7.3 (m, 1H), 7.13 (d, 1H), 6.85 (dd, 1H), 6.65 (s, 1H), 3.2 (m, 4H), 2.56 (m, 4H), 2.3 (s, 3H), 2.28 (s, 3H), 1.5 (m, 6H), 1.3 (m, 6H), 1.1 (m, 6H), 0.85 (m, 9H).

(C) Synthesis of 4-[6-(4-Methyl-piperazin-1-yl)-1-(toluene-4-sulfonyl)-1H-indol-2-yl]-2-nitro-phenylamine

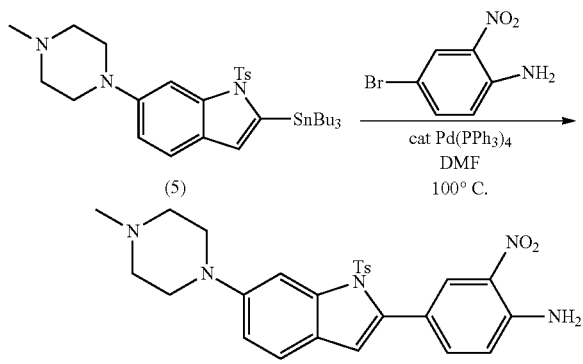

6-(4-Methyl-piperazin-1-yl)-1-(toluene-4-sulfonyl)-2-tributylstannanyl-1H-indole (crude) (5.0 g, 7.6 mmol) and 4-bromo-2-nitroaniline (2.05 g, 9.5 mmol) in DMF (50 mL) were placed in a RB flask followed by evacuating and flushing with nitrogen. Pd(PPh$_3$)$_4$ (0.22 g, 0.19 mmol) was added and under nitrogen was heated to 100° C., overnight. Analysis after this period indicated that all starting material had been consumed. Workup was by diluting with EtOAc (200 ml) and repeatedly washing with sat NH$_4$Cl (5×50 ml). Crude NMR spectrum was complex, attributed to the product nitrogen atoms being in various oxidation states. The crude was chromatographically purified (16 cm×6 cm silicagel column, gradient eluting with dichloromethane to 10% methanol in dichloromethane), and all related fractions were pooled together (orange thick oil) 3.0 g, was taken directly to the next step without further purification or attempting to assign the chemical shifts.

(D) Synthesis of 6-[6-(4-Methyl-piperazin-1-yl)-1-(toluene-4-sulfonyl)-1H-indol-2-yl]-2-pyridin-2-yl-1H-benzoimidazole

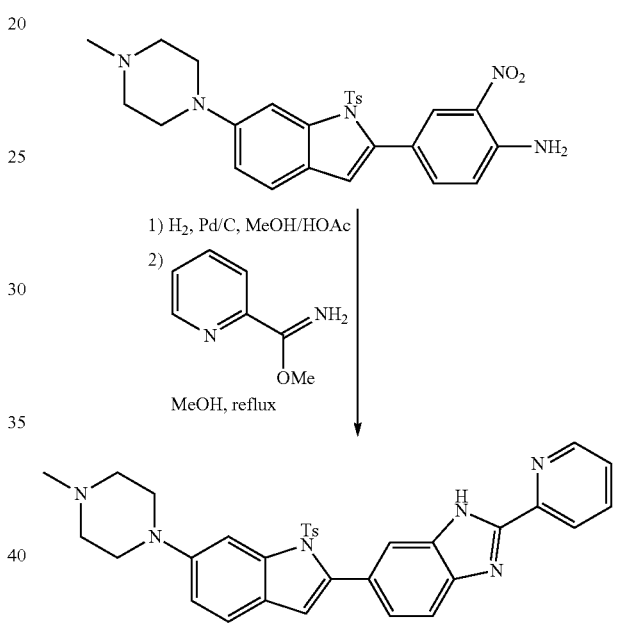

The 4-[6-(4-Methyl-piperazin-1-yl)-1-(toluene-4-sulfonyl)-1H-indol-2-yl]-2-nitro-phenylamine (0.5 g, 0.99 mmol), was dissolved in 7:3 MeOH/HOAc (100 ml), and hydrogenated in the presence of 5% palladium on carbon (100 mg), overnight. The solution was then filtered through celite, washed with methanol (50 ml), and evaporated. The resulting diamine was dissolved in methanol (20 ml). To this was added a solution of 2-cyanopyridine (154 mg, 1.5 mmol) that had been treated (immediately before) with sodium methoxide (0.15 mmol) in methanol (2 mL) at 40° C. for 1.5 hour under nitrogen. To this mixture, acetic acid (0.21 ml, 3.8 mmol) was added. This mixture was heated at 80° C. overnight under nitrogen followed by cooling to room temperature, and removing the solvents under reduced pressure. Next the residue treated with a 5% aqueous ammonia solution, incubated at 5° C. over one day, decanted the aqueous layer, washed well with water. Resulting light tan solid was isolated and washed with ether to give the product 150 mg (15% yield). The material while not completely pure, could be taken to next step.

$^1$H NMR (CD$_3$OD, 400 MHz): (due to lower purity, peak assignment and intensities are approximate) δ 8.6 (unresolved, 1H), 8.2 (d, 1H), 7.9 (m, 2H), 7.8 (unresolved, 1H), 7.65 (m, 3H), 7.4 (m, 1H), 7.3 (d, 1H), 7.2 (m, 1H), 7.1 (d, 1H), 6.95 (dd, 1H), 6.5, (s, 1H), 2.9 (m, 4H), 2.5 (m, 4H), 2.4 (s, 3H), 2.3 (s, 3H)

(E) Synthesis of 2-(5'-(5''-(4'''-methylpiperazin-1'''-yl)-1H-indol-2''-yl)benzimidazol-2'-yl)pyridine

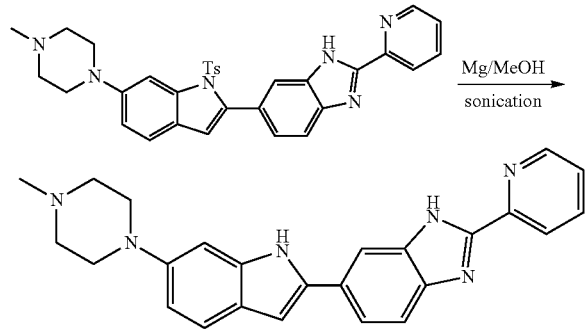

Crude 6-[6-(4-Methyl-piperazin-1-yl)-1-(toluene-4-sulfonyl)-1H-indol-2-yl]-2-pyridin-2-yl-1H-benzoimidazole (0.5 g, 0.9 mmol) was dissolved in methanol (100 mL) and to this Mg turnings (1.2 g) was added. This mixture was sonicated in an ultrasound bath for 3×90 minutes. Resulting slurry was evaporated to remove most of the solvent and was dissolved dichloromethane (250 mL). The organic extract was repeatedly washed with saturated NH$_4$Cl, dried and evaporated. Due to the formation of emulsions, recovery was poor (100 mg) chromatography of this (silicagel, 4 cm×2 cm column—pre-treated with 9:1 dichloromethane:methanolic ammonia: the product was gradient-eluted with 10% methanol in dichloromethane to 20% methanol in dichloromethane and then methanol) yielded 20 mg of product (5% yield) about 80-90% pure.

$^1$H NMR (CD$_3$OD+TFA, 400 MHz): δ 8.9 (unresolved d, 1H), 8.4 (d, 1H), 8.3 (m, 1H), 8.2 (unresolved, 1H), 8.1 (m, 2H), 7.9 (m, 1H), 7.8 (m, 1H), 7.7 (m, 1H), 7.5 (m, 1H), 7.0, (s, 1H), 3.8 (m, 2H), 3.6 (m, 2H), 3.1 (m, 2H), 2.9 (m, 2H)2.9 (s, 3H).

Cytotoxicity and Radioprotection Results

C50=34.1
PF=4.9
DMFm=1.30
DMF10=1.21

Example 54

Synthesis of 2-(5'-(5''-(3'''-hydroxyethyl-1'''-methylamino)benzimidazol-2''-yl)benzimidazol-2'-yl)pyridine (A) Preparation of 2-[(3-Amino-4-nitro-phenyl)-methyl-amino]-ethanol

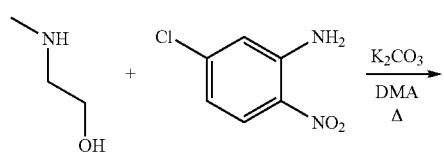

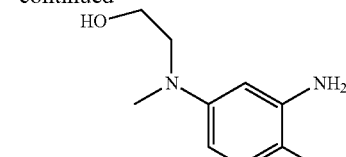

A mixture of 5-chloro-2-nitroaniline (5 g, 29 mmol), 2-Methylamino-ethanol (7 mL, 87 mmol) and anhydrous potassium carbonate (5.3 g, 38 mmol) in N,N-dimethylacetamide (10 ml) were stirred at 125° C. under nitrogen for 1 day. Sample NMR analysis showed complete conversion of the starting material. The resultant mixture was then cooled to room temperature, poured onto cold water (30 mL), stirred vigorously and incubated at 4° C. overnight. The resulting yellow precipitate was collected by filtration, washed well with water then dried on the filter funnel. This was then slurried in diethyl ether, filtered, washed with additional diethyl ether, dried to afford 2-[(3-Amino-4-nitro-phenyl)-methyl-amino]-ethanol (5.4 g, 88% yield) as a yellow solid and used in the next step without further purification.

$^1$H NMR (400 MHz, DMSO): δ 7.75, (d, 1H); 7.2 (broad s, 2H); 6.2, (d, 1H); 5.95, (s, 1H); 4.75 (crude t, 1H); 3.55 (m, 2H); 3.4 (m, 2H); 2.95 (s, 3H)—includes NH$_2$ and OH protons (B) Preparation of [2-(4-Amino-3-nitro-phenyl)-1H-benzoimidazol-5-yl]-methyl-propyl-amine

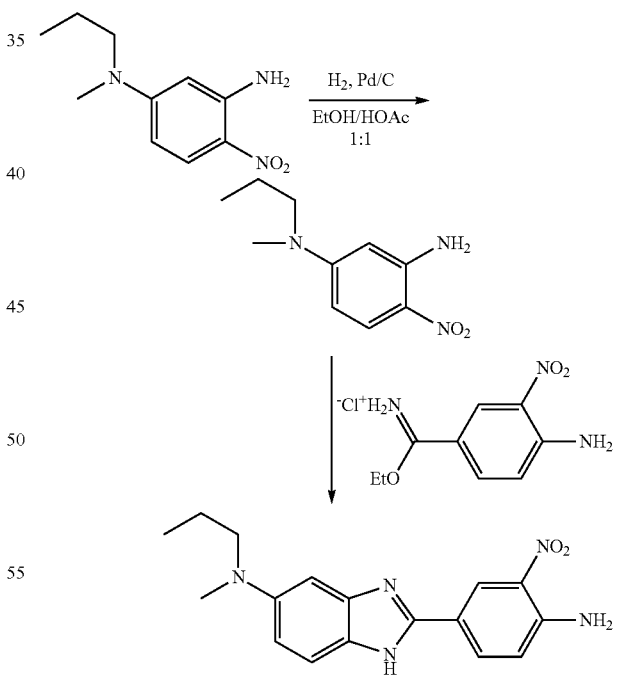

(i) Hydrogenation

To a solution of 2-[(3-Amino-4-nitro-phenyl)-methyl-amino]-ethanol (1.0 g, 4.7 mmol) in 1:1 acetic acid/ethanol (60 ml), under nitrogen, was added 5% palladium on activated carbon (0.075 g). The resulting mixture was evacuated and next, stirred at room temperature under an atmosphere of hydrogen (balloon) for one day. The reaction mixture was then directly filtered through celite into a round bottom flask under a nitrogen atmosphere containing ethyl 4-amino-3-nitrobenzenecarboximidate hydrochloride (1.1 g, 4.5 mmol), and proceeded to the coupling step.

(ii) Coupling Reaction

The resulting slurry from step (i) was heated at 80° C. under nitrogen for 24 h, then cooled to room temperature and solvents removed by rotary evaporator. The resulting dark oil was treated with dilute aqueous ammonia solution (5% in water, 50 ml), mixed vigorously and was kept overnight at 4° C. The supernatant liquid was decanted and the precipitated solid was washed with water again and decanted and the residual water was removed by evaporation.

Resulting black solid was slurried in ether (100 mL) overnight and filtered, giving the product as a 1.0 g black-violet solid (66% crude yield). The crude product was used in the next step without further purification.

$^1$H NMR (400 MHz, DMSO): δ 8.6 (s, 1H); 8.05, (d, 1H); 7.65 (broad s, 2H); 7.3, (unresolved, 1H); 7.0, (d, 1H); 6.65 (unresolved s, 1H); 6.6 (unresolved s, 1H); 4.6 (broad, 1H); 3.55 (crude t, 2H); 3.3 (unresolved-overlapping with $H_2O$, 2H); 2.95 (s, 3H)—includes $NH_2$ and OH protons (C) Synthesis of 2-(5'-(5''-(3'''-hydroxyethyl-1'''-methylamino)benzimidazol-2''-yl)benzimidazol-2'-yl) pyridine

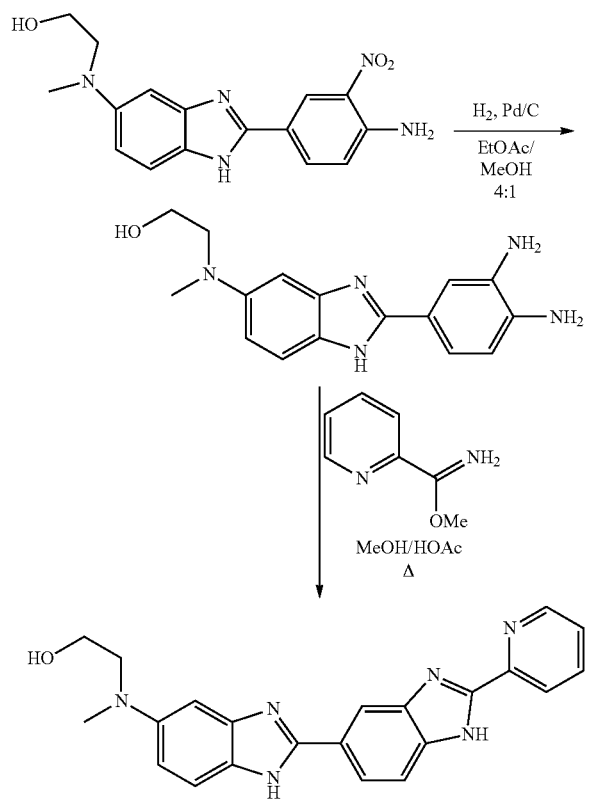

(i) Hydrogenation

To a solution of crude [2-(4-Amino-3-nitro-phenyl)-1H-benzoimidazol-5-yl]-methyl-propyl-amine (0.5 g, 1.5 mmol) in 3:1 ethyl acetate/methanol (60 ml) was added 5% palladium on carbon (100 mg) and the mixture was first evacuated and then stirred at room temperature under an atmosphere of hydrogen (balloon) for 1 day. The reaction mixture was next filtered through celite, washed with methanol, and the combined filtrate and washings were concentrated to give the crude diamine as a dark brown oil that was used in the next step without any purification.

(ii) Coupling Reaction

The crude diamine (prepared as above) was dissolved in methanol (20 ml). To this was added a solution of 2-cyanopyridine (238 mg, 2.3 mmol) that had been treated (immediately before) with sodium methoxide (0.23 mmol) in methanol (2.2 mL) at 40° C. for 1 hour under nitrogen. To this total mixture, acetic acid (0.33 ml, 5.8 mmol) was added next.

This mixture was heated at 80° C. for a day under nitrogen followed by cooling to room temperature, and removing the solvents under reduced pressure. The resulting dark red oil was treated with a 5% aqueous ammonia solution (20 ml), incubated at 5° C. for one day. The supernatant liquid was decanted and the precipitated solid was washed with water again and decanted and the residual water was removed by evaporation. Resulting solid was slurried in acetonitrile (50 mL) over 3 days and filtered to give the crude product as a brown powder 270 mg (48.2% crude yield). 130 mg of this was chromatographed on a 2 cm×9 cm silicagel column pretreated with 9:1 dichloromethane:methanolic ammonia. The product was gradient-eluted with 10% ethanol in dichloromethane to 50% ethanol in dichloromethane. Product was isolated as a red-brown-solid, 30 mg.

$^1$H NMR (400 MHz, $CD_3OD$): δ 8.62 (poorly resolved d, 1H); 8.2 (m, 2H); 7.82 (t, 1H); 7.8 (d, 1H); 7.65 (d, 1H); 7.4, (m, 2H); 7.0, (d, 1H); 6.8 (s, 1H); 3.6 (t, 2H); 3.4 (t, 2H); 2.95 (s, 3H);

Cytotoxicity and Radioprotection Results
C50=94.3
PF=20.2
DMFm=1.87
DMF10=1.15

Example 55

Topical Radioprotection of the Oral Mucosa of Mouse Tongue

Mice

Mice of the inbred C3H/Neu strain were sourced from a breeding colony at the Medical Faculty Carl Gustav Carus, Dresden, Germany. The animals were bred and housed under specified pathogen-free conditions. Housing was under controlled conditions of humidity (30-50%) and temperature (21° C.-24° C.). An automated light programme regulated a 12/12-hour light/dark rhythm with lights on from 6 am to 6 pm. The mice were kept in size 3 Macrolon cages, maximum of 10 per cage, on sawdust bedding. Standard mouse diet (Altromin 1326, Altrogge) and filtered city tap water from standard perspex drinking bottles were provided ad libitum.

Irradiation

A 3 mm×3 mm field at the middle of the lower surface of the mouse tongue was irradiated with 25 kV x-rays from a Darpac 150-MC device (Forward Raytech Ltd, Swinburne, UK) operated with a tube current of 20 milliamps yielding a dose rate of 3.78 Gy per minute and a focus-skin distance of 15 cm. Anaesthetised mice (sodium pentabarbitone; 60 mg per kg) were placed in a supine position in the central cylindrical hole (diameter 25 mm) of a pre-warmed aluminium block (approximately 35° C.). The tongue was guided through a hole (diameter 3 mm) in roof of the block by use of forceps, and the upper surface of the tongue was fixed to the outer surface of the block with double-sided adhesive tape.

The head was supported by a polystyrene wedge to avoid traction of the base of the tongue and consequent hypoxia. The collimator was a 1 mm thick aluminium plate with a 3×3 mm² window positioned centrally over the lower surface of the tongue. Groups of 10 mice, were irradiated with 5 different doses in the range of 10-20 Gy.

Pre-Irradiation Treatment

One hour prior to irradiation, 10 microlitres of formulation was applied to the lower surface of the tongue of anaesthetised mice using a displacement micropipette. Thirty minutes later, a second 10 microlitre aliquot of the formulation was applied and the mice irradiated thirty minutes later.

Topical Formulations

Stock solutions of the appropriate drug in propylene glycol or water were diluted with an aqueous solution of Poloxamer 407 gel (BASF Lutrol F 127) and/or a solution of hydroxypropyl cellulose (approx average MW 80,000; Aldrich cat no 435007) in propylene glycol and with water and/or propylene glycol, producing each of two formulations:

Formulation 1—gel, which contained 10 or 30 mM drug in 20% Poloxamer 407 and 1% hydroxylpropyl cellulose in 30% propylene glycol in water, and Formulation 2—Liquid, which contained 10, 30 or 60 mM drug in propylene glycol containing a final concentration of 1% hydroxypropyl cellulose.

Formulation 3—Liquid, which contained 30 mM drug in water containing a final concentration of 2% hydroxypropyl cellulose.

Scoring and Data Analysis

At various times after irradiation, the lower surface of the tongue of anaesthetised mice was examined daily. The quantal endpoint used was mucosal ulceration, corresponding to confluent mucositis RTOG/EORTC grade 3. The data plotted in the example figures is the percentage of a group of 10 mice in which the endpoint of mucosal ulceration was scored for at least 2 consecutive days. Radiation dose effect curves were generated with a single parameter sigmoidal relationship (logistic function $$S(D) = \frac{1}{1 + e^{-(D-ED_{50})}}),$$

using the Prism 5.0 curve-fitting programme to generate the $ED_{50}$ value, which corresponds to the interpolated radiation dose at which 50% of the mice in the group reached the mucosal ulceration endpoint.

The results are shown in FIGS. 3 to 7.

Example 56

Radioprotection of Mouse Jejunum by Intravenous 2PH

C3H/HeJ mice were administered 2PH by intravenous (tail vein) injection (30 mM solution in acetate-buffered saline, pH5; 150 mg/kg) 2 hours prior to whole body irradiation (up to 19 Gy) with $^{137}Cs$ γ-rays (GammaCell 40 Irradiator, Nordion International Inc., Canada) at a dose rate of 0.73 Gy/min, in groups of 5. The mice were euthanised 3 days 14 hours post-irradiation and the jejunum excised. Five 1 cm jejunum sections were taken from each mouse and bundled with micropore tape before being fixed in neutral buffered formalin. Samples are then paraffin embedded, sectioned and stained with Hematoxylin-Eosin. The densely stained colonies (>10 cells) arising from proliferation of surviving crypt clonogens were counted and scored on the basis of colonies per circumference.

Figure 8:
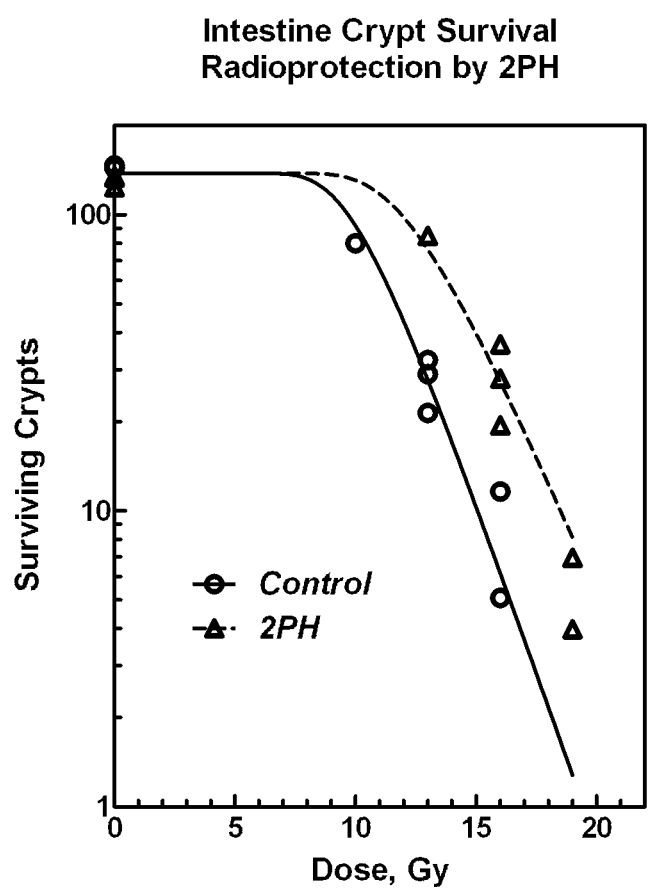
FIG. 8 shows dose (Gy)/effect (surviving crypts) curves for re-populating crypt clonogens and the radioprotective effect of prior intravenous administration of 2PH (Example 2) to mice compared to radiation-only controls.

FIG. 8 shows survival curves for re-populating crypt clonogens for 2PH-treated mice compared to radiation-only controls. The data for each of the two experimental groups was fitted to the expression:

$$N(D)=N_0(1-e^{-Se^{-\alpha D}})$$

Where:

$N_o$ is the initial number of clonogens per circumference, $N(D)$ the number of surviving clonogens per circumference after a radiation dose of D Gy, S is the number of clonogens per crypt, and α is the reciprocal of radiation dose corresponding to a lethal event.

The values for a derived by curve-fitting were:

$$\alpha_{control}=0.529+/-0.048\ Gy-1$$

$$\alpha_{2PH}=0.431+/-0.039\ Gy-1(p<0.0001)$$

These two values yielded a dose modification factor of 1.23+/−0.15.

Example 56

Radioprotection of Mouse Jejunum Subcutaneous M2PB

2-Hydroxypropyl-β-cyclodextrin (HPCD, Sigma-Aldrich, typical MW 1540) vehicle solution was prepared by dissolving 3.6 g of HPCD in 9.3 mL of phosphate buffered saline (PBS) resulting in 30% v/w solution. M2PB/HPCD stock solution was prepared by dissolving approximately 30 mg of M2PB (MW 396.45) in 2 mL of HPCD vehicle solution, which resulted in the formation of a highly aqueous soluble complex. The concentration of M2PB was measured following appropriate dilution in 45% MeOH 0.1% TFA using an extinction coefficient $4\times10^8\ M^{-1}\ cm^{-1}$ at 345 nm. The M2PB/HPCD stock was diluted to 8.75 mg/mL (22 mM) in HPCD vehicle to produce the final M2PB/HPCD formulation, which was injected subcutaneously into mice, between the shoulder blades (scruff of the neck) at a volume of $8\times10^{-3}$ ml/g body weight.

The subsequent irradiation and analysis was as described for Example 56.

Figure 9:
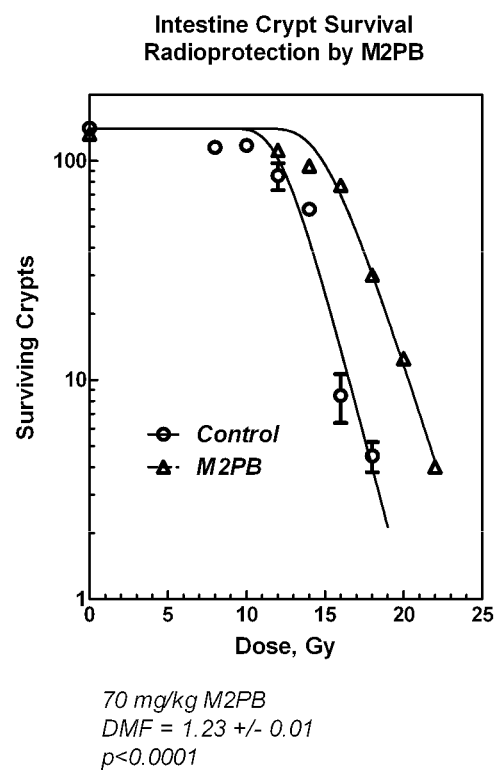
FIG. 9 shows dose (Gy)/effect (surviving crypts) curves for re-populating crypt clonogens and the radioprotective effect of prior subcutaneous administration of M2PB (Example 19), formulated as a complex with 2-hydroxypropyl-β-cyclodextrin, to mice compared to radiation-only controls.

Results are shown in FIG. 9. There was no indication of local reaction or toxicity at the site of subcutaneous injection that had been observed in similar experiments with the jejunum model, using for example subcutaneous administration of solutions of methylproamine, 2PH or M2PB in polyethylene glycol (MW 400).

REFERENCES

1. Waselenko, J. K., MacVittie, T. J., Blakely, W. F., Pesik, N., Wiley, A. L., Dickerson, W. E., Tsu, H., Confer, D. L., Coleman, C. N., Seed, T., Lowry, P., Armitage, J. O., and Dainiak, N., Medical management of the acute radiation syndrome: recommendations of the Strategic National Stockpile Radiation Working Group., *Ann Intern Med,* 140: 1037-1051, 2004.

2. Smith, P. J. and Anderson, C. O., *Int. J. Radiat. Biol.,* 46, 331 (1984).

3. Young, S. D. and Hill, R. P., *Brit. J. Cancer,* 60, 715-721 (1989).

4. Martin R F, Broadhurst S, Reum M E, Squire C J, Clark G R, Lobachevsky P N, White J M, Clark C, Sy D, Spotheim-Maurizot M, Kelly D P. In vitro studies with methylproamine: a potent new radioprotector. *Cancer Res.* 64(3):1067-70 (2004)

5. Kelly, D. P.; Bateman, S. A.; Hook, R. J.; Martin, R. F.; Reum, M. E.; Rose, M.; Whittaker, A. R. D. *Aust. J. Chem.* 1994, 47, 1751-1769

6. Smith P P, Bryant E M, Kaur P, McDougall J K, Cytogenetic analysis of eight human papillomavirus immortalized human keratinocyte cell lines, *Int. J. Cancer,* 1989 Dec. 15; 44(6):1124-31.

7. Kelly, D. P., Bateman, S. A., Martin, R. F., Rose, M. and Whittaker, A. R. D., *Aust. J. Chem.,* 47, 247-262, 1994.

8. Kuznetsov et al, *Zh. Org. Khim.,* 22, 455-6, 1986.

9. Renhowe et al, *J. Med. Chem.,* 52, 278-292, 2009.

10. WO 02/20500 A2.

11. WO 2005/070906 A1.

12. Whittaker, *J. Chem. Soc.,* 1565, 1951.

13. Okumura et al, *Bull. Chem. Soc. Jap.,* 33, 1471-1472, 1960.

14. Ram et al, *J. Heterocyclic Chem.,* 26, 1053-1059, 1989.

15. Metz et al, *Clin Cancer Res.* 10, 6411-17, 2004

16. Burdelya et al, Science 320, 226-30, 2008

17. *J. Med. Chem.* 2007, 50(15), 3561-3572.

The invention claimed is:

1. A radioprotector compound of Formula I:

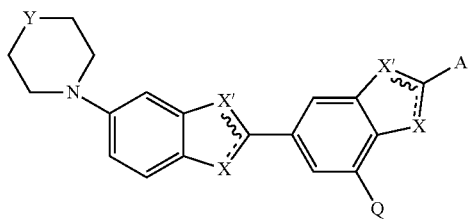

(I)

wherein
- X represents N or NH, where ---- is a double bond when X is N and a single bond when X is NH;
- X' represents N or NH, where X and X' are different and where ∼∼∼ is a double bond when X' is N and a single bond when X' is NH;
- Q represents methoxyl or H;
- Y represents O, methylene, hydroxymethyl or methylamino; and
- A represents optionally substituted 2-pyridyl, optionally substituted 2-pyrimidyl, optionally substituted 2-pyrazinyl, optionally substituted 3-pyrazolyl, optionally substituted 5-pyrazolyl, optionally substituted 2-furanyl, optionally substituted 2-quinolinyl, optionally substituted 1-isoquinolinyl or optionally substituted 3-isoquinolinyl and pharmaceutically acceptable salts, hydrates, solvates or tautomers thereof.

2. The compound of claim 1 wherein Y represents methylamino or hydroxymethyl.

3. The compound of claim 1 wherein A represents optionally substituted 2-pyridyl.

4. A radioprotector compound of Formula II:

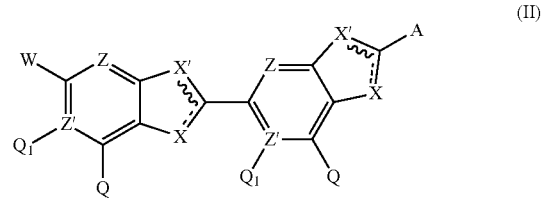

(II)

wherein
- W represents —N($R_1R_2$) where $R_1$ and $R_2$ are not both hydrogen and where they may together form a 5, 6 or 7 membered ring structure, —NHN($R_1R_2$), —NHR$_3$N($R_1R_2$), —NHR$_3$OR$_2$, —N($R_3$)R$_3$OR$_2$, —N($R_1$)R$_3$OR$_3$OR$_3$, —OR$_3$NR$_1R_2$, —OR$_3$ or W represents piperidyl, piperazinyl, morpholinyl, thiomorpholinyl or diazepanyl each of which may be optionally substituted by $C_1$ to $C_4$ alkyl, $C_2$ to $C_4$ alkenyl, —N(CO)N($R_1$ $R_2$), —N(CO)OR$_1$, —N(CO)OR$_3$OH, —(CO)NR$_1R_2$, —R$_3$(CO)NR$_1R_2$, —N($R_1R_2$) or —NH—;
- $R_1$ and $R_2$ are the same or different and are selected from hydrogen, $C_1$ to $C_4$ alkyl or $C_2$ to $C_4$ alkenyl;
- $R_3$ is a $C_1$ to $C_4$ alkyl or $C_2$ to $C_4$ alkenyl group or chain;
- Z is the same or different and represents N or CH;
- Z' is the same or different and represents N or C;
- X represents CH, N or NH, where ---- is a double bond when X is CH or N and a single bond when X is NH;
- X' represents N or NH, wherein when X is CH or N X' is NH and wherein X and X' are different and further where ∼∼∼ is a double bond when X' is N and a single bond when X' is NH;
- Q represents H, alkoxyl, —NR$_1R_2$,F or Cl;
- $Q_1$ is absent when Z' is N and when Z' is C it represents H, alkoxyl, —NR$_1R_2$,F or Cl;
- A represents a five to ten membered single or multiple ring structure with heterocyclic N or O located at the ortho position, said ring including optional double bonds, substitutions and/or other heteroatoms and pharmaceutically acceptable salts, hydrates, solvates or tautomers thereof.

5. The compound of claim 4 wherein A represents optionally substituted 2-pyridyl, optionally substituted 2-pyrimidyl, optionally substituted 2-pyrazinyl, optionally substituted 3-pyrazolyl, optionally substituted 5-pyrazolyl, optionally substituted 2-furanyl, optionally substituted 2-quinolinyl, optionally substituted 1-isoquinolinyl or optionally substituted 3-isoquinolinyl.

6. The compound of claim 5 wherein the optional substitution of A is by chloro, fluoro, $C_1$ to $C_4$ fluoroalkyl, $C_1$ to $C_4$ alkyl, $C_2$ to $C_4$ alkenyl, $C_1$ to $C_4$ alkoxy, $C_1$ to $C_4$ alkoxyalkyl, $C_1$ to $C_4$ alkylamino, $C_2$ to $C_4$ di-alkylamino or $C_1$ to $C_4$ aminoalkyl.

7. The compound of claim 5 wherein the optional substitution of A is by methyl or methoxyl.

8. The compound of claim 4 wherein at least one Q represents methoxyl.

9. The compound of claim 4 selected from:
2-(5'-(5"-(4'"-Methylpiperazin-1'"-yl)benzimidazol-2"-yl)benzimidazol-2'-yl)pyridine
4-Methyl-2-(5'-(5"-(4'"-methylpiperazin-1'"-yl)benzimidazol-2"-yl)benzimidazol-2'-yl)pyridine 4-Chloro-2-(5'-(5"-(4'''-methylpiperazin-1'''-yl)benzimidazol-2"-yl)benzimidazol-2'-yl)pyridine
4-Methoxy-2-(5'-(5"-(4'''-methylpiperazin-1'''-yl)benzimidazol-2"-yl)benzimidazol-2'-yl)pyridine
1-(5'-(5"-(4'''-Methylpiperazin-1'''-yl)benzimidazol-2"-yl)benzimidazol-2'-yl)isoquinoline
3-(5'-(5"-(4'''-Methylpiperazin-1'''-yl)benzimidazol-2"-yl)benzimidazol-2'-yl)isoquinoline
3-(5'-(5"-(4'''-Methylpiperazin-1'''-yl)benzimidazol-2"-yl)benzimidazol-2'-yl)indazole
2-(5'-(5"-Morpholinobenzimidazol-2"-yl)benzimidazol-2'-yl)pyridine
2-(5'-(5"-Morpholinobenzimidazol-2"-yl)benzimidazol-2'-yl)-4-methylpyridine
3-(5'-(5"-Morpholinobenzimidazol-2"-yl)benzimidazol-2'-yl)isoquinoline
2-(5'-(5"-(4'''-Methyl-1''',4'''-diazepan-1'''-yl)benzimidazol-2"-yl)benzimidazol-2'-yl)pyridine
2-(5'-(5"-(4'''-Methoxypiperidin-1'''-yl)benzimidazol-2"-yl)benzimidazol-2'-yl)pyridine
2-(4'-Methoxy-6'-(5"-(4'''-methylpiperazin-1'''-yl)benzimidazol-2"-yl)benzimidazol-2'-yl)pyridine
2-(6'-(5"-(4'''-Methylpiperazin-1'''-yl)benzimidazol-2"-yl)indol-2'-yl)pyridine
2-(5'-(5"-(morpholinoamino)benzimidazol-2"-yl)benzimidazol-2'-yl)pyridine
2-(5'-(5"-(4'''-Isopropylpiperazin-1'''-yl)benzimidazol-2"-yl)benzimidazol-2'-yl)pyridine
2-(5'-(5"-(4'''-Butylpiperazin-1'''-yl)benzimidazol-2"-yl)benzimidazol-2'-yl)pyridine
2-(5'-(5"((2'''-Methoxyethyl)(methyl)amino)benzimidazol-2"-yl)benzimidazol-2'-yl)pyridine
5-Methyl-2-(5'-(5"-(4'''-methylpiperazin-1'''-yl)benzimidazol-2"-yl)benzimidazol-2'-yl)pyridine
2-(5'-methoxy-6"-(5"-(4'''-methylpiperazin-1'''-yl)benzimidazol-2"-yl)benzimidazol-2'-yl)pyridine
3-(5'-(5"-(4'''-hydroxypiperidin-1'''-yl)benzimidazol-2"-yl)benzimidazol-2'-yl)isoquinoline
2-(5'-(5"-(4'''-(2''''methoxyethyl)piperazin-1'''-yl)benzimidazol-2"-yl)benzimidazol-2'-yl)pyridine
2-(5'-(5"-(2'''-(2''''-methoxyethoxy)ethylamino)benzimidazol-2"-yl)benzimidazol-2'-yl)pyridine
5-fluoro-2-(5'-(5"-(4'''-methylpiperazin-1'''-yl)benzimidazol-2"-yl)benzimidazol-2'-yl)pyridine
2-(5'-(5"-(4'''-hydroxypiperidin-1'''-yl)benzimidazol-2"-yl)benzimidazol-2'-yl)-5-methylpyridine.

10. The compound of claim 4 selected from:
2-(5'-(5"-(4'''-Methylpiperazin-1'''-yl)benzimidazol-2"-yl)benzimidazol-2'-yl)pyridine
4-Chloro-2-(5'-(5"-(4'''-methylpiperazin-1'''-yl)benzimidazol-2"-yl)benzimidazol-2'-yl)pyridine
4-Methyl-2-(5'-(5"-(4'''-methylpiperazin-1'''-yl)benzimidazol-2"-yl)benzimidazol-2'-yl)pyridine
2-(5'-(5"-Morpholinobenzimidazol-2"-yl)benzimidazol-2'-yl)pyridine
2-(4'-Methoxy-6'-(5"-(4'''-methylpiperazin-1'''-yl)benzimidazol-2"-yl)benzimidazol-2'-yl)pyridine
2-(5'-(5"-(4'''-Butylpiperazin-1'''-yl)benzimidazol-2"-yl)benzimidazol-2'-yl)pyridine
2-(5'-methoxy-6'-(5"-(4'''-methylpiperazin-1'''-yl)benzimidazol-2"-yl)benzimidazol-2'-yl)pyridine
4-methoxy-2-(5'-(5"-(4'''-methylpiperazin-1'''-yl)benzimidazol-2"-yl)benzimidazol-2'-yl)pyridine
3-(5'-(5"-(4'''-hydroxypiperidin-1'''-yl)benzimidazol-2"-yl)benzimidazol-2'-yl)isoquinoline
2-(5'-(5"-(2'''-(2''''-methoxyethoxy)ethylamino)benzimidazol-2"-yl)benzimidazol-2'-yl)pyridine
2-(5'-(5"-(4'''-Isopropylpiperazin-1'''-yl)benzimidazol-2"-yl)benzimidazol-2'-yl)pyridine
5-fluoro-2-(5'-(5"-(4'''-methylpiperazin-1'''-yl)benzimidazol-2"-yl)benzimidazol-2'-yl)pyridine.

11. A method of protecting biological material from ionising radiation damage comprising administering to said material an effective amount of a compound of claim 1 prior to and/or in conjunction with exposure of the material to ionising radiation.

12. The method of claim 11 wherein said biological material comprises a human or animal patient undergoing radiation therapy.

13. The method of claim 11 wherein said biological material comprises a human or animal patient undergoing a diagnostic procedure involving exposure to ionising radiation.

14. A method of preventing ionising radiation damage in a human at risk of exposure to ionising radiation comprising administration to the human of an effective amount of a compound of claim 1 prior to possible exposure of the human to ionising radiation.

15. A composition comprising a compound of claim 1 in combination with one or more of a pharmaceutically or veterinarily acceptable carrier.

* * * * *